US008338595B2

(12) United States Patent
Dixon et al.

(10) Patent No.: US 8,338,595 B2
(45) Date of Patent: *Dec. 25, 2012

(54) PYRROLOTRIAZINE DERIVATIVES USEFUL FOR TREATING HYPER-PROLIFERATIVE DISORDERS AND DISEASES ASSOCIATED WITH ANGIOGENESIS

(75) Inventors: Julie A. Dixon, Bethany, CT (US);
Catherine Brennan, Durham, NC (US);
Karl Miranda, Lexington, MA (US);
Brent Chandler, New Haven, CT (US);
Barton Phillips, New Haven, CT (US);
Jianmei Fan, Newton, MA (US);
Michael Brands, Wuppertal (DE);
Andrea McClure, West Haven, CT (US); Benjamin D. Jones, New Haven, CT (US); Wenlang Fu, Milford, CT (US); Donald Bierer, Bethany, CT (US);
Steven Magnuson, Wallingford, CT (US); Harold C. E. Kluender, Trumbull, CT (US)

(73) Assignee: Bayer HealthCare LLC, Tarrytown, NY (US)

( * ) Notice: Subject to any disclaimer, the term of this patent is extended or adjusted under 35 U.S.C. 154(b) by 539 days.

This patent is subject to a terminal disclaimer.

(21) Appl. No.: 12/506,033

(22) Filed: Jul. 20, 2009

(65) Prior Publication Data

US 2010/0075958 A1    Mar. 25, 2010

Related U.S. Application Data

(63) Continuation of application No. 11/596,913, filed as application No. PCT/US2005/019472 on Jun. 3, 2005, now Pat. No. 7,563,791.

(60) Provisional application No. 60/576,652, filed on Jun. 3, 2004, provisional application No. 60/626,531, filed on Nov. 9, 2004.

(51) Int. Cl.
*C07D 487/04* (2006.01)
*C07D 417/02* (2006.01)
*C07D 413/02* (2006.01)
*A61K 31/53* (2006.01)
*A61P 35/00* (2006.01)

(52) U.S. Cl. ............... 544/183; 514/243; 514/227.8; 514/231.5; 544/60; 544/111

(58) Field of Classification Search ............... 544/183, 544/60, 111; 514/243, 227.8, 231.5
See application file for complete search history.

(56) References Cited

U.S. PATENT DOCUMENTS

| 7,563,791 | B2 * | 7/2009 | Dixon et al. | 514/243 |
|---|---|---|---|---|
| 8,129,379 | B2 * | 3/2012 | Dixon et al. | 514/243 |
| 8,133,995 | B2 * | 3/2012 | Dixon et al. | 544/183 |
| 8,138,336 | B2 * | 3/2012 | Magnuson et al. | 544/183 |
| 8,143,393 | B2 * | 3/2012 | Dixon et al. | 544/183 |
| 2005/0153966 | A1 | 7/2005 | Gangloff et al. | |
| 2007/0004733 | A1 | 1/2007 | Chen et al. | |
| 2009/0281079 | A1 | 11/2009 | Dixon et al. | |
| 2010/0063038 | A1 | 3/2010 | Dixon et al. | |
| 2010/0179125 | A1 | 7/2010 | Dixon et al. | |
| 2010/0273800 | A1 | 10/2010 | Magnuson et al. | |

FOREIGN PATENT DOCUMENTS

| WO | WO 0071129 A1 | 11/2000 |
|---|---|---|
| WO | WO-2005/121147 A1 | 12/2005 |
| WO | WO-2007/061882 A2 | 5/2007 |

OTHER PUBLICATIONS

Cecil Textbook of Medicine, edited by Bennet, J.C., and Plum F., 20th edition, vol. 1, 1004-1010, 1996.
Freshney et al. "Culture of Animal Cells, A Manual of Basic Technique," Alan R. Liss, Inc. 1983, New York, p. 4.
Dermer et al., Bio/Technology, 1994, 12:320.
Powell et al., British Journal of Dermatology, 141: 802-810, 1999.
Cohen et al., Current Opinion in Chemical Biology, 3, 456-465, 1999.
Golub et al., Science, 286, 531-537, 1999.
Mass, R.D., International Journal of Radiation Oncology Bio Phys. vol. 58(3): 932-940, 2004.
Fabbro et al., Pharmacology & Therapeutics 93, 79-98, 2002.
West—Solid State Chemistry.
Vippagunta et al., Advanced Drug Delivery Reviews 48; 3-26, 2001.
Gautschi et al., Clin. Cancer Research, 14(6), 1639-1648, 2008.
Mountzios et al., Cancer Treatments Reviews, 34, 175-182, 2008.
Ferrara, N., Oncology, 69 suppl. 3, 11-16, 2005.
Jain et al., Nature Clinical Practice Oncology, 3(1), 24-40, 2006.
Ferrara, N. The Oncologist: 9 (Suppl. 1): 2-10, 2004.

\* cited by examiner

*Primary Examiner* — Venkataraman Balasubramanian
(74) *Attorney, Agent, or Firm* — Edwards Wildman Palmer LLP; Ralph A. Loren; Nicholas J. DiCeglie, Jr.

(57) ABSTRACT

This invention relates to pyrrozolotriazine compounds, pharmaceutical compositions containing such compounds and the use of those compounds and compositions for the prevention and/or treatment of hyper-proliferative disorders and diseases associated with angiogenesis.

8 Claims, No Drawings

PYRROLOTRIAZINE DERIVATIVES USEFUL FOR TREATING HYPER-PROLIFERATIVE DISORDERS AND DISEASES ASSOCIATED WITH ANGIOGENESIS

This application is a continuation of U.S. patent application Ser. No. 11/596,913, Nov. 17, 2006, now U.S. Pat. No. 7,563,791, which is the U.S. National Stage application under 35 U.S.C. §371 of International Patent Application Serial No. PCT/US2005/019472, filed Jun. 3, 2005, which claims the benefit under 35 USC 119(e) of U.S. Patent Application No. 60/576,652, filed Jun. 3, 2004, and U.S. Patent Application No. 60/626,531, filed Nov. 9, 2004, the disclosures of each of which are expressly incorporated by reference in their entireties.

This invention relates to novel pyrrozolotriazine compounds, pharmaceutical compositions containing such compounds and the use of those compounds and compositions for the prevention and/or treatment of hyper-proliferative disorders and diseases associated with angiogenesis.

BACKGROUND OF THE INVENTION

To support progressive tumor growth beyond the size of 1-2 mm$^3$, it is recognized that tumor cells require a functional stroma, a support structure consisting of fibroblast, smooth muscle cells, endothelial cells, extracellular matrix proteins, and soluble factors (Folkman, J., *Semin Oncol,* 2002. 29(6 Suppl 16), 15-8). Tumors induce the formation of stromal tissues through the secretion of soluble growth factors such as PDGF and transforming growth factor-beta (TGF-beta), which in turn stimulate the secretion of complimentary factors by host cells such as fibroblast growth factor (FGF), epidermal growth factor (EGF), and vascular endothelial growth factor (VEGF). These stimulatory factors induce the formation of new blood vessels, or angiogenesis, which brings oxygen and nutrients to the tumor and allows it to grow and provides a route for metastasis. It is believed some therapies directed at inhibiting stroma formation will inhibit the growth of epithelial tumors from a wide variety of histological types. (George, D. *Semin Oncol,* 2001. 28(5 Suppl 17), 27-33; Shaheen, R. M., et al., *Cancer Res,* 2001. 61(4), 1464-8; Shaheen, R. M., et al. *Cancer Res,* 1999. 59(21), 5412-6). However, because of the complex nature and the multiple growth factors involved in angiogenesis process and tumor progression, an agent targeting a single pathway may have limited efficacy. It is desirable to provide treatment against a number of key signaling pathways utilized by tumors to induce angiogenesis in the host stroma. These include PDGF, a potent stimulator of stroma formation (Ostman, A. and C. H. Heldin, *Adv Cancer Res,* 2001, 80, 1-38), FGF, a chemoattractant and mitogen for fibroblasts and endothelial cells, and VEGF, a potent regulator of vascularization.

A major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are reported to be highly specific for vascular endothelial cells (for reviews, see: Farrara et al. *Endocr. Rev.* 1992, 13, 18; Neufield et al. *FASEB J.* 1999, 13, 9).

VEGF expression is reported to be induced by hypoxia (Shweiki et al. *Nature* 1992, 359, 843), as well as by a variety of cytokines and growth factors, such as interleukin-1, interleukin-6, epidermal growth factor and transforming growth factor. To date, VEGF and the VEGF family members have been reported to bind to one or more of three transmembrane receptor tyrosine kinases (Mustonen et al. *J. Cell Biol.,* 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependant tyrosine phosphorylation in intact cells, whereas flt-1 displays a weak response. Thus, binding to KDR is believed to be a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. It is believed regulation of the VEGF-mediated signal transduction cascade by some agents can provide a useful mode for control of abnormal angiogenesis and/or hyperpermeability processes.

The vascular endothelial growth factors (VEGF, VEGF-C, VEGF-D) and their receptors (VEGFR2, VEGFR3) are not only key regulators of tumor angiogenesis, but also lymphangiogenesis. VEGF, VEGF-C and VEGF-D are expressed in most tumors, primarily during periods of tumor growth and, often at substantially increased levels. VEGF expression is stimulated by hypoxia, cytokines, oncogenes such as ras, or by inactivation of tumor suppressor genes (McMahon, G. *Oncologist* 2000, 5(Suppl. 1), 3-10; McDonald, N. Q.; Hendrickson, W. A. *Cell* 1993, 73, 421-424)

The biological activities of the VEGFs are mediated through binding to their receptors. VEGFR3 (also called Flt-4) is predominantly expressed on lymphatic endothelium in normal adult tissues. VEGFR3 function is needed for new lymphatic vessel formation, but not for maintenance of the pre-existing lymphatics. VEGFR3 is also upregulated on blood vessel endothelium in tumors. Recently VEGF-C and VEGF-D, ligands for VEGFR3, have been identified as regulators of lymphangiogenesis in mammals. Lymphangiogenesis induced by tumor-associated lymphangiogenic factors could promote the growth of new vessels into the tumor, providing tumor cells access to systemic circulation. Cells that invade the lymphatics could find their way into the bloodstream via the thoracic duct. Tumor expression studies have allowed a direct comparison of VEGF-C, VEGF-D and VEGFR3 expression with clinicopathological factors that relate directly to the ability of primary tumors to spread (e.g., lymph node involvement, lymphatic invasion, secondary metastases, and disease-free survival). In many instances, these studies demonstrate a statistical correlation between the expression of lymphangiogenic factors and the ability of a primary solid tumor to metastasize (Skobe, M. et al. *Nature Med.* 2001, 7(2), 192-198; Stacker, S. A. et al. *Nature Med.* 2001, 7(2), 186-191; Makinen, T. et al. *Nature Med.* 2001, 7(2), 199-205; Mandriota, S. J. et al. *EMBO J.* 2001, 20(4), 672-82; Karpanen, T. et al. *Cancer Res.* 2001, 61(5), 1786-90; Kubo, H. et al. *Blood* 2000, 96(2), 546-53).

Hypoxia appears to be an important stimulus for VEGF production in malignant cells. Activation of p38 MAP kinase is required for VEGF induction by tumor cells in response to hypoxia (Blaschke, F. et al. *Biochem. Biophys. Res. Commun.* 2002, 296, 890-896; Shemirani, B. et al. *Oral Oncology* 2002, 38, 251-257). In addition to its involvement in angiogenesis through regulation of VEGF secretion, p38 MAP kinase promotes malignant cell invasion, and migration of different tumor types through regulation of collagenase activity and urokinase plasminogen activator expression (Laferriere, J. et al. *J. Biol. Chem.* 2001, 276, 33762-33772; Westermarck, J. et al. *Cancer Res.* 2000, 60, 7156-7162; Huang, S. et al. *J. Biol. Chem.* 2000, 275, 12266-12272; Simon, C. et al. *Exp. Cell Res.* 2001, 271, 344-355). Moreover, VEGF activates the extracellular signal-regulated protein kinase (ERK) in human umbilical vein endothelial cells (HUVEC) (Yu, Y.; Sato, D. *J. Cell Physiol* 1999, 178, 235-246).

PDGF is another key regulator of stromal formation which is secreted by many tumors in a paracrine fashion and is believed to promote the growth of fibroblasts, smooth muscle and endothelial cells, promoting stroma formation and angiogenesis. PDGF was originally identified as the v-sis oncogene product of the simian sarcoma virus (Heldin, C. H., et al., *J Cell Sci Suppl*, 1985, 3, 65-76). The growth factor is made up of two peptide chains, referred to as A or B chains which share 60% homology in their primary amino acid sequence. The chains are disulfide cross linked to form the 30 kDa mature protein composed of either AA, BB or AB homo- or heterodimmers. PDGF is found at high levels in platelets, and is expressed by endothelial cells and vascular smooth muscle cells. In addition, the production of PDGF is up regulated under low oxygen conditions such as those found in poorly vascularized tumor tissue (Kourembanas, S., et al., *Kidney Int*, 1997, 51(2), 438-43). PDGF binds with high affinity to the PDGF receptor, a 1106 amino acid 124 kDa transmembrane tyrosine kinase receptor (Heldin, C. H., A. Ostman, and L. Ronnstrand, *Biochim Biophys Acta*, 1998. 1378(1), 79-113). PDGFR is found as homo- or heterodimer chains which have 30% homology overall in their amino acid sequence and 64% homology between their kinase domains (Heldin, C. H., et al. *Embo J*, 1988, 7(5), 1387-93). PDGFR is a member of a family of tyrosine kinase receptors with split kinase domains that includes VEGFR2 (KDR), VEGFR3 (Flt4), c-Kit, and FLT3. The PDGF receptor is expressed primarily on fibroblast, smooth muscle cells, and pericytes and to a lesser extent on neurons, kidney mesangial, Leydig, and Schwann cells of the central nervous system. Upon binding to the receptor, PDGF induces receptor dimerization and undergoes auto- and trans-phosphorylation of tyrosine residues which increase the receptors' kinase activity and promotes the recruitment of downstream effectors through the activation of SH2 protein binding domains. A number of signaling molecules form complexes with activated PDGFR including PI-3-kinase, phospholipase C-gamma, src and GAP (GTPase activating protein for p21-ras) (Soskic, V., et al. *Biochemistry*, 1999, 38(6), 1757-64). Through the activation of PI-3-kinase, PDGF activates the Rho signaling pathway inducing cell motility and migration, and through the activation of GAP, induces mitogenesis through the activation of p21-ras and the MAPK signaling pathway.

In adults, it is believed the major function of PDGF is to facilitate and increase the rate of wound healing and to maintain blood vessel homeostasis (Baker, E. A. and D. J. Leaper, *Wound Repair Regen*, 2000. 8(5), 392-8; Yu, J., A. Moon, and H. R. Kim, *Biochem Biophys Res Commun*, 2001. 282(3), 697-700). PDGF is found at high concentrations in platelets and is a potent chemoattractant for fibroblast, smooth muscle cells, neutrophils and macrophages. In addition to its role in wound healing PDGF is known to help maintain vascular homeostasis. During the development of new blood vessels, PDGF recruits pericytes and smooth muscle cells that are needed for the structural integrity of the vessels. PDGF is thought to play a similar role during tumor neovascularization. As part of its role in angiogenesis PDGF controls interstitial fluid pressure, regulating the permeability of vessels through its regulation of the interaction between connective tissue cells and the extracellular matrix. Inhibiting PDGFR activity can lower interstitial pressure and facilitate the influx of cytotoxics into tumors improving the anti-tumor efficacy of these agents (Pietras, K., et al. *Cancer Res*, 2002. 62(19), 5476-84; Pietras, K., et al. *Cancer Res*, 2001. 61(7), 2929-34).

PDGF can promote tumor growth through either the paracrine or autocrine stimulation of PDGFR receptors on stromal cells or tumor cells directly, or through the amplification of the receptor or activation of the receptor by recombination. Over expressed PDGF can transform human melanoma cells and keratinocytes (Forsberg, K., et al. *Proc Natl Acad Sci USA.*, 1993. 90(2), 393-7; Skobe, M. and N. E. Fusenig, *Proc Natl Acad Sci USA*, 1998. 95(3), 1050-5), two cell types that do not express PDGF receptors, presumably by the direct effect of PDGF on stroma formation and induction of angiogenesis. This paracrine stimulation of tumor stroma is also observed in carcinomas of the colon, lung, breast, and prostate (Bhardwaj, B., et al. *Clin Cancer Res*, 1996, 2(4), 773-82; Nakanishi, K., et al. *Mod Pathol*, 1997, 10(4), 341-7; Sundberg, C., et al. *Am J Pathol*, 1997, 151(2), 479-92; Lindmark, G., et al. *Lab Invest*, 1993, 69(6), 682-9; Vignaud, J. M., et al, *Cancer Res*, 1994, 54(20), 5455-63) where the tumors express PDGF, but not the receptor. The autocrine stimulation of tumor cell growth, where a large faction of tumors analyzed express both the ligand PDGF and the receptor, has been reported in glioblastomas (Fleming, T. P., et al. *Cancer Res*, 1992, 52(16), 4550-3), soft tissue sarcomas (Wang, J., M. D. Coltrera, and A. M. Gown, *Cancer Res*, 1994, 54(2), 560-4) and cancers of the ovary (Henriksen, R., et al. *Cancer Res*, 1993, 53(19), 4550-4), prostate (Fudge, K., C. Y. Wang, and M. E. Stearns, *Mod Pathol*, 1994, 7(5), 549-54), pancreas (Funa, K., et al. *Cancer Res*, 1990, 50(3), 748-53) and lung (Antoniades, H. N., et al., *Proc Natl Acad Sci USA*, 1992, 89(9), 3942-6). Ligand independent activation of the receptor is found to a lesser extent but has been reported in chronic myelomonocytic leukemia (CMML) where the a chromosomal translocation event forms a fusion protein between the Ets-like transcription factor TEL and the PDGF receptor. In addition, activating mutations in PDGFR have been found in gastrointestinal stromal tumors in which c-Kit activation is not involved (Heinrich, M. C., et al., *Science*, 2003, 9, 9).

Certain PDGFR inhibitors will interfere with tumor stromal development and are believed to inhibit tumor growth and metastasis.

The link between activity in tumor cell proliferation assays in vitro and anti-tumor activity in the clinical setting has been well established in the art. For example, the therapeutic utility of taxol (Silvestrini et al. *Stem Cells* 1993, 11(6), 528-35), taxotere (Bissery et al. *Anti Cancer Drugs* 1995, 6(3), 339), and topoisomerase inhibitors (Edelman et al. *Cancer Chemother.*

Cells protect their DNA by adopting a higher-order complex termed chromatin. Chromatin condensation is evident during mitosis and cell death induced by apoptosis while chromatin decondensation is necessary for replication, repair, recombination and transcription. Histones are among some of the DNA-binding proteins that are involved in the regulation of DNA condensation; and post-translational modifications of histone tails serve a critical role in the dynamic condensation/decondensation that occurs during the cell cycle. Phoshorylation of the tails of histone H3 is involved in both transcription and cell division (Prigent et al. *J. Cell Science* 2003, 116, 3677). A number of protein kinases have been reported to phosphorylate H3 and these kinases function both as signal transduction and mitotic kinases.

Pyrrolotriazine derivatives have been described as having kinase inhibitory activity in U.S. application Ser. No. 10/289,010, U.S. Pat. No. 6,670,357, WO 2001/19828, WO 2003/042172, WO 2004/009542, WO2004/009601, WO 2004/009784 and WO 2004/013145.

In one embodiment, the present invention provides a compound of formula (I)

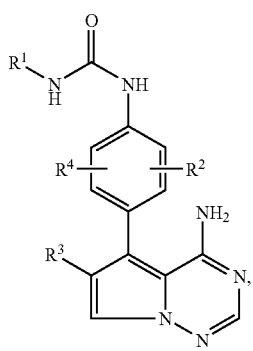

(I)

wherein
$R^1$ is selected from the group consisting of aryl, benzyl, and heteroaryl,
  wherein aryl and heteroaryl can be optionally substituted with 0, 1, 2, 3 or 4 substituents independently selected from the group consisting of
    $(C_1-C_4)$alkyl, wherein $(C_1-C_4)$alkyl can be substituted with 0, 1, 2 or 3 halogen, 0 or 1 heterocyclyl, or 0 or 1 $(C_1-C_3)$alkoxy, wherein
      $(C_1-C_3)$alkoxy can be optionally substituted with $(C_1-C_3)$alkylamino,
    $(C_1-C_3)$alkoxy, wherein $(C_1-C_3)$alkoxy can be optionally substituted with $(C_1-C_3)$alkylamino,
    halogen,
    trifluoromethyl,
    trifluoromethoxy,
    $(C_3-C_6)$cycloalkyl,
    phenyl optionally substituted with 1 or 2 halogen,

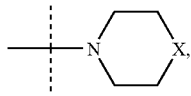

wherein X is $CH_2$, O, S or $NR^{1-1}$, and wherein $R^{1-1}$ is hydrogen or $(C_1-C_6)$alkyl,
    nitro,
    cyano,
    $(C_1-C_3)$alkylthio,
    trifluoromethylthio,
    $(C_1-C_3)$alkylcarbonyl,
    $(C_1-C_6)$alkoxycarbonyl, and
    phenoxy, wherein phenoxy can optionally be substituted with 0, 1 or 2 substituents independently selected from the group consisting of $(C_1-C_6)$alkyl, $(C_1-C_6)$alkoxy, trifluoromethoxy, and halogen,
  and
  wherein benzyl can be substituted with 0, 1, 2 or 3 groups selected from halogen, $(C_1-C_3)$alkyl, and $(C_1-C_3)$alkoxy;

$R^2$ is selected from the group consisting of hydrogen, halogen, $(C_1-C_4)$alkyl and $(C_1-C_4)$alkoxy;
$R^3$ is selected from the group consisting of
  carboxyl,
  formyl,
  $(C_1-C_6)$alkylcarbonyl optionally substituted with 0, 1, 2, or 3 groups selected from fluorine, chlorine, hydroxy, $(C_1-C_6)$alkoxy, and heterocycle,
  $(C_3-C_6)$cycloalkylcarbonyl,
  $(C_1-C_6)$alkoxycarbonyl optionally substituted with 0, 1, 2, or 3 groups selected from amino, and $(C_1-C_6)$alkoxycarbonyl,
  aminocarbonyl,
  $(C_1-C_6)$alkylaminocarbonyl, wherein $(C_1-C_6)$alkylaminocarbonyl can optionally be substituted with 0, 1, 2 or 3 substituents independently selected from the group consisting of $(C_3-C_6)$cycloalkyl, halogen, amino, $(C_1-C_6)$alkylamino, hydroxy, $(C_1-C_6)$alkoxy, $(C_1-C_6)$alkoxycarbonyl, $(C_1-C_6)$alkylthio, $(C_1-C_6)$alkoxycarbonylamino, and methylsulfonyl, and wherein $(C_1-C_6)$alkylaminocarbonyl can optionally be substituted with or 0 or 1 heterocyclyl, wherein heterocyclyl can optionally be substituted with 0 or 1 $(C_1-C_6)$alkyl, and wherein $(C_1-C_6)$alkylaminocarbonyl can optionally be substituted with 0 or 1 phenyl, wherein phenyl can optionally be substituted with 0 or 1 halogen, $(C_1-C_6)$alkyl, or $(C_1-C_6)$alkoxy,
  heterocyclylcarbonyl optionally substituted with 0 or 1 amino, $(C_1-C_6)$alkylamino, cycloalkyl, or $(C_1-C_6)$alkyl, wherein $(C_1-C_6)$alkyl can optionally be substituted with 0 or 1 amino or $(C_1-C_6)$alkylamino,
  $(C_1-C_6)$alkyl optionally substituted with 0, 1, 2 or 3 substituents independently selected from the group consisting of
    a) hydroxyl,
    b) amino,
    c) $(C_1-C_6)$alkylamino, wherein $(C_1-C_6)$alkylamino can be substituted with 0, 1, 2, 3 or 4 substituents independently selected from the group consisting of halogen, amino, alkylamino, methoxy, methylthio, and methylsulfonyl,
    d) arylamino, wherein arylamino can be substituted with 0, 1 or 2 substituents independently selected from the group consisting of $(C_1-C_6)$alkyl, $(C_1-C_6)$alkoxy, and trifluoromethyl,
    e) heterocyclyl, wherein heterocyclyl can be substituted with 0, 1 or 2 $(C_1-C_6)$alkyl, wherein $(C_1-C_6)$alkyl can be substituted with 0, 1 or 2 hydroxy, methoxy or pyridyl,
    f) imidazolyl,
    g) pyridylamino,
    h) $(C_1-C_3)$alkoxy optionally substituted by fluoro up to the perfluoro level, or by heterocycle, wherein heterocycle can optionally be substituted by 0 or 1 $(C_1-C_6)$alkyl,
    i) $(C_1-C_3)$alkoxy$(C_2-C_3)$alkoxy, and
    j) $(C_1-C_6)$alkoxycarbonyl,
    k) $(C_3-C_6)$cycloalkyl,
    l) cyano,
  $(C_1-C_6)$alkoxy optionally substituted with 1, 2 or 3 substituents independently selected from the group consisting of amino, $(C_1-C_6)$alkylamino, and heterocyclyl, wherein heterocyclyl can be substituted with 0, 1, 2 or 3 $(C_1-C_6)$alkyl,
  $(C_3-C_6)$cycloalkylaminocarbonyl optionally substituted with $(C_1-C_3)$alkyl, cyano,
heteroaryl, wherein heteroaryl can be substituted with 0, 1, 2, or 3 groups independently selected from the group consisting of
  a) ($C_1$-$C_6$)alkyl, wherein ($C_1$-$C_6$)alkyl can be substituted with 0, 1, 2, or 3 halogen, 0 or 1 heterocyclyl, 0 or 1 alkylamino, or 0 or 1 hydroxy or methoxy,
  b) halogen,
  c) amino,
  d) alkylamino,
  e) ($C_1$-$C_6$)alkoxycarbonyl, and
  f) ($C_3$-$C_6$)cycloalkyl,
heteroarylcarbonyl, which can be substituted with 0, 1, 2, or 3 groups independently selected from the group consisting of ($C_1$-$C_6$)alkyl, ($C_3$-$C_6$)cycloalkyl and halogen,
heterocyclyl, wherein heterocyclyl can be substituted with 0, 1, 2, or 3 groups independently selected from the group consisting of ($C_1$-$C_6$)alkyl and ($C_1$-$C_6$)alkoxycarbonyl; and
$R^4$ is selected from the group consisting of hydrogen, ($C_1$-$C_6$) alkyl, ($C_1$-$C_6$)alkoxy and halogen;
or a pharmaceutically acceptable salt thereof.

Depending on their structure, the compounds according to the invention can exist in stereoisomeric forms (enantiomers, diastereomers). The invention therefore relates to the enantiomers or diastereomers and to their respective mixtures. Such mixtures of enantiomers and/or diastereomers can be separated into stereoisomerically unitary constituents in a known manner.

The invention also relates to tautomers of the compounds, depending on the structure of the compounds.

A salt for the purposes of the invention is a pharmaceutically acceptable salt of the compound according to the invention.

Pharmaceutically acceptable salts of the compounds (I) include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, malic acid, citric acid, fumaric acid, maleic acid and benzoic acid.

Pharmaceutically acceptable salts of the compounds (I) also include salts of customary bases, such as for example alkali metal salts (for example sodium and potassium salts), alkaline earth metal salts (for example calcium and magnesium salts) and ammonium salts derived from ammonia or organic amines having 1 to 16 carbon atoms, such as ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabietylamine, arginine, lysine, ethylenediamine and methylpiperidine.

Solvates for the purposes of the invention are those forms of the compounds that coordinate with solvent molecules to form a complex in the solid or liquid state. Hydrates are a specific form of solvates, where the coordination is with water.

For the purposes of the present invention, the substituents have the following meanings, unless otherwise specified:

Alkyl represents a linear or branched alkyl radical having generally 1 to 6, 1 to 4 or 1 to 3 carbon atoms, representing illustratively methyl, ethyl, n-propyl, isopropyl, tert-butyl, n-pentyl and n-hexyl.

Alkoxy in general represents a straight-chain or branched hydrocarbon radical having generally 1 to 6, 1 to 4 or 1 to 3 carbon atoms and bound via an oxygen atom. Non-limiting examples include methoxy, ethoxy, propoxy, isopropoxy, butoxy, isobutoxy, pentoxy, isopentoxy, hexoxy, isohexoxy. The terms "alkoxy" and "alkyloxy" can be used synonymously.

Alkylamino represents an amino radical having one or two (independently selected) alkyl substituents, illustratively representing methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Alkylthio in general represents a straight-chain or branched hydrocarbon radical having 1 to 6 carbon atoms and bound via an sulfur atom. Non-limiting examples include methylthio and ethylthio.

Arylamino represents an amino radical having one or two (independently selected) aryl substituents, illustratively representing phenylamino.

Aminoalkyl represents an alkyl radical substituted with an amino group. Non-limiting examples include aminomethyl and aminoethyl.

Aminocarbonyl represents a free amide group.

Alkylcarbonyl represents a carbonyl group having an alkyl substituent. Non-limiting examples include acetyl, propanoyl, butanoyl, 2-methylpropanoyl, and hexanoyl.

Alkylaminocarbonyl represents an aminocarbonyl radical (free amide) having one or two (independently selected) alkyl substituents, illustratively representing methylaminocarbonyl, ethylaminocarbonyl, n-propylaminocarbonyl, isopropylamino-carbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-t-butyl-N-methylaminocarbonyl, N-ethyl-N-n-pentylamino-carbonyl and N-n-hexyl-N-methylaminocarbonyl.

Alkoxycarbonyl represents a carbonyl group having an alkoxy substituent. It illustratively represents methoxycarbonyl, ethoxycarbonyl, n-propoxycarbonyl, isopropoxycarbonyl, tert-butoxycarbonyl, n-pentoxycarbonyl and n-hexoxycarbonyl.

Cycloalkyl represents a monocyclic cycloalkyl radical having generally 3 to 8 or 5 to 7 carbon atoms, illustratively representing cyclopropyl, cyclobutyl, cyclopentyl, cyclohexyl and cycloheptyl.

Aryl represents a mono- to bicyclic carbocyclic radical, which is aromatic at least in one ring, having generally 6 to 10 carbon atoms, illustratively representing phenyl and naphthyl.

Heteroaryl represents an mono- or bicyclic radical having generally 5 to 10 or 5 or 6 ring atoms and up to 5, in another embodiment up to 4 hetero atoms selected from the group consisting of nitrogen, oxygen and sulfur, which is aromatic at least in one ring. It can be attached via a ring carbon atom or a ring nitrogen atom. If it represents a bicycle, wherein one ring is aromatic and the other one is not, it can be attached at either ring. Illustrative examples are thienyl, furyl, pyrrolyl, pyrazolyl, thiazolyl, oxazolyl, imidazolyl, pyridyl, pyrimidyl, pyridazinyl, indolyl, indazolyl, benzofuryl, benzimidazolyl, benzothiophenyl, quinolinyl, isoquinolinyl, 1,3-benzodioxinyl, 1,4-benzodioxinyl, or benzodioxolyl.

Heteroarylcarbonyl represents a heteroaryl residue bonded via a carbonyl carbon atom.

Heterocyclyl represents a mono- or bicyclic, in another embodiment monocyclic, nonaromatic, i.e. saturated or partially unsaturated radical having generally 4 to 10 or 5 to 8 ring atoms and up to 3, in another embodiment up to 2 hetero atoms and/or hetero groups selected from the group consisting of nitrogen, oxygen and sulfur, CO, SO and $SO_2$. If bicyclic, it can be a fused or spiro-connected bicycle. It can be attached via a ring carbon atom or a ring nitrogen atom. Illustrative examples are tetrahydrofuran-2-yl, pyrrolidin-2-yl, pyrrolidin-3-yl, pyrrolinyl, piperidinyl, morpholinyl, perhydroazepinyl.

Heterocyclylcarbonyl represents a heterocyclyl residue bonded via a carbonyl carbon atom.

Methylsulfonyl represents a $—S(O)_2CH_3$ residue.

Halogen or halo represents a substituent selected from the group consisting of fluoro, chloro, bromo and iodo, in another embodiment fluoro and chloro.

$(C_1-C_3)$alkoxy$(C_2-C_3)$alkoxy represents an 2 to 3 carbon alkoxy group substituted at the 2 or 3-position with a 1 to 3 carbon alkoxy group, illustratively representing 2-methoxyethoxy ($CH_3—O—CH_2CH_2—O—$), 3-ethoxypropoxy ($CH_3CH_2—O—CH_2CH_2CH_2—O—$), 2-methoxypropoxy ($CH_3—O(CH_3)CHCH_2—O—$), 2-isopropoxyethoxy ($CH_3(CH_3)CH—O—CH_2CH_2—O—$) 2-methoxy-1-methyl-ethoxy ($CH_3OCH_2(CH_3)CH—O—$) or 3-propoxyethoxy, ($CH_3CH_2CH_2—O—CH_2CH_2—O—$).

$(C_3-C_6)$cycloalkylaminocarbonyl optionally substituted by $(C_1-C_3)$alkyl represents an aminocarbonyl radical (free amide) having one (independently selected) cycloalkyl substituent, which may be optionally substituted on the nitrogen atom by a $(C_1-C_3)$alkyl group and independently substituted on any available carbon atom by 1 or 2 $(C_1-C_3)$alkyl groups, illustratively representing N-cyclopropylaminocarbonyl, N-cyclopropyl-N-methylaminocarbonyl, N-(2-methylcyclopropyl)aminocarbonyl, N-cyclobutylaminocarbonyl, N-(2,2-dimethyl)cyclopropyl)aminocarbonyl, cyclopentylaminocarbonyl, N-(3-ethylcyclopentyl)aminocarbonyl, N-cyclohexylaminocarbonyl, N-cyclohexyl-N-ethylaminocarbonyl, N-(3-propylcyclohexyl)aminocarbonyl, and N-(4,4-dimethylcyclohexyl)aminocarbonyl.

A * symbol next to a bond denotes the point of attachment in the molecule. Alternatively, a dotted line (---) denotes the bond via a radical is attached to the rest of the molecule.

When prefixes such as $(C_1-C_4)$ are used before substituents, they mean to indicate the respective number of carbon atoms, for example 1 to 4 in case of $(C_1-C_4)$.

When more than one substituent is selected from a group, selection can be independent of each other. Unless a maximum number of substituents is indicated, substitution can take place up to the maximum number of available substitution locations, e.g. in case of halogenation to the perhalo level.

In another embodiment, the present invention provides a compound of formula (I), wherein $R^1$ is selected from the group consisting of phenyl and monocyclic heteroaryl having 5 or 6 ring atoms,
wherein phenyl and heteroaryl can be optionally substituted with 0, 1, 2, 3 or 4 substituents independently selected from the group consisting of
$(C_1-C_4)$alkyl, wherein $(C_1-C_4)$alkyl can be substituted with 0, 1, 2 or 3 halogen, 0 or 1 pyrrolidinyl, 0 or 1 morpholinyl, or 0 or 1 $(C_1-C_3)$alkoxy wherein $(C_1-C_3)$alkoxy can be optionally substituted with $(C_1-C_3)$alkylamino,
$(C_1-C_3)$alkoxy, wherein $(C_1-C_3)$alkoxy can be optionally substituted with $(C_1-C_3)$alkylamino,
halogen,
trifluoromethyl,
trifluoromethoxy,
$(C_3-C_6)$cycloalkyl,
phenyl optionally substituted with 1 or 2 halogen,
trifluoromethylthio;

$R^2$ is selected from the group consisting of hydrogen, halogen, $(C_1-C_4)$alkyl and $(C_1-C_4)$alkoxy;

$R^3$ is selected from the group consisting of
carboxyl,
formyl,
$(C_1-C_6)$alkylcarbonyl optionally substituted with 0, 1, 2, or 3 groups selected from fluorine, chlorine, hydroxy, $(C_1-C_6)$alkoxy, and monocyclic heterocycle having 5 or 6 ring atoms,
$(C_3-C_6)$cycloalkylcarbonyl,
$(C_1-C_6)$alkoxycarbonyl optionally substituted with 0, 1, 2, or 3 groups selected from amino, and $(C_1-C_6)$alkoxycarbonyl,
aminocarbonyl,
$(C_1-C_6)$alkylaminocarbonyl, wherein $(C_1-C_6)$alkylaminocarbonyl can optionally be substituted with 0, 1, 2 or 3 substituents independently selected from the group consisting of $(C_3-C_6)$cycloalkyl, halogen, amino, $(C_1-C_6)$alkylamino, hydroxy, $(C_1-C_6)$alkoxy, $(C_1-C_6)$alkoxycarbonyl, $(C_1-C_6)$alkylthio, $(C_1-C_6)$alkoxycarbonylamino, and methylsulfonyl, and wherein $(C_1-C_6)$alkylaminocarbonyl can optionally be substituted with 0 or 1 hydroxyl or 0 or 1 monocyclic heterocyclyl having 5 or 6 ring atoms, wherein heterocyclyl can optionally be substituted with 0 or 1 $(C_1-C_6)$alkyl, and wherein $(C_1-C_6)$alkylaminocarbonyl can optionally be substituted with 0 or 1 phenyl, wherein phenyl can optionally be substituted with 0 or 1 halogen or $(C_1-C_6)$alkyl,
monocyclic heterocyclylcarbonyl having 5 or 6 ring atoms, optionally substituted with 0 or 1 amino, $(C_1-C_6)$alkylamino, $(C_3-C_6)$cycloalkyl, or $(C_1-C_6)$alkyl, wherein $(C_1-C_6)$alkyl can optionally be substituted with 0 or 1 amino or $(C_1-C_6)$alkylamino,
$(C_1-C_6)$alkyl optionally substituted with 0, 1, 2 or 3 substituents independently selected from the group consisting of
a) hydroxyl,
b) amino,
c) $(C_1-C_6)$alkylamino, wherein $(C_1-C_6)$alkylamino can be substituted with 0, 1, 2, 3 or 4 substituents independently selected from the group consisting of halogen, amino, alkylamino, methoxy, methylthio, and methylsulfonyl,
e) monocyclic heterocyclyl having 5 or 6 ring atoms, wherein heterocyclyl can be substituted with 0, 1 or 2 $(C_1-C_6)$alkyl, wherein $(C_1-C_6)$alkyl can be substituted with 0, 1 or 2 hydroxy, methoxy or pyridyl,
f) imidazolyl,
h) $(C_1-C_3)$alkoxy optionally substituted by fluoro up to the perfluoro level, or by monocyclic heterocycle having 5 or 6 ring atoms, wherein heterocycle can optionally be substituted by 0 or 1 $(C_1-C_6)$alkyl,
i) $(C_1-C_3)$alkoxy$(C_2-C_3)$alkoxy, and
j) $(C_1-C_6)$alkoxycarbonyl,
k) $(C_3-C_6)$cycloalkyl,
l) cyano,
$(C_3-C_6)$cycloalkylaminocarbonyl optionally substituted with $(C_1-C_3)$alkyl,
cyano,
heteroaryl, wherein heteroaryl can be substituted with 0, 1, 2, or 3 groups independently selected from the group consisting of
a) $(C_1-C_6)$alkyl, wherein $(C_1-C_6)$alkyl can be substituted with 0, 1, 2, or 3 halogen, 0 or 1 monocyclic heterocyclyl having 5 or 6 ring atoms, 0 or 1 alkylamino, or 0 or 1 hydroxy or methoxy,
b) halogen,
e) $(C_1-C_6)$alkoxycarbonyl, and
f) $(C_3-C_6)$cycloalkyl,
monocyclic heteroarylcarbonyl having 5 or 6 ring atoms,
monocyclic heterocyclyl having 5 or 6 ring atoms, wherein heterocyclyl can be substituted with 0, 1, 2, or 3 groups independently selected from the group consisting of $(C_1-C_6)$alkyl and $(C_1-C_6)$alkoxycarbonyl; and
$R^4$ is selected from the group consisting of hydrogen and halogen;
or a pharmaceutically acceptable salt thereof.

In another embodiment, the present invention provides a compound of formula (I), wherein
$R^1$ is selected from the group consisting of phenyl, pyrazolyl, oxazolyl, isoxazolyl, thiazolyl, pyridinyl, and pyrimidinyl,
wherein phenyl, pyrazolyl, oxazolyl, isoxazolyl, thiazolyl, pyridinyl, and pyrimidinyl can be optionally substituted with 0, 1, 2, 3 or 4 substituents independently selected from the group consisting of
$(C_1-C_4)$alkyl, wherein $(C_1-C_4)$alkyl can be substituted with 0, 1, 2 or 3 halogen,
$(C_1-C_3)$alkoxy, wherein $(C_1-C_3)$alkoxy can be optionally substituted with $(C_1-C_3)$alkylamino,
halogen,
trifluoromethyl,
trifluoromethoxy,
cyclopropyl,
phenyl optionally substituted with 1 or 2 halogen;
$R^2$ is selected from the group consisting of hydrogen, fluoro and chloro;
$R^3$ is selected from the group consisting of
$(C_1-C_6)$alkylcarbonyl optionally substituted with 0, 1, 2, or 3 groups selected from fluorine, chlorine, hydroxy, $(C_1-C_6)$alkoxy, piperazinyl, morpholinyl, pyrrolidinyl, and piperidinyl,
cyclopropylcarbonyl,
aminocarbonyl,
$(C_1-C_6)$alkylaminocarbonyl, wherein $(C_1-C_6)$alkylaminocarbonyl can optionally be substituted with 0, 1, 2 or 3 substituents independently selected from the group consisting of $(C_3-C_6)$cycloalkyl, halogen, amino, $(C_1-C_6)$alkylamino, hydroxy, $(C_1-C_6)$alkoxy, $(C_1-C_6)$alkoxycarbonyl, $(C_1-C_6)$alkylthio, $(C_1-C_6)$alkoxycarbonylamino, and methylsulfonyl, and wherein $(C_1-C_6)$alkylaminocarbonyl can optionally be substituted with 0 or 1 hydroxyl, piperazinyl, morpholinyl, pyrrolidinyl or piperidinyl, wherein piperazinyl, morpholinyl, pyrrolidinyl or piperidinyl can optionally be substituted with 0 or 1 $(C_1-C_6)$alkyl, and wherein $(C_1-C_6)$alkylaminocarbonyl can optionally be substituted with 0 or 1 phenyl, wherein phenyl can optionally be substituted with 0 or 1 halogen or $(C_1-C_6)$alkyl,
heterocyclylcarbonyl selected from piperazinylcarbonyl, morpholinylcarbonyl, pyrrolidinylcarbonyl or piperidinylcarbonyl, optionally substituted with 0 or 1 amino, $(C_1-C_6)$alkylamino, $(C_3-C_6)$cycloalkyl, or $(C_1-C_6)$alkyl, wherein $(C_1-C_6)$alkyl can optionally be substituted with 0 or 1 amino or $(C_1-C_6)$alkylamino,
$(C_1-C_6)$alkyl optionally substituted with 0, 1, 2 or 3 substituents independently selected from the group consisting of
a) hydroxyl,
c) $(C_1-C_6)$alkylamino, wherein $(C_1-C_6)$alkylamino can be substituted with 0, 1, 2, 3 or 4 substituents independently selected from the group consisting of halogen, alkylamino, and methoxy,
e) piperazinyl, morpholinyl, pyrrolidinyl or piperidinyl, wherein piperazinyl, morpholinyl, pyrrolidinyl or piperidinyl can be substituted with 0, 1 or 2 $(C_1-C_6)$alkyl, wherein $(C_1-C_6)$alkyl can be substituted with 0, 1 or 2 hydroxy or methoxy,
f) imidazolyl,
h) $(C_1-C_3)$alkoxy optionally substituted by fluoro up to the perfluoro level, or by monocyclic heterocycle having 5 or 6 ring atoms, wherein heterocycle can optionally be substituted by 0 or 1 $(C_1-C_6)$alkyl,
i) $(C_1-C_3)$alkoxy$(C_2-C_3)$alkoxy, and
j) $(C_1-C_6)$alkoxycarbonyl,
k) $(C_3-C_6)$cycloalkyl,
l) cyano,
$(C_3-C_6)$cycloalkylaminocarbonyl optionally substituted with $(C_1-C_3)$alkyl,
cyano,
pyrazolyl, oxazolyl, isoxazolyl, thiazolyl, isothiazolyl, pyridinyl, imidazolyl or pyrimidinyl, wherein pyrazolyl, oxazolyl, isoxazolyl, thiazolyl, isothiazolyl, pyridinyl, imidazolyl or pyrimidinyl can be substituted with 0, 1, 2, or 3 groups independently selected from the group consisting of
a) $(C_1-C_6)$alkyl, wherein $(C_1-C_6)$alkyl can be substituted with 0, 1, 2, or 3 halogen, 0 or 1 alkylamino, or 0 or 1 methoxy,
b) halogen, and
f) $(C_3-C_6)$cycloalkyl,
pyrazolylcarbonyl, oxazolylcarbonyl, isoxazolylcarbonyl, thiazolylcarbonyl, pyridinylcarbonyl or pyrimidinylcarbonyl; and
$R^4$ is selected from the group consisting of hydrogen and fluoro;
or a pharmaceutically acceptable salt thereof.

In another embodiment, the present invention provides a compound of formula (I), wherein
$R^1$ is selected from the group consisting of phenyl and monocyclic heteroaryl,
wherein aryl and heteroaryl can be optionally substituted with 0, 1, 2, 3 or 4 substituents independently selected from the group consisting of
$(C_1-C_4)$alkyl, wherein $(C_1-C_4)$alkyl can be substituted with 0, 1, 2 or 3 halogen, 0 or 1 pyrrolidinyl or morpholinyl, or 0 or 1 $(C_1-C_3)$alkoxy wherein $(C_1-C_3)$alkoxy can be optionally substituted with $(C_1-C_3)$alkylamino,
$(C_1-C_3)$alkoxy, wherein $(C_1-C_3)$alkoxy can be optionally substituted with $(C_1-C_3)$alkylamino,
halogen,
trifluoromethyl,
trifluoromethoxy,
$(C_3-C_6)$cycloalkyl,
$(C_1-C_3)$alkylthio, and
phenoxy, wherein phenoxy can optionally be substituted with 0, 1 or 2 substituents independently selected from the group consisting of $(C_1-C_6)$alkyl, $(C_1-C_6)$alkoxy, trifluoromethoxy, and halogen,
$R^2$ is selected from the group consisting of hydrogen, halogen, $(C_1-C_4)$alkyl and $(C_1-C_4)$alkoxy;
$R^3$ is selected from the group consisting of
carboxyl,
$(C_1-C_6)$alkylcarbonyl optionally substituted with 0, 1, 2, or 3 groups selected from fluorine, chlorine, hydroxy, $(C_1-C_6)$alkoxy, and heterocycle,
$(C_3-C_6)$cycloalkylcarbonyl, ($C_1$-$C_6$)alkoxycarbonyl, aminocarbonyl, ($C_1$-$C_6$)alkylaminocarbonyl, wherein ($C_1$-$C_6$)alkylaminocarbonyl can optionally be substituted with 0, 1, 2 or 3 substituents independently selected from the group consisting of ($C_3$-$C_6$)cycloalkyl, halogen, ($C_1$-$C_6$)alkylamino, hydroxy and ($C_1$-$C_6$)alkoxy, and wherein ($C_1$-$C_6$)alkylaminocarbonyl can optionally be substituted with or 0 or 1 heterocyclyl, wherein heterocyclyl can optionally be substituted with 0 or 1 ($C_1$-$C_6$)alkyl, and wherein ($C_1$-$C_6$)alkylaminocarbonyl can optionally be substituted with 0 or 1 phenyl, wherein phenyl can optionally be substituted with 0 or 1 halogen, ($C_1$-$C_6$)alkyl, or ($C_1$-$C_6$)alkoxy, heterocyclylcarbonyl optionally substituted with 0 or 1 amino, ($C_1$-$C_6$)alkylamino, cycloalkyl, or ($C_1$-$C_6$)alkyl, wherein ($C_1$-$C_6$)alkyl can optionally be substituted with 0 or 1 amino or ($C_1$-$C_6$)alkylamino, ($C_1$-$C_6$)alkyl optionally substituted with 0, 1, 2 or 3 substituents independently selected from the group consisting of
a) hydroxyl,
c) ($C_1$-$C_6$)alkylamino, wherein ($C_1$-$C_6$)alkylamino can be substituted with 0, 1, 2, 3 or 4 substituents independently selected from the group consisting of halogen, amino, alkylamino, methoxy, methylthio, and methylsulfonyl,
e) heterocyclyl, wherein heterocyclyl can be substituted with 0, 1 or 2 ($C_1$-$C_6$)alkyl, wherein ($C_1$-$C_6$)alkyl can be substituted with 0, 1 or 2 hydroxy, methoxy or pyridyl,
f) imidazolyl,
h) ($C_1$-$C_3$)alkoxy optionally substituted by fluoro up to the perfluoro level, or by heterocycle, wherein heterocycle can optionally be substituted by 0 or 1 ($C_1$-$C_6$)alkyl,
i) ($C_1$-$C_3$)alkoxy($C_2$-$C_3$)alkoxy, and
j) ($C_1$-$C_6$)alkoxycarbonyl,
k) ($C_3$-$C_6$)cycloalkyl, ($C_3$-$C_6$)cycloalkylaminocarbonyl optionally substituted with ($C_1$-$C_3$)alkyl, monocyclic heteroaryl having 5 or 6 ring atoms, wherein heteroaryl can be substituted with 0, 1, 2, or 3 groups independently selected from the group consisting of
g) ($C_1$-$C_6$)alkyl, wherein ($C_1$-$C_6$)alkyl can be substituted with 0, 1, 2, or 3 halogen, 0 or 1 heterocyclyl, 0 or 1 alkylamino, or 0 or 1 hydroxy or methoxy,
h) halogen,
i) amino,
j) alkylamino,
k) ($C_1$-$C_6$)alkoxycarbonyl, and
l) ($C_3$-$C_6$)cycloalkyl, monocyclic heteroarylcarbonyl having 5 or 6 ring atoms, monocyclic heterocyclylcarbonyl having 5 or 6 ring atoms, wherein heterocyclyl can be substituted with 0, 1, 2, or 3 groups independently selected from the group consisting of ($C_1$-$C_6$)alkyl and ($C_1$-$C_6$)alkoxycarbonyl; and $R^4$ is hydrogen or fluoro;

or a pharmaceutically acceptable salt thereof.

In another embodiment, the present invention provides a compound of formula (I), wherein $R^1$ is selected from the group consisting of phenyl, pyrazolyl, oxazolyl, isoxazolyl, thiazolyl, pyridinyl, and pyrimidinyl, wherein phenyl, pyrazolyl, oxazolyl, isoxazolyl, thiazolyl, pyridinyl, and pyrimidinyl can be optionally substituted with 0, 1, 2, 3 or 4 substituents independently selected from the group consisting of ($C_1$-$C_4$)alkyl, wherein ($C_1$-$C_4$)alkyl can be substituted with 0, 1, 2 or 3 halogen, ($C_1$-$C_3$)alkoxy, halogen, trifluoromethyl, and phenoxy, wherein phenoxy can optionally be substituted with 0, 1 or 2 substituents independently selected from the group consisting of alkyl, ($C_1$-$C_6$)alkoxy, trifluoromethoxy, and halogen;

$R^2$ is hydrogen, fluoro, chloro, methyl, ethyl or methoxy;

$R^3$ is selected from the group consisting of ($C_1$-$C_6$)alkoxycarbonyl, ($C_1$-$C_6$)alkylaminocarbonyl, wherein ($C_1$-$C_6$)alkylaminocarbonyl can optionally be substituted with 0, 1, 2 or 3 substituents independently selected from the group consisting of halogen, and ($C_3$-$C_6$)cycloalkylaminocarbonyl optionally substituted with ($C_1$-$C_3$)alkyl, piperazinylcarbonyl, morpholinylcarbonyl, pyrrolidinylcarbonyl or piperidinylcarbonyl; and $R^4$ is hydrogen;

or a pharmaceutically acceptable salt thereof.

In another embodiment, the present invention provides a compound of formula (I), wherein $R^1$ is selected from the group consisting of phenyl, pyrazolyl, thiazolyl, pyridinyl, and pyrimidinyl, wherein phenyl, pyrazolyl, oxazolyl, isoxazolyl, thiazolyl, pyridinyl, and pyrimidinyl can be optionally substituted with 0, 1, 2, 3 or 4 substituents independently selected from the group consisting of methyl, ethyl, propyl or butyl, wherein methyl, ethyl, propyl or butyl can be substituted with 0, 1, 2 or 3 fluoro or chloro, fluoro or chloro, trifluoromethyl, and phenoxy, wherein phenoxy can optionally be substituted with 0, 1 or 2 substituents independently selected from the group consisting of methyl, ethyl, propyl or butyl, methoxy, ethoxy, propoxy, trifluoromethoxy, fluoro and chloro;

$R^2$ is hydrogen;

$R^3$ is selected from the group consisting of methoxycarbonyl, ethoxycarbonyl, propoxycarbonyl or butoxycarbonyl, ($C_1$-$C_4$)alkylaminocarbonyl, wherein ($C_1$-$C_4$)alkylaminocarbonyl can optionally be substituted with 0, 1, 2 or 3 fluoro, and cyclopropylaminocarbonyl optionally substituted with methyl, ethyl or propyl, pyrrolidinylcarbonyl or piperidinylcarbonyl; and $R^4$ is hydrogen;

or a pharmaceutically acceptable salt thereof.

In another embodiment, the present invention provides a compound of formula (Ic)

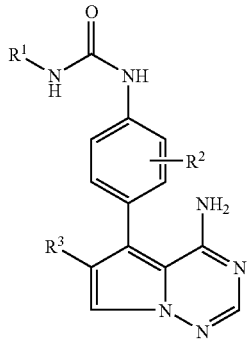

(Ic)

wherein
R¹ is selected from the group consisting of aryl, benzyl, and heteroaryl,
  wherein aryl and heteroaryl can be optionally substituted with 1, 2, 3 or 4 substituents independently selected from the group consisting of
    ($C_1$-$C_4$)alkyl, wherein ($C_1$-$C_4$)alkyl can be substituted with 0, 1, 2 or 3 halogen, 0 or 1 pyrrolidinyl, 0 or 1 morpholinyl, or 0 or 1 ($C_1$-$C_3$)alkoxy wherein ($C_1$-$C_3$)alkoxy can be optionally substituted with ($C_1$-$C_3$)alkylamino,
    ($C_1$-$C_3$)alkoxy, wherein ($C_1$-$C_3$)alkoxy can be optionally substituted with ($C_1$-$C_3$)alkylamino,
    halogen,
    trifluoromethyl,
    trifluoromethoxy,
    ($C_3$-$C_6$)cycloalkyl,
    phenyl optionally substituted with 1 or 2 halogen,

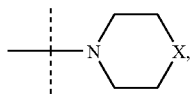

wherein X is $CH_2$, O, S or $NR^{1-1}$, and wherein $R^{1-1}$ is hydrogen or ($C_1$-$C_6$)alkyl,
    nitro,
    cyano,
    ($C_1$-$C_3$)alkylthio,
    trifluoromethylthio,
    ($C_1$-$C_3$)alkylcarbonyl,
    ($C_1$-$C_6$)alkoxycarbonyl, and
    phenoxy
  and
  wherein benzyl can be substituted with 0, 1, 2 or 3 groups selected from halogen, ($C_1$-$C_3$)alkyl, and ($C_1$-$C_3$)alkoxy;
R² is selected from the group consisting of hydrogen, halogen, alkyl and alkoxy;
R³ is selected from the group consisting of
  carboxyl,
  formyl,
  ($C_1$-$C_6$)alkylcarbonyl optionally substituted with 1, 2, or 3 fluorine,
  ($C_1$-$C_6$)alkoxycarbonyl,
  aminocarbonyl,
  ($C_1$-$C_6$)alkylaminocarbonyl, wherein ($C_1$-$C_6$)alkylaminocarbonyl can optionally be substituted with 1, 2 or 3 substituents independently selected from the group consisting of halogen, amino, alkylamino, methoxy, and methylsulfonyl, and wherein ($C_1$-$C_6$)alkylaminocarbonyl can be substituted with 0 or 1 hydroxyl or 0 or 1 heterocyclyl,
  heterocyclylcarbonyl,
  ($C_1$-$C_6$)alkyl optionally substituted with 1, 2 or 3 substituents independently selected from the group consisting of
    a) hydroxyl,
    b) amino,
    c) ($C_1$-$C_6$)alkylamino, wherein ($C_1$-$C_6$)alkylamino can be substituted with 0, 1, 2, 3 or 4 substituents independently selected from the group consisting of halogen, amino, alkylamino, methoxy, methylthio, and methylsulfonyl,
    d) arylamino, wherein arylamino can be substituted with 0, 1 or 2 substituents independently selected from the group consisting of ($C_1$-$C_6$)alkyl, ($C_1$-$C_6$)alkoxy, and trifluoromethyl,
    e) heterocyclyl, wherein heterocyclyl can be substituted with 0, 1 or 2 ($C_1$-$C_6$)alkyl, wherein ($C_1$-$C_6$)alkyl can be substituted with 0, 1 or 2 methoxy or pyridyl,
    f) imidazolyl,
    g) pyridylamino,
    h) ($C_1$-$C_3$)alkoxy optionally substituted by fluoro up to the perfluoro level,
    i) ($C_1$-$C_3$)alkoxy($C_2$-$C_3$)alkoxy, and
    j) ($C_1$-$C_6$)alkoxycarbonyl,
  ($C_1$-$C_6$)alkoxy optionally substituted with 1, 2 or 3 substituents independently selected from the group consisting of amino, ($C_1$-$C_6$)alkylamino, and heterocyclyl, wherein heterocyclyl can be substituted with 0, 1, 2 or 3 ($C_1$-$C_6$)alkyl;
  ($C_3$-$C_6$)cycloalkylaminocarbonyl optionally substituted with ($C_1$-$C_3$)alkyl,
  cyano, and
  heteroaryl wherein heteroaryl can be substituted with 0, 1, 2, or 3 groups independently selected from the group consisting of
    m) ($C_1$-$C_6$)alkyl, wherein ($C_1$-$C_6$)alkyl can be substituted with 0, 1, 2, or 3 halogen, 0 or 1 heterocycyl, 0 or 1 alkylamino, or 0 or 1 methoxy,
    n) halogen,
    o) amino, and
    p) alkylamino;
or a pharmaceutically acceptable salt thereof.

In another embodiment, the present invention provides a compound of formula (Ic):

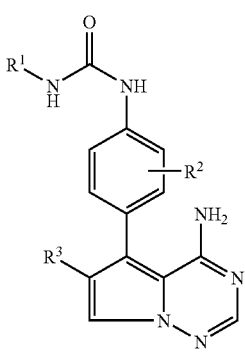

(Ic)

wherein
R¹ is selected from the group consisting of aryl and heteroaryl, wherein aryl and heteroaryl can be substituted with 0, 1, 2, 3 or 4 substituents independently selected from the group consisting of
($C_1$-$C_4$)alkyl,
($C_1$-$C_3$)alkoxy,
halogen,
trifluoromethyl,
trifluoromethoxy,
($C_3$-$C_6$)cycloalkyl,
phenyl optionally substituted with 0, 1 or 2 halogen, and

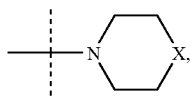

wherein X is $CH_2$, O, S or $NR^{1-1}$; and wherein $R^{1-1}$ is hydrogen or ($C_1$-$C_6$)alkyl;

$R^2$ is selected from the group consisting of hydrogen, halogen, alkyl and alkoxy;

$R^3$ is selected from the group consisting of carboxyl, ($C_1$-$C_6$) alkoxycarbonyl, aminocarbonyl, ($C_1$-$C_6$)alkylaminocarbonyl, and heterocyclylcarbonyl, wherein ($C_1$-$C_6$)alkylaminocarbonyl can optionally be substituted with 0, 1, 2 or 3 substituents independently selected from the group consisting of halogen, amino, alkylamino, methoxy and methylsulfonyl, or $R^3$ is ($C_1$-$C_6$)alkyl optionally substituted with 0, 1, 2 or 3 substituents independently selected from the group consisting of hydroxyl, amino, ($C_1$-$C_6$)alkylamino, arylamino, heterocyclyl, pyridyl, and pyridylamino, wherein ($C_1$-$C_6$)alkylamino can optionally be substituted with 0, 1, 2, 3 or 4 substituents independently selected from the group consisting of halogen, amino, alkylamino, methoxy, methylthio, and methylsulfonyl, and wherein heterocyclyl can optionally be substituted with 0, 1 or 2 ($C_1$-$C_6$)alkyl, wherein ($C_1$-$C_6$)alkyl can optionally be substituted with 1 or 2 methoxy or pyridyl, and wherein arylamino can optionally be substituted with 0, 1 or 2 substituents independently selected from the group consisting of ($C_1$-$C_6$)alkyl, ($C_1$-$C_6$)alkoxy, and trifluoromethyl, or $R^3$ is ($C_1$-$C_6$)alkoxy optionally substituted with 0, 1, 2 or 3 substituents independently selected from the group consisting of amino, ($C_1$-$C_6$)alkylamino, and heterocyclyl, wherein heterocyclyl can optionally be substituted with 0, 1, 2 or 3 ($C_1$-$C_6$)alkyl;

or a pharmaceutically acceptable salt thereof.

In another embodiment, the present invention provides a compound of formula (I), wherein $R^1$ is selected from the group consisting of phenyl and mono- or bicyclic heteroaryl containing 5, 6, 9 or 10 ring atoms and up to 2 hetero atoms selected from the group consisting of nitrogen, oxygen and sulfur, wherein phenyl and heteroaryl can be substituted with 0, 1 or 2 substituents independently selected from the group consisting of ($C_1$-$C_4$)alkyl, $C_1$-$C_3$)alkoxy, halogen, trifluoromethyl, trifluoromethoxy, ($C_3$-$C_6$)cycloalkyl, phenyl optionally substituted with trifluoromethyl, and

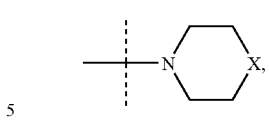

wherein X is $CH_2$, O, S or $NR^{1-1}$;
wherein $R^{1-1}$ is hydrogen or ($C_1$-$C_6$)alkyl;

$R^2$ is selected from the group consisting of hydrogen, fluoro, chloro, methyl, and methoxy;

$R^3$ is selected from the group consisting of carboxyl, ($C_1$-$C_6$) alkoxycarbonyl, aminocarbonyl, and ($C_1$-$C_6$)alkylaminocarbonyl, wherein ($C_1$-$C_6$)alkylaminocarbonyl can optionally be substituted with 0, 1 or 2 substituents independently selected from the group consisting of halogen, amino, alkylamino, methoxy and methylsulfonyl, or $R^3$ is ($C_1$-$C_6$)alkyl substituted with amino, ($C_1$-$C_6$)alkylamino, pyridyl, or 5- to 6 membered heterocyclyl containing 1 or 2 heteroatoms selected from the group consisting of nitrogen, oxygen and sulfur, wherein ($C_1$-$C_6$)alkylamino can optionally be substituted with 0, 1 or 2 substituents independently selected from the group consisting of halogen, amino, alkylamino, methoxy and methylsulfonyl, and wherein heterocyclyl can optionally be substituted with 0, 1 or 2 ($C_1$-$C_6$)alkyl, wherein ($C_1$-$C_6$) alkyl can optionally be substituted with 0 or 1 methoxy or pyridyl, or $R^3$ is ($C_1$-$C_6$)alkoxy optionally substituted with 0, 1, 2 or 3 substituents independently selected from the group consisting of amino, ($C_1$-$C_6$)alkylamino, and a 5- to 6 membered heterocyclyl containing 1 or 2 heteroatoms selected from the group consisting of nitrogen, oxygen and sulfur, wherein heterocyclyl can optionally be substituted with 0, 1, 2 or 3 ($C_1$-$C_6$)alkyl;

or a pharmaceutically acceptable salt thereof.

In another embodiment, the present invention provides a compound of formula (Ic),

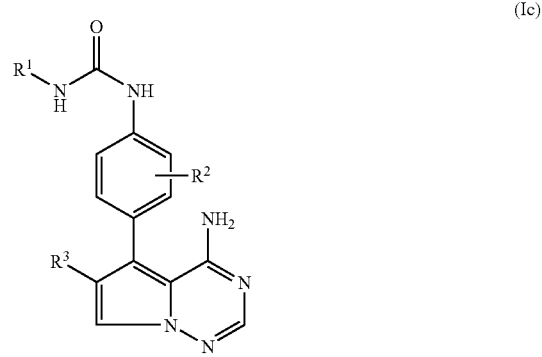

(Ic)

wherein
$R^1$ is selected from the group consisting of
phenyl optionally substituted with 1-2 groups selected from halo, ($C_1$-$C_4$)alkyl, $OCF_3$, $CF_3$, and

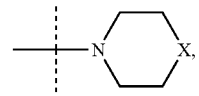

wherein X is CH$_2$, O, S or NR$^{1-1}$, wherein R$^{1-1}$ is hydrogen or (C$_1$-C$_6$)alkyl,
pyridyl optionally substituted with CF$_3$,
pyrazolyl option substituted with 1-2 groups selected from (C$_1$-C$_4$)alkyl, (C$_3$-C$_6$)cycloalkyl, and phenyl optionally substituted with CF$_3$,
isoxazolyl optionally substituted with (C$_1$-C$_4$)alkyl,
pyrimid-4-yl optionally substituted with (C$_1$-C$_3$)alkoxy
indazolyl, optionally substituted on N with (C$_1$-C$_4$)alkyl;
R$^2$ is hydrogen;
R$^3$ is selected from the group consisting of
CO$_2$R$^{3-1}$
CONR$^{3-2}$R$^{3-3}$
—(CH$_2$)$_m$NR$^{3-4}$R$^{3-5}$

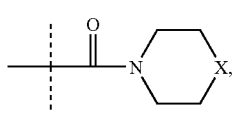

wherein X is O or NH,

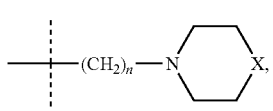

wherein X is O or NH,

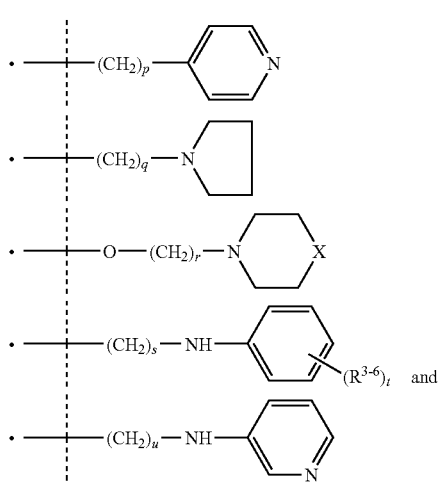

and m is 1, 2 or 3
n is 1, 2, or 3;
p is 1, 2 or 3;
q is 2 or 3;
r is 2 or 3
s is 1, 2 or 3;
t is 0, 1 or 2;
u is 1, 2 or 3;
R$^{3-1}$ is H or (C$_1$-C$_6$)alkyl;
R$^{3-2}$ and R$^{3-3}$ are independently selected from H and (C$_1$-C$_6$)alkyl;
R$^{3-4}$ and R$^{3-5}$ are independently selected from H and (C$_1$-C$_6$)alkyl;
R$^{3-6}$ is CF$_3$, (C$_1$-C$_4$)alkoxy or (C$_1$-C$_4$)alkyl;
or a pharmaceutically acceptable salt thereof.

In another embodiment, the present invention provides a compound of the formula (Ia),

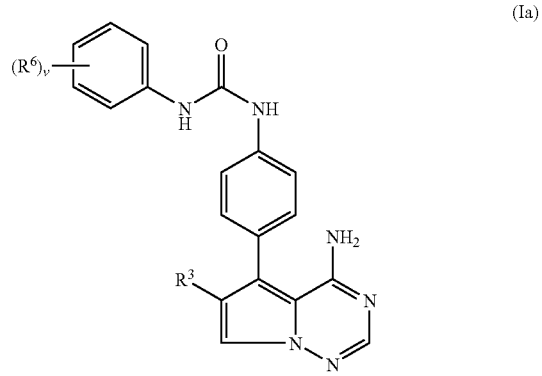

wherein
R$^3$ is selected from the group consisting of

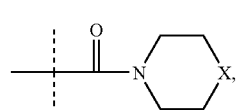

wherein X is O or NH,

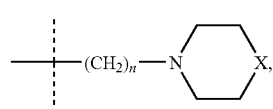

wherein X is O or NH, and
aminocarbonyl or (C$_1$-C$_6$)alkylaminocarbonyl substituted as described above;
n is 1, 2, or 3;
R$^5$ is independently selected from the group consisting of fluoro, chloro, methyl, ethyl, propyl, isopropyl, trifluoromethyl, trifluoromethoxy, and morpholino; and
v is 0, 1 or 2;
or a pharmaceutically acceptable salt thereof.

In another embodiment, the present invention provides a compound of the formula (Ib),

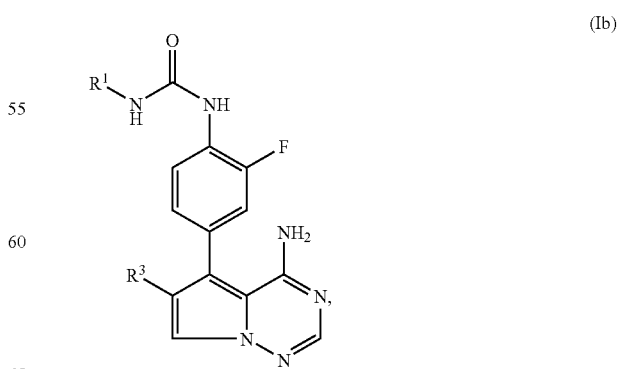

or a pharmaceutically acceptable salt thereof.

In another embodiment, the present invention provides a compound of the formula (Ic), wherein $R^1$ represents

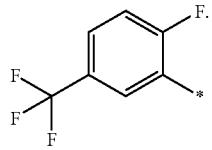

In another embodiment, the present invention provides a compound of the formula (Ic), wherein $R^3$ represents ethoxycarbonyl.

In another embodiment, the present invention provides a compound of the formula (Ic), wherein $R^3$ is $(C_1-C_6)$alkylaminocarbonyl, wherein $(C_1-C_6)$alkylaminocarbonyl can optionally be substituted with 1 or 2 substituents independently selected from the group consisting of halogen, amino, alkylamino, methoxy and methylsulfonyl, and wherein arylamino can optionally be substituted with 1 or 2 methoxy or trifluoromethyl.

In another embodiment, the present invention provides a compound as described as an Operational Example Examples section of the present application.

In another embodiment, the present invention relates to a compound capable of being metabolized or hydrolyzed to a compound of formula (I) under physiological conditions. This includes e.g. ester and amide derivatives (which can be hydrolyzed to the respective acids, alcohols and amines) as well as orthoesters and aminal esters (which can be hydrolyzed to the respective acids), acetals and hemiacetals (which can be hydrolyzed to the respective keto derivatives, e.g. the oxo group of the 4-oxopyrimidine ring moiety).

In another embodiment, the present invention provides a process for preparing a compound of formula (I), wherein a compound of formula (II)

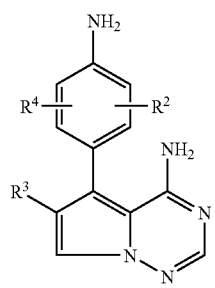

wherein $R^2$, $R^3$ and $R^4$ have the meaning indicated above, is reacted with an isocyanate compound of formula (III)

  (III)

or with an carbamate of formula (VI)

  (VI), wherein $R^1$ has the meaning indicated above; or a compound of formula (IV)

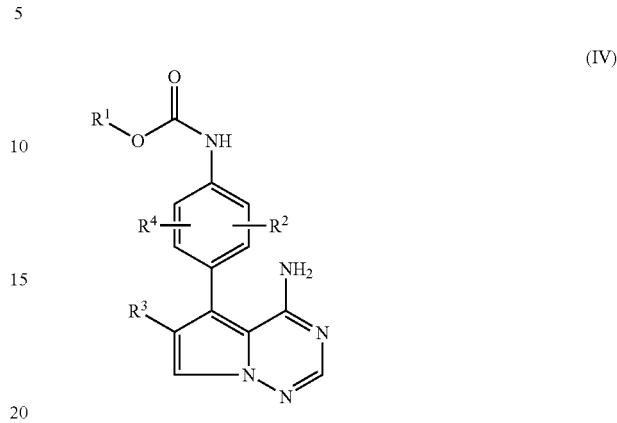

wherein $R^1$, $R^2$, $R^3$ and $R^4$ have the meaning indicated above, is reacted with an anine of formula (V)

  (V), wherein $R^1$ has the meaning indicated above.

The preparation of the compounds according to the invention can be illustrated by means of the following synthetic schemes. Unless specifically defined otherwise, the substituent placeholders such as $R^1$ to $R^3$ have the meaning indicated above.

Methods for preparing pyrrolotriazines are also disclosed in published U.S. application Ser. No. 10/289,010 (Publication No. US 2003-0186982 A1), U.S. Pat. No. 6,670,357 (U.S. application Ser. No. 10/036,293), as well as WO 2003/042172, WO 2004/009542, WO2004/009601, WO 2004/009784 and WO 2004/013145, all of which are hereby incorporated by reference in their entirety.

General Methods of Preparation of Invention Compounds

Compounds of the present invention of Formula (I) can be conveniently prepared from the corresponding amino compounds of Formula (II) by straightforward means as described in the Reaction Schemes below or by means well known to those skilled in the art. In these Reaction Schemes, unless otherwise specifically defined, the meanings of $R^1$-$R^3$, $R^{3-2}$, $R^{3-3}$, $R^{3-4}$, $R^4$ and r are identical to those described above.

Reaction Scheme 1 illustrates the general method of preparing Formula (I) compounds from the corresponding amino compounds of Formula (II) by standard methods of urea formation. In this scheme, a Formula (II) compound is allowed to react with either an isocyanate of Formula (III), or more preferably a carbamate of Formula (VI), generally in an inert solvent, to give the compound of Formula (I) directly. Alternatively, the amine of Formula (II) can be treated first with a chloroformate of Formula (VII), in an inert solvent, to provide an intermediate carbamate of Formula (IV). The Formula (IV) compound is then allowed to react with an amine of Formula (V), in an inert solvent, to provide the compound of Formula (I).

Reaction Scheme 1

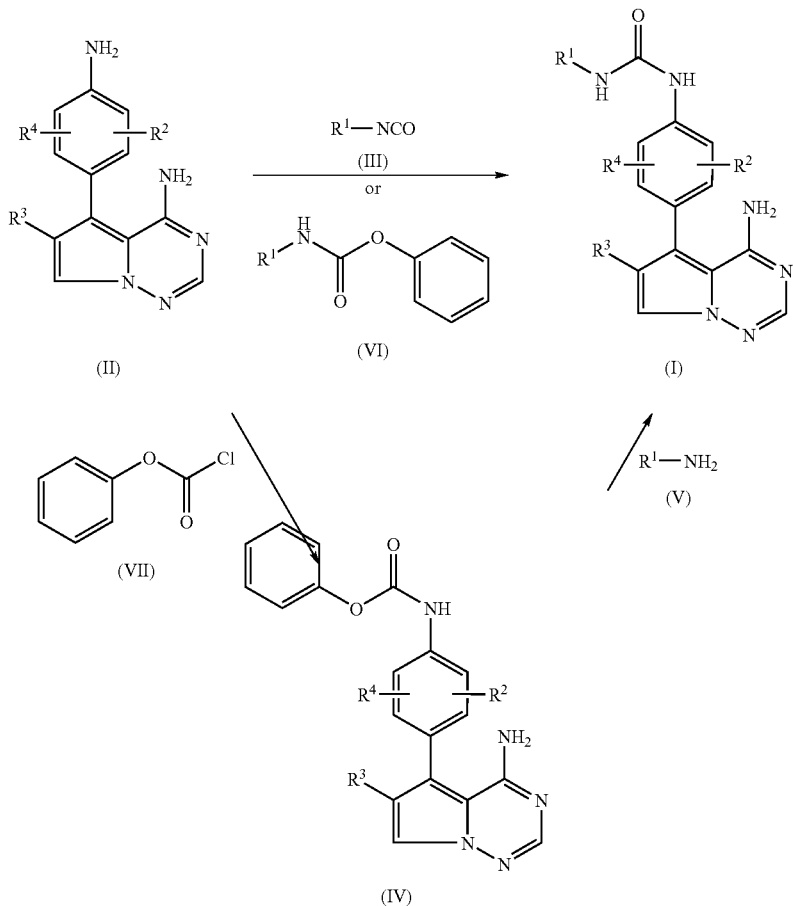

A more specific example of the Reaction Scheme 1 method is illustrated in Reaction Scheme 2 below. In this scheme, the amine of Formula (II-1) [Formula (II), where $R^3$ is $CO_2Et$], is used as the starting material, reacting with an isocyanate ((III), carbamate (VI), or in a two step sequence using (VII) followed by (V), to give the compound of Formula (I-1) [Formula (I) where $R^3$ is $CO_2Et$]. The Formula (I-1) compound can then be used as a starting material to prepare other compounds of Formula (I) as shown, for example, in Reaction Scheme 3 below.

Reaction Scheme 2

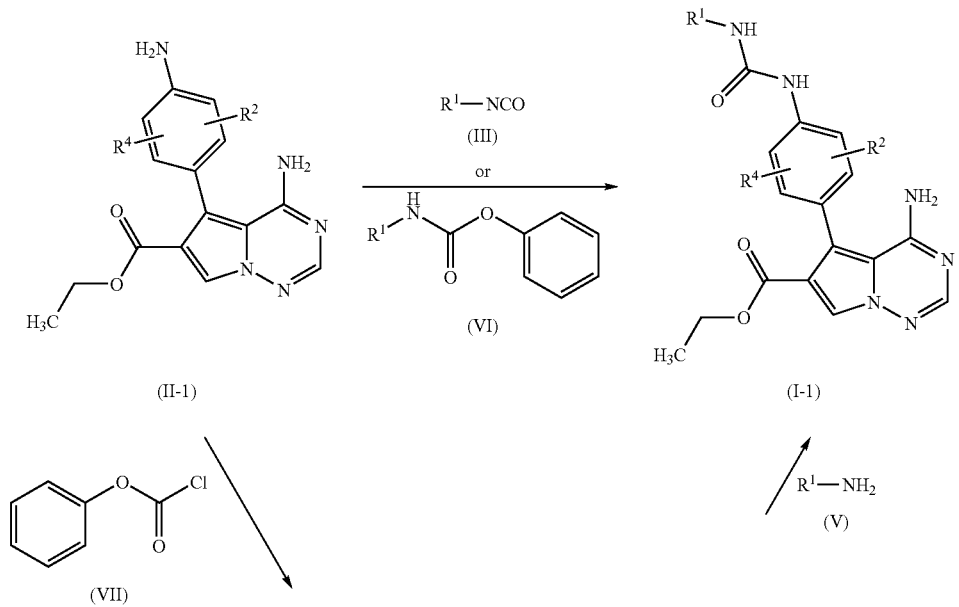

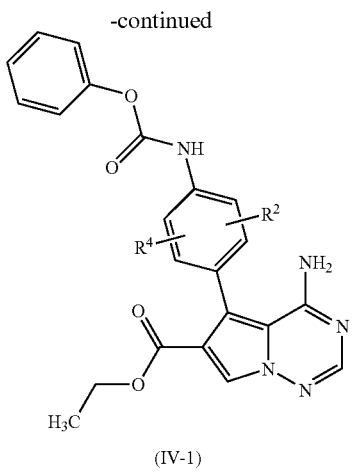

(IV-1)

Reaction Scheme 3 illustrates the preparation of compounds of Formula (I) in which $R^3$ is a variety of substituents, starting from the compound of Formula (I-1) in which $R^3$ is $CO_2Et$. For example, hydrolysis of (I-1), in either aqueous base or acid, provides the carboxylic acid compound of Formula (I-2). Coupling of this acid with an amine of Formula $(R^{3-2})(R^{3-3})NH$ gives amide compounds of Formula (I-3).

Reduction of the Formula (I-1) ester with a reducing agent such as DIBAL, provides the alcohol of Formula (I-4). Oxidation of the alcohol by standard means such as the Dess-Martin periodinane gives the aldehyde of Formula (I-5). Conversion of the aldehyde to an amine compound of Formula (I-6) is accomplished by a reductive amination sequence. In this sequence, a primary amine of Formula $R^{3-4}$—$NH_2$ is added to the compound of Formula (I-5) in the presence of acetic acid, and the intermediate imine compound is not isolated but is selectively reduced with a reagent such as sodium triacetoxyborohydride to give the amine of Formula (I-6).

Reaction Scheme 3

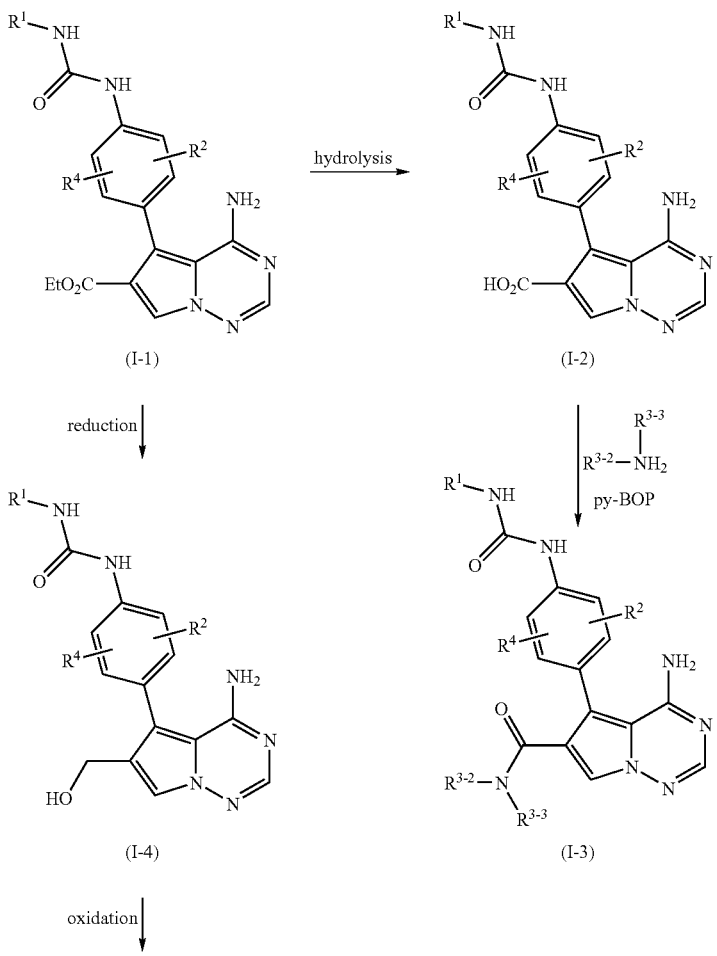

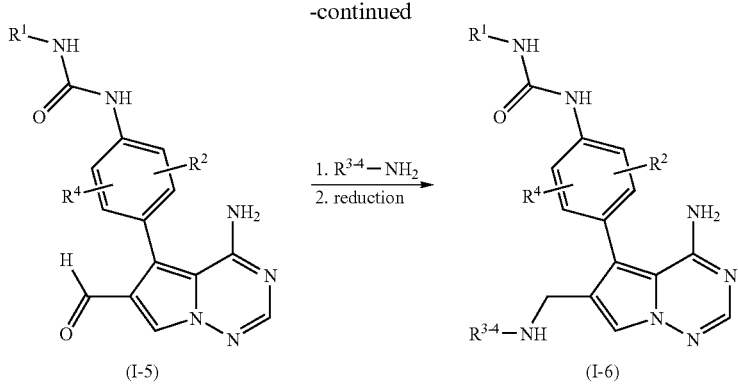

The alcohol of Formula (I-4) is further elaborated in Reaction Scheme 4, and the aldehyde of Formula (I-5) is further elaborated in Reaction Scheme 5, below.

In Reaction Scheme 4, the alcohol is converted to the homologous aldehyde by standard means, namely, conversion to a tosylate or mesylate with tosyl or mesyl chloride, respectively, and a base such as pyridine or $Et_3N$, to give the intermediate of Formula (I-7). Reaction of (I-7) with a cyanide source, e.g., KCN or NaCN, in a polar solvent such as DMF gives the nitrile of Formula (I-8). Selective reduction with DIBAL with hydrolytic workup gives aldehyde of Formula (I-9). The Formula (I-9) aldehyde is converted to the compound of Formula (I-10) [(I) where $R^3$ is $(R^{3-4})NHCH_2CH_2$—] by the reductive amination sequence as described for preparation of (I-6) in Reaction Scheme 3.

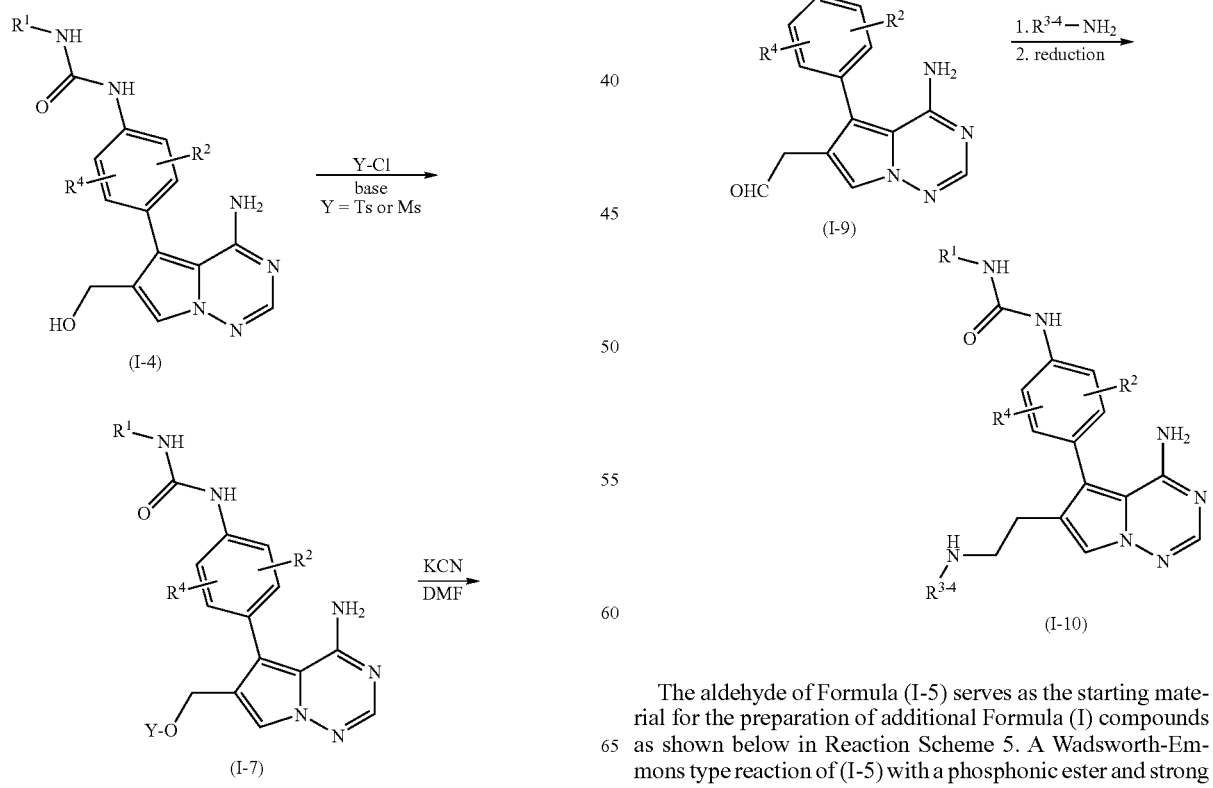

The aldehyde of Formula (I-5) serves as the starting material for the preparation of additional Formula (I) compounds as shown below in Reaction Scheme 5. A Wadsworth-Emmons type reaction of (I-5) with a phosphonic ester and strong base such as LiH gives the unsaturated ester of Formula (I-11); reduction of this ester to the saturated compound of Formula (I-12) is accomplished by hydrogenation using a platinum oxide catalyst in acetic acid. Reduction of the ester to the alcohol of Formula (I-13) is followed by oxidation to the compound of Formula (I-14), a 2-carbon homologue of the aldehyde of Formula (I-5). Reductive amination of (I-14), as previously described above in Reactions Schemes 3 and 4 provides the compound of Formula (I-15) [Formula (I) where $R^3$ is $(R^{3-4})NHCH_2CH_2CH_2$—].

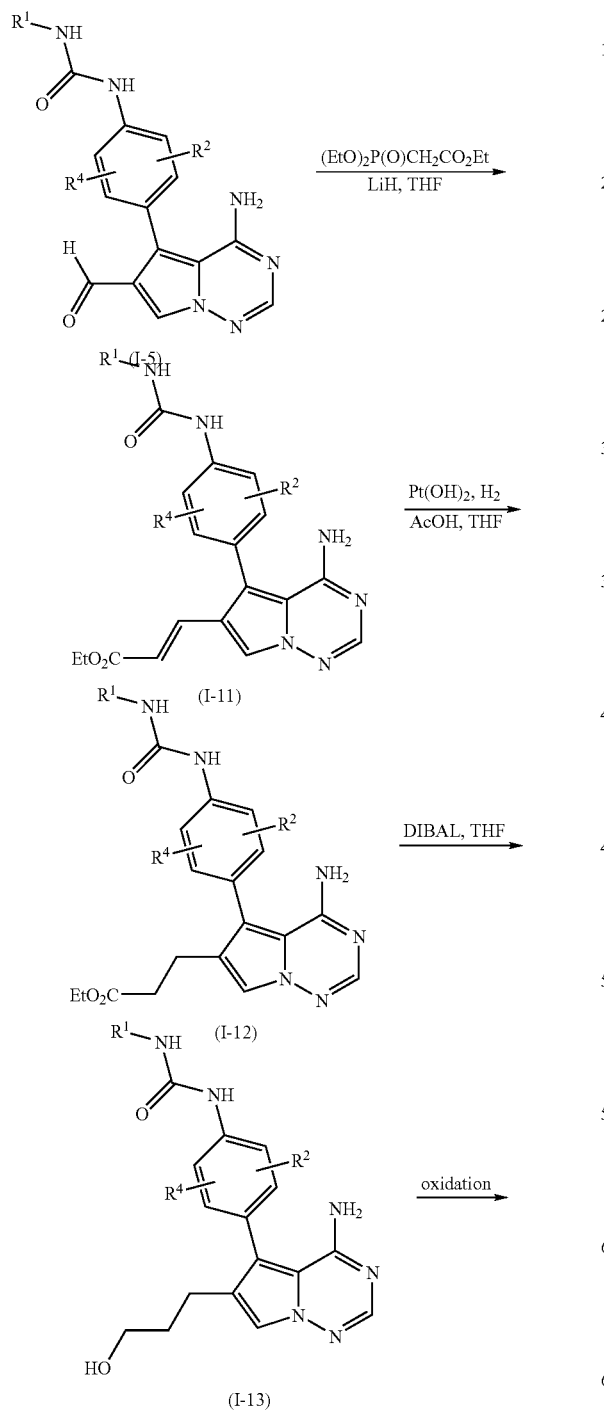

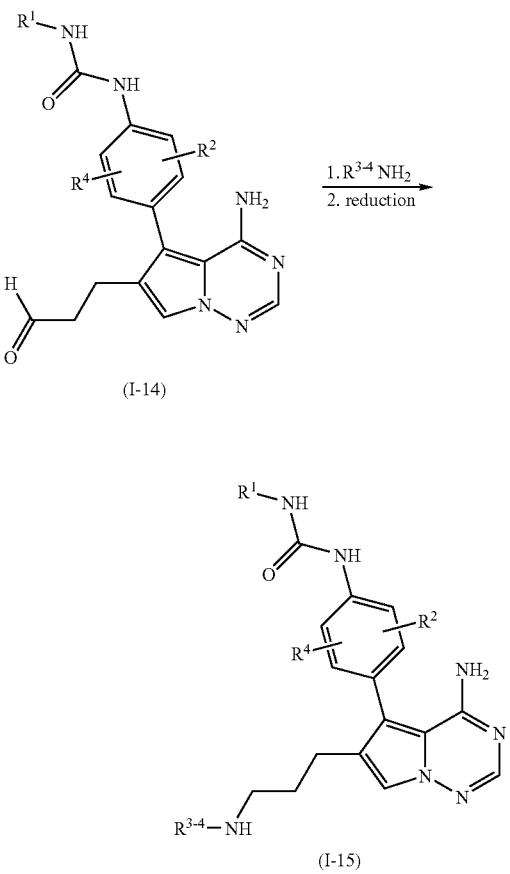

General Methods of Preparation of Intermediates

The preparation of key intermediate (II-1) shown above as starting material for Reaction Scheme 2, is prepared as illustrated below in Reaction Scheme 6. A 4-nitrocinnamate of Formula (VIII) is allowed to react with the isocyanide reagent of Formula (IX) in the presence of a strong base such as lithium hexamethyldisilazide (LHMDS) in an aprotic solvent such as THF, to give the substituted pyrrole of Formula (X). Formylation of (X) under Vilsmeier conditions (e.g., DMF, POCl$_3$) gives the 2-formylpyrrole of Formula (XI). The aldehyde (XI) is converted to the nitrile of Formula (XII) by reaction with hydroxylamine hydrochloride to form an intermediate oxime, which is dehydrated in situ to a nitrile of Formula (XII), using a reagent such as acetic anhydride. The nitrile of Formula (XII) is then N-aminated using a strong base such as NaH and an aminating reagent such as $(Ph)_2P(O)$—O—NH$_2$, to provide the N-amino nitrile of Formula (XIII). Reaction of (XIII) with formamide [HC(O)NH$_2$] gives the pyrrolotriazine intermediate of Formula (XIV-1). Selective reduction of the nitro substituent of the phenyl ring is accomplished in the final step using a catalyst such as Raney-Nickel in THF, providing the intermediate (II-1). These same reduction conditions are used to convert addition compounds of general formula (XIV), prepared as shown in Reaction Schemes 8-11 below, to the corresponding formula (II) intermediates.

Reaction Scheme 6

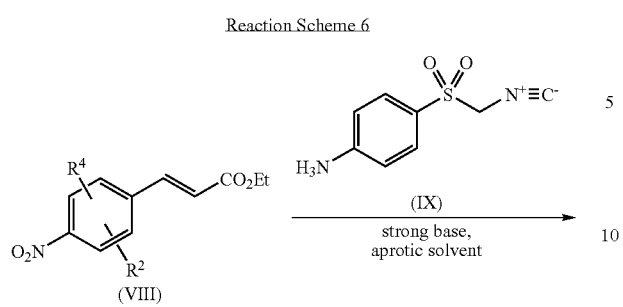

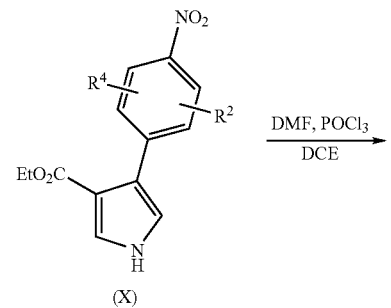

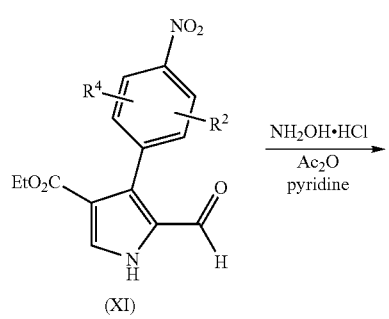

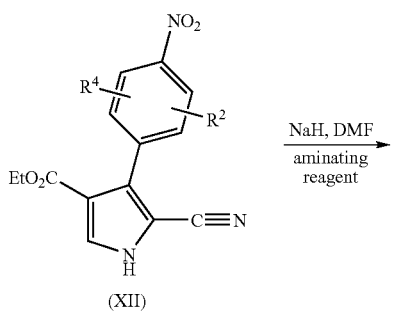

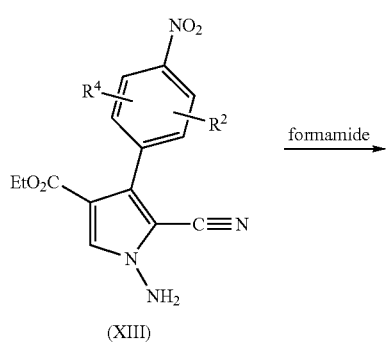

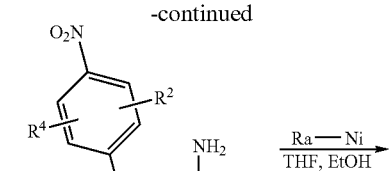

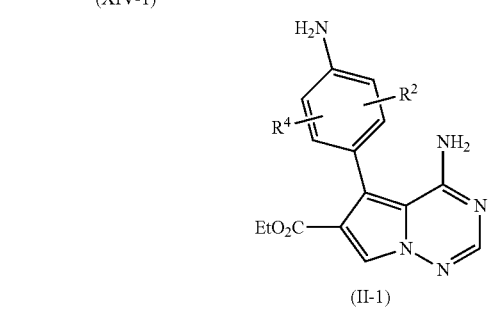

The cinnamates of Formula (VIII) are either commercially available or prepared as shown in Reaction Scheme 7. In this sequence, a substituted nitrotoluene of Formula (XV) is oxidized with a reagent such as potassium permanganate to give the corresponding acid of Formula (XVI); this acid is reduced to the alcohol of Formula (XVII) with a reducing agent such as borane and then oxidized to the aldehyde of Formula (XVIII) using a reagent such as the Dess-Martin periodinane. Wadsworth-Emmons type reaction of (XVIII) using $(EtO)_2P(O)CH_2CO_2Et$ and a strong base such as LiH gives the cinnamate of Formula (VIII).

Reaction Scheme 7

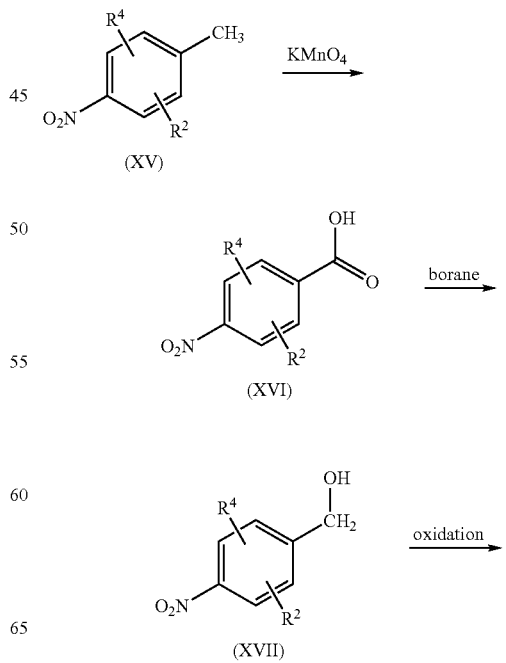

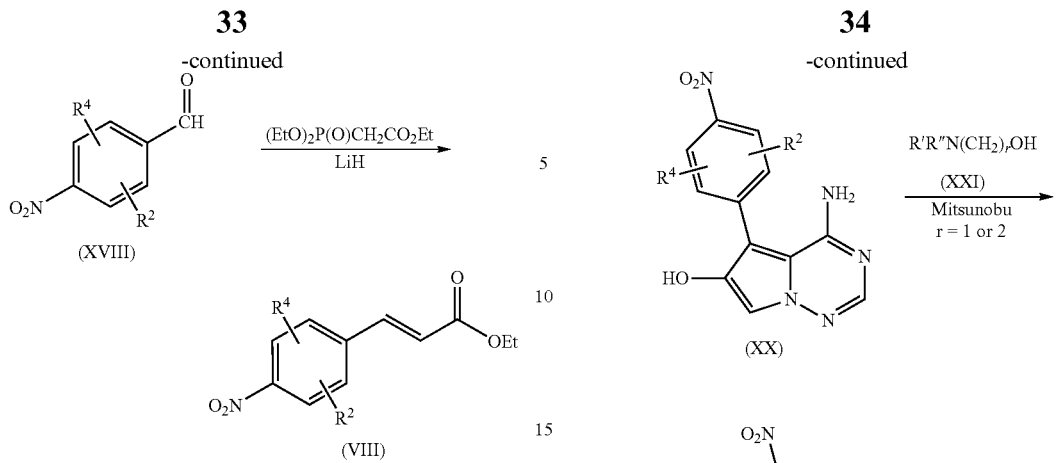

The use of intermediate (XIV-1) for the preparation of the intermediate of Formula (II-2) is shown in Reaction Scheme 8 below. The Formula (XIV-1) compound is allowed to react with excess methyl Grignard reagent to give the tertiary alcohol of Formula (XIX). This compound is subjected to oxidative rearrangement and hydrolysis using hydrogen peroxide and a Lewis acid, such as $BF_3$, to give the hydroxy compound of Formula (XX). Reaction of (XX) with a substituted alcohol of Formula (XXI) under Mitsunobu conditions, e.g., DEAD, TPP, gives the intermediate of Formula (XIV-2). Reduction of the nitro group in Formula (XIV-2), as described for preparation of Formula (II-1) in Reaction Scheme 6, gives the intermediate of Formula (II-2) [Formula (II) where $R^3$ is $R'R''N(CH_2)_rO$— and R" and R' are as described in Reaction Scheme 8].

The compound of Formula (II-2) can be used to prepare the compound of Formula (I) [where $R^3$ is a group of Formula $R'R''N(CH_2)_rO$—, and R" and R' are as described in Reaction Scheme 8] by the route outlined in Reaction Scheme 1.

Reaction Scheme 8

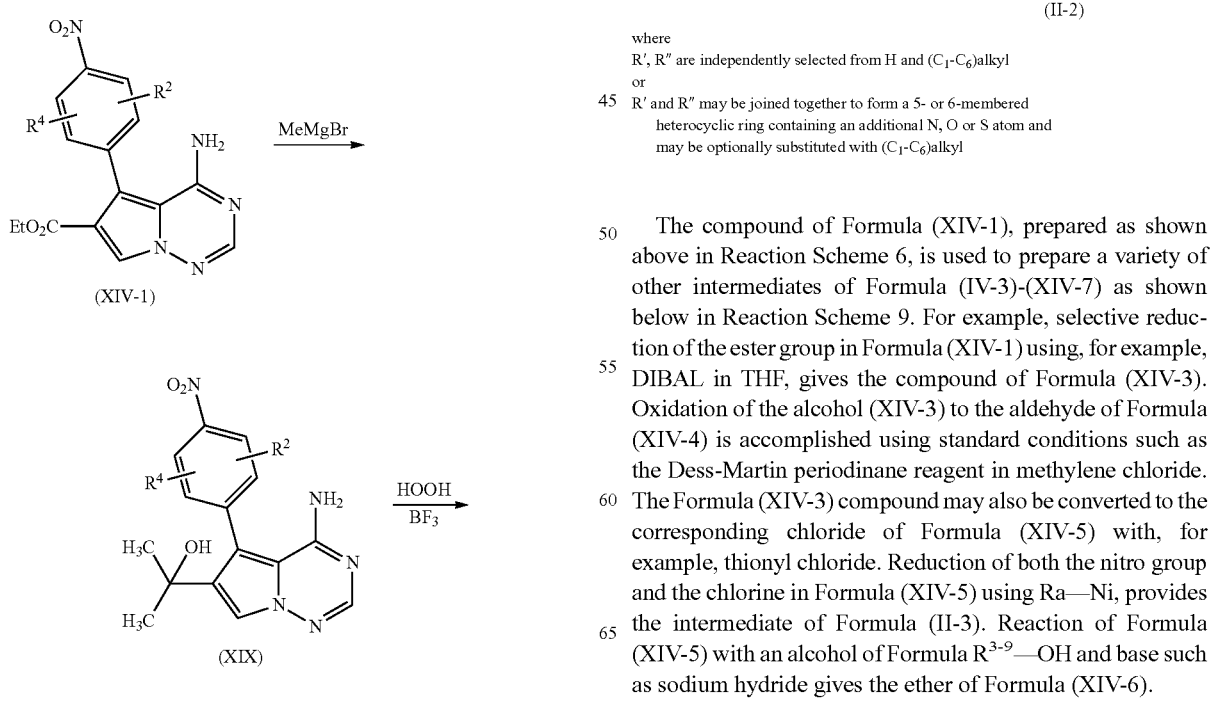

where
R', R" are independently selected from H and $(C_1-C_6)$alkyl
or
R' and R" may be joined together to form a 5- or 6-membered heterocyclic ring containing an additional N, O or S atom and may be optionally substituted with $(C_1-C_6)$alkyl The compound of Formula (XIV-1), prepared as shown above in Reaction Scheme 6, is used to prepare a variety of other intermediates of Formula (IV-3)-(XIV-7) as shown below in Reaction Scheme 9. For example, selective reduction of the ester group in Formula (XIV-1) using, for example, DIBAL in THF, gives the compound of Formula (XIV-3). Oxidation of the alcohol (XIV-3) to the aldehyde of Formula (XIV-4) is accomplished using standard conditions such as the Dess-Martin periodinane reagent in methylene chloride. The Formula (XIV-3) compound may also be converted to the corresponding chloride of Formula (XIV-5) with, for example, thionyl chloride. Reduction of both the nitro group and the chlorine in Formula (XIV-5) using Ra—Ni, provides the intermediate of Formula (II-3). Reaction of Formula (XIV-5) with an alcohol of Formula $R^{3-9}$—OH and base such as sodium hydride gives the ether of Formula (XIV-6).

Reaction Scheme 9

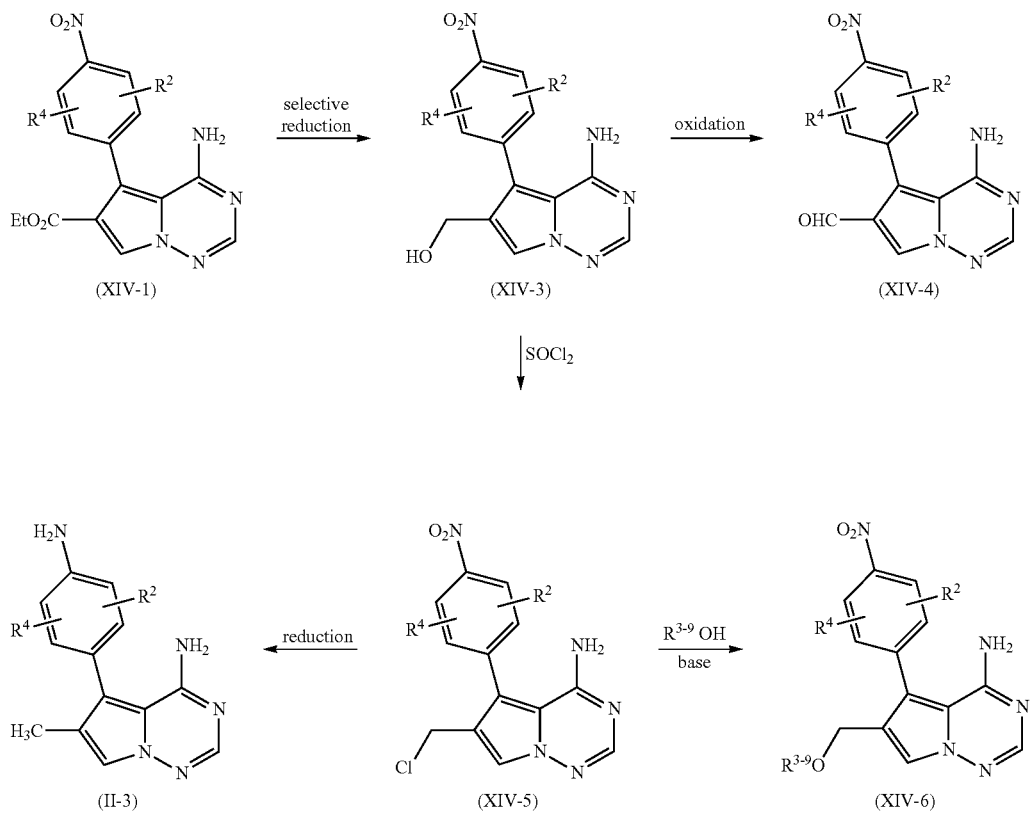

As shown below in Reaction Scheme 9, the compound of Formula (XIV-4) may also be used for the preparation of the nitrile of Formula (XIV-7), by a two step procedure: reaction with hydroxylamine hydrochloride and pyridine, followed by dehydration of the intermediate oxime using acetic anhydride. The Formula (XIV-4) aldehyde may also be converted to an isoxazole intermediate of Formula (XIV-8) by reaction with tosylmethylisocyanide (TosMIC) in the presence of a base such as potassium carbonate, in a protic solvent such as methanol.

Reaction Scheme 10

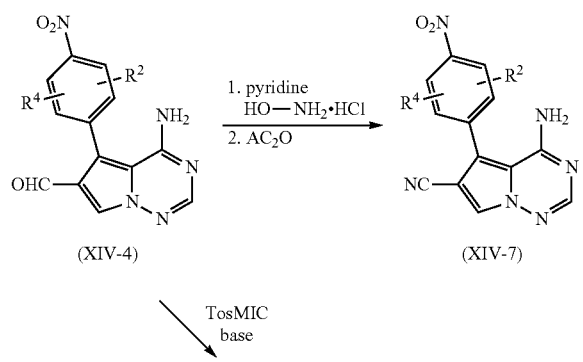

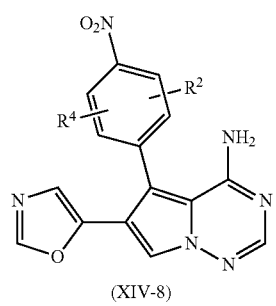

The intermediate of Formula (XIV-1) may also be used for the preparation of other amides and heterocycles as shown in Reaction Scheme 11. Hydrolysis of (XIV-1) under standard conditions to the corresponding acid of Formula (XIV-9) is followed by conversion to the amide of Formula (XIV-11), either directly using an amine of formula $R^{3-11-1}$—$NH_2$, BOP, and a base such as TEA, or by prior conversion to the acid chloride of Formula (XIV-10), which is then allowed to react with the amine of formula $R^{3-11-1}$—$NH_2$. The acid chloride of Formula (XIV-10) is also used for the preparation of oxadia zoles of Formulae (XIV-12) and (XIV-13), by reaction with either 1) hydrazine and trimethyl orthoformate to give the oxadiazole of Formula (XIV-12), or 2) hydrazine, a carboxylic acid of formula $R^{3-11-2}$—$CO_2H$, and a dehydrating agent such as $POCl_3$, to give the substituted oxadiazole Formula (XIV-13).

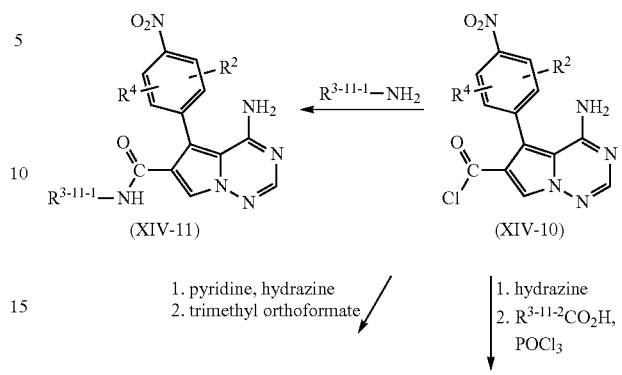

Reaction Scheme 11

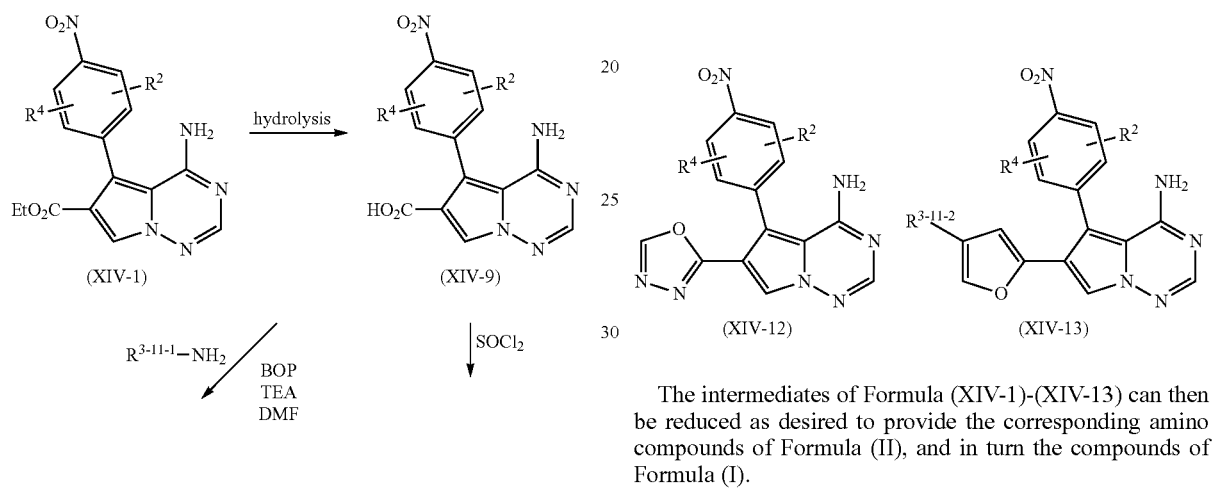

The intermediates of Formula (XIV-1)-(XIV-13) can then be reduced as desired to provide the corresponding amino compounds of Formula (II), and in turn the compounds of Formula (I).

Reaction Scheme 12

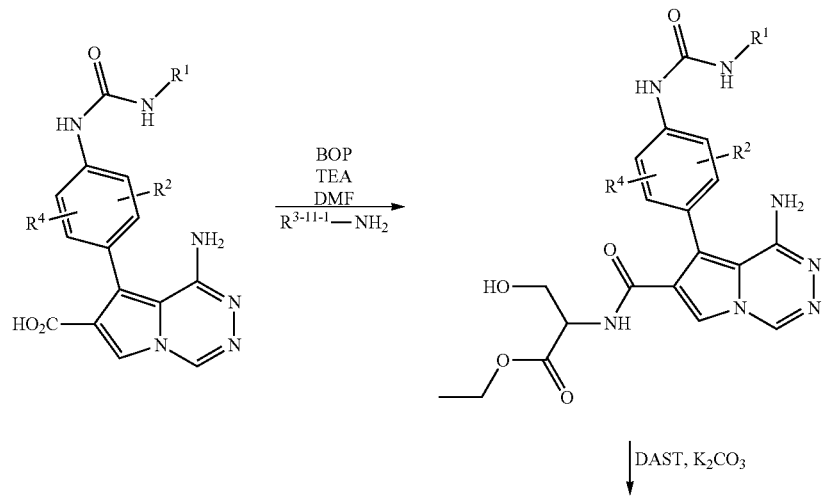

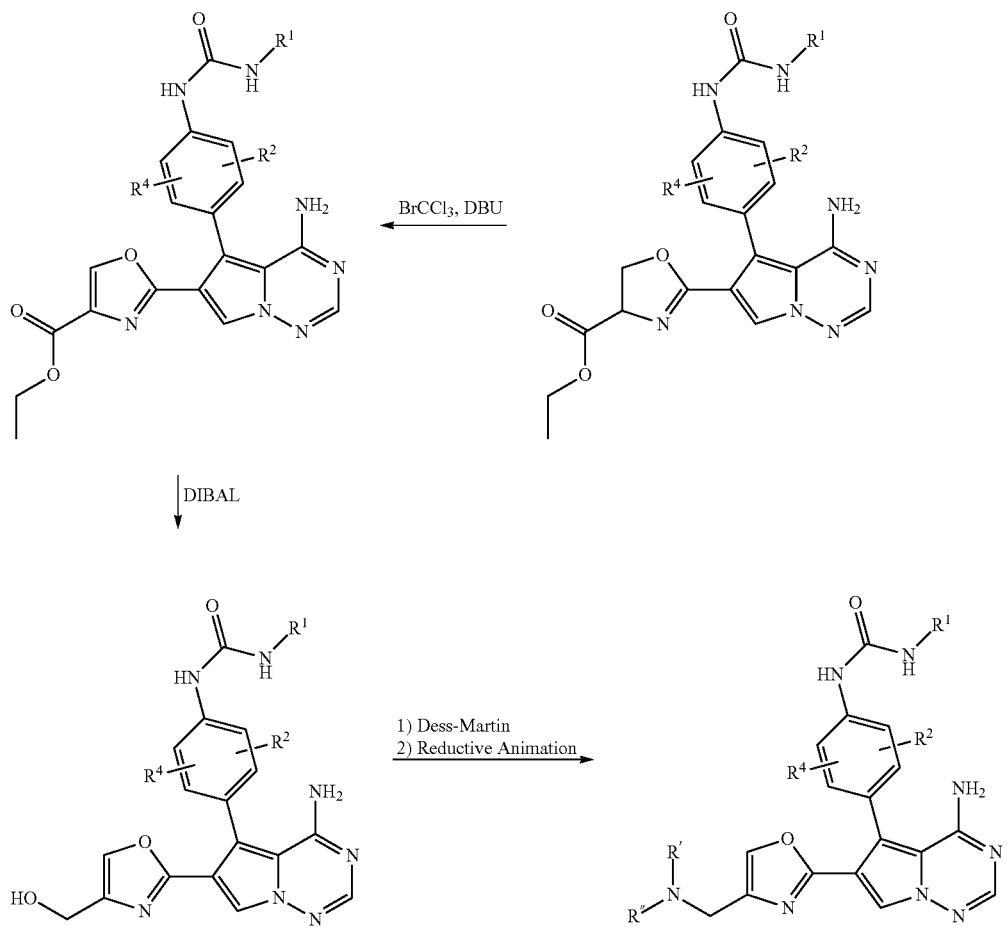
where
R′, R″ are independently selected from H and (C$_1$-C$_6$)alkyl
or
R′ and R″ may be joined together to form a 5- or 6-membered heterocyclic ring containing an additional N, O or S atom and may be optionally substituted with (C$_1$-C$_6$)alkyl
Reaction Scheme 13

-continued

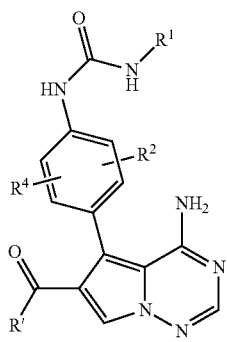

where
R′, R″ are independently selected from substituted
(C$_1$-C$_6$)alkyl and (C$_3$-C$_6$)cycloalkyl It is also to be understood that starting materials are commercially available or readily prepared by standard methods well known in the art. Such methods include, but are not limited to the transformations listed herein.

If not mentioned otherwise, the reactions are usually carried out in inert organic solvents which do not change under the reaction conditions. These include ethers, such as diethyl ether, 1,4-dioxane or tetrahydrofuran, halogenated hydrocarbons, such as dichloromethane, trichloromethane, carbon tetrachloride, 1,2-dichloroethane, trichloroethane or tetrachloroethane, hydrocarbons, such as benzene, toluene, xylene, hexane, cyclohexane or mineral oil fractions, alcohols, such as methanol, ethanol or iso-propanol, nitromethane, dimethylformamide or acetonitrile. It is also possible to use mixtures of the solvents.

The reactions are generally carried out in a temperature range of from 0° C. to 150° C., preferably from 0° C. to 70° C. The reactions can be carried out under atmospheric, elevated or under reduced pressure (for example from 0.5 to 5 bar). In general, they are carried out under atmospheric pressure of air or inert gas, typically nitrogen.

Pro-drugs of this invention in general may be made by conventional methods well known in the art. For example, hydroxyl groups may be converted to esters by reacting the compounds with carboxylic acid chlorides or anhydrides under standard conditions. A hydroxyl group may also be converted to carbonates by reacting the compounds with chloroformates under standard conditions.

Salts of the compounds identified herein can be obtained by isolating the compounds as hydrochloride salts, prepared by treatment of the free base with anhydrous HCl in a suitable solvent such as THF. Generally, a desired salt of a compound of this invention can be prepared in situ during the final isolation and purification of a compound by means well known in the art. Or, a desired salt can be prepared by separately reacting the purified compound in its free base form with a suitable organic or inorganic acid and isolating the salt thus formed. These methods are conventional and would be readily apparent to one skilled in the art.

Additionally, sensitive or reactive groups on the compound of this invention may need to be protected and deprotected during any of the above methods. Protecting groups in general may be added and removed by conventional methods well known in the art (see, for example, T. W. Greene and P. G. M. Wuts, *Protective Groups in Organic Synthesis*; Wiley: New York, (1999).

If used as active compounds, the compounds according to the invention are preferably isolated in more or less pure form, that is more or less free from residues from the synthetic procedure. The degree of purity can be determined by methods known to the chemist or pharmacist (see especially Remington's Pharmaceutical Sciences, 18$^{th}$ ed. 1990, Mack Publishing Group, Enolo). Preferably the compounds are greater than 99% pure (w/w), while purities of greater than 95%, 90% or 85% can be employed if necessary.

The compounds according to the invention exhibit an unforeseeable, useful pharmacological and pharmacokinetic activity spectrum. They are therefore suitable for use as medicaments for the treatment and/or prophylaxis of disorders in humans and animals.

Because of their antiproliferative properties, the compounds according to the invention are useful alone or in combination with other active components for treating and/or preventing mammalian hyper-proliferative disorders. Indications mediated by hyperproliferative disorders means diseases or conditions whose progression proceeds, at least in part, via proliferation.

The present invention also relates to a method of using the compounds or compositions described herein for the treatment or prevention of, or in the manufacture of a medicament for treating or preventing, mammalian hyper-proliferative disorders. This method comprises administering to a patient (or a mammal) in need thereof, including a human, an amount of a compound, a pharmaceutically acceptable salt or ester thereof, or a composition of this invention which is effective to treat or prevent the disorder.

The present invention also relates to a method for using the compounds of this invention as prophylactic or chemopreventive agents for prevention of the mammalian hyper-proliferative disorders described herein. This method comprises administering to a mammal in need thereof, including a human, an amount of a compound of this invention, or a pharmaceutically acceptable salt or ester thereof, which is effective to delay or diminish the onset of the disorder.

Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

The present invention also relates to a method for using the compounds of this invention as prophylactic or chemopreventive agents for prevention of the mammalian hyper-proliferative disorders described herein. This method comprises administering to a mammal in need thereof, including a human, an amount of a compound of this invention, or a pharmaceutically acceptable salt or ester thereof, which is effective to delay or diminish the onset of the disorder.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, and also exist with a similar etiology in other mammals which can also be treated by the administration of the compounds and/or pharmaceutical compositions of the present invention.

The assay described in this application is one of the methods by which compound activity relating to treatment of the disorders identified herein can be determined.

In another embodiment, the present invention provides a medicament containing at least one compound according to the invention. In another embodiment, the present invention provides a medicament containing at least one compound according to the invention together with one or more pharmacologically safe excipient or carrier substances, for example hydroxypropylcellulose, and also their use for the abovementioned purposes.

The active component can act systemically and/or locally. For this purpose, it can be applied in a suitable manner, for example orally, parenterally, pulmonally, nasally, sublingually, lingually, buccally, rectally, transdermally, conjunctivally, otically or as an implant.

For these application routes, the active component can be administered in suitable application forms. An overview of application forms is given in Remington's Pharmaceutical Sciences, 18$^{th}$ ed. 1990, Mack Publishing Group, Enolo.

Useful oral application forms include application forms which release the active component rapidly and/or in modified form, such as for example tablets (non-coated and coated tablets, for example with an enteric coating), capsules, sugar-coated tablets, granules, pellets, powders, emulsions, suspensions, solutions and aerosols. Such sustained-release pharmaceutical compositions are described in Part 8, Chapter 91 of Remington's Pharmaceutical Sciences, 18$^{th}$ ed. 1990, Mack Publishing Group, Enolo.

Parenteral application can be carried out with avoidance of an absorption step (intravenously, intraarterially, intracardially, intraspinally or intralumbarly) or with inclusion of an absorption (intramuscularly, subcutaneously, intracutaneously, percutaneously or intraperitoneally). Useful parenteral application forms include injection and infusion preparations in the form of solutions, suspensions, emulsions, lyophilisates and sterile powders. Such parenteral pharmaceutical compositions are described in Part 8, Chapter 84 of Remington's Pharmaceutical Sciences, 18$^{th}$ ed. 1990, Mack Publishing Group, Enolo.

In one embodiment, the invention relates to intravenous (i.v.) application of the active compound, e.g. as bolus injection (that is as single dose, e.g. per syringe), infusion over a short period of time (e.g. for up to one hour) or infusion over a long period of time (e.g. for more than one hour). The application can also be done by intermittent dosing. The applied volume can vary dependent on the conditions and usually is 0.5 to 30, or 1 to 20 ml for bolus injection, 25 to 500, or 50 to 250 ml for infusion over a short period of time and 50 to 1000, or 100 to 500 ml for infusion over a long period of time.

The application forms have to be sterile and free of pyrogens. They can be based on aqueous solvents or mixtures of aqueous and organic solvents. Examples are ethanol, polyethyleneglycol (PEG) 300 or 400, aqueous solutions containing cyclodextrins or emulsifiers, such as lecithin, Pluronic F68®, Solutol HS15® or Cremophor®. Aqueous solutions are preferred.

For intravenous application the solutions are generally isotonic and euhydric, for example with a pH of 3 to 11, 6 to 8 or about 7.4.

Glass or plastic containers can be employed as packaging for i.v.-solutions, e.g. rubber seal vials. They can contain liquid volumes of 1 to 1000, or 5 to 50 ml. The solution can directly be withdrawn from the vial to be applied to the patient. For this purpose, it can be advantageous to provide the active compound in solid form (e.g. as lyophilisate) and dissolve by adding the solvent to the vial directly before administration.

Solutions for infusion can advantageously be packaged in containers made from glass or plastic, for example bottles or collapsible containers such as bags. They can contain liquid volumes of 1 to 1000, or 50 to 500 ml.

Forms suitable for other application routes include for example inhalatory pharmaceutical forms (including powder inhalers, nebulizers), nasal drops/solutions, sprays; tablets or capsules to be administered lingually, sublingually or buccally, suppositories, ear and eye preparations, vaginal capsules, aqueous suspensions (lotions, shake mixtures), lipophilic suspensions, ointments, creams, milk, pastes, dusting powders or implants.

The active components can be converted into the recited application forms in a manner known per se. This is carried out using inert non-toxic, pharmaceutically suitable excipients. These include inter alia carriers (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odor corrigents.

For human use, in the case of oral administration, it is recommended to administer doses of from 0.001 to 100 mg/kg, or from 0.01 to 20 mg/kg. In the case of parenteral administration such as, for example, intravenously or via mucous membranes nasally, buccally or inhalationally, it is recommended to use doses of 0.001 to 0.60 mg/kg, in particular 0.01 to 30 mg/kg.

In spite of this, it can be necessary in certain circumstances to depart from the amounts mentioned, namely as a function of body weight, application route, individual behaviour towards the active component, manner of preparation and time or interval at which application takes place. It can for instance be sufficient in some cases to use less than the aforementioned minimum amount, while in other cases the upper limit mentioned will have to be exceeded. In the case of the application of larger amounts, it can be advisable to divide them into a plurality of individual doses spread through the day.

The percentages in the tests and examples which follows are, unless otherwise stated, by weight; parts are by weight. Solvent ratios, dilution ratios and concentrations reported for liquid/liquid solutions are each based on the volume.

A. EXAMPLES

General Preparative Methods

Unless otherwise stated, the term 'concentrated under reduced pressure' refers to use of a Buchi rotary evaporator at approximately 15 mm of Hg.

Thin-layer chromatography (TLC) was performed on Whatman® pre-coated glass-backed silica gel 60A F-254 250 μm plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, and/or (d) immersion of the plate in a cerium sulfate solution followed by heating. Column chromatography (flash chromatography) was performed using 230-400 mesh EM Science® silica gel.

"Shaker block" refers to the use of a shaker model BTS3000 from J-Kem Scientific at a speed of 150-180.

Proton ($^1$H) nuclear magnetic resonance (NMR) spectra were measured with a Varian 400 Mercury Plus (400 MHz) spectrometer with either Me$_4$Si ($\delta$ 0.00) or residual protonated solvent (CHCl$_3$ $\delta$ 7.26; MeOH $\delta$ 3.30; DMSO $\delta$ 2.49) as standard. Carbon ($^{13}$C) NMR spectra were measured with a Varian 400 Mercury Plus (400 MHz) (100 MHz) spectrometer with solvent (CDCl$_3$ $\delta$ 77.0; d$_3$-MeOD; $\delta$ 49.0; d$_6$-DMSO $\delta$ 39.5) as standard.

HPLC—electrospray mass spectra (HPLC ES-MS) for characterization were obtained using a Gilson HPLC system equipped with a variable wavelength detector set at 254 nm, a YMC pro C-18 column (2×23 mm, 120A), and a Finnigan LCQ ion trap mass spectrometer with electrospray ionization. Spectra were scanned from 120-1200 amu using a variable ion time according to the number of ions in the source. The eluants were A: 2% acetonitrile in water with 0.02% TFA and B: 2% water in acetonitrile with 0.018% TFA. Gradient elution from 10% B to 95% over 3.5 minutes at a flow rate of 1.0 mL/min was used with an initial hold of 0.5 minutes and a final hold at 95% B of 0.5 minutes. Total run time was 6.5 minutes.

Preparative high performance liquid chromatography (HPLC), when needed, was run using either a Gilson 215 Liquid Handler with a Gilson 322 pump and a Gilson UV-VIS-155 detector set at 254 nm or a Shimadzu LC-8A pump with a Shimadzu SPD-10A detector set at 220 nM both equipped with a YMC Pac ProC18 column (150×20 mm). Eluant A is acetonitrile with 0.01% of trifluoroacetic acid and Eluant B is water with 0.01% trifluoroacetic acid. Typically, a gradient was run from 10% A/90% B to 90% A/10% B over a period of 15-25 min. The fractions of interest were collected and the solvent removed in vacuo to give the final compound as a trifluoroacetic acid salt.

HPLC using a chiral column may be used to separate enantiomers. Analytical conditions used a Chiralcel OD-H® (4.6×150 mm) column on a Shimadzu HPLC. 30% Eluent A=Hexane (0.1% Et$_3$N) and 70% eluent B=1:1 MeOH-EtOH (0.1% Et$_3$N) for 15 min. with a flowrate of 1.0 mL/min, detection by UV at 235 nm. Preparative conditions used a Chiralcel OD® (20×150 mm) column on a Gilson 215 HPLC. 30% Eluent A=Hexane (0.1% Et$_3$N) and 70% eluent B=1:1 MeOH-EtOH (0.1% Et$_3$N) for 15 min. with a flowrate of 1.0 mL/min, detection by UV at 235 nm using approximately 75 mg material per injection.

RPMI growth media was obtained from GIBCO®.

The IUPAC names were generated using ACD/Name Version 7.0 from Advanced Chemistry Development (U.S.A.).

Abbreviations and Acronyms $^1$H-NMR proton nuclear magnetic resonance spectroscopy
$^{31}$P-NMR phosphorus-31 nuclear magnetic resonance spectroscopy
AcOH acetic acid
(Ac)$_2$O acetic anhydride
abs absolute
aq aqueous
ap approximate
atm atmosphere
br broad
BOP benzotriazole-1-yloxy-tris(dimethylamino)phosphonium hexafluorophosphate
Bu butyl
ACN acetonitrile
Ac$_2$O acetic anhydride
AcOH acetic acid
Celite® brand of diatomaceous earth from Celite Corp.
CD$_3$CN acetonitrile-d$_3$
CD$_3$OD methanol-d$_4$
d doublet
DCE dichloroethane
DCM dichloromethane
dd double doublet
DIBAL diisobutylaluminum hydride
DMF N,N-dimethylformamide
DMSO dimethylsulfoxide
DMSO-d$_6$ dimethylsulfoxide-d$_6$
equiv equivalent(s)
ES-MS electrospray mass spectrometry
Et$_3$N triethylamine
Et$_2$O diethyl ether
EtOAc ethyl acetate
EtOH ethanol
FBS fetal bovine serum
g gram(s)
h hour(s)
HPLC high performance liquid chromatography
Hz hertz
J NMR coupling constant
L liter(s)
LCMS liquid chromatography-mass spectrometry
LHMDS lithium hexamethyldisilazide
M molar
Me methyl
MeOH methanol
mg milligram(s)
MHz megahertz min minute(s)
mL milliliter
mmol millimole
MPLC medium pressure liquid chromatography
MS mass spectrometry
Ms methanesulfonyl
N normal
nM nanomolar
Pr propyl
py-BOP benzotriazol-1-yl-oxytripyrrolidineophosphonium hexafluorophosphate
q quartet
Ra—Ni Raney-Nickel
$R_f$ TLC retention factor
Rochelle's salt potassium sodium tartrate
RPMI Roswell Park Memorial Institute
RT retention time
rt room temperature
s singlet
t triplet
TEA triethylamine
TFA trifluoroacetic acid
THF tetrahydrofuran
TLC thin layer chromatography
TosMIC Tosylmethyl isocyanide
TPP triphenylphosphine
Ts p-toluenesulfonyl
v/v volume-to-volume proportion
v/v/v volume-to-volume-to-volume proportion
μL microliter
μm micrometer Preparation of Intermediates Intermediate A Preparation of ethyl 4-amino-5-(4-nitrophenyl)pyrrolo[2,1-f][1,2,4]triazine-6-carboxylate

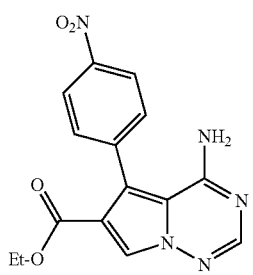

Step 1: Preparation of ethyl 4-(4-nitrophenyl)-1H-pyrrole-3-carboxylate

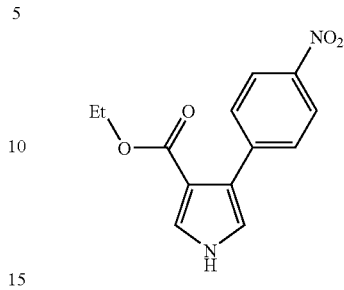

To a solution of 1M lithium hexamethyldisilazide in THF (102.4 mL, 102.4 mmol) cooled to −77° C. was added 1-[(isocyanomethyl)sulfonyl]-4-methylbenzene (20.0 g, 102.4 mmol) as a solution in THF (100 mL) dropwise over 30 min. The solution was allowed to stir an additional 15 min, and then ethyl (2E)-3-(4-nitrophenyl)acrylate was added dropwise (22.66 g, 102.4 mmol) as a solution in THF (250 mL) over 1 h. The reaction was allowed to warm to rt over 17 h. Aqueous saturated $NaHCO_3$ (200 mL) was added to the reaction mixture followed by EtOAc (500 mL). The solution was transferred to a separatory funnel, and the organic layer was isolated and washed with $H_2O$ (100 mL). The aqueous layers were back extracted with EtOAc (2×150 mL). The combined organic layers were collected, dried ($MgSO_4$), concentrated onto silica gel, and purified by column chromatography (100% $CH_2Cl_2$ ramping to 95:5 v/v $CH_2Cl_2$-EtOAc) to afford 16.65 g of the above compound as an orange/yellow solid (63.98 mmol, yield 62%). $^1$H-NMR (DMSO-$d_6$) δ 11.78 (br s, 1H), 8.19 to 8.15 (m, 2H), 7.76 to 7.73 (m, 2H), 7.57 to 7.56 (m, 1H), 7.22 to 7.21 (m, 1H), 4.18 to 4.13 (q, J=7.1 Hz, 2H), 1.21 (t, J=7.1 Hz, 3H); LCMS RT=2.90 min; TLC $R_f$=0.47 (95:5 v/v $CH_2Cl_2$-EtOAc).

Step 2: Preparation of ethyl 5-formyl-4-(nitrophenyl)-1H-pyrrole-3-carboxylate

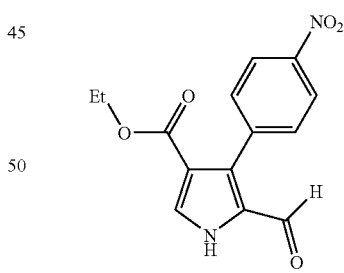

To a solution of DCE (100 mL) was added DMF (14.96 mL, 194.4 mmol), which was cooled in an ice-salt bath. As $POCl_3$ (18.12 mL, 194.4 mmol) was slowly added a white precipitate formed. The solution was allowed to warm to rt while vigorously stirring over 30 min. The slurry was again cooled in an ice-salt bath. Ethyl 4-(4-nitrophenyl)-1H-pyrrole-3-carboxylate (46.00 g, 176.8 mmol) was added as a suspension in DCE (500 mL). The reaction proceeded while cooling in an ice-salt bath for 1 h, and then was allowed to warm to rt over 17 h. Sodium Acetate (79.75 g, 972.2 mmol) in water (600 mL) was added to the reaction, and the solution was heated to 80° C. for 1 h. Upon cooling to rt the solution was transferred to a separatory funnel and the organic layer was isolated while the aqueous layer was back extracted with CH$_2$Cl$_2$ (2×150 mL). The combined organic layers were collected, dried (MgSO$_4$), filtered, and concentrated to dryness. The crude material was heated to reflux in toluene (2 L) and to the hot solution was added hexanes (200 mL). The solution was allowed to slowly cool, and over the following 2 days crystals formed. The crystals were collected, washed with Et$_2$O (500 mL), and dried under vacuum to afford 25.53 g of the above compound as golden needles (88.57 mmol, yield 50%). $^1$H-NMR (DMSO-d$_6$) δ 12.94 (br s, 1H), 9.29 (d, J=0.8 Hz, 1H), 8.25 to 8.22 (m, 2H), 7.81 (d, J=2.7 Hz, 1H), 7.74 to 7.71 (m, 2H), 4.12 to 4.06 (q, J=7.1 Hz, 2H), 1.15 to 1.11 (t, J=7.0 Hz, 3H); LCMS RT=2.75 min; TLC R$_f$=0.16 (95:5 v/v CH$_2$Cl$_2$-EtOAc).

Step 3: Preparation of ethyl 5-cyano-4-(nitrophenyl)-1H-pyrrole-3-carboxylate

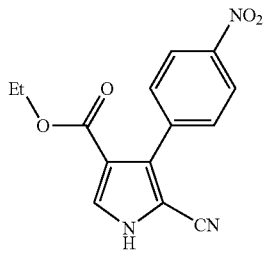

To a solution of pyridine (400 mL) was added ethyl 5-formyl-4-(nitrophenyl)-1H-pyrrole-3-carboxylate (24.55 g, 85.17 mmol) followed by hydroxylamine hydrochloride (6.51 g, 93.7 mmol). The solution was stirred at rt for 2 h, acetic anhydride (17.68 mL, 187.4 mmol) was added, and the solution was heated to 80° C. for 17 h. Upon cooling to it the reaction mixture was partially concentrated in vacuo and then diluted with EtOAc (300 mL) and H$_2$O (300 mL). The solution was transferred to a separatory funnel, and the organic layer was isolated while the aqueous layers were back extracted with EtOAc (2×100 mL). The combined organic layers were collected, dried (Na$_2$SO$_4$), filtered, and concentrated to dryness. The crude material was then triturated with CH$_2$Cl$_2$-Et$_2$O (1:1 v/v, 300 ml). The solid was collected, washed with Et$_2$O (150 mL), and dried under vacuum to afford 18.94 g of the above compound as a fluffy white solid (66.40 mmol, yield 78%). $^1$H-NMR (DMSO-d$_6$) δ 13.24 (br s, 1H), 8.30 to 8.27 (m, 2H), 7.92 (s, 1H), 7.74 to 7.71 (m, 2H), 4.16 to 4.10 (q, J=7.2 Hz, 2H), 1.18 to 1.15 (t, J=7.0 Hz, 3H); LCMS RT=2.97 min; TLC R$_f$=0.20 (95:5 v/v CH$_2$Cl$_2$-EtOAc).

Step 4: Preparation of (aminooxy)(diphenyl)phosphine oxide

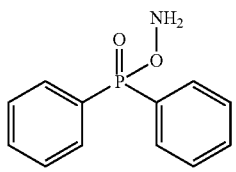

To hydroxylamine hydrochloride (15.86 g, 228.2 mmol) in H$_2$O (35 mL) cooled in an ice-salt bath was added 7.1 N NaOH (27.4 mL, 194.4 mmol) followed by 1,4-dioxane (100 mL). The solution was vigorously stirred for 15 min and then chlorodiphenylphosphine oxide (20.00 g, 84.52 mmol) was added as a solution in 1,4-dioxane (100 mL). The solution was stirred an additional 15 min as a white precipitate formed which was filtered. The solid was suspended in 0.25 N NaOH (250 mL) while stirring in an ice-salt bath for 1 h. The solid was then collected, washed with H$_2$O (100 mL), and thoroughly dried under vacuum to afford 7.09 g of the above compound as a white powder (30.4 mmol, yield 36%). $^1$H-NMR (DMSO-d$_6$) δ 7.72 to 7.67 (m, 4H), 7.50 to 7.40 (m, 6H); $^{31}$P-NMR (DMSO-d$_6$) δ 23.11 (br s, 1P).

Step 5: Preparation of ethyl 1-amino-5-cyano-4-(nitrophenyl)-1H-pyrrole-3-carboxylate

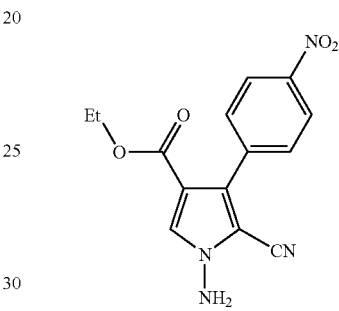

To a solution of DMF (625 mL) was added ethyl 5-cyano-4-(nitrophenyl)-1H-pyrrole-3-carboxylate (17.97 g, 63.00 mmol) followed by NaH, 60% dispersion in mineral oil (3.02 g, 75.59 mmol). The solution was stirred at rt for 15 min and then (aminooxy)(diphenyl)phosphine oxide (17.63 g, 75.59 mmol) was added, and the solution was heated to 80° C. for 17 h. Upon cooling to rt aqueous saturated NaHCO$_3$ (500 mL) was added followed by EtOAc (400 mL), which was transferred to a separatory funnel and the organic layer was isolated while the aqueous layer was back extracted with EtOAc (2×200 mL). The combined organic layers were collected, dried (Na$_2$SO$_4$), filtered, and concentrated to dryness. The crude material was then triturated with CH$_2$Cl$_2$-hexanes (1:1 v/v 400 mL). The solid was collected, washed with hexanes (100 mL), dried under vacuum, suspended in EtOAc which was heated to reflux for 15 min, and then filtered. The filtrate was concentrated in vacuo and then dried under vacuum to afford 14.15 g of the above compound as a yellow powder (47.12 mmol, yield 75%). $^1$H-NMR (DMSO-d$_6$) δ 8.29 to 8.27 (m, 2H), 7.73 (s, 1H), 7.71 to 7.69 (m, 2H), 6.71 (br s, 2H), 4.14 to 4.09 (q, J=7.1 Hz, 2H), 1.17 to 1.14 (t, J=7.1 Hz, 3H); LCMS RT=2.91 min; TLC R$_f$=0.30 (95:5 v/v CH$_2$Cl$_2$-EtOAc).

Step 6: Preparation of the Title Compound

To a solution of formamide (74.9 mL, 1.88 mol) was added ethyl 1-amino-5-cyano-4-(nitrophenyl)-1H-pyrrole-3-carboxylate (14.15 g, 47.12 mmol). The solution was heated to 195° C. for 2 h and was then allowed to cool to rt over 17 h. The crystalline solid was collected and washed with EtOAc (2×100 mL) and then with H$_2$O (100 mL). The solid was dried under vacuum to afford 10.20 g of the above compound as a bronze crystalline solid (31.16 mmol, yield 66%). $^1$H-NMR (DMSO-d$_6$) δ 8.27 to 8.25 (m, 2H), 8.20 (s, 1H), 8.05 (br s, 1H), 7.97 (s, 1H), 7.66 to 7.64 (m, 2H), 5.52 (br s, 1H), 4.10 to 4.05 (q, J=7.1 Hz, 2H), 1.11 to 1.07 (t, J=7.1 Hz, 3H); MS [M+H]$^+$=328; LCMS RT=2.51 min; TLC R$_f$=0.20 (3:1 v/v CH$_2$Cl$_2$-EtOAc).

Intermediate B

Preparation of ethyl 4-amino-5-(4-aminophenyl)pyrrolo[2,1-f][1,2,4]triazine-6-carboxylate

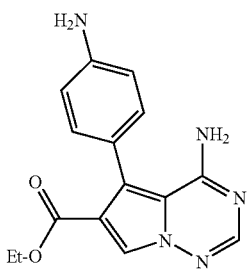

Raney nickel was added to a flask containing 20 mL abs EtOH. The catalyst was triturated with abs EtOH (3×20 mL). A suspension of ethyl 4-amino-5-(4-nitrophenyl)pyrrolo[2,1-f][1,2,4]triazine-6-carboxylate (4.0 g, 12.2 mmol) in abs EtOH (600 mL)/THF (200 mL) was added to the flask with the catalyst. The flask was evacuated and refilled with hydrogen gas (3×) and the reaction was then placed under a hydrogen atmosphere (1 atm) and allowed to stir at rt overnight. The reaction was filtered through a Celite® pad and washed with copious amounts of EtOH/THF (3:1) to afford 3.60 g of the above compound as a brown solid (yield 96%) $^1$H-NMR (DMSO-d$_6$) δ 8.05 (s, 1H), 8.04 (br s, 2H), 7.88 (s, 1H), 7.01 (d, J=8.0 Hz, 2H), 6.61 (d, J=8.0 Hz, 2H), 5.31 (br s, 2H), 4.07 (q, J=7.4 Hz, 2H), 1.12 (t, J=7.2 Hz, 3H); MS [M+H]$^+$=298; LCMS RT=1.64 min; TLC R$_f$=0.30 (Acetone/CH$_2$Cl$_2$ 1:3).

Intermediate C

Preparation of ethyl 4-amino-5-{4-[(phenoxycarbonyl)amino]phenyl}pyrrolo[2,1-f][1,2,4]triazine-6-carboxylate

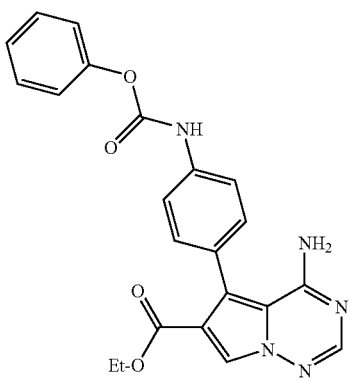

To a stirred solution of Intermediate B (1.0 g, 3.4 mmol) in THF (33 mL) was added pyridine (0.33 mL, 4.0 mmol), then phenyl chloroformate (0.42 mL, 3.4 mmol) at −40° C. Some solid precipitated out. The mixture was stirred at rt for 2 h. Then more phenyl chloroformate (0.02 mL, 0.10 mmol) was added and the mixture was stirred at rt for another half hour. The reaction was filtered, washed with water (3×5 mL) and EtOAc-hexanes (9:1 v/v) (3×5 mL) to afford the above compound as a light yellow solid (600 mg, 43%). The filtrate was concentrated in vacuo and further purified by column chromatography (30:70:1 to 80:20:1 v/v/v EtOAc-hexanes-NH$_4$OH) to afford more of the title compound (570 mg, 40%). $^1$H-NMR (DMSO-d$_6$) δ 10.42 (s, 1H), 8.13 (s, 1H), 8.06 (br s, 1H), 7.93 (s, 1H), 7.58 (d, J=8.4 Hz, 2H), 7.46 to 7.39 (m, 2H), 7.35 (d, J=8.5 Hz, 2H), 7.29 to 7.21 (m, 3H), 5.07 (br s, 1H), 4.06 (q, J=7.2 Hz, 2H), 1.08 (t, J=7.2 Hz, 3H); MS [M+H]$^+$=418; LCMS RT=2.81 min.

Intermediate D

Preparation of ethyl 4-amino-5-(4-{[(4-nitrophenoxy)carbonyl]amino}phenyl)pyrrolo[2,1-f][1,2,4]triazine-6-carboxylate

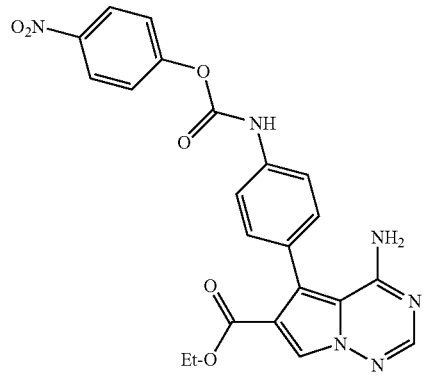

The procedure used for the preparation of Intermediate C was used to prepare the title compound by substituting 4-nitrophenyl chloroformate for phenyl chloroformate. $^1$H-NMR (DMSO-d$_6$) δ 10.66 (s, 1H), 8.32 (d, J=9.3 Hz, 2H), 8.16 (s, 1H), 7.95 (s, 1H), 7.61 (d, J=8.8 Hz, 2H), 7.56 (d, J=8.9 Hz, 2H), 7.38 (d, J=8.9 Hz, 2H), 4.07 (q, J=7.2 Hz, 2H), 1.09 (t, J=7.2 Hz, 3H); MS [M+H]$^+$=463; LCMS RT=3.29 min.

Intermediate E

Preparation of ethyl 4-amino-5-{4-[({[2-fluoro-5-(trifluoromethyl)phenyl]amino}carbonyl)amino]phenyl}pyrrolo[2,1-f][1,2,4]triazine-6-carboxylate

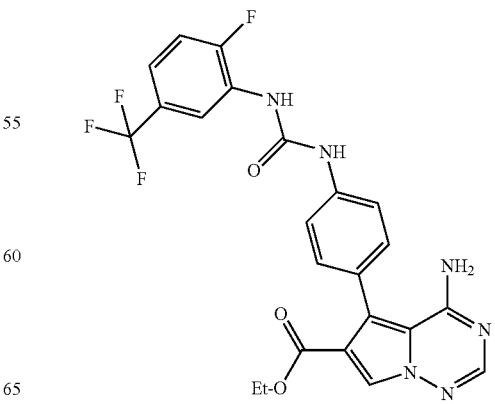

To a suspension of Intermediate C (210 mg, 0.45 mmol) in THF:DMF 4:1 (8 mL) was added Et$_3$N (0.20 mL, 1.4 mmol) and 2-fluoro-5-(trifluoromethyl)aniline (0.18 mL, 1.36 mmol). This was stirred at rt until reaction was complete upon which the reaction was evaporated to dryness and purified via HPLC (10-90% ACN/H$_2$O) to give the product as a yellow solid (80 mg, 35%). $^1$H-NMR (DMSO-d$_6$) δ 9.33 (s, 1H), 8.97 (d, J=4.0 Hz, 1H), 8.62 (d, J=12.0 Hz, 1H), 8.12 (s, 1H), 8.11 (br s, 1H), 7.92 (s, 1H), 7.6-7.3 (m, 5H), 4.10 (q, J=8.0 Hz, 2H), 1.11 (t, J=8.0 Hz, 3H); MS [M+H]$^+$=503; LCMS RT=3.50 min; TLC R$_f$=0.40 (3:1 v/v CH$_2$Cl$_2$-Acetone).

Intermediate F

Preparation of N-[4-(4-amino-6-formylpyrrolo[2,1-f][1,2,4]triazin-5-yl)phenyl]-N'-[2-fluoro-5-(trifluoromethyl)phenyl]urea

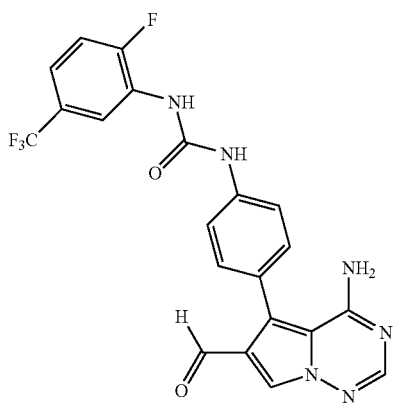

Step 1: Preparation of N-{4-[4-amino-6-(hydroxymethyl)pyrrolo[2,1-f][1,2,4]triazin-5-yl]phenyl}-N'-[2-fluoro-5-(trifluoromethyl)phenyl]urea

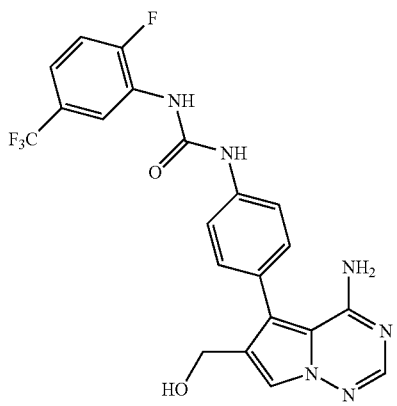

To a solution of THF (8.0 mL) was added Intermediate E (80.0 mg, 0.16 mmol) followed by DIBAL (0.8 mL, 0.8 mmol, 1.0M solution in THF). The reaction was stirred at rt with addition of DIBAL (2.4 mL, 2.4 mmol, 1.0M solution in THF) in three batches until HPLC indicated completion of reaction. The reaction was diluted with EtOAc and quenched with saturated aqueous Rochelle's salt. Reaction was extracted with EtOAc (4×). Organic was dried (Na$_2$SO$_4$) and evaporated to give a crude oil that was purified via HPLC (10-90% ACN/H$_2$O) yielding a yellow solid (40.0 mg, 55%). $^1$H-NMR (CD$_3$CN) δ 8.61 (d, J=8.0 Hz, 1H), 7.80 (s, 1H), 7.66-7.60 (m, 3H), 7.42-7.32 (m, 4H), 4.50 (s, 2H); MS [M+H]$^+$=461; LCMS RT=2.87 min.

Step 2: Preparation of the Title Compound

N-{4-[4-amino-6-(hydroxymethyl)pyrrolo[2,1-f][1,2,4]triazin-5-yl]phenyl}-N'-[2-fluoro-5-(trifluoromethyl)phenyl]urea (40.0 mg, 0.09 mmol) was dissolved in THF (5.0 mL) and to it was added Dess-Martin Periodinane reagent (44.0 mg, 0.10 mmol). The reaction was stirred at rt until HPLC indicated completion of reaction. Reaction was diluted with EtOAc and washed with saturated aqueous NaHCO$_3$/Na$_2$S$_2$O$_3$ 1:1 (3×). The aqueous layer was back extracted with EtOAc (2×). Organic was dried (Na$_2$SO$_4$) and evaporated to give a crude oil that was purified via HPLC (10-90% ACN/H$_2$O) to give a yellow solid (35.0 mg, 88%). $^1$H-NMR (CD$_3$OD) δ 9.76 (s, 1H), 8.61 (d, J=8.0 Hz, 1H), 8.11 (s, 1H), 7.87 (s, 1H), 7.65 (d, J=8.0 Hz, 1H), 7.46 (d, J=8.0 Hz, 1H), 7.30 (d, J=8.0 Hz, 1H); MS [M+H]$^+$=459; LCMS RT=2.95 min.

Intermediate G

Preparation of 4-amino-5-{4-[({[2-fluoro-5-(trifluoromethyl)phenyl]amino}carbonyl)amino]phenyl}pyrrolo[2,1-f][1,2,4]triazine-6-carboxylic acid

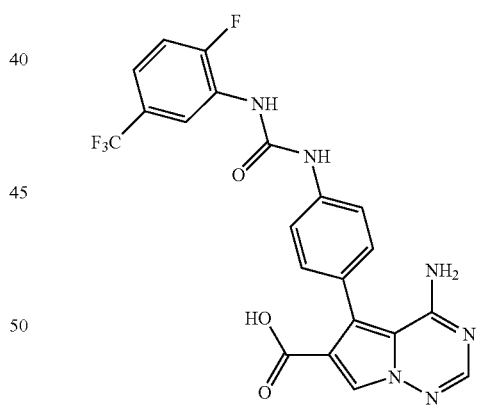

To a solution of Intermediate E (720.0 mg, 1.433 mmol) in 5 mL MeOH and 3 mL THF was added 1M NaOH (3.58 mL, 3.58 mmol.) and the reaction left to stir at 60° C. for 12 h. The reaction mixture was cooled and partitioned between CHCl$_3$ and pH 2 sulfate buffer. The organic layer was washed with brine, dried (Na$_2$SO$_4$) and concentrated to yield a brown solid (623 mg, 92% yield). $^1$H-NMR (DMSO-d$_6$) δ 12.17 (bs, 1H), 9.34 (s, 1H), 8.98 (d, J=2 Hz, 1H), 8.62 (dd, J=2 Hz, 8 Hz, 1H), 8.07 (3, 1H), 8.0 (bs, 1H), 7.91 (s, 1H), 7.53 (d, J=8 Hz, 2H), 7.55-7.45 (m, 1H), 7.42-7.35 (m, 1H), 7.32 (d, J=8 Hz, 2H), 5.0 (bs, 1H); MS [M+H]$^+$=475.2; LCMS RT=2.56 min; TLC R$_f$=0.26 (1:1:0.02 v/v/v THF:CH$_2$Cl$_2$:MeOH).

Intermediate H

Preparation of ethyl 3-[4-amino-5-(4-aminophenyl) pyrrolo[2,1-f][1,2,4]triazin-6-yl]propanoate

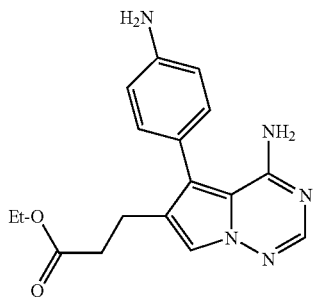

Step 1: Preparation of [4-amino-5-(4-nitrophenyl) pyrrolo[2,1-f][1,2,4]triazin-6-yl]methanol

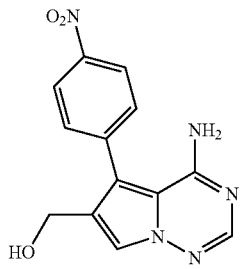

To a solution of THF (10 mL) was added Intermediate A (500 mg, 1.53 mmol) followed by DIBAL (3 mL, 3 mmol, 1.0M solution in toluene). The reaction was stirred at rt for 1 h. Additional DIBAL (1.5 mL, 1.5 mmol, 1.0M solution in toluene) was added and stirred at rt for another 1 h. The reaction was diluted with EtOAc and quenched with saturated aqueous Rochelle's salt. Reaction was extracted with EtOAc (4×). The organic was dried ($Na_2SO_4$) and evaporated to give a crude solid (435 mg, 100%) that was used directly in the next step without further purification. $^1$H-NMR (DMSO-$d_6$) δ 8.29 (d, J=9.2 Hz, 2H), 7.89 (s, 1H), 7.73 (s, 1H), 7.67 (d, J=9.3 Hz, 2H), 5.07 (t, J=5.5 Hz, 1H), 4.38 (d, J=5.2 Hz, 2H); MS [M+H]$^+$=286; LCMS RT=0.59 min.

Step 2: Preparation of 4-amino-5-(4-nitrophenyl) pyrrolo[2,1-f][1,2,4]triazine-6-carbaldehyde

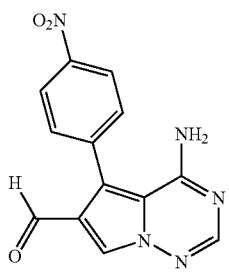

To a solution of THF (80 mL) was added 4-amino-5-(4-nitrophenyl)pyrrolo[2,1-f][1,2,4]triazin-6-yl]methanol (435 mg, 1.53 mmol) followed by Dess-Martin Periodinane reagent (4 mL, 1.89 mmol, 15% wt in $CH_2Cl_2$). The reaction was stirred at rt until HPLC indicated completion of reaction (5 h). The reaction was diluted with EtOAc and washed with saturated aqueous $NaHCO_3/Na_2S_2O_3$ (1:1 v/v) (3×). The aqueous layer was back extracted with EtOAc (2×). The organic was dried ($Na_2SO_4$) and evaporated to give a crude yellow solid (433 mg, 100%) that was used directly in the next step without further purification. $^1$H-NMR (DMSO-$d_6$) δ 9.79 (s, 1H), 8.39 (s, 1H), 8.29 (d, J=8.7 Hz, 2H), 8.00 (s, 1H), 7.73 (d, J=8.8 Hz, 2H); MS [M+H]$^+$=284; LCMS RT=2.48 min.

Step 3: Preparation of ethyl (2E)-3-[4-amino-5-(4-nitrophenyl)pyrrolo[2,1-f][1,2,4]triazin-6-yl]acrylate

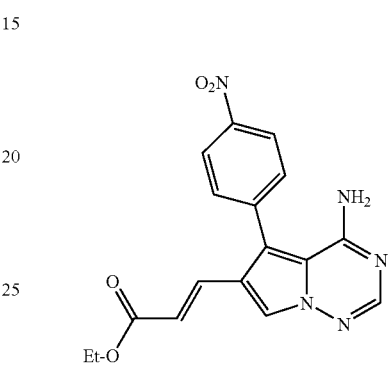

To a suspension of lithium hydride (68 mg, 4.0 mmol) in THF (5 mL) under $N_2$ atmosphere was added triethyl phosphonoacetate (498 mg, 2.22 mmol). The mixture was stirred at rt for 30 min and to the reaction mixture was added a slurry of 4-amino-5-(4-nitrophenyl)pyrrolo[2,1-f][1,2,4] triazine-6-carbaldehyde (433 mg, 1.53 mmol) in THF (15 ml). The mixture was heated at reflux for 2 h. After it was cooled to rt, aqueous $NaHCO_3$ was slowly added followed by EtOAc. The organic layer was collected and the aqueous layer was back extracted with EtOAc (2×). The combined organic layers were dried ($Na_2SO_4$) and evaporated to give a crude yellow solid that was purified by column chromatography (10:90 to 90:10 v/v EtOAc-hexanes) to afford the title compound (480 mg, 89%). $^1$H-NMR (CD$_3$OD) δ 8.42 (d, J=8.0 Hz, 2H), 8.17 (s, 1H), 7.88 (s, 1H), 7.68 (d, J=8.0 Hz, 2H), 7.43 (d, J=16 Hz, 1H), 6.36 (d, J=16 Hz, 1H), 4.16 (q, J=7.1 Hz, 2H), 1.23 (t, J=7.1 Hz, 3H); MS [M+H]$^+$=354; LCMS RT=3.12 min.

Step 4: Preparation of the Title Compound

A suspension of $PtO_2$ (16 mg, 0.070 mmol) in acetic acid (0.5 ml) was added to a suspension of ethyl (2E)-3-[4-amino-5-(4-nitrophenyl)pyrrolo[2,1-f][1,2,4]triazin-6-yl]acrylate (144 mg, 0.408 mmol) in acetic acid (2 ml) under $N_2$ atmosphere. The flask was evacuated and refilled with hydrogen gas (3×) and the reaction proceeded under a hydrogen atmosphere (1 atm) for 1 d. Additional $PtO_2$ (50 mg, 0.22 mmol) in acetic acid (0.5 ml) was added and the reaction proceeded under $H_2$ atmosphere for an additional 1 d. The reaction was filtered through a Celite pad and washed with MeOH. It was evaporated to dryness, diluted with EtOAc and washed with aqueous $Na_2CO_3$. The aqueous layer was back extracted with EtOAc (2×). Organic was dried ($Na_2SO_4$), filtered, and evaporated to dryness to afford the above compound as a yellow solid (120 mg, yield 90%). ¹H-NMR (CD₃OD) δ 7.70 (s, 1H), 7.47 (s, 1H), 7.12 (d, J=8.3 Hz, 2H), 6.84 (d, J=8.3 Hz, 2H), 4.06 (q, J=7.8 Hz, 2H), 2.82 (t, J=7.8 Hz, 2H), 2.48 (t, J=7.7 Hz, 2H), 1.18 (t, J=7.8 Hz, 3H); MS [M+H]⁺=326; LCMS RT=1.20 min.

Intermediate I

Preparation of N-{4-[4-amino-6-(3-oxopropyl)pyrrolo[2,1-f][1,2,4]triazin-5-yl]phenyl}-N'-[2-fluoro-5-(trifluoromethyl)phenyl]urea

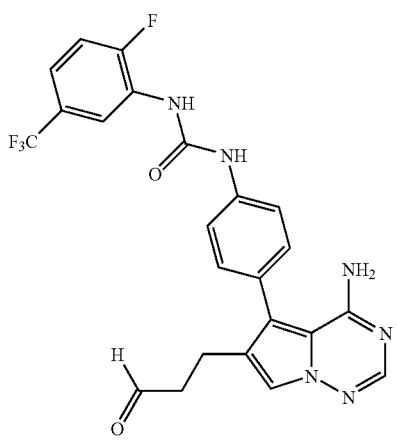

Step 1: Preparation of phenyl[2-fluoro-5-(trifluoromethyl)phenyl]carbamate

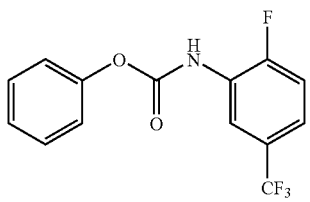

To a stirred solution of 2-fluoro-5-(trifluoromethyl)aniline (3.00 g, 16.7 mmol) in THF (80 mL) was added pyridine (2.71 mL, 33.5 mmol), followed by phenyl chloroformate (3.15 mL, 25.1 mmol) at rt. Some solid precipitated out. The mixture was stirred at rt overnight. Water was added to the reaction and it was extracted with EtOAc. The organic solution was washed with water (2×) and dried over MgSO₄ and then filtered. The filtrate was concentrated in vacuo and purified by column chromatography (10:90 to 30:70 v/v EtOAc-hexanes) to afford the title compound (3.1 g, 62%). ¹H-NMR (DMSO-d₆) δ 10.36 (br s, 1H), 8.15 (d, J=7.1 Hz, 1H), 7.59 to 7.47 (m, 2H), 7.46 to 7.38 (m, 2H), 7.30 to 7.20 (m, 3H); TLC R_f=0.39 (9:1 v/v hexanes-EtOAc).

Step 2: Preparation of ethyl 3-(4-amino-5-{4-[({[2-fluoro-5-(trifluoromethyl)phenyl]amino}carbonyl)amino]phenyl}pyrrolo[2,1-f][1,2,4]triazin-6-yl)propanoate

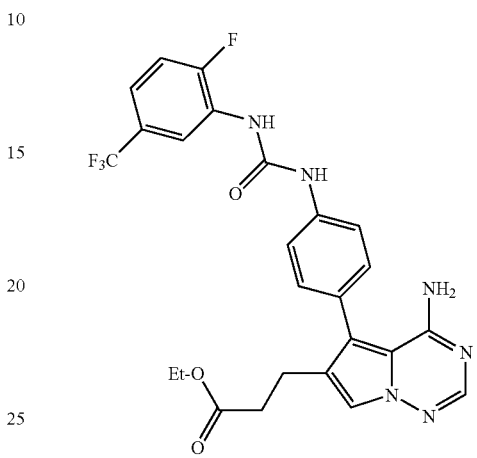

To a solution of THF (2.0 mL) was added Intermediate H (80 mg, 0.25 mmol) followed by phenyl[2-fluoro-5-(trifluoromethyl)phenyl]carbamate (74 mg, 0.25 mmol) and triethylamine (34 μL, 0.25 mmol). The reaction was stirred at 0° C. and was allowed to slowly warm to rt overnight. The solution was concentrated in vacuo to dryness and then purified by column chromatography (5:95 to 50:50 v/v EtOAc-hexanes) to afford the title compound (66 mg, 50%). ¹H-NMR (CD₃OD) δ 8.62 (d, J=7.4 Hz, 1H), 7.74 (s, 1H), 7.63 (d, J=8.6 Hz, 2H), 7.52 (s, 1H), 7.40 to 7.31 (m, 4H), 4.06 (q, J=7.0 Hz, 2H), 2.84 (t, J=7.5 Hz, 2H), 2.50 (t, J=7.4 Hz, 2H), 1.18 (t, J=7.0 Hz, 3H); MS [M+H]⁺=531; LCMS RT=3.29 min.

Step 3: Preparation of N-{4-[4-amino-6-(3-hydroxypropyl)pyrrolo[2,1-f][1,2,4]triazin-5-yl]phenyl}-N'-[2-fluoro-5-(trifluoromethyl)phenyl]urea

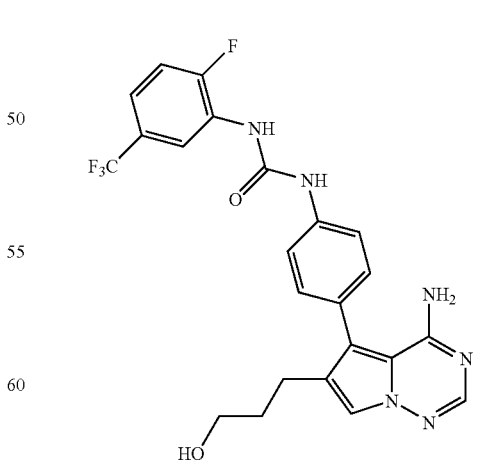

To a solution of THF (6 mL) was added ethyl 3-(4-amino-5-{4-[({[2-fluoro-5-(trifluoromethyl)phenyl]amino}carbonyl)amino]phenyl}pyrrolo[2,1-f][1,2,4]triazin- 6-yl)propanoate (62 mg, 0.12 mmol) followed by DIBAL (0.6 mL, 0.6 mmol, 1.0M solution in toluene). The reaction was stirred at rt for 1 h. Additional DIBAL (1.2 mL, 1.2 mmol, 1.0M solution in toluene) was added and stirred at rt for an additional 1 h. The reaction was diluted with EtOAc and quenched with saturated aqueous Rochelle's salt. Reaction was extracted with EtOAc (4×). The combined organic layers were dried ($Na_2SO_4$), filtered, and evaporated to dryness to afford a crude yellow solid (56 mg, 98%) that was used directly in the next step without further purification. $^1$H-NMR ($CD_3OD$) δ 8.62 (d, J=7.6 Hz, 1H), 7.74 (s, 1H), 7.61 (d, J=7.6 Hz, 2H), 7.52 (s, 1H), 7.38 to 7.31 (m, 4H), 3.50 (t, J=7.1 Hz, 2H), 2.61 (t, J=7.8 Hz, 2H), 1.77 to 1.65 (m, 2H); MS $[M+H]^+$=489; LCMS RT=2.50 min.

Step 4: Preparation of the Title Compound

To a solution of THF (5 mL) was added N-{4-[4-amino-6-(3-hydroxypropyl)pyrrolo[2,1-f][1,2,4]triazin-5-yl]phenyl}-N'-[2-fluoro-5-(trifluoromethyl)phenyl]urea (55 mg, 0.11 mmol) followed by Dess-Martin Periodinane reagent (0.29 mL, 0.14 mmol, 15% wt in $CH_2Cl_2$). The reaction was stirred until HPLC indicated completion of reaction (2 h). The reaction was diluted with EtOAc and washed with saturated aqueous $NaHCO_3$/$Na_2S_2O_3$ 1:1 (3×). The aqueous layer was back extracted with EtOAc (2×). The combined organic layers were dried ($Na_2SO_4$), filtered, and evaporated to give a crude yellow solid (53 mg, 96%) that was used without further purification. $^1$H-NMR (DMSO-$d_6$) δ 9.35 (s, 1H), 8.98 (s, 1H), 8.62 (d, J=7.2 Hz, 1H), 7.80 (s, 1H), 7.62 to 7.28 (m, 6H), 2.71 (t, J=7.5 Hz, 2H), 2.41 (t, J=7.4 Hz, 2H); MS $[M+H]^+$=487; LCMS RT=2.62 min.

Intermediate J

Preparation of 4-amino-5-{4-[({[2-chloro-5-(trifluoromethyl)phenyl]amino}carbonyl)amino]phenyl}pyrrolo[2,1-f][1,2,4]triazine-6-carboxylic acid

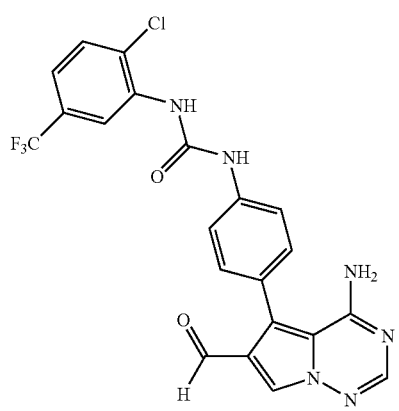

Step 1: Preparation of ethyl 4-amino-5-{4-[({[2-chloro-5-(trifluoromethyl)phenyl]amino}carbonyl)amino]phenyl}pyrrolo[2,1-f][1,2,4]triazine-6-carboxylate

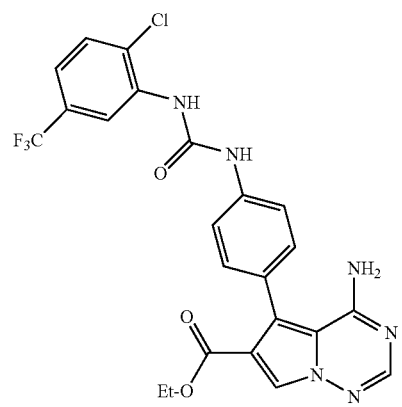

To a solution of DCE (5 mL) was added Intermediate B (300 mg, 1.01 mmol) followed by 2-chloro-1-isocyanato-4-(trifluoromethyl)benzene (0.32 mL, 2.12 mmol). The reaction was stirred under $N_2$ at rt for 1 h, and then aq 2N HCl (0.50 mL, 1.01 mmol) was added to the reaction followed by DMF (5 mL). The solution was heated at 80° C. for 1 h. Upon cooling to rt the solution was diluted with EtOAc, transferred to a separatory funnel, and washed with aq saturated $NaHCO_3$. The aq layer was back extracted with EtOAc. The combined organic layers were collected, dried, concentrated, and purified by column chromatography (95:5 v/v $CH_2Cl_2$-MeOH). The resulting fractions containing product were concentrated and triturated using $CH_2Cl_2$ and hexanes. The product was filtered and dried in vacuo to afford 408 mg of the above compound as a white solid (0.79 mmol, yield 78%). $^1$H-NMR (DMSO-$d_6$) δ 9.72 (s, 1H), 8.67 (s, 1H), 8.64 (s, 1H), 8.13 (s, 1H), 8.08 (br s, 1H), 7.93 (s, 1H), 7.72 (d, J=8.5 Hz, 1H), 7.56 (d, J=8.8 Hz, 2H), 7.39 to 7.36 (m, 1H), 7.34 (d, J=8.6 Hz, 2H), 5.10 (br s, 1H), 4.09 (q, J=7.0 Hz, 2H), 1.12 (t, J=7.1 Hz, 3H); MS $[M+H]^+$=519; LCMS RT=3.58 min; TLC $R_f$=0.26 (95:5 v/v $CH_2Cl_2$-MeOH).

Step 2: Preparation of the Title Compound

To a solution of MeOH (20 mL) and THF (50 mL) was added ethyl 4-amino-5-{4-[({[2-chloro-5-(trifluoromethyl)phenyl]amino}carbonyl)amino]phenyl}pyrrolo[2,1-f][1,2,4]triazine-6-carboxylate (381 mg, 0.73 mmol) followed by aq 1N NaOH (7.34 mL, 7.34 mmol). The reaction was then heated under $N_2$ at 60° C. for 17 h. Upon cooling to rt the solution was partially rotavapped and was then treated with 1N HCl (7.34 mL, 7.34 mmol). A precipitate formed which was collected and washed with water yielding 324 mg of the above compound as a white solid (0.66 mmol, yield 90%). $^1$H-NMR (DMSO-$d_6$) δ 12.29 (br s, 1H), 9.75 (s, 1H), 8.69 (s, 1H), 8.63 (s, 1H), 8.08 (s, 1H), 8.03 (br s, 1H), 7.92 (s, 1H), 7.72 (d, J=8.3 Hz, 1H), 7.55 (d, J=8.4 Hz, 2H), 7.37 (m, 1H), 7.33 (d, J=8.6 Hz, 2H), 5.05 (br s, 1H); MS [M+H]⁺=491; LCMS RT=3.15 min; TLC $R_f$<0.1 (5:4:1 v/v/v CH$_2$Cl$_2$-EtOAc-MeOH).

Intermediate K

Preparation of 4-amino-5-(4-nitrophenyl)pyrrolo[2,1-f][1,2,4]triazine-6-carboxylic acid

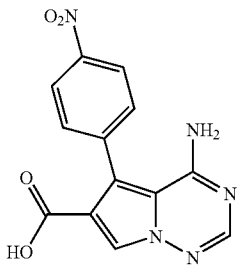

A suspension of Intermediate A (1.04 g, 3.18 mmol) in EtOH (10 mL), THF (5 mL) and 1N NaOH (5.56 mL, 5.56 mmol) was stirred at 80° C. for 6 h. The homogeneous solution was cooled to rt and treated dropwise with 1N HCl (5.56 mL). The reaction was concentrated in vacuo and the resulting solid triturated with water to give the above compound as a tan solid. MS [M+H]⁺=300.2; LCMS RT=1.37 min.

Intermediate L

Preparation of 4-amino-5-(4-aminophenyl)-N-(tert-butyl)pyrrolo[2,1-f][1,2,4]triazine-6-carboxamide

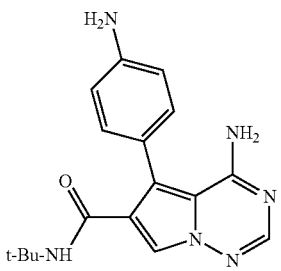

Step 1: Preparation of 4-amino-N-(tert-butyl)-5-(4-nitrophenyl)pyrrolo[2,1-f][1,2,4]triazine-6-carboxamide

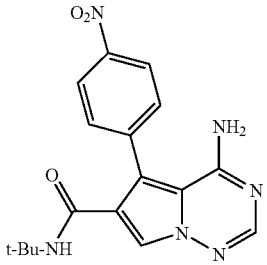

To a solution of toluene (10 mL) was added 2M trimethyl aluminum in hexanes (1.37 mL, 2.75 mmol) followed by 2-methylpropan-2-amine (0.14 mL, 1.37 mmol). The solution was stirred at rt for 15 min and then Intermediate A (300 mg, 0.92 mmol) was added. The solution was heated at 110° C. for 17 h. Upon cooling to rt 1N HCl was slowly added until bubbling ceased. EtOAc was added followed by careful addition of aq NaHCO$_3$. The solution was transferred to a separatory funnel, the organic was collected and the aqueous was back extracted with EtOAc (3×20 mL). The combined organics were dried (MgSO$_4$), concentrated, and purified by column chromatography (50:45:5 v/v/v CH$_2$Cl$_2$/EtOAc/MeOH) to afford 181 mg of the above compound (0.51 mmol, yield 56%). ¹H-NMR (DMSO-d$_6$) 8.25 (d, J=8.9 Hz, 2H), 8.16 (s, 1H), 7.94 (s, 1H), 7.59 (d, J=8.8 Hz, 2H), 7.39 (s, 1H) 1.25 (s, 9H); MS [M+H]⁺=355; LCMS RT=2.42 min.

Step 2: Preparation of the Title Compound

The procedure used for the preparation of Intermediate B was used to prepare the title compound by substituting 4-amino-N-(tert-butyl)-5-(4-nitrophenyl)pyrrolo[2,1-f][1,2,4]triazine-6-carboxamide for Intermediate A. ¹H-NMR (DMSO-d$_6$) δ 7.91 (s, 1H), 7.89 (br s, 1H), 7.84 (s, 1H), 7.07 (d, J=8.2 Hz, 2H), 6.69 (d, J=8.3 Hz, 2H), 6.15 (s, 1H), 5.44 (s, 2H), 5.04 (br s, 1H), 1.14 (s, 9H); MS [M+H]⁺=325; LCMS RT=1.38 min; TLC $R_f$=0.15 (95:5 v/v CH$_2$Cl$_2$-MeOH).

Intermediate M

Preparation of 4-amino-5-(4-aminophenyl)-N-(2,2,2-trifluoroethyl)pyrrolo[2,1-f][1,2,4]triazine-6-carboxamide

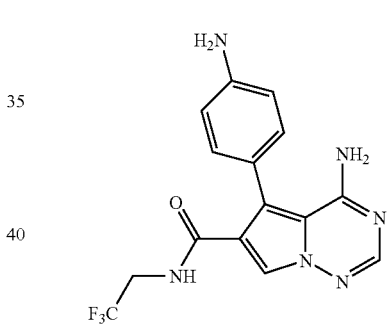

Step 1: Preparation of 4-amino-5-(4-nitrophenyl)-N-(2,2,2-trifluoroethyl)pyrrolo[2,1-f][1,2,4]triazine-6-carboxamide

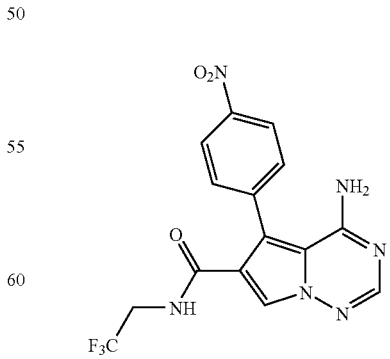

To a solution of thionyl chloride (15 mL) was added Intermediate K (495 mg, 1.73 mmol) which was heated at 50° C. for 3 h. Upon cooling to rt the reaction mixture was concentrated to dryness chasing with THF. The reaction mixture was then diluted with 2,2,2-trifluoro-ethylamine hydrochloride salt (587 mg, 4.33 mmol) and triethylamine (1.15 ml, 8.66 mmol) in THF (8 mL) and stirred at rt overnight. The solution was rotavapped to dryness, diluted with EtOAc (50 mL), transferred to a separatory funnel, and washed with water (50 mL). The water layer was back extracted with EtOAc (4×20 mL), dried ($Na_2SO_4$), filtered, and concentrated to dryness. Then it was triturated with EtOAc/MeOH. The product was collected to afford 490 mg of the above compound as a yellow solid (yield 74%). $^1$H-NMR (DMSO-$d_6$) δ 8.77 (t, J=6.2 Hz, 1H), 8.29 (s, 1H), 8.23 (d, J=8.9 Hz, 2H), 7.97 (s, 1H), 7.59 (d, J=8.9 Hz, 2H), 3.97 to 3.91 (m, 2H); MS [M+H]$^+$=381.1; LCMS RT=2.33 min).

Step 2: Preparation of the Title Compound

The procedure used for the preparation of Intermediate B was used to prepare the title compound by substituting 4-amino-5-(4-nitrophenyl)-N-(2,2,2-trifluoroethyl)pyrrolo[2,1-f][1,2,4]triazine-6-carboxamide for Intermediate A. $^1$H-NMR (CD$_3$OD) δ 8.00 (s, 1H), 7.81 (s, 1H), 7.17 (d, J=8.5 Hz, 2H), 6.84 (d, J=8.6 Hz, 2H), 4.03 to 3.85 (m, 2H); MS [M+H]$^+$=351.2; LCMS RT=1.14 min.

Intermediate N

Preparation of 2-(trimethylsilyl)ethyl (5-(4-aminophenyl)-6-{[(2-methoxyethyl)amino]carbonyl}pyrrolo[2,1-f][1,2,4]triazin-4-yl)carbamate

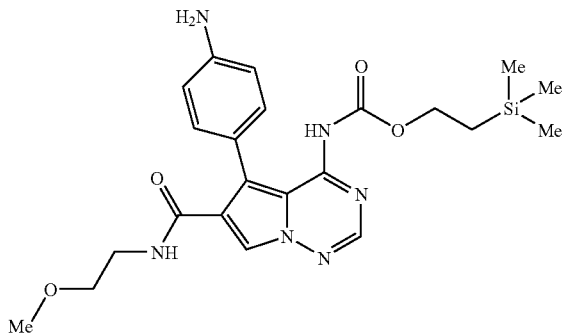

Step 1: Preparation of 4-amino-N-(2-methoxyethyl)-5-(4-nitrophenyl)pyrrolo[2,1-f][1,2,4]triazine-6-carboxamide

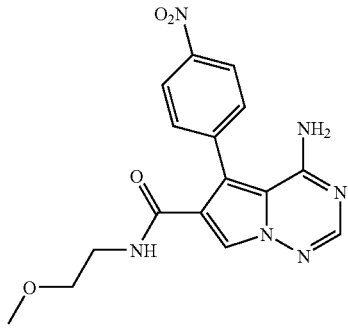

The procedure used for the preparation of 4-amino-N-(tert-butyl)-5-(4-nitrophenyl)pyrrolo[2,1-f][1,2,4]triazine-6-carboxamide (intermediate L Step 1) was used to prepare the title compound by substituting 2-methoxyethanamine for 2-methylpropan-2-amine. $^1$H-NMR (DMSO-$d_6$) δ 8.22 (d, J=8.7 Hz, 2H), 8.18 (s, 1H), 8.11 (t, J=5.6 Hz, 1H), 7.93 (s, 1H), 7.58 (d, J=8.9 Hz, 2H), 3.28 to 3.26 (m, 2H), 3.21 (s, 3H), 3.16 to 3.14 (m, 2H); MS [M+H]$^+$=357; LCMS RT=1.83 ruin.

Step 2: Preparation of 2-(trimethylsilyl)ethyl[6-{[(2-methoxyethyl)amino]carbonyl}-5-(4-nitrophenyl)pyrrolo[2,1-f][1,2,4]triazin-4-yl]carbamate

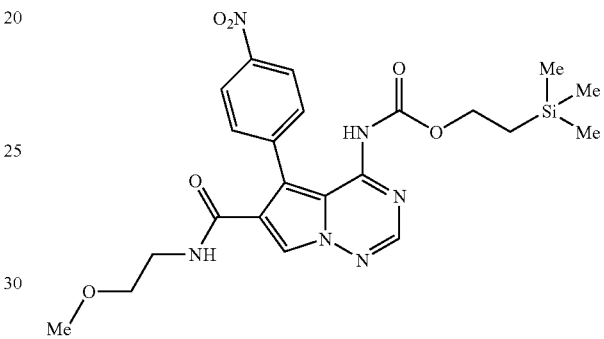

To a solution of DMF (100 mL) was added 4-amino-N-(2-methoxyethyl)-5-(4-nitrophenyl)pyrrolo[2,1-f][1,2,4]triazine-6-carboxamide (4.03 g, 11.3 mol) followed by 60% NaH by weight in mineral oil (1.13 g, 28.3 mmol). The solution was stirred for 15 min and then 4-nitrophenyl 2-(trimethylsilyl)ethyl carbonate (3.52 g, 12.4 mmol) was added. The solution was stirred under $N_2$ for 2 h. MeOH was added to the reaction until bubbling ceased and then EtOAc (50 mL) was added. The solution was transferred to a separatory funnel and was washed with 1N NaOH (20 mL) and water (20 mL). The organic was collected, dried ($Na_2SO_4$), and purified by column chromatography to afford 3.60 g of the above compound (7.15 mmol, yield 63%). $^1$H-NMR (CDCl$_3$) δ 8.38 (d, J=8.5 Hz, 2H), 8.16 (s, 1H), 8.14 (s, 1H), 7.69 (d, J=8.5 Hz, 2H) 5.87 to 5.86 (m, 1H), 4.17 (t, J=8.3 Hz, 2H), 3.48 to 3.46 (m, 2H), 3.36 (t, J=5.0 Hz 2H), 3.21 (s, 3H), 0.93 (t, J=8.1 Hz 2H), −0.01 (s, 9H); MS [M+H]$^+$=501; LCMS RT=3.17 min.

Step 3: Preparation of the Title Compound

The procedure used for the preparation of Intermediate B was used to prepare the title compound by substituting 2-(trimethylsilyl)ethyl[6-{[(2-methoxyethyl)amino]carbonyl}-5-(4-nitrophenyl)pyrrolo[2,1-f][1,2,4]triazin-4-yl]carbamate for Intermediate A. $^1$H-NMR (DMSO-$d_6$) δ 8.26 (s, 1H), 8.23 (s, 1H), 8.16 (s, 1H), 7.42 (br s, 1H), 7.04 (d, J=8.3 Hz, 2H), 6.61 (d, J=8.3 Hz, 2H), 5.36 (br s, 2H), 3.99 (t, J=8.3 Hz, 2H), 3.29 to 3.25 (m, 4H), 3.18 (s, 3H), 0.88 to 0.84, (m, 2H), −0.01 (s, 9H); MS [M+H]$^+$=471; LCMS RT=3.04 min.

Intermediate O

Preparation of 4-amino-5-(4-nitrophenyl)pyrrolo[2,1-f][1,2,4]-triazine-6-carbonitrile

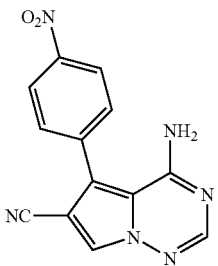

To a solution of pyridine (8.75 mL) was added 4-amino-5-(4-nitrophenyl)pyrrolo[2,1-f][1,2,4]triazine-6-carbaldehyde (Intermediate H, Step 2) (500 mg, 1.77 mmol) followed by hydroxylamine hydrochloride (135 mg, 1.94 mmol). The solution was stirred at rt for 1 h, acetic anhydride (0.366 mL, 3.88 mmol) was added, and the solution was heated to 80° C. for 17 h. Upon cooling to rt the reaction mixture was partially rotavapped and then diluted with EtOAc (50 mL) and H$_2$O (50 mL). The solution was transferred to a separatory funnel, and the organic layer was isolated while the aqueous layers were back extracted with EtOAc (2×25 mL). The combined organic layers were collected, dried (Na$_2$SO$_4$), filtered, and concentrated to dryness to afford a brown solid. This proved to be a 1:1 ratio of the title compound and N-[6-cyano-5-(4-nitro-phenyl)-pyrrolo[2,1-f][1,2,4]triazin-4-yl]-acetamide. $^1$H-NMR (DMSO-d$_6$) δ 10.67 (s, 1H), 8.96 (s, 1H), 8.62 (s, 1H), 8.57 (s, 1H), 8.40 to 8.30 (m, 4H), 8.05 (s, 1H), 7.79 to 7.68 (m, 4H), 1.74 (s, 3H); MS [M+H]$^+$=281.2, 323.0; LCMS RT=2.48 min.

Intermediate P

Preparation of 4-amino-5-(4-aminophenyl)pyrrolo[2,1-f][1,2,4]triazine-6-carbonitrile

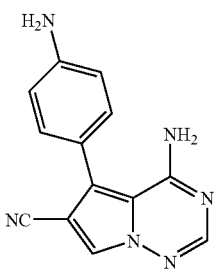

The procedure used for the preparation of Intermediate B was used to prepare the title compound by substituting Intermediate O for Intermediate A $^1$H-NMR (CD$_3$OD) δ 8.29 (s, 1H), 7.98 (s, 1H), 7.57 (d, J=9.0 Hz, 2H), 7.33 (d, J=9.0 Hz, 2H); MS [M+H]$^+$=251.3; LCMS RT=0.40 min.

Intermediate Q

Preparation of 4-amino-5-(4-aminophenyl)pyrrolo[2,1-f][1,2,4]triazine-6-carboxamide

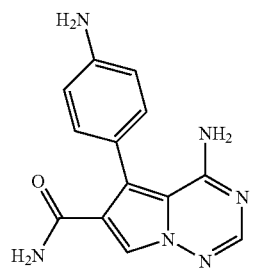

Step 1: Preparation of 4-amino-5-(4-nitrophenyl)pyrrolo[2,1-f][1,2,4]triazine-6-carboxamide

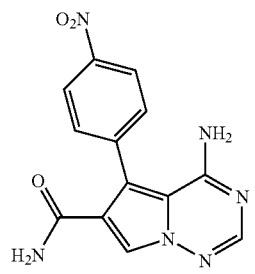

A mixture of Intermediate O (80 mg, 0.29 μmmol) in sulfuric acid (1 mL) was stirred at rt overnight. The reaction mixture was slowly quenched with saturated sodium bicarbonate solution until gas evolution ceased. The reaction mixture was then extracted with EtOAc (3×5 mL) and THF (3×5 mL), dried (Na$_2$SO$_4$), filtered, and concentrated to dryness to afford a brown solid. $^1$H-NMR (CD$_3$OD) δ 8.22 (d, J=9.0 Hz, 2H), 8.04 (s, 1H), 7.80 (s, 1H), 7.59 (d, J=8.6 Hz, 2H); MS [M+H]$^+$=299.1; LCMS RT=1.15 min.

Step 2: Preparation of the Title Compound

The procedure used for the preparation of Intermediate B was used to prepare the title compound by substituting 4-amino-5-(4-nitrophenyl)pyrrolo[2,1-f][1,2,4]triazine-6-carboxamide for Intermediate A. $^1$H-NMR (CD$_3$OD) δ 8.26 (s, 1H), 8.02 (s, 1H), 7.98 (br s, 2H), 7.53 (d, J=9.0 Hz, 2H), 7.33 (d, J=9.0 Hz, 2H); MS [M+H]$^+$=269.3; LCMS RT=0.19 min.

Intermediate R

Preparation of [4-amino-5-(4-nitrophenyl)pyrrolo[2,1-f][1,2,4]triazin-6-yl]methanol

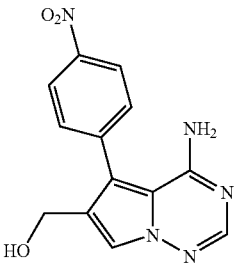

To a solution of THF (10 mL) was added Intermediate A (500 mg, 1.53 mmol) followed by DIBAL (3 mL, 3 mmol, 1.0 M solution in toluene). The reaction was stirred at rt for 1 h. Additional DIBAL (1.5 mL, 1.5 mmol, 1.0 M solution in toluene) was added and stirring continued at rt for another 1 h. The reaction was diluted with EtOAc and quenched with saturated aqueous Rochelle's salt. The reaction was extracted with EtOAc (4×). The organic was dried (Na$_2$SO$_4$) and evaporated to give a crude solid (435 mg, 100%) that was used directly in the next step without further purification. $^1$H-NMR (DMSO-d$_6$) δ 8.29 (d, J=9.2 Hz, 2H), 7.89 (s, 1H), 7.73 (s, 1H), 7.67 (d, J=9.3 Hz, 2H), 5.07 (t, J=5.5 Hz, 1H), 4.38 (d, J=5.2 Hz, 2H); MS [M+H]$^+$=286; LCMS RT=0.59 min.

Intermediate S

Preparation of 6-(chloromethyl)-5-(4-nitrophenyl)pyrrolo[2,1-f][1,2,4]triazin-4-amine

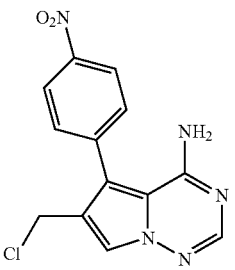

A mixture Intermediate R (522 mg, 1.83 mmol) in thionyl chloride (10 mL) was stirred at 50° C. for 1 h. It was then concentrated to dryness to afford a brown solid. $^1$H-NMR (DMSO-d$_6$) δ 8.37 (d, J=8.9 Hz, 2H), 8.19 (s, 1H), 8.16 (s, 1H), 7.74 (d, J=8.9 Hz, 2H), 4.70 (s, 2H); MS [M+H]$^+$=304.3; LCMS RT=2.44 min.

Intermediate T

Preparation of 5-(4-aminophenyl)-6-methylpyrrolo[2,1-f][1,2,4]triazin-4-amine

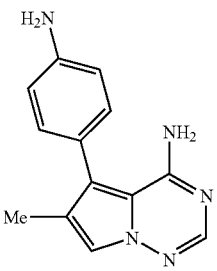

The procedure used for the preparation of Intermediate B was used to prepare the title compound by substituting Intermediate S for Intermediate A. $^1$H-NMR (CD$_3$OD) δ 7.74 (s, 1H), 7.52 (s, 1H), 7.13 (d, J=8.2 Hz, 2H), 6.86 (d, J=8.5 Hz, 2H), 2.11 (s, 3H); MS [M+H]$^+$=240.3; LCMS RT=1.06 min.

Intermediate U

Preparation of 5-(4-aminophenyl)-6-(methoxymethyl)pyrrolo[2,1-f][1,2,4]triazin-4-amine

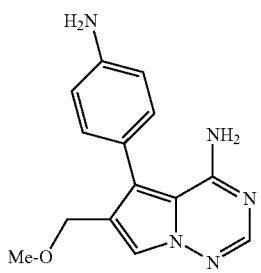

Step 1: Preparation of 6-(methoxymethyl)-5-(4-nitrophenyl)pyrrolo[2,1-f][1,2,4]triazin-4-amine

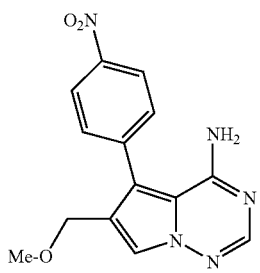

To a solution of thionyl chloride (20 mL) was added Intermediate R (873 mg, 3.06 mmol) which was heated to reflux under N$_2$ for 2 h. Upon cooling to rt the reaction mixture was rotavapped to dryness chasing with CH$_2$Cl$_2$. The reaction mixture was then diluted with MeOH (20 mL) and then 60% by weight NaH with mineral oil (489 mg, 12.2 mmol) was added. The solution was heated to reflux for 6 h. Upon cooling to rt the solution was rotavapped to dryness, diluted with EtOAc (50 mL), transferred to a separatory funnel, and washed with water (50 mL). The water layer was back extracted with EtOAc (4×20 mL), dried (MgSO$_4$), filtered, and purified by column chromatography (95:5 v/v CH$_2$CL$_2$:MeOH). The resulting clean fractions were combined, evaporated, and triturated with CH$_2$Cl$_2$/diethyl ether. The product was collected to afford 470 mg of the above compound as a yellow solid (1.57 mmol, yield 51%). $^1$H-NMR (DMSO-d$_6$) δ 8.30 (d, J=8.9 Hz, 2H), 7.91 (s, 1H), 7.84 (s, 1H), 7.65 (d, J=8.9 Hz, 2H), 4.29 (s, 2H), 3.21 (s, 3H); MS [M+H]$^+$=300; LCMS RT=2.07 min; TLC R$_f$=0.54 (95:5 v/v CH$_2$Cl$_2$-MeOH).

Step 2: Preparation of the Title Compound

The procedure used for the preparation of Intermediate B was used to prepare the title compound by substituting 6-(methoxymethyl)-5-(4-nitrophenyl)pyrrolo[2,1-f][1,2,4]triazin-4-amine for Intermediate A. $^1$H-NMR (DMSO-d$_6$) δ7.79 (s, 1H), 7.67 (s, 1H), 7.03 (d, J=8.4 Hz, 2H), 6.64 (d, J=8.7 Hz, 2H), 5.30 (s, 2H), 4.24 (s, 2H), 3.19 (s, 3H); MS [M+H]$^+$=270; LCMS RT=0.26 min; TLC R$_f$=0.30 (95:5 v/v CH$_2$Cl$_2$-MeOH).

Intermediate V

Preparation of 4-amino-5-(4-aminophenyl)-N-(2,3-dihydroxypropyl)pyrrolo[2,1-f][1,2,4]triazine-6-carboxamide

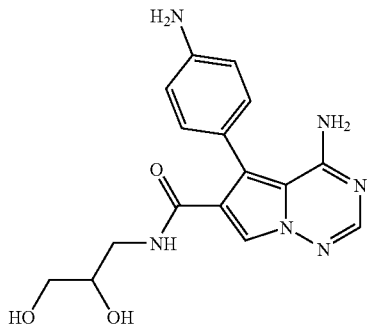

Step 1: Preparation of 4-amino-N-(2,3-dihydroxypropyl)-5-(4-nitrophenyl)pyrrolo[2,1-f][1,2,4]triazine-6-carboxamide

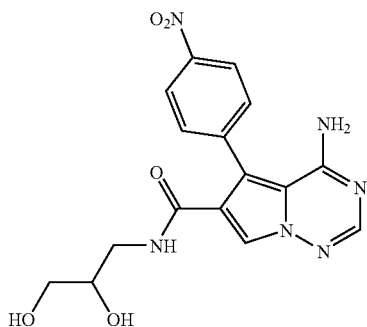

To a solution of Intermediate K (550 mg, 1.84 mmol), 3-amino-1,2-propanediol (251 mg, 2.76 mmol), triethylamine (1.0 mL, 7.4 mmol), and DMF (20 mL) was added py-BOP (1051 mg, 2.02 mmol) and the reaction was left to stir for 1 h. The reaction mixture was concentrated in vacuo and the residue triturated first with water and then with 30% aqueous ethanol to afford 318 mg of the above compound as an orange/yellow solid (yield 47%). MS [M+H]$^+$=373.2; LCMS RT=1.21.

Step 2: Preparation of the Title Compound

The procedure used for the preparation of Intermediate B was used to prepare the title compound by 4-amino-N-(2,3-dihydroxypropyl)-5-(4-nitrophenyl)pyrrolo[2,1-f][1,2,4]triazine-6-carboxamide for Intermediate A. $^1$H-NMR (DMSO-d$_6$) δ 8.02 (s, 1H), 7.84 (s, 1H), 7.28 (t, J=6 Hz, 1H) 7.02 (d, J=8 Hz, 2H), 5.34 (s, 2H), 5.05 (bs, 1H), 4.75 (bs, 1H), 4.52 (bs, 1H), 4.38 to 3.43 (m, 1H), 3.36 to 3.16 (m, 3H), 3.03 to 2.85 (m, 1H). MS [M+H]$^+$=343.2; LCMS RT=1.02 min.

Intermediate W

Preparation of 4-amino-5-(4-aminophenyl)-N-cyclopropylpyrrolo[2,1-f][1,2,4]triazine-6-carboxamide

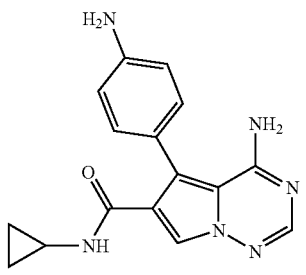

Step 1: Preparation of 4-amino-N-cyclopropyl-5-(4-nitrophenyl)pyrrolo[2,1-f][1,2,4]triazine-6-carboxamide

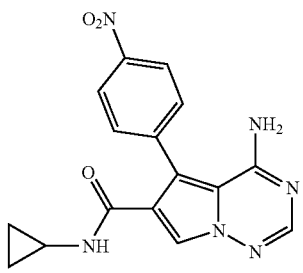

The procedure used for the preparation of 4-amino-N-(tert-butyl)-5-(4-nitrophenyl)pyrrolo[2,1-f][1,2,4]triazine-6-carboxamide (Intermediate L Step 1) was used to prepare the title compound by substituting cyclopropylamine for 2-methylpropan-2-amine. $^1$H-NMR (DMSO-d$_6$) δ 8.23 (d, J=8.8 Hz, 2H), 8.14 (s, 1H), 8.13 (br s, 1H), 7.93 (d, J=8.4 Hz, 2H), 7.58 (s, 1H), 2.67 to 2.59 (m, 1H), 0.62 to 0.54 (m, 2H), 0.46 to 0.41 (m, 2H); MS [M+H]$^+$=339.2; LCMS RT=1.40 min.

Step 2: Preparation of the Title Compound

The procedure used for the preparation of Intermediate B was used to prepare the title compound by substituting 4-amino-N-cyclopropyl-5-(4-nitrophenyl)pyrrolo[2,1-f][1,2,4]triazine-6-carboxamide for Intermediate A. $^1$H-NMR (CD$_3$OD) δ 7.68 (s, 1H), 7.58 (s, 1H), 7.07 (s, 1H), 6.73 (d, J=8.6 Hz, 2H), 6.33 (d, J=8.3 Hz, 2H), 5.05 (s, 2H), 2.38 to 2.28 (m, 1H), 0.34 to 0.24 (m, 2H), 0.067 to −0.032 (m, 2H); MS [M+H]⁺=309.3; LCMS RT=0.23 min.

Intermediate X

Preparation of 4-amino-5-(4-aminophenyl)-N-methylpyrrolo[2,1-f][1,2,4]triazine-6-carboxamide

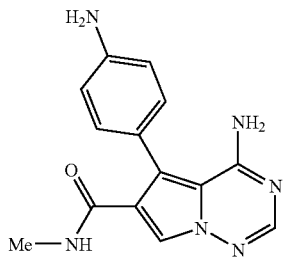

Step 1: Preparation of 4-amino-N-methyl-5-(4-nitrophenyl)pyrrolo[2,1-f][1,2,4]triazine-6-carboxamide

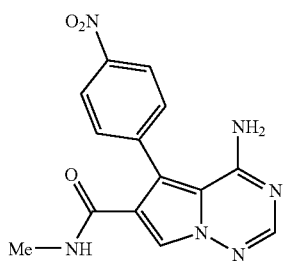

To a solution of thionyl chloride (10 mL) was added Intermediate K (300 mg, 1.00 mmol) which was heated at 50° C. for 3 h. Upon cooling to rt the reaction mixture was rotavapped to dryness chasing with THF. The reaction mixture was then diluted with 2M methylamine in THF (40 mL) and stirred at rt overnight. The solution was rotavapped to dryness, diluted with EtOAc (50 mL), transferred to a separatory funnel, and washed with water (50 mL). The water layer was back extracted with EtOAc (4×20 mL), dried (Na₂SO₄), filtered, and rotavapped to dryness. Then it was triturated with EtOAc/MeOH. The product was collected to afford 240 mg of the above compound as a yellow solid (240 mg, yield 76%). ¹H-NMR (DMSO-d₆) δ 8.22 (d, J=8.9 Hz, 2H), 8.15 (s, 1H), 7.94 (s, 1H), 7.58 (d, J=8.9 Hz, 2H), 3.60 to 3.55 (m, 1H), 2.62 (d, J=4.6 Hz, 3H); MS [M+H]⁺=313.2; LCMS RT=0.58 min).

Step 2: Preparation of the Title Compound

The procedure used for the preparation of Intermediate B was used to prepare the title compound by substituting 4-amino-N-methyl-5-(4-nitrophenyl)pyrrolo[2,1-f][1,2,4]triazine-6-carboxamide for Intermediate A. ¹H-NMR (DMSO-d₆) δ 8.00 (s, 1H), 7.84 (s, 1H), 7.00 (d, J=8.4 Hz, 2H), 6.61 (d, J=8.5 Hz, 2H), 5.31 (s, 2H), 4.19 to 4.12 (m, 1H), 2.59 (d, J=4.6 Hz, 3H); MS [M+H]⁺=281.3; LCMS RT=1.03 min Intermediate Y Preparation of 4-amino-5-(4-aminophenyl)-N-(2-morpholin-4-ylethyl)pyrrolo[2,1-f][1,2,4]triazine-6-carboxamide

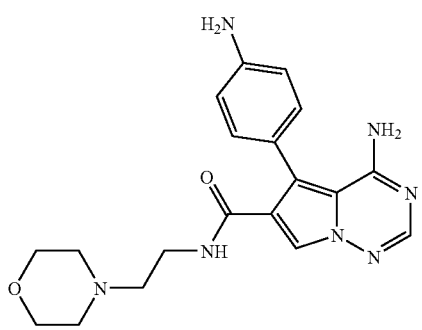

Step 1: Preparation of 4-amino-N-(2-morpholin-4-ylethyl)-5-(4-nitrophenyl)pyrrolo[2,1-f][1,2,4]triazine-6-carboxamide

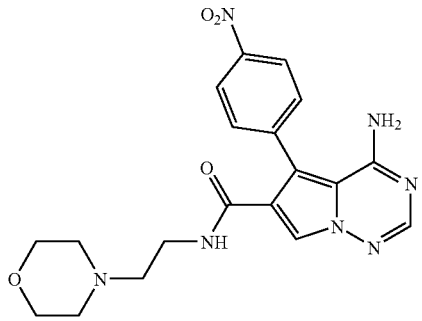

The procedure used for the preparation of 4-amino-N-methyl-5-(4-nitrophenyl)pyrrolo[2,1-f][1,2,4]triazine-6-carboxamide (Intermediate X Step 1) was used to prepare the title compound by substituting 2-morpholin-4-yl-ethylamine for methylamine. ¹H-NMR (CD₃OD) δ 8.34 (d, J=8.8 Hz, 2H), 8.07 (s, 1H), 7.89 (s, 1H), 7.69 (d, J=8.8 Hz, 2H), 3.66 to 3.61 (m, 4H), 3.39 (t, J=6.6 Hz, 2H), 2.49 to 2.40 (m, 6H); MS [M+H]⁺=412.2; LCMS RT=0.28 min.

Step 2: Preparation of the Title Compound

The procedure used for the preparation of Intermediate B was used to prepare the title compound by substituting 4-amino-N-(2-morpholin-4-ylethyl)-5-(4-nitrophenyl)pyrrolo[2,1-f][1,2,4]triazine-6-carboxamide for Intermediate A. ¹H-NMR (CD₃OD) δ 8.04 (br s, 2H), 7.99 (s, 1H), 7.80 (s, 1H), 7.20 (d, J=8.4 Hz, 2H), 6.85 (d, J=8.4 Hz, 2H), 3.64 to 3.57 (m, 4H), 3.42 to 3.36 (m, 2H), 2.35 to 2.27 (m, 6H); MS [M+H]⁺=382.3; LCMS RT=0.17 min.

Intermediate Z

Preparation of 5-(4-aminophenyl)-6-[(2-methoxyethoxy)methyl]pyrrolo[2,1-f][1,2,4]triazin-4-amine

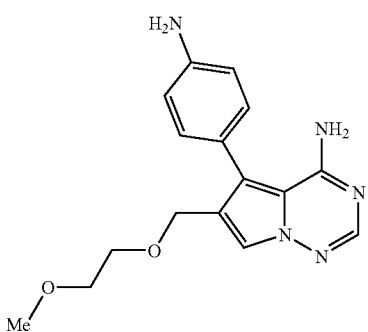

Step 1: Preparation of 6-[(2-methoxyethoxy)methyl]-5-(4-nitrophenyl)pyrrolo[2,1-f][1,2,4]triazin-4-amine

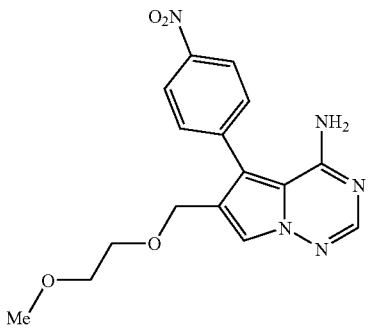

The procedure used for the preparation of 6-(methoxymethyl)-5-(4-nitrophenyl)pyrrolo[2,1-f][1,2,4]triazin-4-amine (Intermediate U Step 1) was used to prepare the title compound by substituting 2-methoxy-ethanol for methanol. ¹H-NMR (CD₃OD) δ8.35 (d, J=8.7 Hz, 2H), 7.85 (s, 1H), 7.77 (s, 1H), 7.75 (d, J=8.7 Hz, 2H), 4.45 (s, 2H), 3.59 to 3.49 (m, 4H), 3.33 (s, 3H); MS [M+H]⁺=344.1; LCMS RT=2.14 min.

Step 2: Preparation of the Title Compound

The procedure used for the preparation of Intermediate B was used to prepare the title compound by substituting 6-[(2-methoxyethoxy)methyl]-5-(4-nitrophenyl)pyrrolo[2,1-f][1,2,4]triazin-4-amine for Intermediate A. ¹H-NMR (CD₃OD)- 7.74 (s, 1H), 7.65 (s, 1H), 7.17 (d, J=8.5 Hz, 2H), 6.81 (d, J=8.5 Hz, 2H), 4.42 (s, 2H), 3.57 to 3.47 (m, 4H), 3.32 (s, 3H); MS [M+H]⁺=314.3; LCMS RT=0.25 min.

Intermediate AA

Preparation of 5-(4-aminophenyl)-6-[(2,2,2-trifluoroethoxy)methyl]pyrrolo[2,1-f][1,2,4]triazin-4-amine

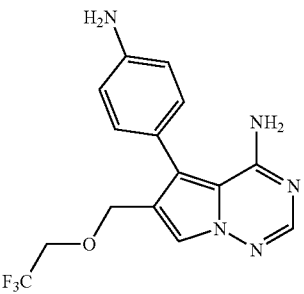

Step 1: Preparation of 5-(4-nitrophenyl)-6-[(2,2,2-trifluoroethoxy)methyl]pyrrolo[2,1-f][1,2,4]triazin-4-amine

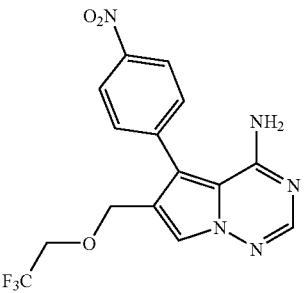

The procedure used for the preparation of 6-(methoxymethyl)-5-(4-nitrophenyl)pyrrolo[2,1-f][1,2,4]triazin-4-amine (Intermediate U Step 1) was used to prepare the title compound by substituting 2,2,2-trifluoro-ethanol for methanol. ¹H-NMR (Acetone-d₆) δ 8.36 (d, J=8.6 Hz, 2H), 7.89 (s, 1H), 7.85 (s, 1H), 7.81 (d, J=8.6 Hz, 2H), 4.68 (s, 2H), 4.04 to 3.94 (m, 2H); MS [M+H]⁺=368.3; LCMS RT=2.68 min.

Step 2: Preparation of the Title Compound

The procedure used for the preparation of Intermediate B was used to prepare the title compound by 5-(4-nitrophenyl)-6-[(2,2,2-trifluoroethoxy)methyl]pyrrolo[2,1-f][1,2,4]triazin-4-amine for Intermediate A. ¹H-NMR (CD₃OD) δ 7.75 (s, 1H), 7.65 (s, 1H), 7.15 (d, J=8.6 Hz, 2H), 6.81 (d, J=8.6 Hz, 2H), 4.53 (s, 2H), 3.93 to 3.72 (m, 2H); MS [M+H]⁺=338.2; LCMS RT=1.69 min.

Intermediate AB

Preparation of 5-(4-aminophenyl)-6-(1,3-oxazol-5-yl)pyrrolo[2,1-f][1,2,4]triazin-4-amine

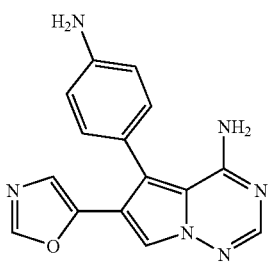

Step 1: Preparation of 5-(4-nitrophenyl)-6-(1,3-oxazol-5-yl)pyrrolo[2,1-f][1,2,4]triazin-4-amine

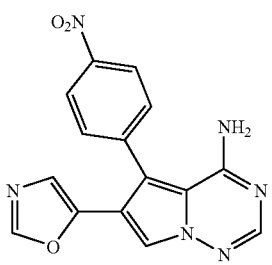

To a solution of 4-amino-5-(4-nitrophenyl)pyrrolo[2,1-f][1,2,4]triazine-6-carbaldehyde (Intermediate H, Step 2) (692 mg, 2.44 mmol) was added tosylmethyl isocyanide (477 mg, 2.44 mmol) and potassium carbonate (338 mg, 2.44 mmol) in MeOH. The solution was allowed to stir at reflux overnight. The solution was dried and diluted with EtOAc (50 mL) and THF (50 mL). Water (50 mL) was added to the reaction mixture. The solution was transferred to a separatory funnel, and the organic layer was isolated and washed with brine (50 mL). The aqueous layers were back extracted with EtOAc (2×50 mL). The combined organic layers were collected, dried ($Na_2SO_4$), concentrated onto silica gel, and purified by column chromatography (100% $CH_2Cl_2$ ramping to 95:5 v/v $CH_2Cl_2$-EtOAc) to afford 310 mg of the above compound as an yellow solid (yield 39%). $^1$H-NMR (DMSO-$d_6$) δ 11.70 (s, 1H), 8.31 (d, J=8.5 Hz, 2H), 8.28 (s, 1H), 8.17 (s, 1H), 7.66 (d, J=7.1 Hz, 2H), 6.75 (s, 1H); MS [M+H]$^+$=323.2; LCMS RT=2.57 min.

Step 2: Preparation of the Title Compound

The procedure used for the preparation of Intermediate B was used to prepare the title compound by substituting 5-(4-nitrophenyl)-6-(1,3-oxazol-5-yl)pyrrolo[2,1-f][1,2,4]triazin-4-amine for Intermediate A. $^1$H-NMR (CD$_3$OD) δ 8.11 (s, 1H), 7.91 (s, 1H), 7.79 (s, 1H), 7.15 (d, J=8.6 Hz, 2H), 6.87 (d, J=8.6 Hz, 2H), 6.45 (s, 1H); MS [M+H]$^+$=293.2; LCMS RT=1.23 min.

Intermediate AC

Preparation of 4-amino-5-{4-[({[2-chloro-5-(trifluoromethyl)phenyl]amino}carbonyl)amino]phenyl}-N-(1,1-dimethyl-2-oxoethyl)pyrrolo[2,1-f][1,2,4]triazine-6-carboxamide

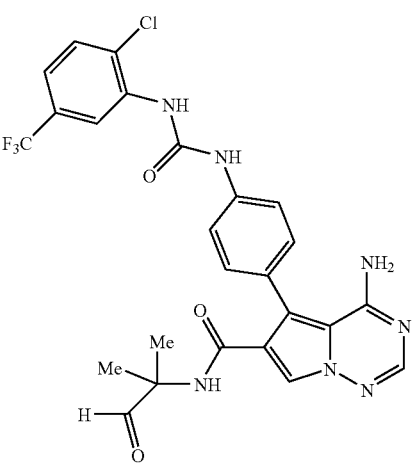

The procedure used for the preparation of Intermediate F (Step 2) was used to prepare the title compound by substituting 4-amino-5-{4-[({[2-chloro-5-(trifluoromethyl)phenyl]amino}carbonyl)amino]phenyl}-N-(2-hydroxy-1,1-dimethylethyl)pyrrolo[2,1-f][1,2,4]triazine-6-carboxamide for N-{4-[4-amino-6-(hydroxymethyl)pyrrolo[2,1-f][1,2,4]triazin-5-yl]phenyl}-N'-[2-fluoro-5-(trifluoromethyl)phenyl]urea. $^1$H-NMR (DMSO-$d_6$) δ 9.69 (s, 1H), 9.21 (s, 1H), 8.65 (s, 1H), 8.62 (d, J=2.1 Hz, 1H), 8.23 (s, 1H), 8.20 (s, 1H), 7.90 (s, 1H), 7.70 (d, J=8.8 Hz, 1H), 7.53 (d, J=9.1 Hz, 2H), 7.35 (dd, J=8.8, 1.6 Hz, 1H), 7.30 (d, J=8.6 Hz, 2H), 3.30 (s, 6H); MS [M+H]$^+$=560.1; LCMS RT=3.36 min.

Intermediate AD

Preparation of 5-(4-aminophenyl)-6-(1,3,4-oxadiazol-2-yl)pyrrolo[2,1-f][1,2,4]triazin-4-amine

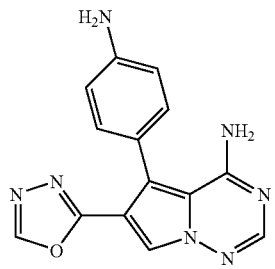

Step 1: Preparation of 5-(4-nitrophenyl)-6-(1,3,4-oxadiazol-2-yl)pyrrolo[2,1-f][1,2,4]triazin-4-amine

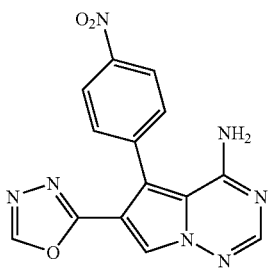

To a solution of thionyl chloride (5 mL) was added Intermediate K (183 mg, 0.613 mmol) which was heated at 50° C. for 3 h. Upon cooling to rt the reaction mixture was rotavapped to dryness chasing with THF. The reaction mixture was then diluted with pyridine (5 mL), added hydrazine (100 mg, 3.15 mmol), and stirred at rt overnight. The solution was rotavapped to dryness, diluted with trimethoxy-methane (10 mL), and stirred at reflux for 5 h. The solution was rotavapped to dryness, and purified by HPLC to afford the title compound (27 mg, 14%); $^1$H-NMR (CD$_3$OD) δ 8.71 (s, 1H), 8.24 (d, J=9.1 Hz, 2H), 8.20 (s, 1H), 7.84 (s, 1H), 7.73 (d, J=8.9 Hz, 2H); MS [M+H]$^+$=324.2; LCMS RT=2.07 min.

Step 2: Preparation of the Title Compound

The procedure used for the preparation of Intermediate B was used to prepare the title compound by substituting 5-(4-nitrophenyl)-6-(1,3,4-oxadiazol-2-yl)pyrrolo[2,1-f][1,2,4]triazin-4-amine for Intermediate A. $^1$H-NMR (CD$_3$OD) δ 8.64 (s, 1H), 8.06 (s, 1H), 7.75 (s, 1H), 7.08 (d, J=8.7 Hz, 2H), 6.66 (d, J=8.9 Hz, 2H); MS [M+H]$^+$=294.2; LCMS RT=0.21 min.

Intermediate AE

Preparation of 5-(4-Amino-phenyl)-6-imidazol-1-ylmethyl-pyrrolo[2,1-f][1,2,4]triazin-4-ylamine

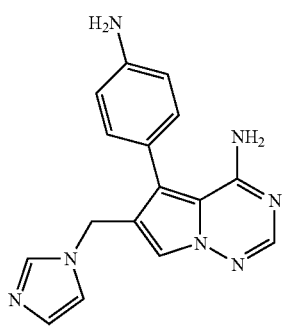

Step 1: Preparation of 6-imidazol-1-ylmethyl-5-(4-nitro-phenyl)-pyrrolo[2,1-f][1,2,4]triazin-4-ylamine

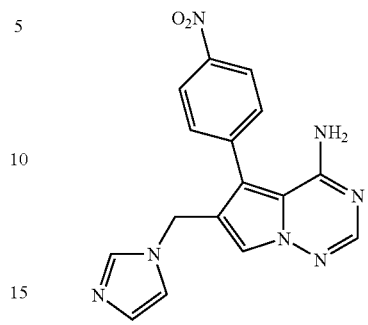

The procedure used for the preparation of 6-(methoxymethyl)-5-(4-nitrophenyl)pyrrolo[2,1-f][1,2,4]triazin-4-amine (Intermediate U Step 1) was used to prepare the title compound by substituting imidazole for methanol. $^1$H-NMR (Acetone-d$_6$) δ 8.22 (d, J=8.8 Hz, 2H), 7.77 (s, 1H), 7.66 (s, 1H), 7.54 (d, J=8.8 Hz, 2H), 7.27 (s, 1H), 6.82 (s, 1H), 6.73 (s, 1H), 5.14 (s, 2H); MS [M+H]$^+$=336.0; LCMS RT=0.25 min.

Step 2: Preparation of the Title Compound

The procedure used for the preparation of Intermediate B was used to prepare the title compound by substituting 6-imidazol-1-ylmethyl-5-(4-nitro-phenyl)-pyrrolo[2,1-f][1,2,4]triazin-4-ylamine for Intermediate A. MS [M+H]$^+$=306.0; LCMS RT=1.02 min.

Intermediate AF

Preparation of N-{4-[4-amino-6-(hydroxymethyl)pyrrolo[2,1-f][1,2,4]triazin-5-yl]phenyl}-N'-[4-(trifluoromethyl)pyridin-2-yl]urea

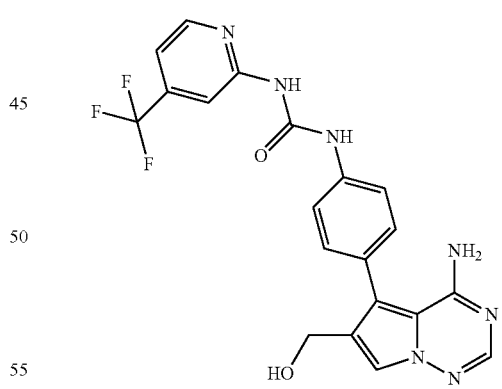

Example 51 (0.25 g, 0.515 mmol) was suspended in THF (5 mL) and treated with 1M solution of DIBAL in THF (2 mL, 2.06 mmol). The resulting solution was stirred at room temperature for 3 hours and quenched with saturated NH$_4$Cl solution. The mixture was stirred for 1 hour. The mixture was transferred to a sep. funnel and the crude product was extracted with EtOAc. The organic layer was then washed with water and saturated NaCl solution. The organic layer was then dried over MgSO$_4$, filtered and concentrated under reduced pressure. The remaining solid was then triturated with EtOAc and filtered providing 0.22 g of product as a tan solid (0.496 mmol, 96% yield). ¹H-NMR (DMSO) δ 11.66 (s, 1H), 9.86 (s, 1H), 9.73 (s, 1H), 8.53 (d, J=8.7 Hz, 1H), 8.05 (s, 1H), 7.82 (s, 1H), 7.65 (s, 1H), 7.61 (d, J=6.6 Hz, 2H), 7.38-7.35 (m, 3H), 4.95 (t, J=5.2 Hz, 1H), 4.37 (d, J=5.1 Hz, 2H); MS [M+H]⁺=444.0; LCMS RT=2.3 min.

Intermediate AG

Preparation of N-[4-(4-amino-6-formylpyrrolo[2,1-f][1,2,4]triazin-5-yl)phenyl]-N'-[4-(trifluoromethyl)pyridin-2-yl]urea

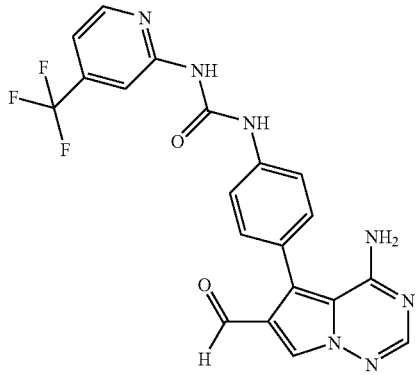

Intermediate AF (1.9 g, 4.29 mmol) was suspended in THF (20 mL) and treated with Dess-Martin periodinane (2.0 g, 4.71 mmol). The mixture was stirred at room temperature overnight and quenched with saturated NHCO₃ solution with Na₂S₂O₃. The mixture was stirred for 1 hour then transferred to a sep. funnel. The crude product was extracted with EtOAc and washed with water and saturated NaCl solution. The organic layer was then dried over MgSO₄, filtered and concentrated under reduced pressure. The remaining solid was then triturated with EtOAc and filtered providing 1.8 g of product as a tan solid (4.08 mmol, 95% yield). ¹H-NMR (DMSO) δ 10.05 (bs, 1H), 9.82 (s, 1H), 9.72 (s, 1H), 8.52 (d, J=5.1 Hz, 1H), 8.26 (s, 1H), 8.07 (s, 1H), 7.95 (s, 1H), 7.64 (d, J=8.6 Hz, 2H), 7.44 (d, J=8.6 Hz, 2H), 7.35 (d, J=5.8 Hz, 1H); MS [M+H]⁺=442.0; LCMS RT=2.81 min.

Intermediate AH

Preparation of 4-amino-5-{4-[({[6-(trifluoromethyl)pyridin-2-yl]amino}carbonyl)amino]phenyl}pyrrolo[2,1-f][1,2,4]triazine-6-carboxylic acid

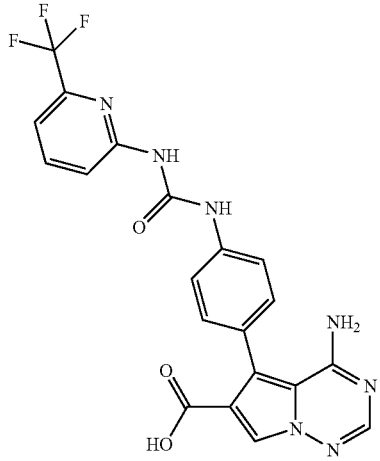

The procedure used for the preparation of Intermediate G was used to prepare the title compound by substituting Example 144 for Intermediate E. ¹H-NMR (DMSO) δ 10.29 (bs, 1H), 8.03 to 7.96 (m, 3H), 7.86 (s, 1H), 7.53 (d, J=8.5 Hz, 2H), 7.45 (d, J=7.0 Hz, 1H), 7.33 (d, J=8.6 Hz, 2H); MS [M+H]⁺=458.1; LCMS RT=2.51 min.

Intermediate AI

Preparation of ethyl 4-amino-5-(3-fluoro-4-nitrophenyl)pyrrolo[2,1-f][1,2,4]triazine-6-carboxylate

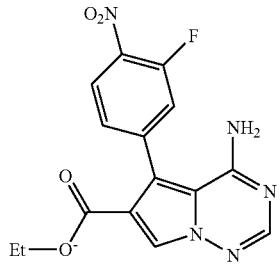

Step 1: Preparation of 3-fluoro-N-methoxy-N-methyl-4-nitrobenzamide

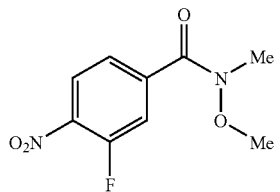

To a solution of CH₂Cl₂ (1 L) was added 3-fluoro-4-nitrobenzoic acid (100 g, 540 mmol) and EDCI (155.3 g, 810 mmol) followed by NMM (178 mL, 1.62 mol) and N-methoxymethanamine hydrochloride (79.0 g, 810 mmol). The solution was allowed to stir under N₂ at rt for 17 h. The reaction mixture was then diluted with 1N HCl (1 L), transferred to separatory funnel, and separated. The organic phase was washed with 1N NaOH (2×500 mL) and water (250 mL). All aqueous layers were back extracted with EtOAc (2×500 mL). The organic layers were combined, dried (MgSO₄), filtered, and concentrated in vacuo. to afford 102.3 g of the above compound as a yellow solid (448 mmol, yield 83%). ¹H-NMR (DMSO-d₆) δ 8.22 to 8.18 (t, J=8.0 Hz, 1H), 7.79 to 7.76 (d, J=11.5 Hz, 1H), 7.60 to 7.58 (d, J=8.3 Hz, 1H), 3.56 (s, 3H), 3.28 (s, 3H); MS [M+H]⁺=229.1; LCMS RT=2.27 min.

Step 2: Preparation of ethyl 3-fluoro-4-nitrobenzaldehyde

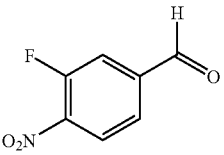

To a solution of THF (800 mL) cooled in an ice-salt/water bath was added 3-fluoro-N-methoxy-N-methyl-4-nitrobenzamide followed by addition of 1 M DIBAL in THF by addition funnel over 30 min. The solution was allowed to stir under $N_2$ for 1 h. The reaction mixture was then carefully diluted with 1N HCl (500 mL) and EtOAc (500 mL), transferred to separatory funnel, and separated. The organic phase was washed with 1N HCl (3×250 mL), 1N NaOH (2×250 mL), and water (250 mL). All aqueous layers were back extracted with EtOAc (2×250 mL). The organic layers were combined, dried ($MgSO_4$), filtered, and concentrated in vacuo to afford 67 g of the above compound (396 mmol, yield 88%). $^1$H-NMR (DMSO-$d_6$) δ 10.06 (s, 1H), 8.36 to 8.32 (t, J=7.8 Hz, 1H), 8.06 to 8.03 (d, J=11.2 Hz, 1H), 7.95 to 7.93 (d, J=9.1 Hz, 1H).

Step 3: Preparation of ethyl (2E)-3-(3-fluoro-4-nitrophenyl)acrylate

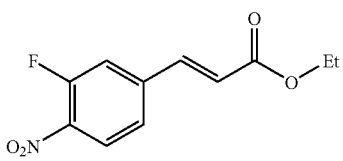

The procedure used for the preparation of Intermediate H Step 3 was used to prepare the title compound by substituting ethyl 3-fluoro-4-nitrobenzaldehyde for 4-amino-5-(4-nitrophenyl)pyrrolo[2,1-f][1,2,4]triazine-6-carbaldehyde. $^1$H-NMR (DMSO-$d_6$) δ 8.17 to 8.13 (t, J=8.2 Hz, 1H), 8.04 to 8.01 (d, J=12.7 Hz, 1H), 7.79 to 7.77 (d, J=8.4 Hz, 1H), 7.71 to 7.67 (d, J=16.1 Hz, 1H), 6.93 to 6.87 (d, J=15.9 Hz, 1H), 4.24 to 4.18 (q, J=7.1 Hz, 2H), 1.29 to 1.25 (t, J=7.1 Hz, 3H); LCMS RT=3.18.

Step 4: Preparation of ethyl 4-(3-fluoro-4-nitrophenyl)-1H-pyrrole-3-carboxylate

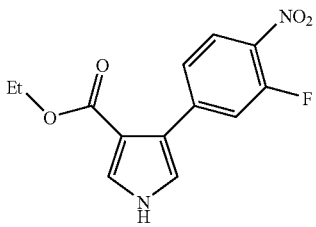

The procedure used for the preparation of Intermediate A Step 1 was used to prepare the title compound by substituting ethyl (2E)-3-(3-fluoro-4-nitrophenyl)acrylate for (2E)-3-(4-nitrophenyl)acrylate. $^1$H-NMR (DMSO-$d_6$) δ 11.86 (s, 1H), 8.10 to 8.06 (t, J=8.5 Hz, 1H), 7.74 to 7.71 (d, J=13.5 Hz, 1H), 7.57 to 7.54 (m, 2H), 7.31 to 7.30 (m, 1H), 4.18 to 4.13 (q, J=7.1 Hz, 2H), 1.25 to 1.21 (t, J=7.0 Hz, 3H); LCMS RT=3.05 min.

Step 5: Preparation of ethyl 4-(3-fluoro-4-nitrophenyl)-5-formyl-1H-pyrrole-3-carboxylate

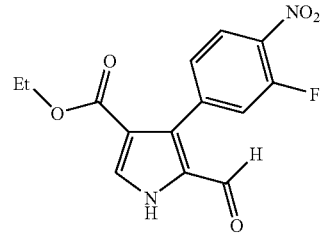

The procedure used for the preparation of Intermediate A Step 2 was used to prepare the title compound by substituting ethyl 4-(3-fluoro-4-nitrophenyl)-1H-pyrrole-3-carboxylate for ethyl 4-(4-nitrophenyl)-1H-pyrrole-3-carboxylate. $^1$H-NMR (DMSO-$d_6$) δ 12.99 (s, 1H), 9.33 (s, 1H), 8.17 to 8.13 (t, J=8.2 Hz, 1H), 7.81 to 7.74 (m, 2H), 7.52 to 7.50 (d, J=6.6 Hz, 1H) 4.13 to 4.07 (q, J=7.2 Hz, 2H), 1.16 to 1.13 (t, J=7.0 Hz, 3H); LCMS RT=2.92.

Step 6: Preparation of ethyl 5-cyano-4-(3-fluoro-4-nitrophenyl)-1H-pyrrole-3-carboxylate

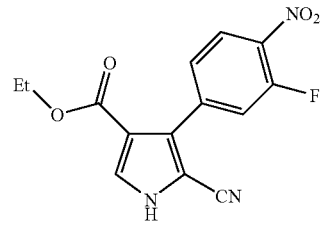

The procedure used for the preparation of Intermediate A Step 3 was used to prepare the title compound by substituting of ethyl 4-(3-fluoro-4-nitrophenyl)-5-formyl-1H-pyrrole-3-carboxylate for 5-formyl-4-(nitrophenyl)-1H-pyrrole-3-carboxylate. $^1$H-NMR (DMSO-$d_6$) δ 13.29 (s, 1H), 8.22 to 8.18 (t, J=8.2 Hz, 1H), 7.91 (s, 1H), 7.74 to 7.71 (d, J=10.9 Hz, 1H), 7.51 to 7.50 (d, J=6.5 Hz, 1H), 4.16 to 4.10 (q, J=7.0 Hz, 2H), 1.18 to 1.15 (t, J=7.0 Hz, 3H).

Step 7: Preparation of ethyl 1-amino-5-cyano-4-(3-fluoro-4-nitrophenyl)-1H-pyrrole-3-carboxylate

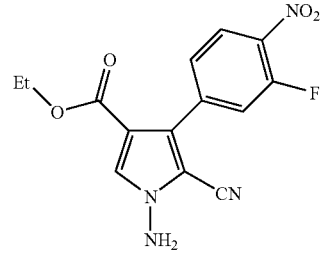

The procedure used for the preparation of Intermediate A Step 5 was used to prepare the title compound by substituting ethyl 5-cyano-4-(3-fluoro-4-nitrophenyl)-1H-pyrrole-3-carboxylate for ethyl 5-cyano-4-(nitrophenyl)-1H-pyrrole-3- carboxylate. $^1$H-NMR (DMSO-d$_6$) δ 8.23 8.21 (t, J=8.3 Hz, 1H), 7.72 (s, 1H), 7.69 (d, J=1.8 Hz, 1H), 7.49 to 7.47 (d, J=8.5 Hz, 1H), 6.72 (s, 2H).

Step 8-Preparation of the Title Compound

To a solution of EtOH (75 mL) was added ethyl 1-amino-5-cyano-4-(3-fluoro-4-nitrophenyl)-1H-pyrrole-3-carboxylate (1.68 g, 5.28 mmol) and formamidine acetate (5.49 g, 52.8 mmol). The solution was heated to 80° C. for 17 h. Upon cooling to rt the solution was treated with water and a precipitate formed which was filtered and washed with additional water. The solid was then suspended in DCM and Et$_2$O. The solid was collected and washed with Et$_2$O yielding 1.22 g of an orange-yellow solid (3.52 mmol, yield 67%). $^1$H-NMR (DMSO-d$_6$) δ 8.20 (s, 1H), 8.18 to 8.14 (t, J=8.2 Hz, 1H), 7.97 (s, 1H), 7.66 to 7.63 (d, J=12.4 Hz, 1H), 7.41 to 7.39 (d, J=8.4 Hz, 1H), 4.12 to 4.07 (q, J=7.0 Hz, 2H), 1.13 to 1.10 (t, J=7.0 Hz, 3H); MS [M+H]$^+$=346.2; LCMS RT=2.77 min.

Intermediate AJ

Preparation of ethyl 4-amino-5-(4-amino-3-fluorophenyl)pyrrolo[2,1-f][1,2,4]-triazine-6-carboxylate

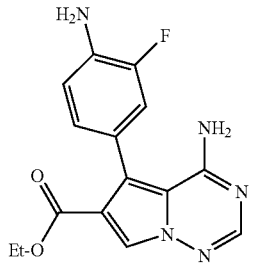

The procedure used for the preparation of Intermediate B was used to prepare the title compound by substituting Intermediate 2 for Intermediate A. $^1$H-NMR (DMSO-d$_6$) δ 8.07 (s, 1H), 7.90 (s, 1H), 7.04 to 7.01 (d, J=12.3 Hz, 1H), 6.88 to 6.85 (m, 2H), 6.81 to 6.77 (m, 1H), 5.36 (s, 2H), 4.11 to 4.06 (q, J=7.1 Hz, 2H), 1.15 to 1.11 (t, J=7.0 Hz, 3H); MS [M+H]$^+$=316.1; LCMS RT=2.16 min.

Intermediate AK

Preparation of N-[4-(4-amino-6-formylpyrrolo[2,1-f][1,2,4]triazin-5-yl)phenyl]-N'-(4-methylpyridin-2-yl)urea

The procedure used for the preparation of Intermediate F was used to prepare the title compound by substituting Example 258 for Intermediate E. $^1$H-NMR (DMSO-d$_6$) δ 10.90 (s, 1H), 9.74 (s, 1H), 9.48 (s, 1H), 8.26 (s, 1H), 8.15 to 8.14 (d, J=5.2 Hz, 1H), 7.96 (s, 1H), 7.68 to 7.66 (d, J=8.6 Hz, 2H), 7.45 to 7.43 (d, J=8.4 Hz, 2H), 7.28 (s, 1H), 6.87 to 6.85 (m, 1H), 2.30 (s, 3H); MS [M+H]$^+$=388.1; LCMS RT=2.09 min.

Intermediate AL

Preparation of N-[4-(4-amino-6-formylpyrrolo[2,1-f][1,2,4]triazin-5-yl)-2-fluorophenyl]-N'-[4-(trifluoromethyl)pyridin-2-yl]urea

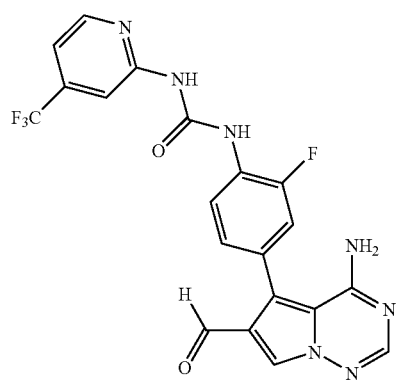

The procedure used for the preparation of Intermediate F was used to prepare the title compound by substituting Example 242 for Intermediate E. $^1$H-NMR (DMSO-d$_6$) δ 10.16 (s, 1H), 10.13 to 10.08 (br s, 1H), 9.76 (s, 1H), 8.55 to 8.54 (d, J=5.3 Hz, 1H), 8.34 to 8.29 (t, J=8.6 Hz, 1H), 8.28 (s, 1H), 8.01 (s, 1H), 7.97 (s, 1H), 7.48 to 7.45 (d, J=11.2 Hz, 1H), 7.39 to 7.38 (d, J=5.7 Hz, 1H), 7.29 to 7.27 (d, J=8.1 Hz, 1H); MS [M+H]$^+$=459.9; LCMS RT=2.96 min.

Intermediate AM

Preparation of N-{4-[4-amino-6-(4-formyl-1,3-oxazol-2-yl)pyrrolo[2,1-f][1,2,4]triazin-5-yl]phenyl}-N'-[2-fluoro-5-(trifluoromethyl)phenyl]urea

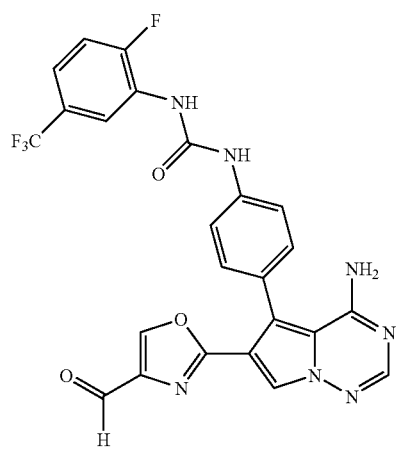

The procedure used for the preparation of Intermediate F was used to prepare the title compound by substituting Example 237 for Intermediate E. ¹H-NMR (DMSO-d₆) δ 9.79 (s, 1H), 9.37 (s, 1H), 8.97 (s, 1H), 8.87 (s, 1H), 8.63 to 8.61 (d, J=7.5 Hz, 1H), 8.34 (s, 1H), 7.96 (s, 1H), 7.60 to 7.58 (d, J=8.6 Hz, 2H), 7.53 to 7.48 (m, 1H), 7.42 to 7.40 (m, 3H); MS [M+H]⁺=526.1; LCMS RT=2.93 min.

Intermediate AN

Preparation of N-[4-(4-amino-6-formylpyrrolo[2,1-f][1,2,4]triazin-5-yl)-2-fluorophenyl]-N'-[2-fluoro-5-(trifluoromethyl)phenyl]urea

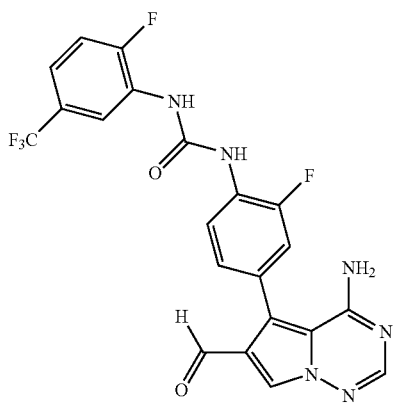

The procedure used for the preparation of Intermediate F was used to prepare the title compound by substituting Example 249 for Intermediate E. ¹H-NMR (DMSO-d₆) δ 9.75 (s, 1H), 9.45 (s, 1H), 9.33 (s, 1H), 8.65 to 8.64 (d, J=7.1 Hz, 1H), 8.34 to 8.29 (m, 2H), 7.97 (s, 1H), 7.54 to 7.40 (m, 3H), 7.27 to 7.25 (d, J=9.4 Hz, 1H); MS [M+H]⁺=477.1; LCMS RT=3.07 min.

Intermediate AO

Preparation of phenyl {4-[4-amino-6-(1,3-oxazol-5-yl)pyrrolo[2,1-f][1,2,4]triazin-5-yl]phenyl}carbamate

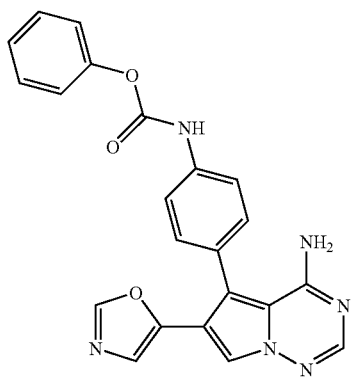

The procedure used for the preparation of Intermediate C was used to prepare the title compound by substituting Intermediate AB for Intermediate B. ¹H-NMR (DMSO-d₆) δ 10.48 (s, 1H), 8.29 (s, 1H), 8.09 (s, 1H), 7.90 (s, 1H), 7.67 to 7.65 (d, J=8.4 Hz, 2H), 7.45 to 7.38 (m, 4H), 7.28 to 7.23 (m, 3H), 6.54 (s, 1H); MS [M+H]⁺=413.1; LCMS RT=2.51 min.

Example 1

Preparation of ethyl 4-amino-5-{4-[({[2-fluoro-5-(trifluoromethyl)phenyl]amino}carbonyl)amino]phenyl}pyrrolo[2,1-f][1,2,4]triazine-6-carboxylate

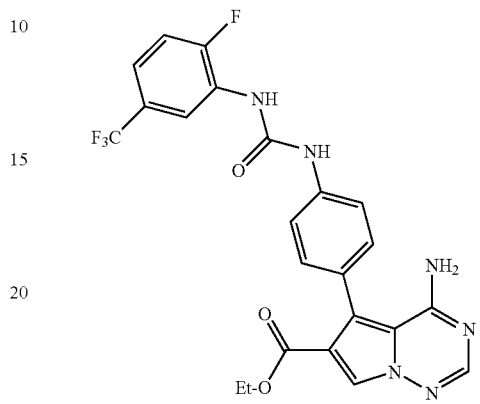

To a solution of DCE (2 mL) was added Intermediate B (75 mg, 0.25 mmol) followed by 1-fluoro-2-isocyanato-4-(trifluoromethyl)benzene (52 mg, 0.25 mmol). The reaction was stirred at rt for 2 h. The solution was concentrated in vacuo to dryness and then purified by preparative HPLC (10-90% ACN/H₂O with 0.1% TFA). The resulting fractions were transferred to a separatory funnel, diluted with EtOAc (20 mL), washed with aqueous saturated NaHCO₃ (20 mL) and H₂O (20 mL). The organic layer was isolated, dried (MgSO₄), filtered, and concentrated to dryness to afford 30 mg of the above compound (0.060 mmol, yield 24%) ¹H-NMR (DMSO-d₆) δ 9.33 (s, 1H), 8.95 (d, J=2.3 Hz, 1H), 8.63 to 8.61 (m, 1H), 8.13 (s, 1H), 8.07 (br s, 1H), 7.93 (s, 1H), 7.56 to 7.53 (m, 2H), 7.51 to 7.48 (m, 1H), 7.40 (br s, 1H), 7.34 to 7.32 (m, 2H), 5.09 (br s, 1H), 4.11 to 4.06 (q, J=6.9 Hz, 2H), 1.13 to 1.10 (t, J=7.1 Hz, 3H); MS [M+H]⁺=503; LCMS RT=3.22 min; TLC R_f=0.15 (95:5 v/v CH₂Cl₂-MeOH).

Example 2

Preparation of ethyl 4-amino-5-{4-[({[4-chloro-3-(trifluoromethyl)phenyl]amino}carbonyl)amino]phenyl}pyrrolo[2,1-f][1,2,4]triazine-6-carboxylate

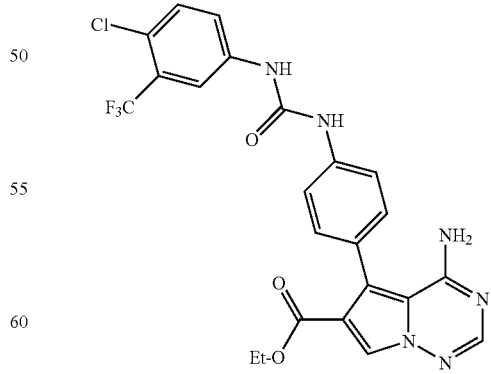

The procedure used for the preparation of Example 1 was used to prepare the title compound by substituting 1-chloro-4-isocyanato-2-(trifluoromethyl)benzene for 1-fluoro-2-isocyanato-4-(trifluoromethyl)benzene and purifying by column chromatography (5:4:1 v/v/v CH$_2$Cl$_2$-EtOAc-MeOH). $^1$H-NMR (DMSO-d$_6$) δ 9.22 (br s, 1H), 9.02 (br s, 1H), 8.12 (s, 1H), 8.11 (d, J=2.4 Hz, 1H), 7.92 (s, 1H), 7.63 (d, J=2.3 Hz, 1H), 7.62 (s, 1H), 7.55 to 7.53 (m, 2H), 7.32 to 7.30 (m, 2H), 4.10 to 4.05 (q, J=7.1 Hz, 2H), 1.12 to 1.09 (t, J=7.0 Hz, 3H); MS [M+H]$^+$=519; LCMS RT=3.06 min; TLC R$_f$=0.48 (5:4:1 v/v/v CH$_2$Cl$_2$-EtOAc-MeOH).

Example 3

Preparation of ethyl 4-amino-5-{4-[({[4-fluoro-3-(trifluoromethyl)phenyl]amino}carbonyl)amino]phenyl}pyrrolo[2,1-f][1,2,4]triazine-6-carboxylate

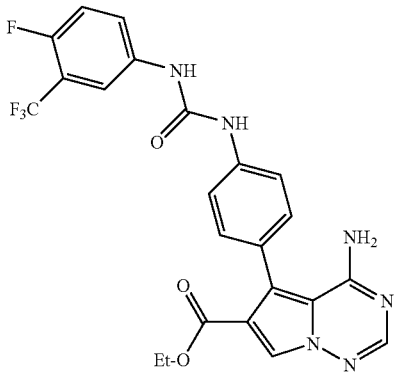

To a solution of THF (1 mL) was added Intermediate C (55 mg, 0.13 mmol) followed by 4-fluoro-3-(trifluoromethyl) aniline (30 μL, 0.24 mmol) and triethylamine (55 μL, 0.40 mmol). The reaction was stirred at 40° C. for 48 h. The solution was concentrated in vacuo to dryness and then purified by preparative HPLC (10-100% ACN/H$_2$O with 0.1% TFA). The resulting fractions were combined, concentrated in vacuo, diluted with EtOAc (5 mL), and washed with aqueous saturated Na$_2$CO$_3$ (5 mL). The aqueous layer was back extracted with EtOAc (5 mL). The organic layer was combined, dried (Na$_2$SO$_4$), filtered, and concentrated to dryness to afford 37 mg of the above compound (0.074 mmol, yield 56%). $^1$H-NMR (CD$_3$OD) δ 8.08 (s, 1H), 7.92 (dd, J=6.4, 2.7 Hz, 1H), 7.84 (s, 1H), 7.69 to 7.62 (m, 1H), 7.57 (d, J=8.3 Hz, 2H), 7.36 (d, J=8.7 Hz, 2H), 7.26 (t, J=8.7 Hz, 1H), 4.10 (q, J=7.1 Hz, 2H), 1.16 (t, J=7.1 Hz, 3H); MS [M+H]$^+$=503; LCMS RT=3.02 min.

Example 4

Preparation of ethyl 4-amino-5-[4-({[(2,2,4,4-tetrafluoro-4H-1,3-benzodioxin-6-yl)amino]carbonyl}amino)phenyl]pyrrolo[2,1-f][1,2,4]triazine-6-carboxylate

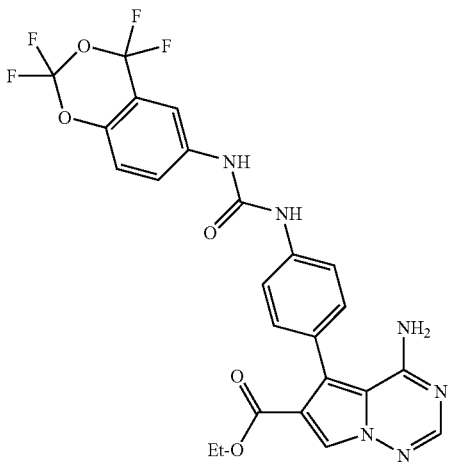

The procedure used for the preparation of Example 3 was used to prepare the title compound by substituting Intermediate D for Intermediate C, and 2,2,4,4-tetrafluoro-4H-1,3-benzodioxin-6-amine for 4-fluoro-3-(trifluoromethyl) aniline. $^1$H-NMR (CD$_3$OD) δ 8.38 (s, 1H), 8.02 (s, 1H), 8.01 (d, J=2.2 Hz, 1H), 7.67 (dd, J=8.5, 2.2 Hz, 1H), 7.62 (d, J=8.2 Hz, 2H), 7.42 (d, J=8.2 Hz, 2H), 7.24 (d, J=8.4 Hz, 1H), 4.17 (q, J=7.2 Hz, 2H), 1.16 (t, J=7.2 Hz, 3H); MS [M+H]$^+$=547; LCMS RT=3.29 min.

Example 5

Preparation of ethyl 4-amino-5-{4-[({[3-(trifluoromethyl)phenyl]amino}carbonyl)amino]phenyl}pyrrolo[2,1-f][1,2,4]triazine-6-carboxylate

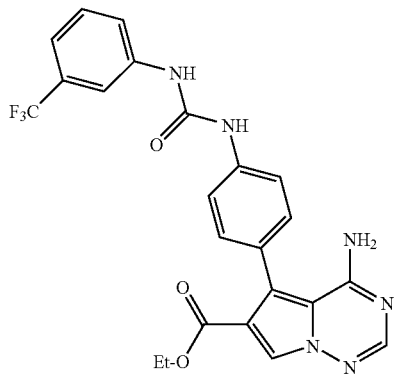

The procedure used for the preparation of Example 3 was used to prepare the title compound by substituting 3-(trifluoromethyl)aniline for 4-fluoro-3-(trifluoromethyl)aniline. $^1$H-NMR (CD$_3$OD) δ 8.08 (s, 1H), 7.93 (br s, 1H), 7.84 (s, 1H), 7.63 (d, J=8.4 Hz, 1H), 7.58 (d, J=8.7 Hz, 2H), 7.48 (t, J=8.0 Hz, 1H), 7.38 (d, J=8.4 Hz, 2H), 7.30 (d, J=8.2 Hz, 1H), 4.10 (q, J=7.3 Hz, 2H), 1.16 (t, J=7.3 Hz, 3H); MS [M+H]$^+$=485; LCMS RT=3.43 min.

Example 6

Preparation of ethyl 4-amino-5-{-4-[({[4-(trifluoromethyl)phenyl]amino}carbonyl)amino]phenyl}pyrrolo[2,1-f][1,2,4]triazine-6-carboxylate

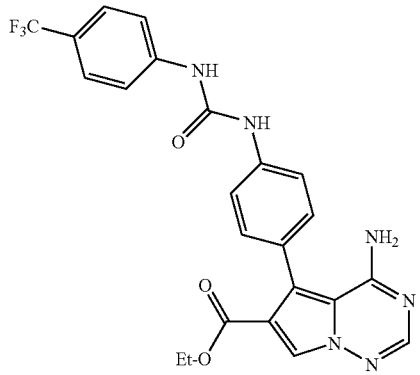

The procedure used for the preparation of Example 3 was used to prepare the title compound by substituting 4-(trifluoromethyl)aniline for 4-fluoro-3-(trifluoromethyl)aniline. ¹H-NMR (CD₃OD) δ 8.07 (s, 1H), 7.83 (s, 1H), 7.66 (d, J=8.3 Hz, 2H), 7.60 to 7.55 (m, 4H), 7.36 (d, J=8.6 Hz, 2H), 4.14 (q, J=7.2 Hz, 2H), 1.16 (t, J=7.2 Hz, 3H); MS [M+H]⁺=485; LCMS RT=3.47 min.

Example 7

Preparation of ethyl 4-amino-5-{4-[({[2-(trifluoromethyl)phenyl]amino}carbonyl)amino]phenyl}pyrrolo[2,1-f][1,2,4]triazine-6-carboxylate

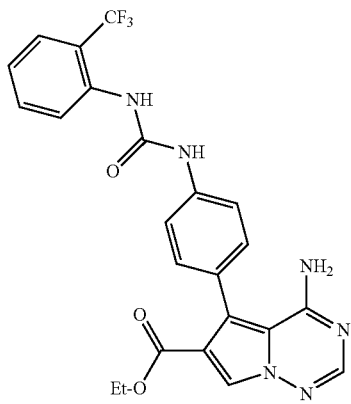

The procedure used for the preparation of Example 3 was used to prepare the title compound by substituting 2-(trifluoromethyl)aniline for 4-fluoro-3-(trifluoromethyl)aniline. ¹H-NMR (CD₃OD) δ 8.07 (s, 1H), 7.96 (d, J=8.7 Hz, 1H), 7.83 (s, 1H), 7.70 to 7.56 (m, 4H), 7.37 (d, J=8.7 Hz, 2H), 7.30 (t, J=7.9 Hz, 1H), 4.11 (q, J=7.1 Hz, 2H), 1.16 (t, J=7.1 Hz, 3H); MS [M+H]⁺=485; LCMS RT=2.80 min.

Example 8

Preparation of ethyl 4-amino-5-{4-[({[2-(trifluoromethoxy)phenyl]amino}carbonyl)amino]phenyl}pyrrolo[2,1-f][1,2,4]triazine-6-carboxylate

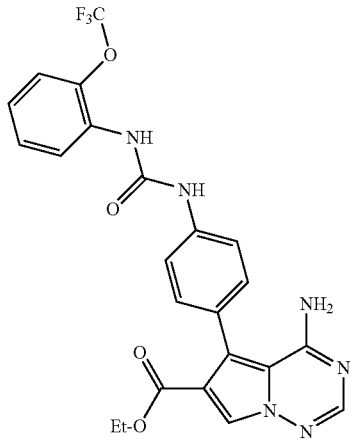

The procedure used for the preparation of Example 3 was used to prepare the title compound by substituting 2-(trifluoromethoxy)aniline for 4-fluoro-3-(trifluoromethyl)aniline. ¹H-NMR (CD₃OD) δ 8.26 (dd, J=8.5, 2.1 Hz, 1H), 8.07 (s, 1H), 7.83 (s, 1H), 7.59 (d, J=8.6 Hz, 2H), 7.40 to 7.28 (m, 4H), 7.14 to 7.07 (m, 1H), 4.08 (q, J=7.2 Hz, 2H), 1.16 (t, J=7.2 Hz, 3H); MS [M+H]⁺=501; LCMS RT=3.07 min.

Example 9

Preparation of ethyl 4-amino-5-{4-[({[3-(trifluoromethoxy)phenyl]amino}carbonyl)amino]phenyl}pyrrolo[2,1-f][1,2,4]triazine-6-carboxylate

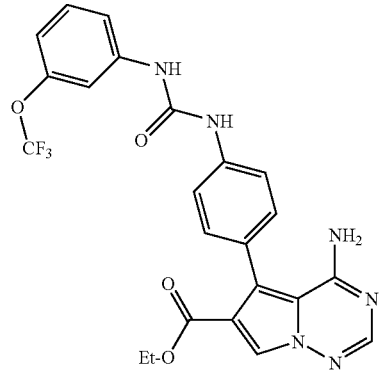

The procedure used for the preparation of Example 3 was used to prepare the title compound by substituting 3-(trifluoromethoxy)aniline for 4-fluoro-3-(trifluoromethyl)aniline. ¹H-NMR (CD₃OD) δ 8.07 (s, 1H), 7.83 (s, 1H), 7.64 (br s, 1H), 7.56 (d, J=8.4 Hz, 2H), 7.39 to 7.28 (m, 5H), 4.10 (q, J=7.1 Hz, 2H), 1.57 (t, J=7.1 Hz, 3H); MS [M+H]⁺=501; LCMS RT=3.08 min.

Example 10

Preparation of ethyl 4-amino-5-{4-[({[4-bromo-3-(trifluoromethyl)phenyl]amino}carbonyl)amino]phenyl}pyrrolo[2,1-f][1,2,4]triazine-6-carboxylate

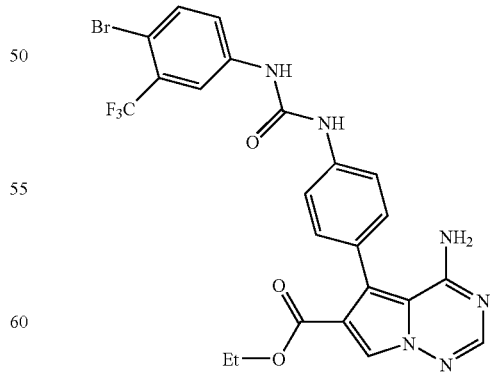

The procedure used for the preparation of Example 3 was used to prepare the title compound by substituting 4-bromo-3-(trifluoromethyl)aniline for 4-fluoro-3-(trifluoromethyl)aniline. ¹H-NMR (CD₃OD) δ 8.07 (s, 1H), 8.01 (d, J=2.5 Hz, 1H), 7.83 (s, 1H), 7.68 (d, J=8.8 Hz, 1H), 7.60 to 7.54 (m, 3H), 7.36 (d, J=8.5 Hz, 2H), 4.08 (q, J=7.2 Hz, 2H), 1.16 (t, J=7.2 Hz, 3H); MS [M+H]⁺=563; LCMS RT=3.19 min.

Example 11

Preparation of ethyl 4-amino-5-{4-[({[4-(trifluoromethoxy)phenyl]amino}carbonyl)amino]phenyl}pyrrolo[2,1-f][1,2,4]triazine-6-carboxylate

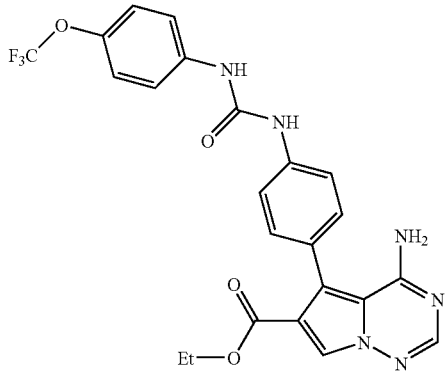

The procedure used for the preparation of Example 3 was used to prepare the title compound by substituting 4-(trifluoromethoxy)aniline for 4-fluoro-3-(trifluoromethyl)aniline. ¹H-NMR (CD₃OD) δ 8.07 (s, 1H), 7.83 (s, 1H), 7.57 (d, J=7.3 Hz, 2H), 7.54 (d, J=6.8 Hz, 2H), 7.35 (d, J=8.5 Hz, 2H), 7.20 (d, J=8.8 Hz, 2H), 4.10 (q, J=7.2 Hz, 2H), 1.14 (t, J=7.2 Hz, 3H); MS [M+H]⁺=501; LCMS RT=3.11 min.

Example 12

Preparation of ethyl 4-amino-5-[4-({[(1-methyl-1H-indazol-5-yl)amino]carbonyl}amino)phenyl]pyrrolo[2,1-f][1,2,4]triazine-6-carboxylate

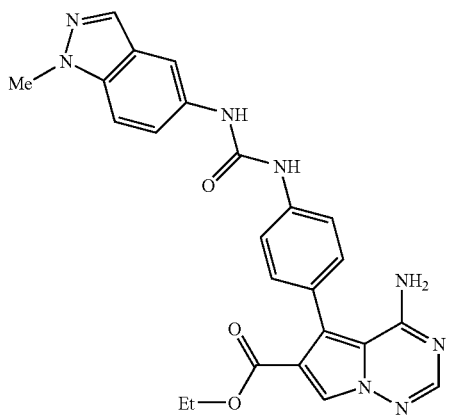

The procedure used for the preparation of Example 3 was used to prepare the title compound by substituting 1-methyl-1H-indazol-5-amine for 4-fluoro-3-(trifluoromethyl)aniline. ¹H-NMR (CD₃OD) δ 8.12 (s, 1H), 7.93 (d, J=5.6 Hz, 2H), 7.91 (s, 1H), 7.59 to 7.51 (m, 3H), 7.36 (d, J=8.6 Hz, 1H), 7.29 (d, J=8.6 Hz, 2H), 4.07 (q, J=7.2 Hz, 2H), 4.00 (s, 3H), 1.09 (t, J=7.2 Hz, 3H); MS [M+H]⁺=471; LCMS RT=2.90 min.

Example 13

Preparation of ethyl 4-amino-5-(4-{[(1,3-benzodioxol-5-ylamino)carbonyl]amino}phenyl)pyrrolo[2,1-f][1,2,4]triazine-6-carboxylate

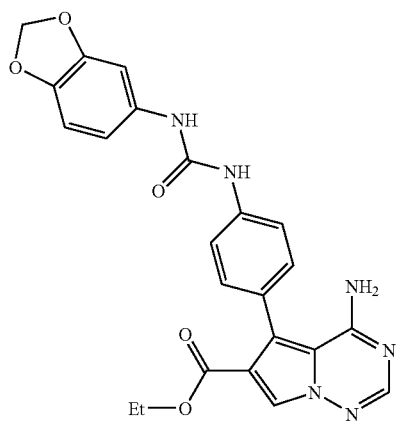

The procedure used for the preparation of Example 3 was used to prepare the title compound by substituting 1,3-benzodioxol-5-amine for 4-fluoro-3-(trifluoromethyl)aniline. ¹H-NMR (CD₃OD) δ 8.08 (s, 1H), 7.84 (s, 1H), 7.55 (d, J=9.0 Hz, 2H), 7.35 (d, J=9.0 Hz, 2H), 7.13 (t, J=1.4 Hz, 1H), 6.92 (br s, 1H), 6.76 (d, J=1.2 Hz, 2H), 5.92 (s, 2H), 4.08 (q, J=7.1 Hz, 2H), 1.16 (t, J=7.1 Hz, 3H); MS [M+H]⁺=461; LCMS RT=3.04 min.

Example 14

Preparation of ethyl 4-amino-5-[4-({[(2,2-difluoro-1,3-benzodioxol-5-yl)amino]carbonyl}amino)phenyl]pyrrolo[2,1-f][1,2,4]triazine-6-carboxylate

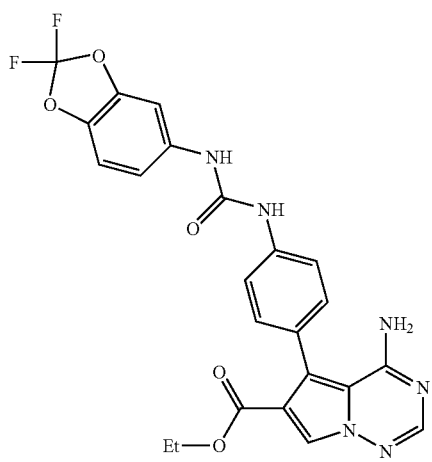

The procedure used for the preparation of Example 3 was used to prepare the title compound by substituting 2,2-difluoro-1,3-benzodioxol-5-amine for 4-fluoro-3-(trifluoromethyl)aniline. $^1$H-NMR (CD$_3$OD) δ 8.08 (s, 1H), 7.84 (s, 1H), 7.59 (d, J=2.1 Hz, 1H), 7.56 (d, J=8.9 Hz, 2H), 7.36 (d, J=8.9 Hz, 2H), 7.12 (d, J=8.7 Hz, 1H), 7.03 (dd, J=8.7, 2.1 Hz, 1H), 6.92 (br s, 1H), 4.09 (q, J=7.2 Hz, 2H), 1.15 (t, J=7.2 Hz, 3H); MS [M+H]$^+$=497; LCMS RT=3.44 min.

Example 15

Preparation of ethyl 4-amino-5-[4-({[(3-chloro-4-fluorophenyl)amino]carbonyl}amino)phenyl]pyrrolo[2,1-f][1,2,4]triazine-6-carboxylate

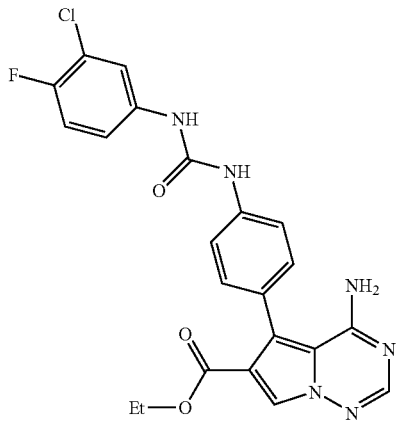

The procedure used for the preparation of Example 3 was used to prepare the title compound by substituting 3-chloro-4-fluoroaniline for 4-fluoro-3-(trifluoromethyl)aniline. $^1$H-NMR (CD$_3$OD) δ 8.08 (s, 1H), 7.84 (s, 1H), 7.73 (dd, J=6.3, 2.4 Hz, 1H), 7.56 (d, J=8.8 Hz, 2H), 7.36 (d, J=8.4 Hz, 2H), 7.33 to 7.27 (m, 1H), 7.17 (t, J=9.2 Hz, 1H), 4.09 (q, J=7.1 Hz, 2H), 1.16 (t, J=7.1 Hz, 3H); MS [M+H]$^+$=469; LCMS RT=3.37 min.

Example 16

Preparation of ethyl 4-amino-5-[4-({[(3-isopropylphenyl)amino]carbonyl}amino)phenyl]pyrrolo[2,1-f][1,2,4]triazine-6-carboxylate

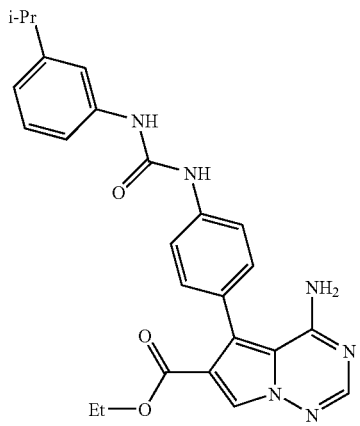

The procedure used for the preparation of Example 3 was used to prepare the title compound by substituting 3-isopropylaniline for 4-fluoro-3-(trifluoromethyl)aniline. $^1$H-NMR (CD$_3$OD) δ 8.08 (s, 1H), 7.84 (s, 1H), 7.56 (d, J=8.6 Hz, 2H), 7.39 to 7.32 (m, 3H), 7.26 to 7.19 (m, 2H), 6.92 (d, J=7.2 Hz, 1H), 4.15 (q, J=7.1 Hz, 2H), 1.16 (t, J=7.1 Hz, 3H); MS [M+H]$^+$=459; LCMS RT=3.07 min.

Example 17

Preparation of ethyl 4-amino-5-[4-({[(4-isopropylphenyl)amino]carbonyl}amino)phenyl]pyrrolo[2,1-f][1,2,4]triazine-6-carboxylate

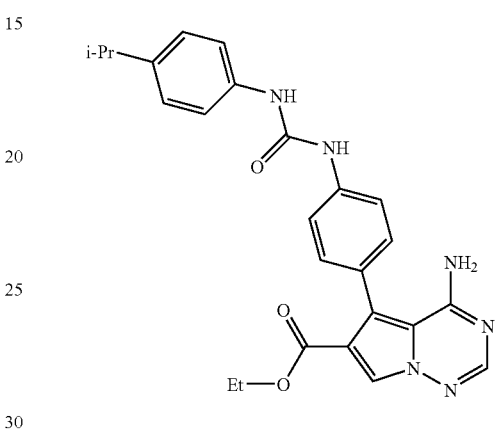

The procedure used for the preparation of Example 3 was used to prepare the title compound by substituting 4-isopropylaniline for 4-fluoro-3-(trifluoromethyl)aniline. $^1$H-NMR (CD$_3$OD) δ 8.08 (s, 1H), 7.84 (s, 1H), 7.56 (d, J=8.3 Hz, 2H), 7.37 to 7.32 (m, 4H), 7.18 (d, J=8.4 Hz, 2H), 4.15 (q, J=7.1 Hz, 2H), 1.16 (t, J=7.1 Hz, 3H); MS [M+H]$^+$=459; LCMS RT=3.09 min.

Example 18

Preparation of ethyl 4-amino-5-[4-({[(3,4-dichlorophenyl)amino]carbonyl}amino)phenyl]pyrrolo[2,1-f][1,2,4]triazine-6-carboxylate

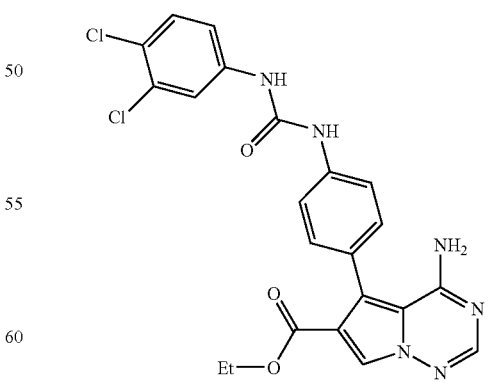

The procedure used for the preparation of Example 3 was used to prepare the title compound by substituting 3,4-dichloroaniline for 4-fluoro-3-(trifluoromethyl)aniline. $^1$H-NMR (CD$_3$OD) δ 8.09 (s, 1H), 7.84 (s, 1H), 7.82 (d, J=2.1 Hz, 1H), 7.57 (d, J=8.3 Hz, 2H), 7.44 to 7.29 (m, 4H), 6.92 (s, 2H), 4.15 (q, J=7.2 Hz, 2H), 1.16 (t, J=7.2 Hz, 3H); MS [M+H]⁺=485; LCMS RT=3.14 min.

Example 19

Preparation of ethyl 4-amino-5-[4-({[(4-bromo-2-fluorophenyl)amino]carbonyl}amino)phenyl]pyrrolo[2,1-f][1,2,4]triazine-6-carboxylate

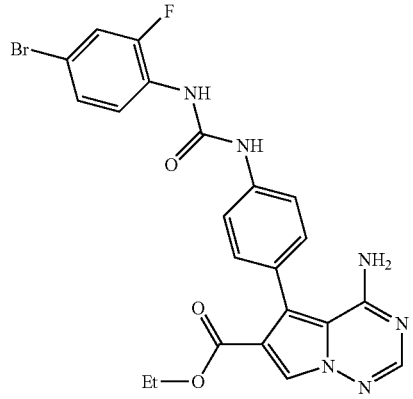

The procedure used for the preparation of Example 3 was used to prepare the title compound by substituting 4-bromo-2-fluoroaniline for 4-fluoro-3-(trifluoromethyl)aniline. ¹H-NMR (CD₃OD) δ 8.14 (s, 1H), 8.12 to 8.07 (m, 1H), 7.88 (s, 1H), 7.59 (d, J=8.7 Hz, 2H), 7.42 to 7.27 (m, 3H), 6.92 (s, 1H), 4.15 (q, J=7.1 Hz, 2H), 1.16 (t, J=7.1 Hz, 3H); MS [M+H]⁺=513; LCMS RT=3.42 min.

Example 20

Preparation of ethyl 4-amino-5-{4-[({[3-methoxy-5-(trifluoromethyl)phenyl]amino}carbonyl)amino]phenyl}pyrrolo[2,1-f][1,2,4]triazine-6-carboxylate

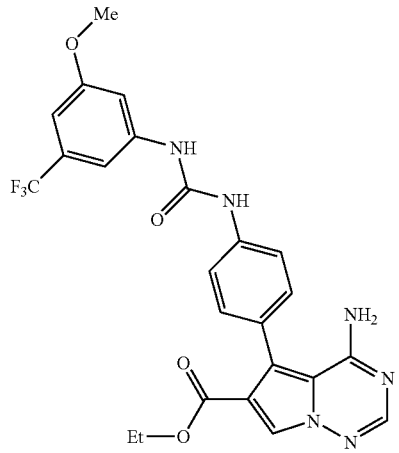

The procedure used for the preparation of Example 3 was used to prepare the title compound by substituting 3-methoxy-5-(trifluoromethyl)aniline for 4-fluoro-3-(trifluoromethyl)aniline. ¹H-NMR (CD₃OD) δ 8.08 (s, 1H), 7.84 (s, 1H), 7.57 (d, J=8.9 Hz, 2H), 7.40 to 7.35 (m, 4H), 6.83 (s, 1H), 4.10 (q, J=7.1 Hz, 2H), 1.16 (t, J=7.1 Hz, 3H); MS [M+H]⁺=515; LCMS RT=3.11 min.

Example 21

Preparation of ethyl 4-amino-5-{4-[({[3-fluoro-5-(trifluoromethyl)phenyl]amino}carbonyl)amino]phenyl}pyrrolo[2,1-f][1,2,4]triazine-6-carboxylate

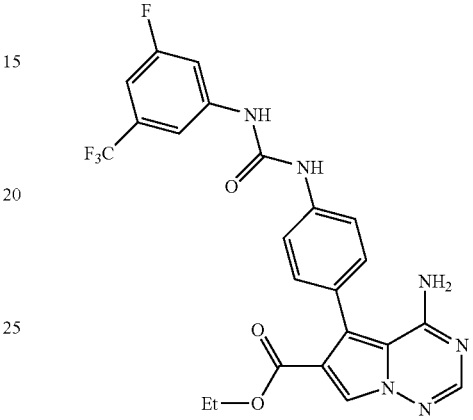

The procedure used for the preparation of Example 3 was used to prepare the title compound by substituting 3-fluoro-5-(trifluoromethyl)aniline for 4-fluoro-3-(trifluoromethyl)aniline. ¹H-NMR (CD₃OD) δ 8.08 (s, 1H), 7.84 (s, 1H), 7.65 (d, J=10.9 Hz, 1H), 7.59 (s, 1H), 7.58 (d, J=8.3 Hz, 2H), 7.38 (d, J=8.5 Hz, 2H), 7.05 (d, J=9.1 Hz, 1H), 4.15 (q, J=7.2 Hz, 2H), 1.16 (t, J=7.2 Hz, 3H); MS [M+H]⁺=503; LCMS RT=3.56 min.

Example 22

Preparation of ethyl 4-amino-5-[4-({[(2,2,3,3-tetrafluoro-2,3-dihydro-1,4-benzodioxin-6-yl)amino]carbonyl}amino)phenyl]pyrrolo[2,1-f][1,2,4]triazine-6-carboxylate

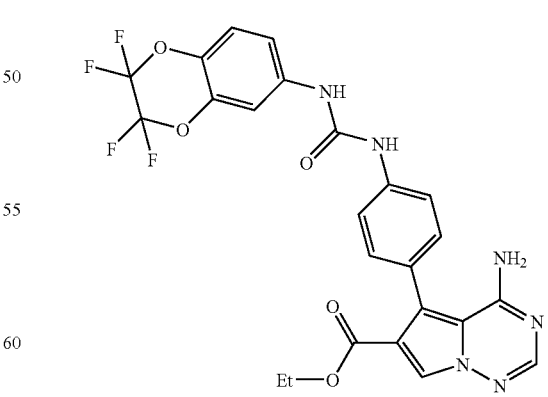

The procedure used for the preparation of Example 3 was used to prepare the title compound by substituting 2,2,3,3-tetrafluoro-2,3-dihydro-1,4-benzodioxin-6-amine for 4-fluoro-3-(trifluoromethyl)aniline. ¹H-NMR (CD₃OD) δ

8.07 (s, 1H), 7.83 (s, 1H), 7.63 (t, J=1.3 Hz, 1H), 7.56 (d, J=8.7 Hz, 2H), 7.35 (d, J=8.6 Hz, 2H), 7.20 (d, J=1.3 Hz, 2H), 4.12 (q, J=7.2 Hz, 2H), 1.15 (t, J=7.2 Hz, 3H); MS [M+H]⁺=547; LCMS RT=3.66 min.

Example 23

Preparation of ethyl 4-amino-5-{4-[(anilinocarbonyl)amino]phenyl}pyrrolo[2,1-f][1,2,4]triazine-6-carboxylate

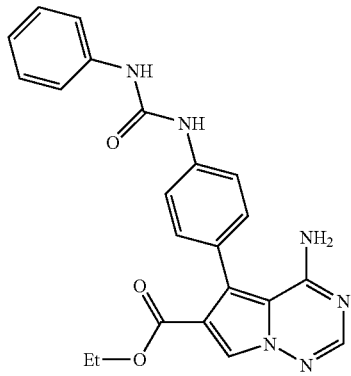

The procedure used for the preparation of Example 3 was used to prepare the title compound by substituting aniline for 4-fluoro-3-(trifluoromethyl)aniline. ¹H-NMR (CD₃OD) δ 8.09 (s, 1H), 7.84 (s, 1H), 7.56 (d, J=8.8 Hz, 2H), 7.44 (d, J=8.0 Hz, 2H), 7.36 (d, J=8.8 Hz, 2H), 7.33 to 7.27 (m, 2H), 7.03 (t, J=7.4 Hz, 1H), 4.15 (q, J=7.1 Hz, 2H), 1.15 (t, J=7.1 Hz, 3H); MS [M+H]⁺=417; LCMS RT=2.53 min.

Example 24

Preparation of ethyl 4-amino-5-[4-({[(2-isopropylphenyl)amino]carbonyl}amino)phenyl]pyrrolo[2,1-f][1,2,4]triazine-6-carboxylate

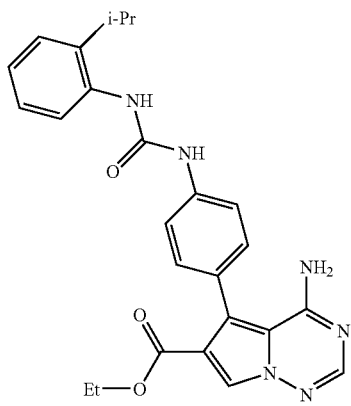

Step 1: Preparation of phenyl (2-isopropylphenyl)carbamate

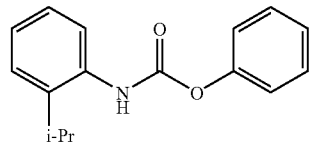

To a stirred solution of 2-isopropylaniline (200 mg, 1.5 mmol) in THF (9 mL) was added pyridine (0.24 mL, 3.0 mmol), then phenyl chloroformate (0.28 mL, 2.2 mmol) at rt. Some solid precipitated out. The mixture was stirred at rt for 4.5 h. Water was added to the reaction and it was extracted with EtOAc. The organic solution was washed with water (5 mL) and dried over MgSO₄ and then filtered. The filtrate was concentrated in vacuo and crystallized from EtOAc-hexanes (1:9 v/v) to afford the title compound (130 mg, 34%). ¹H-NMR (DMSO-d₆) δ 9.45 (s, 1H), 7.44 to 7.36 (m, 2H), 7.35 to 7.28 (m, 2H), 7.25 to 7.14 (m, 5H), 3.27 (m, 1H), 1.17 (d, J=6.9 Hz, 2H); TLC R_f=0.33 (9:1 v/v hexanes-EtOAc).

Step 2: Preparation of the Title Compound

To a solution of THF (1.5 mL) was added phenyl (2-isopropylphenyl)carbamate (43 mg, 0.17 mmol) followed by Intermediate B (50 mg, 0.17 mmol) and triethylamine (23 mL, 0.17 mmol). The reaction was stirred at 50° C. for 36 h. The solution was concentrated in vacuo to dryness and then purified by preparative HPLC (10-100% ACN/H₂O with 0.1% TFA). The resulting fractions were combined and concentrated in vacuo. EtOAc (5 mL) was added and washed with aqueous saturated Na₂CO₃ (5 mL). The aqueous layer was back extracted with EtOAc (5 mL). The organic layer was combined, dried (Na₂SO₄), filtered, and concentrated to dryness to afford 19 mg of the above compound (0.042 mmol, yield 25%). ¹H-NMR (CD₃OD) δ 8.08 (s, 1H), 7.84 (s, 1H), 7.57 (d, J=8.6 Hz, 2H), 7.53 to 7.49 (m, 1H), 7.38 to 7.32 (m, 3H), 7.21 to 7.16 (m, 2H), 6.92 (s, 1H), 4.09 (q, J=7.1 Hz, 2H), 3.28 to 3.18 (m, 1H), 1.16 (t, J=7.1 Hz, 3H); MS [M+H]⁺=459; LCMS RT=3.31 min.

Example 25

Preparation of ethyl 4-amino-5-{4-[({[3-tert-butyl-1-(4-fluorophenyl)-1H-pyrazol-5-yl]amino}carbonyl)amino]phenyl}pyrrolo[2,1-f][1,2,4]triazine-6-carboxylate

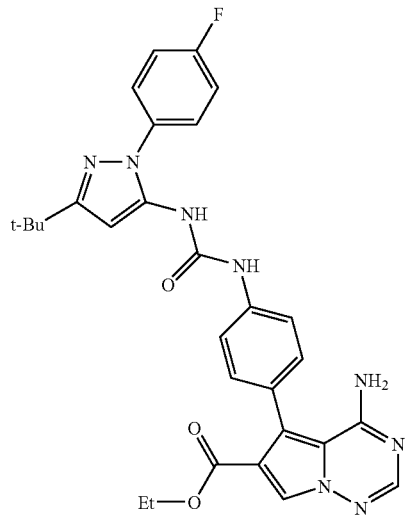

The procedure used for the preparation of Example 24 was used to prepare the title compound by substituting 3-tert-butyl-1-(4-fluorophenyl)-1H-pyrazol-5-amine for 2-isopropylaniline. ¹H-NMR (DMSO-d₆) δ 9.15 (s, 1H), 8.44 (s, 1H), 8.12 (s, 1H), 8.05 (br s, 1H), 7.93 (s, 1H), 7.57 (dd, J=9.1, 5.0 Hz, 2H), 7.49 (d, J=8.6 Hz, 2H), 7.37 (t, J=8.8 Hz, 2H), 7.28 (d, J=9.1 Hz, 2H), 6.38 (s, 1H), 5.05 (br s, 1H), 4.02 (q, J=7.1 Hz, 2H), 1.27 (s, 9H), 1.08 (t, J=7.1 Hz, 3H); MS [M+H]⁺=557; LCMS RT=3.12 min.

Example 26

Preparation of ethyl 4-amino-5-{4-[({[3,5-bis(trifluoromethyl)phenyl]amino}carbonyl)amino]phenyl}pyrrolo[2,1-f][1,2,4]triazine-6-carboxylate

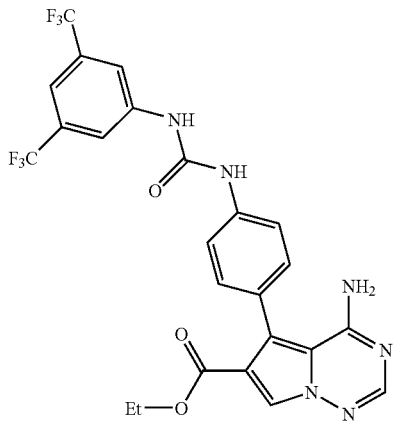

The procedure used for the preparation of Example 24 was used to prepare the title compound by substituting 3,5-bis(trifluoromethyl)aniline for 2-isopropylaniline. ¹H-NMR (CD₃OD) δ 8.11 (s, 2H), 8.09 (s, 1H), 7.86 (s, 1H), 7.60 (d, J=8.8 Hz, 2H), 7.52 (s, 1H), 7.35 (d, J=8.5 Hz, 2H), 4.07 (q, J=7.1 Hz, 2H), 1.14 (t, J=7.1 Hz, 3H); MS [M+H]⁺=553; LCMS RT=3.40 min.

Example 27

Preparation of ethyl 4-amino-5-{4-[({[2-morpholin-4-yl-5-(trifluoromethyl)phenyl]amino}carbonyl)amino]phenyl}pyrrolo[2,1-f][1,2,4]triazine-6-carboxylate

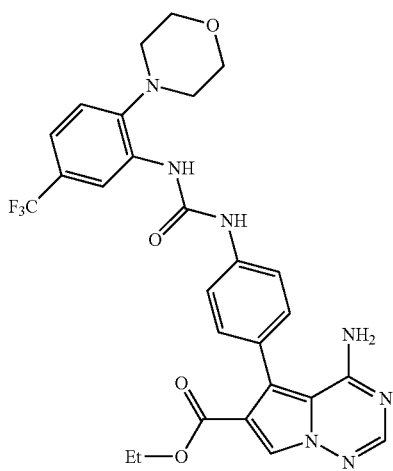

The procedure used for the preparation of Example 24 was used to prepare the title compound by substituting 2-morpholin-4-yl-5-(trifluoromethyl)aniline for 2-isopropylaniline. ¹H-NMR (CD₃OD) δ 8.50 (s, 1H) 8.09 (s, 1H), 7.85 (s, 1H), 7.62 (d, J=8.9 Hz, 2H), 7.42 to 7.29 (d, J=8.7 Hz, 4H), 4.08 (q, J=7.1 Hz, 2H), 3.98 to 3.93 (m, 4H), 2.98 to 2.89 (m, 4H), 1.16 (t, J=7.1 Hz, 3H); MS [M+H]⁺=570; LCMS RT=3.18 min.

Example 28

Preparation of ethyl 4-amino-5-[4-({[(2,2,3,3-tetrafluoro-2,3-dihydro-1,4-benzodioxin-5-yl)amino]carbonyl}amino)phenyl]pyrrolo[2,1-f][1,2,4]triazine-6-carboxylate

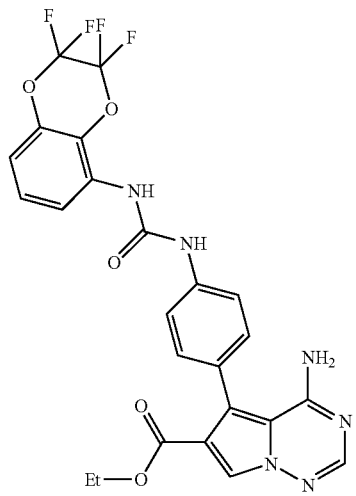

The procedure used for the preparation of Example 24 was used to prepare the title compound by substituting 2,2,3,3-tetrafluoro-2,3-dihydro-1,4-benzodioxin-5-amine for 2-isopropylaniline. ¹H-NMR (CD₃OD) δ 8.10 (d, J=8.0 Hz, 1H), 8.08 (s, 1H), 7.84 (s, 1H), 7.59 (d, J=8.2 Hz, 2H), 7.38 (d, J=8.2 Hz, 2H), 7.23 (t, J=8.2 Hz, 1H), 6.93 (d, J=8.2 Hz, 1H), 4.10 (q, J=7.1 Hz, 2H), 1.16 (t, J=7.1 Hz, 3H); MS [M+H]⁺=547; LCMS RT=3.27 min.

Example 29

Preparation of ethyl 4-amino-5-[4-({[(6-methoxypyrimidin-4-yl)amino]carbonyl}amino)phenyl]pyrrolo[2,1-f][1,2,4]triazine-6-carboxylate

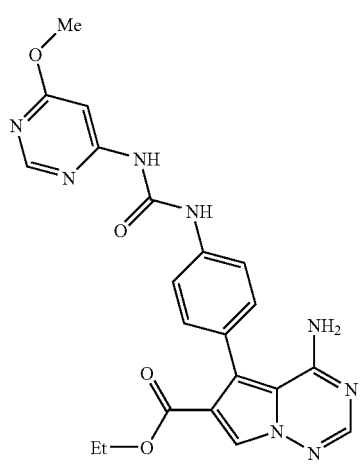

The procedure used for the preparation of Example 24 was used to prepare the title compound by substituting 6-methoxypyrimidin-4-amine for 2-isopropylaniline. $^1$H-NMR (DMSO-d$_6$) δ 9.82 (s, 1H), 9.60 (s, 1H), 8.50 (s, 1H), 8.13 (s, 1H), 7.93 (s, 1H), 7.56 (d, J=8.5 Hz, 2H), 7.33 (d, J=8.5 Hz, 2H), 7.09 (d, J=1.1 Hz, 1H), 4.07 (q, J=7.1 Hz, 2H), 3.89 (s, 3H), 1.09 (t, J=7.1 Hz, 3H); MS [M+H]$^+$=449; LCMS RT=2.94 min.

Example 30

Preparation of N-{4-[4-amino-6-(morpholin-4-ylmethyl)pyrrolo[2,1-f][1,2,4]triazin-5-yl]phenyl}-N'-[2-fluoro-5-(trifluoromethyl)phenyl]urea

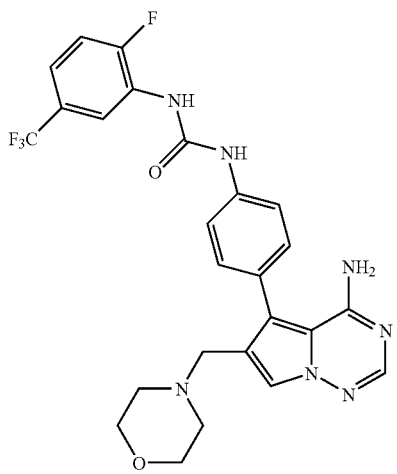

To a solution of Intermediate F (40.0 mg, 0.08 mmol) in CH$_2$Cl$_2$ (3.0 mL) was added AcOH (0.03 mL, 0.46 mmol) and morpholine (0.01 mL, 0.11 mmol). The reaction was stirred at rt for 1 h after which sodium triacetoxyborohydride (49.0 mg, 0.23 mmol) was added. The reaction was stirred at rt until completion. Reaction was diluted with CH$_2$Cl$_2$, transferred to a separatory funnel and washed with saturated aq NaHCO$_3$ (2×). Aqueous phase was back extracted with CH$_2$Cl$_2$ (2×). The organic was dried (Na$_2$SO$_4$) and evaporated to give a crude oil that was purified via HPLC (10-90% ACN/H$_2$O) to give the title compound (30 mg, 70%). $^1$H-NMR (CD$_3$OD) δ 8.61 (d, J=8.0 Hz, 1H), 7.76 (s, 1H), 7.66 (s, 1H), 7.62 (s, 1H), 7.60 (s, 1H), 7.40 (d, J=8.0 Hz, 2H), 7.33 (d, J=8.0 Hz, 2H), 3.65-3.62 (m, 4H), 3.48 (s, 2H), 2.40-2.36 (m, 4H); MS [M+H]$^+$=530; LCMS RT=2.22 min; TLC R$_f$=0.27 (1:3 v/v Acetone: CH$_2$Cl$_2$).

Example 31

Preparation of N-(4-{4-amino-6-[(4-methylpiperazin-1-yl)methyl]pyrrolo[2,1-f][1,2,4]triazin-5-yl}phenyl)-N'-[2-fluoro-5-(trifluoromethyl)phenyl]urea

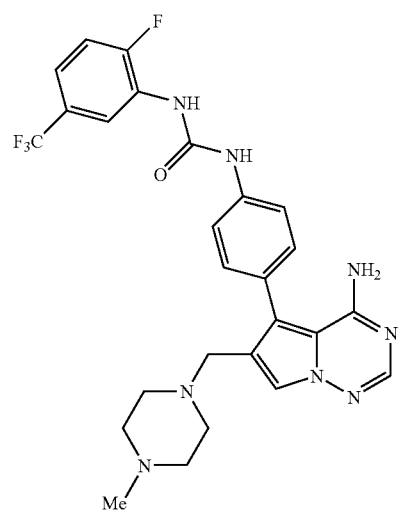

The procedure used for the preparation of Example 30 was used to prepare the title compound by substituting 1-methylpiperazine for morpholine and purifying by preparative TLC (20:180:1 v/v/v MeOH—CH$_2$Cl$_2$—NH$_4$OH). $^1$H-NMR (CD$_3$OD) δ 8.61 (d, J=8.0 Hz, 1H), 7.77 (s, 1H), 7.67 (s, 1H), 7.61 (d, J=8.0 Hz, 2H), 7.41-7.33 (m, 4H), 3.53 (s, 2H), 3.35 (s, 3H), 2.50 (br s, 4H), 2.32 (m, 4H); MS [M+H]$^+$=543; LCMS RT=2.15 min; TLC R$_f$=0.23 (20:180:1 v/v/v MeOH—CH$_2$Cl$_2$—NH$_4$OH).

Example 32

Preparation of N-[4-(4-amino-6-{[(2-methoxyethyl)amino]methyl}pyrrolo[2,1-f][1,2,4]triazin-5-yl)phenyl]-N'-[2-fluoro-5-(trifluoromethyl)phenyl]urea

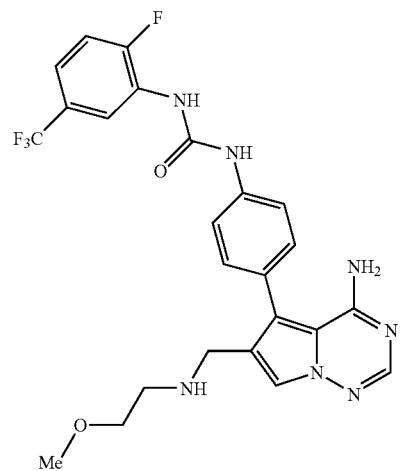

The procedure used for the preparation of Example 30 was used to prepare the title compound by substituting 2-methoxyethanamine for morpholine and purifying by MPLC (Analogix) using 0-15% MeOH—CH$_2$Cl$_2$. $^1$H-NMR (CD$_3$OD) δ 8.61 to 8.59 (d, J=7.8 Hz, 1H), 7.80 (s, 1H), 7.79 (s, 1H), 7.67 to 7.65 (d, J=8.6 Hz, 2H), 7.41 to 7.39 (d, J=8.6 Hz, 2H), 7.35 to 7.33 (d, J=8.9 Hz, 2H), 3.99 (s, 2H), 3.48 to 3.46 (t, J=5.1 Hz, 2H), 3.31 (s, 3H), 2.91 to 2.89 (t, J=5.2 Hz, 2H); MS [M+H]$^+$=518; LCMS RT=2.26 nm; TLC R$_f$=0.30 (15:85 v/v MeOH—CH$_2$Cl$_2$).

Example 33

Preparation of N-{4-[4-amino-6-({[2-(methylthio)ethyl]amino}methyl)pyrrolo[2,1-f][1,2,4]triazin-5-yl]phenyl}-N'-[2-fluoro-5-(trifluoromethyl)phenyl]urea

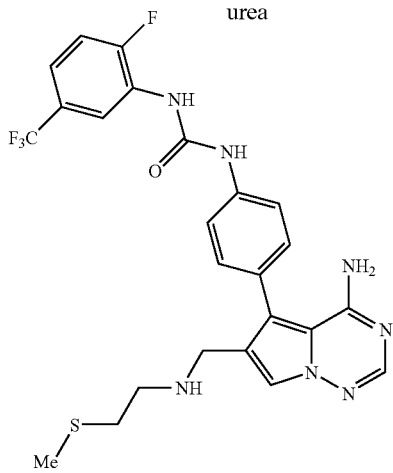

The procedure used for the preparation of Example 30 was used to prepare the title compound by substituting 2-(methylthio)ethanamine for morpholine and purifying by MPLC (Analogix) using 0-15% MeOH—CH$_2$Cl$_2$. $^1$H-NMR (CD$_3$OD) δ 8.62 to 8.60 (d, J=7.7 Hz, 1H), 7.78 (s, 1H), 7.71 (s, 1H), 7.65 to 7.63 (d, J=8.6 Hz, 2H), 7.42 to 7.40 (d, J=8.5 Hz, 2H), 7.35 to 7.33 (d, J=8.8 Hz, 2H), 3.80 (s, 2H), 2.75 to 2.72 (t, J=6.5 Hz, 2H), 2.58 to 2.55 (t, J=6.6 Hz, 2H), 1.99 (s, 3H); MS [M+H]$^+$=534; LCMS RT=2.36 min; TLC R$_f$=0.50 (15:85 v/v MeOH—CH$_2$Cl$_2$).

Example 34

Preparation of N-[4-(4-amino-6-{[(2-methoxyethyl)(methyl)amino]methyl}pyrrolo[2,1-f][1,2,4]triazin-5-yl)phenyl]-N'-[2-fluoro-5-(trifluoromethyl)phenyl]urea

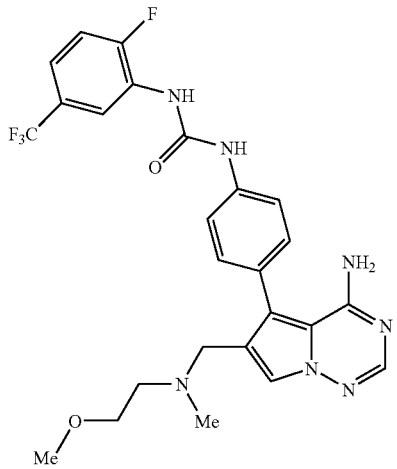

The procedure used for the preparation of Example 30 was used to prepare the title compound by substituting 2-methoxy-N-methylethanamine for morpholine and purifying by MPLC (Analogix) using 0-15% MeOH—CH$_2$Cl$_2$. $^1$H-NMR (CD$_3$OD) δ 8.61 to 8.59 (d, J=7.9 Hz, 1H), 7.80 (s, 1H), 7.78 (s, 1H), 7.66 to 7.64 (d, J=8.6 Hz, 2H), 7.40 to 7.38 (d, J=8.5 Hz, 2H), 7.35 to 7.32 (d, J=8.9 Hz, 2H), 3.90 (s, 2H), 3.47 to 3.44 (t, J=5.4 Hz, 2H), 3.29 (s, 3H), 2.79 to 2.77 (t, J=5.4 Hz, 2H), 2.39 (s, 3H); MS [M+H]$^+$=532; LCMS RT=2.69 min; TLC R$_f$=0.16 (15:85 v/v MeOH—CH$_2$Cl$_2$).

Example 35

Preparation of N-{4-[4-amino-6-(pyrrolidin-1-ylmethyl)pyrrolo[2,1-f][1,2,4]triazin-5-yl]phenyl}-N'-[2-fluoro-5-(trifluoromethyl)phenyl]urea

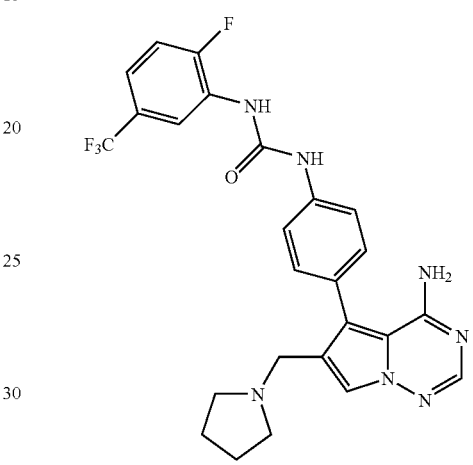

The procedure used for the preparation of Example 30 was used to prepare the title compound by substituting pyrrolidine for morpholine and purifying by MPLC (Analogix) using 0-15% MeOH—CH$_2$Cl$_2$. $^1$H-NMR (CD$_3$OD) δ 8.62 to 8.60 (d, J=7.8 Hz, 1H), 7.78 (s, 1H), 7.74 (s, 1H), 7.64 to 7.62 (d, J=8.4 Hz, 2H), 7.39 to 7.37 (d, J=8.6 Hz, 2H), 7.35 to 7.33 (d, J=8.8 Hz, 2H), 3.77 (s, 2H), 2.63 to 2.60 (m, 4H), 1.82 to 1.78 (m, 4H); MS [M+H]$^+$=514; LCMS RT=2.69 min; TLC R$_f$<0.10 (15:85 v/v MeOH—CH$_2$Cl$_2$).

Example 36

Preparation of N-{4-[4-amino-6-({[2-(methylsulfonyl)ethyl]amino}methyl)pyrrolo[2,1-f][1,2,4]triazin-5-yl]phenyl}-N'-[2-fluoro-5-(trifluoromethyl)phenyl]urea

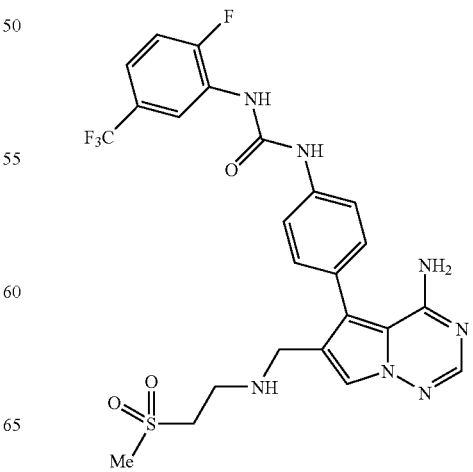

The procedure used for the preparation of Example 30 was used to prepare the title compound by substituting 2-(methylsulfonyl)ethanamine hydrochloride for morpholine and purifying by MPLC (Analogix) using 0-15% MeOH—CH$_2$Cl$_2$. $^1$H-NMR (CD$_3$OD) δ 8.62 to 8.60 (d, J=7.5 Hz, 1H), 7.77 (s, 1H), 7.69 (s, 1H), 7.64 to 7.62 (d, J=8.7 Hz, 2H), 7.42 to 7.40 (d, J=8.9 Hz, 2H), 7.35 to 7.33 (d, J=8.9 Hz, 2H), 3.77 (s, 2H), 3.22 to 3.19 (t, J=6.5 Hz, 2H), 3.03 to 2.99 (t, J=6.7 Hz, 2H), 2.96 (s, 3H); MS [M+H]$^+$=566; LCMS RT=2.25 min; TLC R$_f$=0.21 (15:85 v/v MeOH—CH$_2$Cl$_2$).

Example 37

Preparation of N-{4-[4-amino-6-({[2-(dimethylamino)ethyl]amino}methyl)pyrrolo[2,1-f][1,2,4]triazin-5-yl]phenyl}-N'-[2-fluoro-5-(trifluoromethyl)phenyl]urea

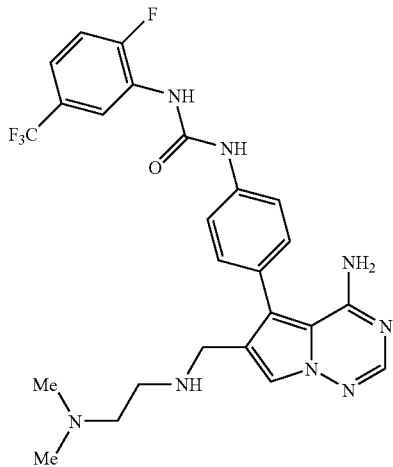

The procedure used for the preparation of Example 30 was used to prepare the title compound by substituting N,N-dimethylethane-1,2-diamine for morpholine and purifying by via HPLC (10-90% ACN/H$_2$O). $^1$H-NMR (CD$_3$OD) δ 8.62 (d, J=7.4 Hz, 1H), 7.77 (s, 1H), 7.71 (s, 1H), 7.64 (d, J=8.5 Hz, 2H), 7.40 (d, J=8.5 Hz, 2H), 7.33 (d, J=8.0 Hz, 2H), 3.73 (s, 2H), 2.61 (t, J=6.5 Hz, 2H), 2.37 (t, J=6.9 Hz, 2H), 2.17 (s, 6H); MS [M+H]$^+$=531; LCMS RT=1.96 min.

Example 38

Preparation of N-{4-[4-amino-6-(piperidin-1-ylmethyl)pyrrolo[2,1-f][1,2,4]triazin-5-yl]phenyl}-N'-[2-fluoro-5-(trifluoromethyl)phenyl]urea

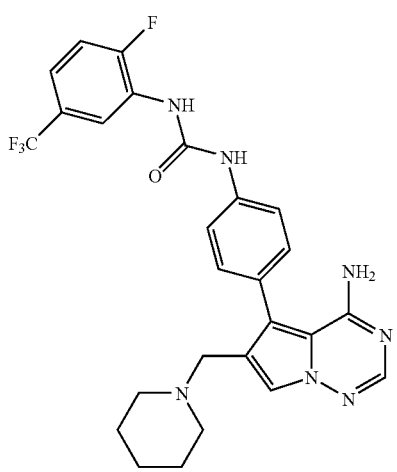

The procedure used for the preparation of Example 30 was used to prepare the title compound by substituting piperidine for morpholine and purifying by via HPLC (10-90% ACN/H$_2$O). $^1$H-NMR (CD$_3$OD) δ 8.63 (d, J=8.2 Hz, 1H), 7.77 (s, 1H), 7.73 (s, 1H), 7.62 (d, J=8.6 Hz, 2H), 7.37 (d, J=8.8 Hz, 2H), 7.34 (d, J=8.8 Hz, 2H), 3.50 (s, 2H), 2.36 to 2.27 (m, 4H), 1.60 to 1.50 (m, 4H), 1.40 to 1.35 (m, 2H); MS [M+H]$^+$=528; LCMS RT=2.34 nm.

Example 39

Preparation of N-[4-(4-ammo-6-{[(3,3,3-trifluoropropyl)amino]methyl}pyrrolo[2,1-f][1,2,4]triazin-5-yl)phenyl]-N'-[2-fluoro-5-(trifluoromethyl)phenyl]urea

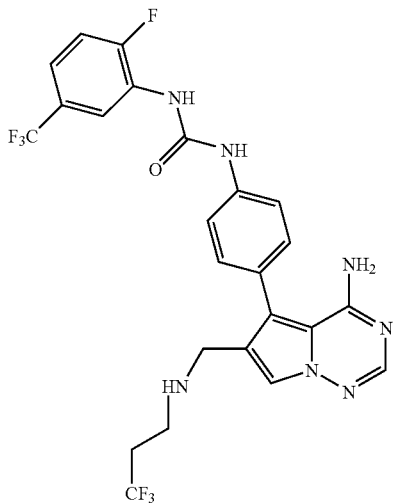

The procedure used for the preparation of Example 30 was used to prepare the title compound by substituting 3,3,3-trifluoropropan-1-amine for morpholine and purifying by via HPLC (10-90% ACN/H$_2$O). $^1$H-NMR (CD$_3$OD) δ 8.62 (d, J=7.3 Hz, 1H), 7.77 (s, 1H), 7.70 (s, 1H), 7.63 (d, J=8.3 Hz, 2H), 7.39 (d, J=7.9 Hz, 2H), 7.34 (d, J=7.4 Hz, 2H), 3.73 (s, 2H), 2.74 (t, J=7.3 Hz, 2H), 2.37 to 2.22 (m, 2H); MS [M+H]$^+$=556; LCMS RT=2.41 nm.

Example 40

Preparation of N-[4-(4-amino-6-{[4-(pyridin-4-ylmethyl)piperazin-1-yl]methyl}pyrrolo[2,1-f][1,2,4]triazin-5-yl)phenyl]-N'-[2-fluoro-5-(trifluoromethyl)phenyl]urea

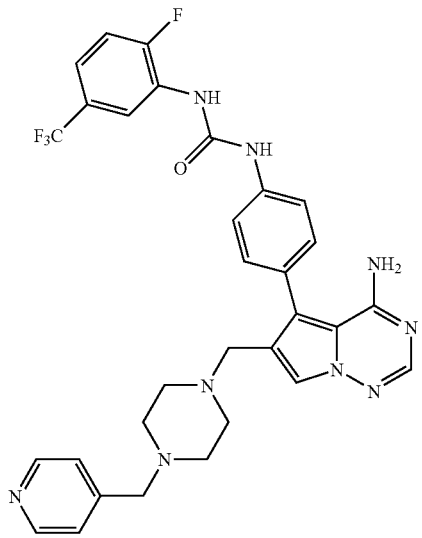

The procedure used for the preparation of Example 30 was used to prepare the title compound by substituting 1-(pyridin-4-ylmethyl)piperazine for morpholine and purifying by via HPLC (10-90% ACN/H$_2$O). $^1$H-NMR (CD$_3$OD) δ 8.62 (d, J=7.3 Hz, 1H), 8.43 (dd, J=4.6, 1.6 Hz, 2H), 7.97 (s, 1H), 7.77 (s, 1H), 7.67 (s, 1H), 7.62 (d, J=8.5 Hz, 2H), 7.41 to 7.31 (m, 6H), 3.54 (s, 2H), 3.51 (s, 2H), 3.32 to 3.29 (m, 4H); MS [M+H]$^+$=620; LCMS RT=2.32 min.

Example 41

Preparation of N-[4-(4-amino-6-{[4-(2-methoxyethyl)piperazin-1-yl]methyl}pyrrolo[2,1-f][1,2,4]triazin-5-yl)phenyl]-N'-[2-fluoro-5-(trifluoromethyl)phenyl]urea

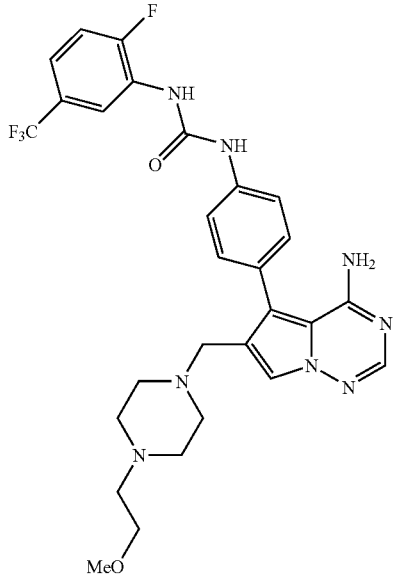

The procedure used for the preparation of Example 30 was used to prepare the title compound by substituting 1-(2-methoxyethyl)piperazine for morpholine and purifying by via HPLC (10-90% ACN/H$_2$O). $^1$H-NMR (CD$_3$OD) δ 8.61 (d, J=7.1 Hz, 1H), 7.77 (s, 1H), 7.67 (s, 1H), 7.62 (d, J=8.9 Hz, 2H), 7.39 (d, J=8.9 Hz, 2H), 7.34 (d, J=8.3 Hz, 2H), 3.50 (s, 3H), 3.48 (t, J=5.3 Hz, 2H), 3.29 (s, 2H), 2.58 to 2.38 (m, 10H); MS [M+H]$^+$=587; LCMS RT=2.55 min.

Example 42

Preparation of N-[4-(4-amino-6-{[(4-methoxyphenyl)amino]methyl}pyrrolo[2,1-f][1,2,4]triazin-5-yl)phenyl]-N'-[2-fluoro-5-(trifluoromethyl)phenyl]urea

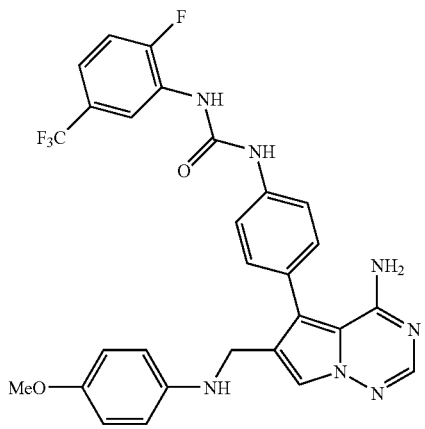

The procedure used for the preparation of Example 30 was used to prepare the title compound by substituting 4-methoxyaniline for morpholine and purifying by via HPLC (10-90% ACN/H$_2$O). $^1$H-NMR (CD$_3$OD) δ 8.62 (d, J=7.4 Hz, 1H), 7.75 (s, 1H), 7.65 to 7.58 (m, 3H), 7.41 (d, J=8.1 Hz, 2H), 7.34 (d, J=8.1 Hz, 2H), 6.70 (d, J=8.8 Hz, 2H), 6.56 (d, J=8.9 Hz, 2H), 4.16 (s, 2H), 3.68 (s, 3H); MS [M+H]$^+$=566; LCMS RT=2.93 min.

Example 43

Preparation of N-(4-{4-amino-6-[(dimethylamino)methyl]pyrrolo[2,1-f][1,2,4]triazin-5-yl}phenyl)-N'-[2-fluoro-5-(trifluoromethyl)phenyl]urea

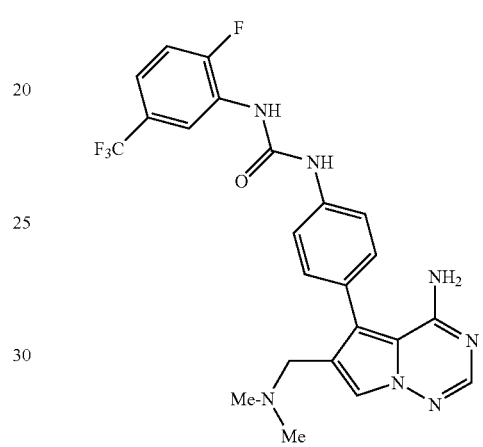

The procedure used for the preparation of Example 30 was used to prepare the title compound by substituting N-methylmethanamine for morpholine and purifying by via HPLC (10-90% ACN/H$_2$O). $^1$H-NMR (CD$_3$OD) δ 8.62 (d, J=8.0 Hz, 1H), 7.78 (s, 1H), 7.70 (s, 1H), 7.63 (d, J=8.6 Hz, 2H), 7.37 (d, J=8.6 Hz, 2H), 7.34 (d, J=8.4 Hz, 2H), 3.52 (s, 2H), 2.18 (s, 6H); MS [M+H]$^+$=488; LCMS RT=2.55 min.

Example 44

Preparation of N-(4-{4-amino-6-[(methylamino)methyl]pyrrolo[2,1-f][1,2,4]triazin-5-yl}phenyl)-N'-[2-fluoro-5-(trifluoromethyl)phenyl]urea

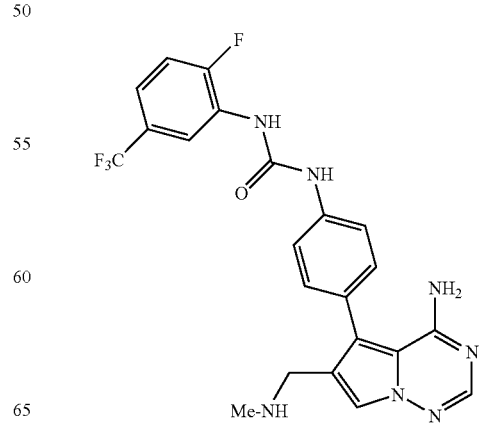

The procedure used for the preparation of Example 30 was used to prepare the title compound by substituting methanamine for morpholine and purifying by via HPLC (10-90% ACN/H$_2$O). $^1$H-NMR (CD$_3$OD) δ 8.62 (d, J=7.4 Hz, 1H), 7.77 (s, 1H), 7.70 (s, 1H), 7.64 (d, J=8.6 Hz, 2H), 7.39 (d, J=8.6 Hz, 2H), 7.34 (d, J=8.5 Hz, 2H), 3.70 (s, 2H), 2.33 (s, 3H); MS [M+H]$^+$=474; LCMS RT=2.55 min.

Example 45

Preparation of N-{4-[4-amino-6-({[3-(dimethylamino)propyl]amino}methyl)pyrrolo[2,1-f][1,2,4]triazin-5-yl]phenyl}-N'-[2-fluoro-5-(trifluoromethyl)phenyl]urea

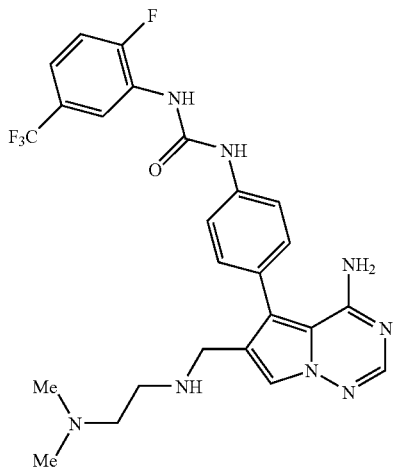

The procedure used for the preparation of Example 30 was used to prepare the title compound by substituting N,N-dimethylethane-1,2-diamine for morpholine and purifying by via HPLC (10-90% ACN/H$_2$O). $^1$H-NMR (CD$_3$OD) δ 8.60 (d, J=8.0 Hz, 1H), 7.97 (s, 1H), 7.84 (s, 1H), 7.69 (d, J=8.0 Hz, 2H), 7.43 (d, J=8.0 Hz, 2H), 7.35 (d, J=8.6 Hz, 2H), 4.20 (s, 2H), 3.04 (t, J=7.3 Hz, 2H), 2.94 (t, J=7.3 Hz, 2H), 2.79 (s, 6H), 2.00 to 1.89 (m, 2H); MS [M+H]$^+$=545; LCMS RT=2.28 min.

Example 46

Preparation of N-{4-[4-amino-6-({[4-(trifluoromethyl)phenyl]amino}methyl)pyrrolo[2,1-f][1,2,4]triazin-5-yl]phenyl}-N'-[2-fluoro-5-(trifluoromethyl)phenyl]urea

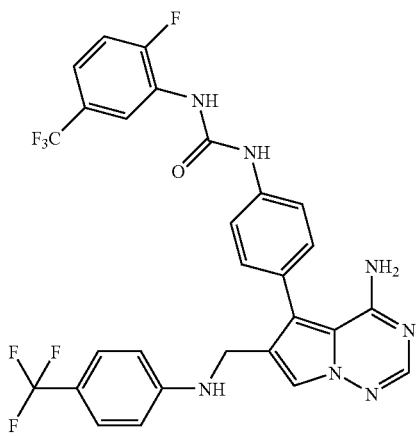

The procedure used for the preparation of Example 30 was used to prepare the title compound by substituting 4-(trifluoromethyl)aniline for morpholine and purifying via HPLC (10-90% ACN/H$_2$O). $^1$H-NMR (CD$_3$OD) δ 8.68 (d, J=8.0 Hz, 1H), 7.76 (s, 1H), 7.67 to 7.62 (m, 3H), 7.43 (d, J=8.8 Hz, 2H), 7.36 to 7.27 (m, 4H), 6.61 (d, J=8.7 Hz, 2H), 4.67 (s, 2H); MS [M+H]$^+$=604; LCMS RT=3.31 min.

Example 47

Preparation of N-(4-{4-amino-6-[(pyridin-3-ylamino)methyl]pyrrolo[2,1-f][1,2,4]triazin-5-yl}phenyl)-N'-[2-fluoro-5-(trifluoromethyl)phenyl]urea

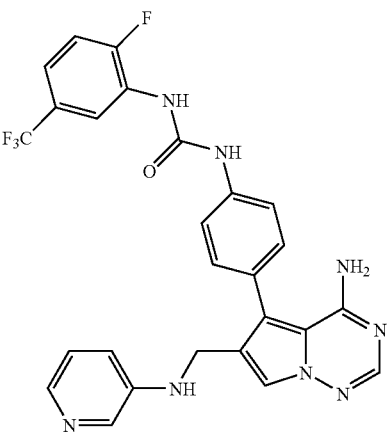

The procedure used for the preparation of Example 30 was used to prepare the title compound by substituting pyridin-3-amine for morpholine and purifying by via HPLC (10-90% ACN/H$_2$O). $^1$H-NMR (CD$_3$OD) δ 8.61 (d, J=8.2 Hz, 1H), 7.82 (d, J=2.9 Hz, 1H), 7.75 (s, 1H), 7.72 (dd, J=5.5, 1.6 Hz, 1H), 7.64 to 7.59 (m, 3H), 7.41 (d, J=7.8 Hz, 2H), 7.33 (d, J=8.4 Hz, 2H), 7.09 (dd, J=8.3, 4.8 Hz, 1H), 6.94 to 6.88 (m, 1H), 4.24 (s, 2H); MS [M+H]$^+$=537; LCMS RT=2.08 min.

Example 48

Preparation of ethyl 4-amino-5-{4-[({[5-(trifluoromethyl)pyridin-2-yl]amino}carbonyl)amino]phenyl}pyrrolo[2,1-f][1,2,4]triazine-6-carboxylate

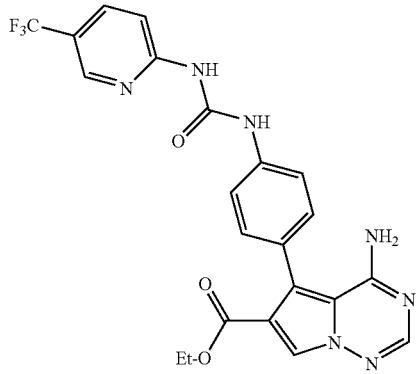

Step 1: Preparation of phenyl[5-(trifluoromethyl)pyridin-2-yl]carbamate

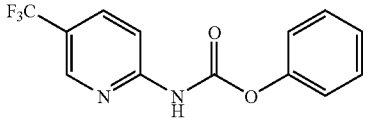

A solution of 5-(trifluoromethyl)pyridin-2-amine (100 mg, 0.617 mmol) and N,N-diisopropylethylamine (159.5 mg, 215 μL, 1.234 mmol) in 5 mL $CH_2Cl_2$ was treated with phenyl chloroformate (106 mg, 85 μL, 0.68 mmol) and left to stir for 3 h at rt. Solution was diluted with EtOAc and washed twice with 1 N HCl and 1 time with brine. The organic layer was dried ($Na_2SO_4$) and concentrated to provide a white solid. Tituration with 10% EtOAc in hexanes gave 120 mg (69%, 0.42 mmol) of the above compound as a white solid. $^1$H-NMR (DMSO-$d_6$) δ 11.26 (s, 1H), 8.70 (s, 1H), 8.22 to 8.16 (m, 1H), 7.99 (d, J=8 Hz, 1H), 7.45 to 7.40 (m, 2H), 7.30 to 7.20 (m, 3H)

Step 2: Preparation of the Title Compound

A mixture of Intermediate B (57.9 mg, 0.195 mmol) and triethylamine in 2 mL THF was heated to 55° C., providing a cloudy solution. Phenyl[5-(trifluoromethyl)pyridin-2-yl]carbamate (50 mg, 0.177 mmol) was added as a solid, and the mixture left to stir overnight. After 16 h, the solid precipitate was filtered, washed with ethyl acetate and dried to provide 66 mg (77%, 0.14 mmol) of the above compound as a yellow solid. $^1$H-NMR (DMSO-$d_6$) δ 9.33 (s, 1H), 8.95 (d, J=2.3 Hz, 1H), 8.63 to 8.61 (m, 1H), 8.13 (s, 1H), 8.07 (br s, 1H), 7.93 (s, 1H), 7.56 to 7.53 (m, 2H), 7.51 to 7.48 (m, 1H), 7.40 (br s, 1H), 7.34 to 7.32 (m, 2H), 5.09 (br s, 1H), 4.11 to 4.06 (q, J=6.9 Hz, 2H), 1.13 to 1.10 (t, J=7.1 Hz, 3H); MS [M+H]$^+$=486.0; LCMS RT=3.36 ml; TLC $R_f$=0.46 (100% EtOAc).

Example 49

Preparation of ethyl 4-amino-5-[4-({[(3-tert-butyl-1-methyl-1H-pyrazol-5-yl)amino]carbonyl}amino)phenyl]pyrrolo[2,1-f][1,2,4]triazine-6-carboxylate

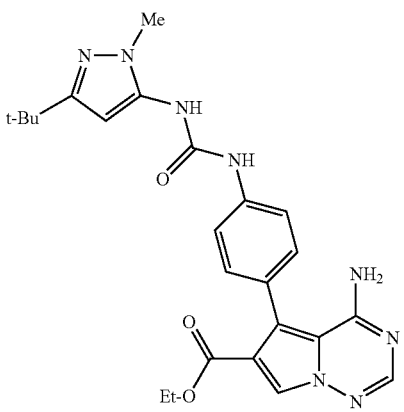

The procedure used for the preparation of Example 48 was used to prepare the title compound by substituting 3-tert-butyl-1-methyl-1H-pyrazol-5-amine for 5-(trifluoromethyl)pyridin-2-anine and purifying by recrystallization (EtOAc/EtOH). $^1$H-NMR (DMSO-$d_6$) δ 9.08 (s, 1H), 8.56 (s, 1H), 8.12 (s, 1H), 8.11-8.04 (bs, 1H), 7.92 (s, 1H), 7.53 (d, J=8.7 Hz, 2H), 7.30 (d, J=8.7 Hz, 2H), 6.05 (s, 1H), 5.14-5.01 (bs, 1H) 4.03 (q, J=7.2 Hz, 2H), 1.09 (t, J=7.2 Hz, 3H); MS [M+H]$^+$=477.2; LCMS RT=2.60 min.

Example 50

Preparation of ethyl 4-amino-5-[4-({[(4-tert-butylpyridin-2-yl)amino]carbonyl}amino)phenyl]pyrrolo[2,1-f][1,2,4]triazine-6-carboxylate

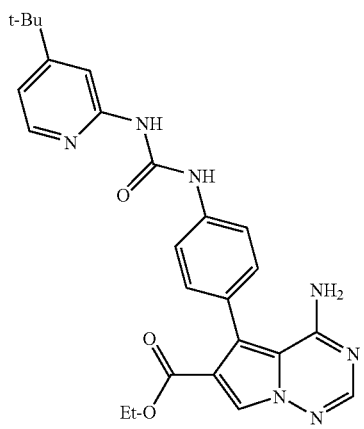

The procedure used for the preparation of Example 48 was used to prepare the title compound by substituting 4-tert-butylpyridin-2-amine for 5-(trifluoromethyl)pyridin-2-amine and purifying by HPLC (10-90% ACN/$H_2O$). $^1$H-NMR (DMSO-$d_6$) δ10.88 (s, 1H), 9.44 (s, 1H), 8.19 (d, J=5.7 Hz), 8.12 (s, 1H), 8.11-8.10 (bs, 1H), 7.92 (s, 1H), 7.61 (d, J=8.4 Hz, 2H), 7.49 (s, 1H), 7.32 (d, J=8.4 Hz, 2H) 7.09-7.03 (m, 1H), 5.01-5.18 (bs, 1H), 4.07 (q, J=7.2 Hz, 2H), 1.25 (s, 9H), 1.08 (t, J=7.2 Hz, 3H); MS [M+H]$^+$=474.2; LCMS RT=2.63 min; TLC $R_f$=0.27 (3:7 v/v THF—$CH_2Cl_2$).

Example 51

Preparation of ethyl 4-amino-5-{4-[({[4-(trifluoromethyl)pyridin-2-yl]amino}carbonyl)amino]phenyl}pyrrolo[2,1-f][1,2,4]triazine-6-carboxylate

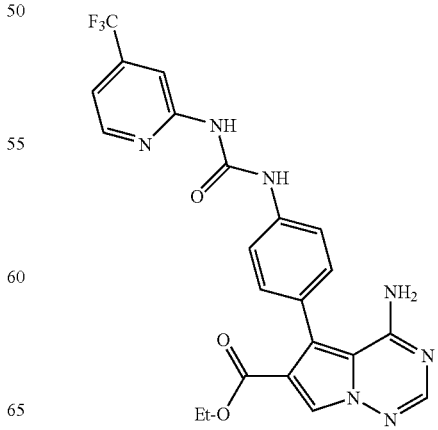

The procedure used for the preparation of Example 48 was used to prepare the title compound by substituting 4-(trifluoromethyl)pyridin-2-amine for 5-(trifluoromethyl)pyridin-2-amine and purifying by flash chromatography (1:3 v/v THF—CH$_2$Cl$_2$). $^1$H-NMR (DMSO-d$_6$) δ 10.19 (s, 1H), 9.89 (s, 1H), 8.52 (d, J=5.4 Hz, 1H), 8.12 (s, 1H), 8.12 to 8.10 (m, 2H), 7.93 (s, 1H), 7.59 (d, J=6.9 Hz, 2H), 7.48 to 7.30 (m, 3H), 5.15 to 5.10 (m, 1H), 4.06 (q, J=7.2 Hz, 2H), 1.11 (t, J=7.2 Hz, 3H); MS [M+H]$^+$=486.1; LCMS RT=3.33 min; TLC R$_f$=0.27 (3:7 v/v THF—CH$_2$Cl$_2$).

Example 52

Preparation of ethyl 4-amino-5-[4-({[(3-tert-butylisoxazol-5-yl)amino]carbonyl}amino)phenyl]pyrrolo[2,1-f][1,2,4]triazine-6-carboxylate

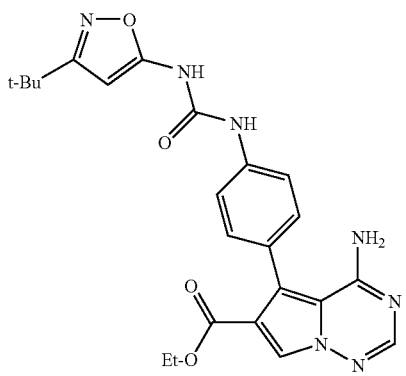

The procedure used for the preparation of Example 48 was used to prepare the title compound by substituting 3-tert-butylisoxazol-5-amine for 5-(trifluoromethyl)pyridin-2-amine and purifying by washing the precipitate formed during the reaction (1:1 v/v EtOAC-hexanes). $^1$H-NMR (DMSO-d$_6$) δ 10.17 (s, 1H), 9.02 (s, 1H), 8.13 (s, 1H), 8.0-8.1 (bs, 1H), 7.93 (s, 1H), 7.54 (d, J=8.7 Hz, 2H), 7.32 (J=8.7 Hz, 2H), 6.07 (s, 1H), 5.2-5.0 (bs, 1H), 4.07 (q, J=6.9 Hz, 2H), 1.25 (ms, 9H), 1.09 (t, J=6.9 Hz, 3H); MS [M+H]$^+$=464.2; LCMS RT=3.25 min; TLC R$_f$=0.33 (3:7 v/v THF—CH$_2$Cl$_2$).

Example 53

Preparation of 4-amino-5-{4-[({[4-chloro-3-(trifluoromethyl)phenyl]amino}carbonyl)amino]phenyl}pyrrolo[2,1-f][1,2,4]triazine-6-carboxylic acid

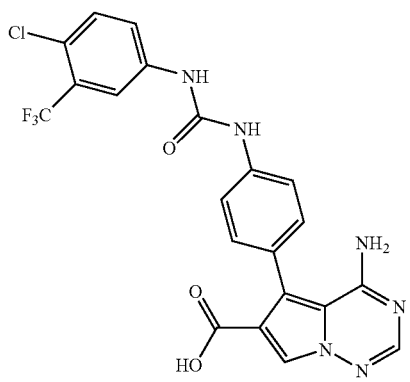

To a solution of MeOH (1.5 mL) was added ethyl 4-amino-5-{4-[({[4-chloro-3-(trifluoromethyl)phenyl]amino}carbonyl)amino]phenyl}pyrrolo[2,1-f][1,2,4]triazine-6-carboxylate, Example 2, (22 mg, 0.042 mol), THF (3.0 mL), and 1N NaOH (0.42 mL, 0.42 mmol). The reaction was heated to 65° C. for 17 h. Upon cooling to rt the reaction was filtered through a plug of Celite®/Silica gel eluting with 85:15 v/v CH$_2$Cl$_2$-MeOH. The filtrate was concentrated in vacuo to dryness, diluted with CH$_2$Cl$_2$, dried (MgSO4), filtered, and concentrated in vacuo to dryness producing 3.8 mg of the above compound (0.0077 mmol, yield 18%). $^1$H-NMR (DMSO-d$_6$) δ 8.18 (br s, 1H), 7.98 (br s, 1H), 7.88 (s, 1H), 7.67 (br s, 1H), 7.59 to 7.57 (d, J=8.6 Hz, 1H), 7.53 to 7.51 (d, J=7.7 Hz, 2H), 7.34 to 7.32 (d, J=8.0 Hz, 2H), 6.56 (s, 1H), 5.06 (br s, 1H); MS [M+H]$^+$=491; LCMS RT=3.18 min; TLC R$_f$=0.20 (85:15 v/v CH$_2$Cl$_2$-MeOH).

Example 54

Preparation of methyl 4-amino-5-{4-[({[2-fluoro-5-(trifluoromethyl)phenyl]amino}carbonyl)amino]phenyl}pyrrolo[2,1-f][1,2,4]triazine-6-carboxylate

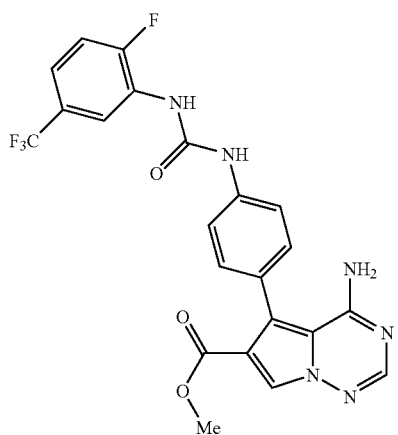

To a solution of MeOH (4.0 mL) was added Intermediate E (30 mg, 0.060 mmol), THF (2.0 mL), and 1N NaOH (0.24 mL, 0.24 mmol). The reaction was stirred at rt for 2 d. The solution was transferred to a Biotage Samplet and dried in a vacuum oven. The material was purified by flash chromatography (Biotage) eluting with 5:4:1 v/v/v CH$_2$Cl$_2$-EtOAc-MeOH. The clean fractions were combined, concentrated in vacuo to dryness producing 14 mg of the above compound (0.029 mmol, yield 48%). $^1$H-NMR (DMSO-d$_6$) δ 9.33 (s, 1H), 8.96 (d, 1H, J=2.4 Hz), 8.63 to 8.61 (dd, 7.3 Hz, 2.4 Hz, 1H), 8.15 (s, 1H), 8.09 (br s, 1H), 7.93 (s, 1H), 7.56 to 7.54 (m, 2H), 7.50 to 7.47 (m, 1H), 7.40 (m, 1H), 7.34 to 7.32 (m, 2H), 5.09 (br s, 1H), 3.63 (s, 3H); MS [M+H]$^+$=489; LCMS RT=2.85 min; TLC R$_f$=0.55 (5:4:1 v/v/v CH$_2$Cl$_2$-EtOAc-MeOH).

Example 55

Preparation of 4-amino-N-[3-(dimethylamino)propyl]-5-{4-[({[2-fluoro-5-(trifluoromethyl)phenyl]amino}carbonyl)amino]phenyl}pyrrolo[2,1-f][1,2,4]triazine-6-carboxamide

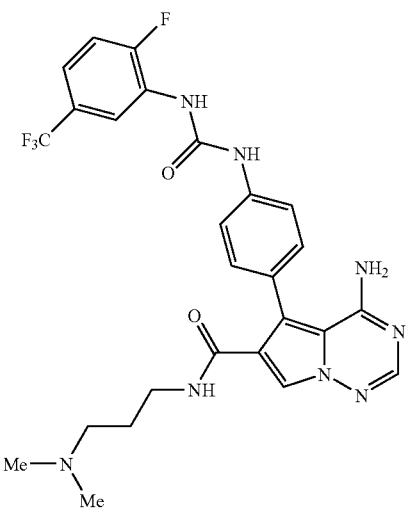

To a solution of Intermediate G (41 mg, 0.09 mmol) in 0.5 mL DMF was added py-BOP (32.0 mg, 0.13 mmol N,N-dimethylpropane-1,3-diamine (13.25 mg, 0.13 mmol) as a solution in THF, diisopropylethylamine (24.9 mg, 0.19 mmol) and 4-dimethylaminopyridine (4 mg, 0.04 mmol). After 12 h the reaction was diluted with 150 mL $CH_2Cl_2$, washed with water and brine, then dried with sodium sulfate. This solution was concentrated and the residue purified by flash column (20% THF in $CH_2Cl_2$) to yield 25.4 mg of impure material. Tituration with ethyl acetate gave 10.3 mg of the desired product (0.018 mmol, 21 mg). $^1$H-NMR (MeOD-$d_4$) δ 8.60 (d, J=8 Hz, 1H), 7.97 (3, 1H), 7.84 (s, 1H), 7.65 (d, J=9 Hz, 1H), 7.43 (d, J=9 Hz, 2H), 7.33 (d, J=9 Hz, 2H), 3.25 (t, J=7 Hz, 2H), 2.23 (t, J=7 Hz, 2H), 2.21 (s, 6H), 1.61 (ap quintet, J=7 Hz, 2H); MS [M+H]$^+$=559.3; LCMS RT=2.63 min; TLC R$_f$=0.14 (1:2 v/v THF:$CH_2Cl_2$).

Example 56

Preparation of 4-amino-N-[2-(dimethylamino)ethyl]-5-{4-[({[2-fluoro-5-(trifluoromethyl)phenyl]amino}carbonyl)amino]phenyl}pyrrolo[2,1-f][1,2,4]triazine-6-carboxamide

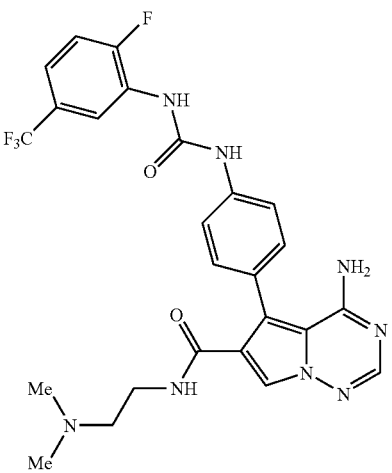

Preparation of this compound is described in Example 55, substituting N,N-dimethylethane-1,2-diamine for N,N-dimethylpropane-1,3-diamine providing 23.7 mg of product as a white solid (0.044 mmol, 34% yield). $^1$H-NMR (CD$_3$OD) δ 8.62 (d, J=8 Hz, 1H), 8.01 (s, 1H), 7.84 (s, 1H), 7.66 (d, J=8 Hz, 1H), 7.42 (d, J=8 Hz, 2H), 7.35 (d, J=8 Hz, 2H), 3.90 (t, J=7 Hz, 2H), 2.40 (t, J=7 Hz, 2H), 2.20 (s, 6H); MS [M+H]$^+$=545.2; LCMS RT=2.13 min; TLC R$_f$=0.31 (1:3:9 v/v/v 2 M NH$_3$ in MeOH:THF:$CH_2Cl_2$).

Example 57

Preparation of N-{4-[4-amino-6-(morpholin-4-ylcarbonyl)pyrrolo[2,1-f][1,2,4]triazin-5-yl]phenyl}-N'-[2-fluoro-5-(trifluoromethyl)phenyl]urea

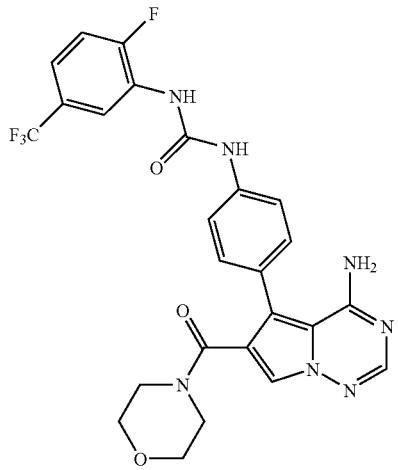

This compound was prepared via the same procedure as Example 55, substituting morpholine for N,N-dimethylpropane-1,3-diamine providing 7.2 mg of product as a white solid (0.013 mmol, 16%). $^1$H-NMR (CD$_3$OD) δ 8.62 (d, J=8 Hz, 1H), 7.91 (s, 1H), 7.80 (s, 1H), 7.66 (d, J=9 Hz, 1H), 7.43-7.39 (m, 2H), 7.34 (d, J=9 Hz, 2H), 3.26-3.45 (m, 4H), 3.2-3.0 (m, 4H), MS [M+H]$^+$=544.6; LCMS RT=2.49 min; TLC R$_f$=0.34 (1:2 v/v THF:$CH_2Cl_2$).

Example 58

Preparation of 4-amino-5-{4-[({[2-fluoro-5-(trifluoromethyl)phenyl]amino}carbonyl)amino]phenyl}-N,N-dimethylpyrrolo[2,1-f][1,2,4]triazine-6-carboxamide

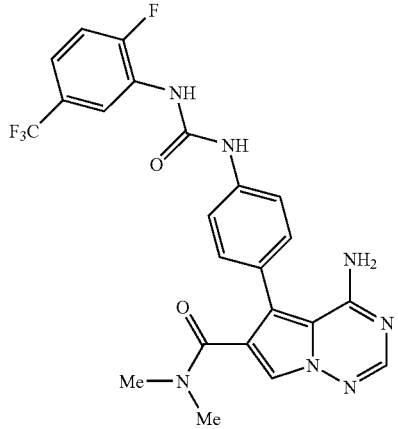

This compound was prepared via the same procedure as Example 55, substituting N-methylmethanamine for N,N-dimethylpropane-1,3-diamine providing 7.0 mg of product as a white solid (0.014 mmol, 17%). $^1$H-NMR (CD$_3$OD) δ 8.61 (d, J=8 Hz, 1H), 7.85 (s, 1H), 7.79 (s, 1H), 7.60 (d, J=9 Hz, 1H), 7.38 (d, J=9 Hz, 2H), 7.34 (d, J=9 Hz, 2H), 2.93 (s, 3H), 2.72 (s, 3H); MS [M+H]$^+$=502.2; LCMS RT=2.54 min; TLC R$_f$=0.29 (1:2 v/v THF:CH$_2$Cl$_2$).

Example 59

Preparation of 4-amino-5-{4-[({[2-fluoro-5-(trifluoromethyl)phenyl]amino}carbonyl)amino]phenyl}-N-methylpyrrolo[2,1-f][1,2,4]triazine-6-carboxamide

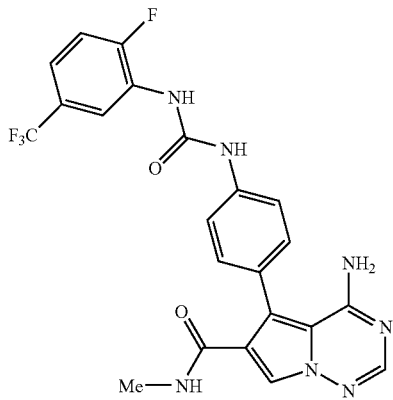

This compound was prepared via the same procedure as Example 55, substituting methanamine for N,N-dimethylpropane-1,3-diamine providing mg of product as a white solid (mol, yield). $^1$H-NMR (CD$_3$OD) δ 8.61 (d, J=8 Hz, 1H), 7.85 (s, 1H), 7.97 (s, 1H), 7.83 (d, J=9 Hz, 1H), 7.61 (d, J=9 Hz, 2H), 7.43-7.39 (m, 2H) 7.34 (d, J=9 Hz, 2H), 2.93 (s, 3H); MS [M+H]$^+$=488.5; LCMS RT=2.50 min; TLC R$_f$=0.26 (1:2 v/v THF:CH$_2$Cl$_2$).

Example 60

Preparation of N-(4-{4-amino-6-[(4-methylpiperazin-1-yl)carbonyl]pyrrolo[2,1-f][1,2,4]triazin-5-yl}phenyl)-N'-[2-fluoro-5-(trifluoromethyl)phenyl]urea

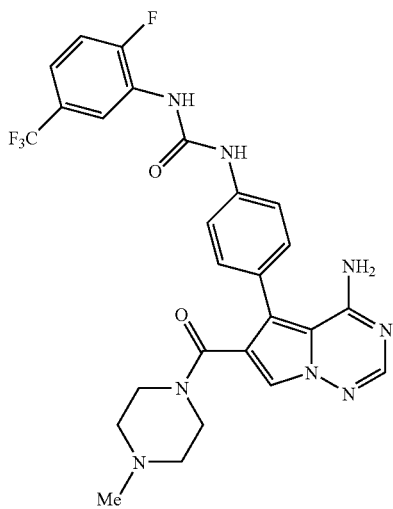

This compound was prepared via the same procedure as Example 55, substituting 1-methylpiperazine for N,N-dimethylpropane-1,3-diamine providing 6.2 mg of product as a white solid (0.011 mmol, 9% yield). $^1$H-NMR (CD$_3$OD) δ 8.62-8.59 (m, 1H), 7.86 (s, 1H), 7.80 (d, J=9 Hz, 1H), 7.64 (d, J=9 Hz, 2H), 7.42-7.39 (m, 2H) 7.34 (d, J=9 Hz, 2H), 3.65-3.57 (m, 2H), 3.56-3.50 (m, 2H), 3.20-3.11 (m, 2H), 2.13 (s, 3H); MS [M+H]$^+$=557.0; LCMS RT=2.13 min; TLC R$_f$=0.21 (1:1 v/v THF:CH$_2$Cl$_2$).

Example 61

Preparation of 4-amino-5-{4-[({[2-fluoro-5-(trifluoromethyl)phenyl]amino}carbonyl)amino]phenyl}-N-(4-pyrrolidin-1-ylbutyl)pyrrolo[2,1-f][1,2,4]triazine-6-carboxamide

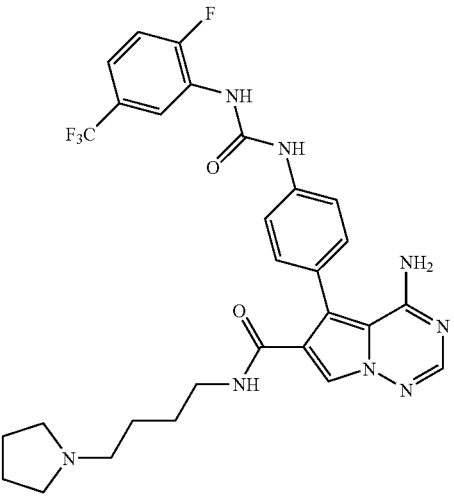

The procedure used for the preparation of Example 55 was used to prepare the title compound by substituting 4-pyrrolidin-1-ylbutan-1-amine for N,N-dimethylpropane-1,3-diamine and purifying via HPLC (10-90% ACN/H$_2$O). $^1$H-NMR (CD$_3$OD) δ 8.61 (d, J=7.4 Hz, 1H), 7.98 (s, 1H), 7.83 (s, 1H), 7.66 (d, J=7.3 Hz, 2H), 7.43 (d, J=8.4 Hz, 2H), 7.34 (d, J=8.3 Hz, 2H), 3.24 (t, J=5.8 Hz, 2H), 2.73 to 2.63 (m, 4H), 2.57 (t, J=5.8 Hz, 2H), 1.86 to 1.78 (m, 4H), 1.48 to 1.39 (m, 4H); MS [M+H]$^+$=599; LCMS RT=2.66 min.

Example 62

Preparation of 4-amino-5-{4-[({[2-fluoro-5-(trifluoromethyl)phenyl]amino}carbonyl)amino]phenyl}-N-(3-pyrrolidin-1-ylpropyl)pyrrolo[2,1-f][1,2,4]triazine-6-carboxamide

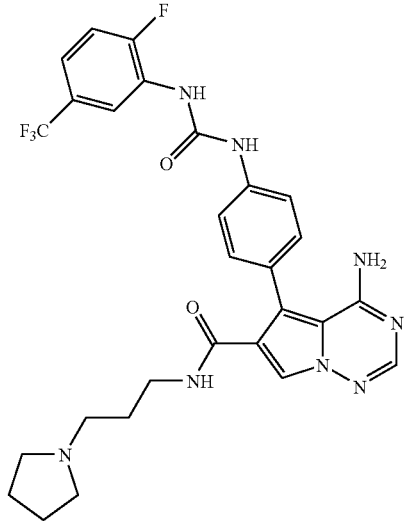

The procedure used for the preparation of Example 55 was used to prepare the title compound by substituting 3-pyrrolidin-1-ylpropan-1-amine for N,N-dimethylpropane-1,3-diamine and purifying by via HPLC (10-90% ACN/H$_2$O). $^1$H-NMR (CD$_3$OD) δ 8.62 (d, J=7.7 Hz, 1H), 8.03 (s, 1H), 7.84 (s, 1H), 7.66 (d, J=8.0 Hz, 2H), 7.43 (d, J=8.4 Hz, 2H), 7.35 (d, J=8.2 Hz, 2H), 3.28 to 3.21 (m, 2H), 2.64 to 2.55 (m, 4H), 2.44 to 2.36 (m, 2H), 1.84 to 1.76 (m, 4H), 1.71 to 1.60 (m, 2H); MS [M+H]$^+$=585; LCMS RT=2.63 min.

Example 63

Preparation of 4-amino-5-{4-[({[2-fluoro-5-(trifluoromethyl)phenyl]amino}carbonyl)amino]phenyl}-N-(2-pyrrolidin-1-ylethyl)pyrrolo[2,1-f][1,2,4]triazine-6-carboxamide

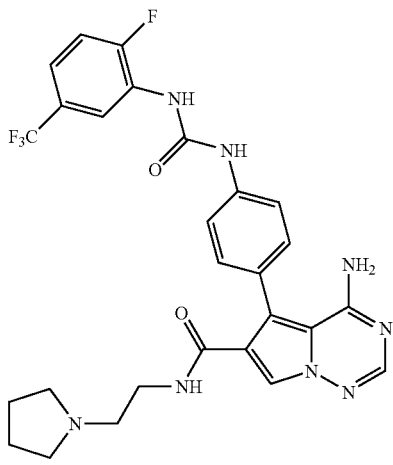

The procedure used for the preparation of Example 55 was used to prepare the title compound by substituting 2-pyrrolidin-1-ylethanamine for N,N-dimethylpropane-1,3-diamine and purifying via HPLC (10-90% ACN/H$_2$O). $^1$H-NMR (CD$_3$OD) δ 8.62 (d, J=7.6 Hz, 1H), 7.97 (s, 1H), 7.84 (s, 1H), 7.66 (d, J=7.8 Hz, 2H), 7.43 (d, J=8.2 Hz, 2H), 7.35 (d, J=8.5 Hz, 2H), 3.25 to 3.20 (m, 2H), 2.64 to 2.50 (m, 6H), 1.82 to 1.74 (m, 4H); MS [M+H]$^+$=571; LCMS RT=2.23 min.

Example 64

Preparation of 4-amino-5-{4-[({[2-fluoro-5-(trifluoromethyl)phenyl]amino}carbonyl)amino]phenyl}-N-(3-morpholin-4-ylpropyl)pyrrolo[2,1-f][1,2,4]triazine-6-carboxamide

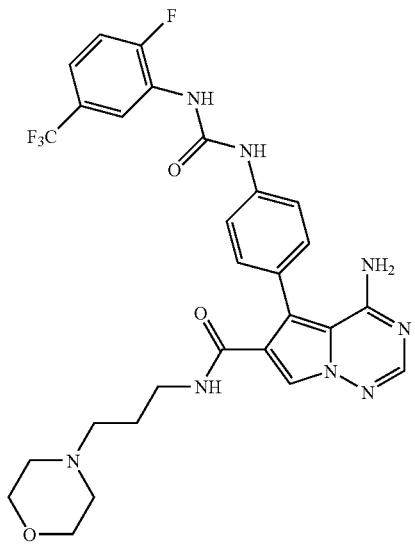

The procedure used for the preparation of Example 55 was used to prepare the title compound by substituting 3-morpholin-4-ylpropan-1-amine for N,N-dimethylpropane-1,3-diamine and purifying by via HPLC (10-90% ACN/H$_2$O). $^1$H-NMR (CD$_3$OD) δ 8.62 (d, J=7.2 Hz, 1H), 7.97 (s, 1H), 7.84 (s, 1H), 7.66 (d, J=8.3 Hz, 2H), 7.44 (d, J=8.3 Hz, 2H), 7.34 (d, J=8.7 Hz, 2H), 3.64 (t, J=3.6 Hz, 4H), 3.26 (t, J=6.1 Hz, 2H), 2.43 to 2.37 (m, 4H), 2.21 (t, J=7.7 Hz, 2H), 1.68 to 1.54 (m, 2H); MS [M+H]$^+$=601; LCMS RT=2.21 min.

Example 65

Preparation of 4-amino-5-{4-[({[2-fluoro-5-(trifluoromethyl)phenyl]amino}carbonyl)amino]phenyl}-N-(2-morpholin-4-ylethyl)pyrrolo[2,1-f][1,2,4]triazine-6-carboxamide

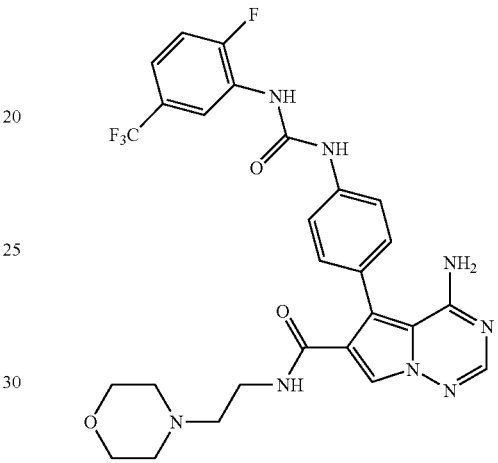

The procedure used for the preparation of Example 55 was used to prepare the title compound by substituting 2-morpholin-4-ylethanamine for N,N-dimethylpropane-1,3-diamine and purifying via HPLC (10-90% ACN/H$_2$O). $^1$H-NMR (CD$_3$OD) δ 8.61 (d, J=7.8 Hz, 1H), 8.03 (s, 1H), 7.84 (s, 1H), 7.69 (d, J=8.4 Hz, 2H), 7.46 (d, J=8.5 Hz, 2H), 7.35 (d, J=8.2 Hz, 2H), 3.60 (t, J=5.0 Hz, 4H), 3.39 to 3.33 (m, 2H), 2.37 to 2.30 (m, 6H); MS [M+H]$^+$=587; LCMS RT=2.21 min.

Example 66

Preparation of N-{4-[4-amino-6-(3-morpholin-4-ylpropyl)pyrrolo[2,1-f][1,2,4]triazin-5-yl]phenyl}-N'-[2-fluoro-5-(trifluoromethyl)phenyl]urea

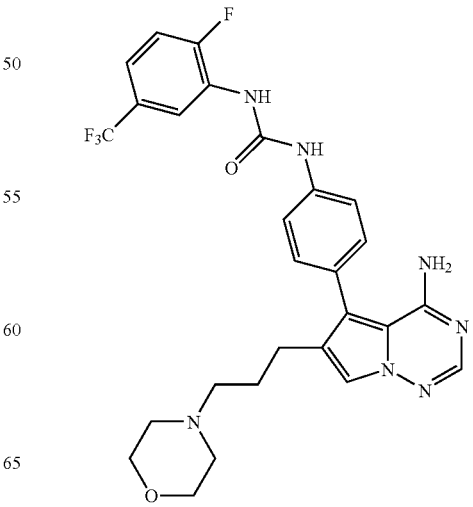

To a solution of Intermediate I (53 mg, 0.11 mmol) in CH$_2$Cl$_2$ (3.0 mL) was added AcOH (0.036 mL, 0.63 mmol) and morpholine (0.019 mL, 0.22 mmol). The reaction was stirred at rt for 1 h after which sodium triacetoxyborohydride (66 mg, 0.31 mmol) was added. The reaction was stirred at rt until completion. Reaction was diluted with CH$_2$Cl$_2$, transferred to a separatory funnel and washed with saturated aq NaHCO$_3$ (2×). Aqueous phase was back extracted with CH$_2$Cl$_2$ (2×). The organic was dried (Na$_2$SO$_4$) and evaporated to give a crude oil that was purified via HPLC (10-90% ACN/H$_2$O) to give the title compound (15 mg, 24%). $^1$H-NMR (CD$_3$OD) δ 8.62 (d, J=7.8 Hz, 1H), 7.74 (s, 1H), 7.62 (d, J=8.2 Hz, 2H), 7.53 (s, 1H), 7.38 to 7.31 (m, 4H), 3.62 (t, J=5.2 Hz, 4H), 2.59 (t, J=7.3 Hz, 2H), 2.38 to 2.23 (m, 6H), 1.74 to 1.62 (m, 2H); MS [M+H]$^+$=558; LCMS RT=2.18 min.

Example 67

Preparation of N-{4-[4-amino-6-(3-pyrrolidin-1-ylpropyl)pyrrolo[2,1-f][1,2,4]triazin-5-yl]phenyl}-N'-[2-fluoro-5-(trifluoromethyl)phenyl]urea

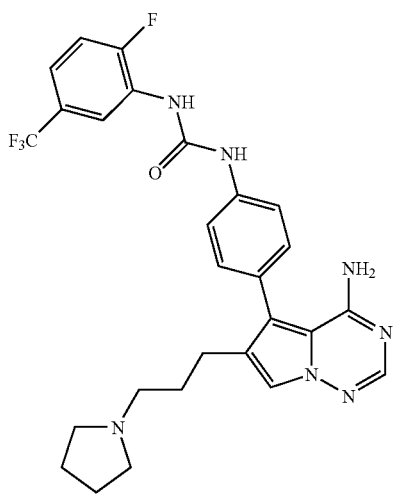

The procedure used for the preparation of Example 66 was used to prepare the title compound by substituting pyrrolidine for morpholine and purifying via HPLC (10-90% ACN/H$_2$O). $^1$H-NMR (CD$_3$OD) δ 8.61 (d, J=7.8 Hz, 1H), 7.74 (s, 1H), 7.63 (d, J=8.3 Hz, 2H), 7.55 (s, 1H), 7.39 to 7.31 (m, 4H), 2.72 to 2.55 (m, 8H), 1.86 to 1.70 (m, 6H); MS [M+H]$^+$=542; LCMS RT=2.15 min.

Example 68

Preparation of ethyl 4-amino-5-[4-({[(3,4-dimethoxyphenyl)amino]carbonyl}amino)phenyl]pyrrolo[2,1-f][1,2,4]triazine-6-carboxylate

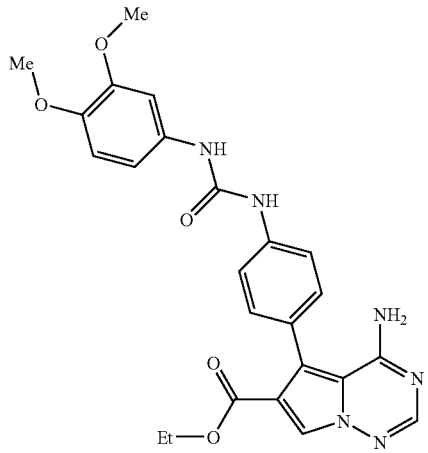

The procedure used for the preparation of Example 3 was used to prepare the title compound by substituting 3,4-dimethoxyaniline for 4-fluoro-3-(trifluoromethyl)aniline. $^1$H-NMR (CD$_3$OD) δ 8.27 (s, 1H), 8.15 (s, 1H), 8.06 (s, 1H), 7.98 (s, 1H), 7.67 (d, J=8 Hz, 2H), 7.39 (d, J=8 Hz, 2H), 7.34 (s, 1H), 6.95 (d, J=9 Hz, 1H), 6.86 (d, J=9 Hz, 3H), 4.15 (q, j=7, 2H), 3.81 (s, 3H), 3.78 (s, 3H), 1.18 (t, j=7 Hz, 3H); MS [M+H]$^+$=477.1 LCMS RT=2.50 min.

Example 69

Preparation of 4-amino-N-cyclopropyl-5-{4-[({[2-fluoro-5-(trifluoromethyl)phenyl]amino}carbonyl)amino]phenyl}pyrrolo[2,1-f][1,2,4]triazine-6-carboxamide

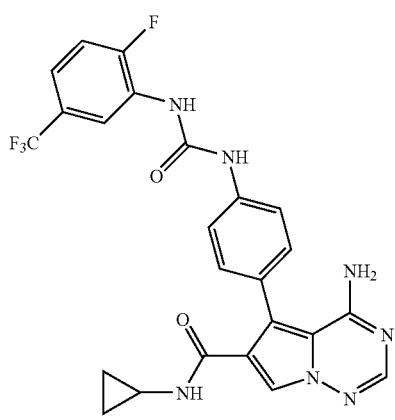

A solution of Intermediate G (50 mg, 0.105 mmol), cyclopropylamine (11 μL, 0.106 mmol), py-BOP (82 mg, 0.158 mmol) and triethylamine (22 μL, 0.158 mmol) was allowed to stir at rt for 15 min and then concentrated in vacuo. The residue was purified by silica chromatography using 20% THF in CH$_2$Cl$_2$ and the product then triturated with 30% aqueous methanol, affording 31.5 mg of the above compound (0.061 mmol, yield 71%). $^1$H-NMR (DMSO-d$_6$) δ 9.32 (s, 1H), 8.96 (s, 1H), 8.64 (bd, J=6 Hz, 1H), 8.06 (s, 1H), 7.90 (s, 1H), 7.85 to 7.82 (m, 1H), 7.54 (d, J=8 Hz, 2H), 7.53 to 7.50 (m, 2H), 7.45 to 7.35 (m, 1H), 7.31 (d, J=8 Hz, 1H), 5.03 (bs, 1H), 2.63-2.59 (m 1H), 0.62 to 0.58 (m, 2H), 0.41 to 0.39 (m, 2H). MS [M+H]$^+$=514.2; LCMS RT=3.11 min; TLC R$_f$=0.33 (2:1 v/v CH$_2$Cl$_2$-THF).

Example 70

Preparation of 4-amino-5-{4-[({[2-fluoro-5-(trifluoromethyl)phenyl]amino}carbonyl)amino]phenyl}-N-(2,2,2-trifluoroethyl)pyrrolo[2,1-f][1,2,4]triazine-6-carboxamide

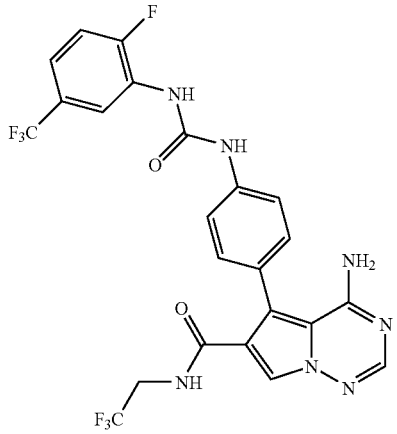

The procedure used for the preparation of Example 69 was used to prepare the title compound by substituting 2,2,2-trifluoroethanamine hydrochloride for cyclopropanamine. $^1$H-NMR (DMSO-d$_6$) δ 9.29 (s, 1H), 8.93 (s, 1H), 8.64-8.58 (m, 1H), 8.51 (t, J=6 Hz, 1H), 8.18 (s, 1H), 8.00 (bs, 1H), 7.91 (s, 1H), 7.52 (d, J=8 Hz, 2H), 7.51 to 7.46 (m, 1H), 7.40 to 7.30 (m, 1H), 7.28 (d, J=8 Hz, 2H), 5.05 (bs, 1H), 4.00 to 3.85 (m, 2H). MS [M+H]$^+$=556.2; LCMS RT=3.32 min; TLC R$_f$=0.33 (2:1 v/v CH$_2$Cl$_2$-THF).

Example 71

Preparation of 4-amino-N-ethyl-5-{4-[({[2-fluoro-5-(trifluoromethyl)phenyl]amino}carbonyl)amino]phenyl}pyrrolo[2,1-f][1,2,4]triazine-6-carboxamide

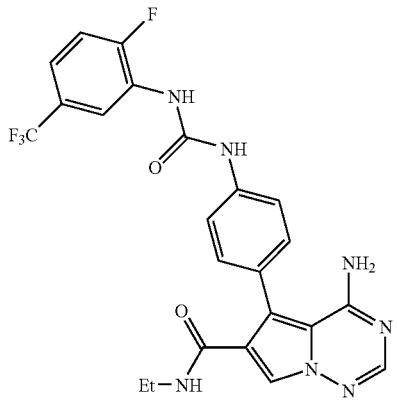

The procedure used for the preparation of Example 69 was used to prepare the title compound by substituting ethanamine for cyclopropanamine. $^1$H-NMR (CD$_3$OD) δ 8.62 to 8.60 (m, 1H), 7.98 (s, 1H), 7.84 (s, 1H), 7.63 (d, J=9 Hz, 2H), 7.42 to 7.41 (m, 1H), 7.34 (d, J=7 Hz, 2H), 1.04 (t, J=7 Hz, 3H); MS [M+H]$^+$=502.1; LCMS RT=2.68 min; TLC R$_f$=0.44 (3:2 v/v CH$_2$Cl$_2$-THF).

Example 72

Preparation of N-(4-{4-amino-6-[3-(4-methylpiperazin-1-yl)propyl]pyrrolo[2,1-f][1,2,4]triazin-5-yl}phenyl)-N'-[2-fluoro-5-(trifluoromethyl)phenyl]urea

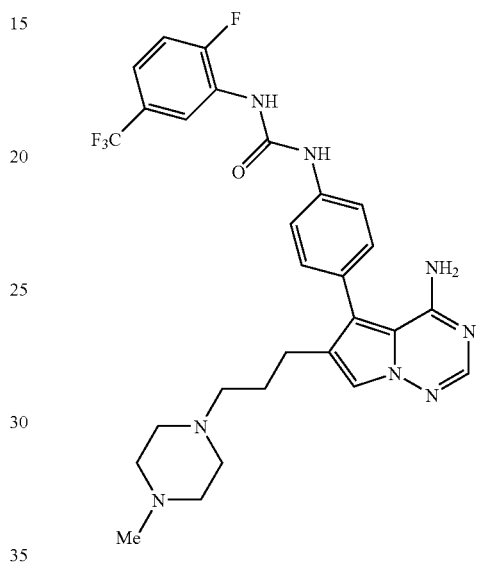

The procedure used for the preparation of Example 66 was used to prepare the title compound by substituting 1-methylpiperazine for morpholine and purifying via HPLC (10-90% ACN/H$_2$O). $^1$H-NMR (CD$_3$OD) δ 8.61 (d, J=8.0 Hz, 1H), 7.74 (s, 1H), 7.63 (d, J=8.7 Hz, 2H), 7.54 (s, 1H), 7.37 (d, J=8.0 Hz, 2H), 7.34 (d, J=8.1 Hz, 2H), 2.79 to 2.37 (m, 12H), 2.47 (s, 3H), 1.75 to 1.62 (m, 2H); MS [M+H]$^+$=571.4; LCMS RT=2.48.

Example 73

Preparation of 4-amino-5-[4-({[(4-tert-butylpyridin-2-yl)amino]carbonyl}amino)phenyl]-N-methylpyrrolo[2,1-f][1,2,4]triazine-6-carboxamide

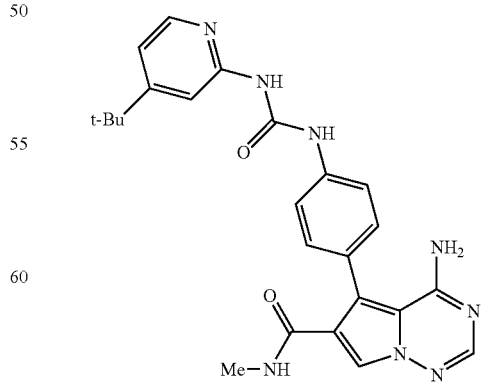

To a solution of DMF (1 mL) was added Intermediate X (50 mg, 0.18 mmol) followed by phenyl (4-tert-butylpyridin-2- yl)carbamate (48 mg, 0.18 mmol) and triethylamine (25 μL, 0.18 mmol). The reaction was stirred at rt overnight, concentrated to dryness, and purified by HPLC to afford 22 mg of the above compound (0.04 mmol, yield 26%). $^1$H-NMR (DMSO-$d_6$) δ 10.9 (s, 1H), 9.48 (s, 1H), 8.17 (d, J=5.4 Hz, 1H), 8.06 (s, 1H), 7.88 (s, 1H), 7.02 (d, J=5.0 Hz, 1H), 7.61 to 7.54 (m, 3H), 7.29 (d, J=8.3 Hz, 2H), 7.04 (dd, J=5.5, 1.6 Hz, 1H), 2.61 (d, J=4.7 Hz, 3H), 1.25 (s, 9H); MS [M+H]$^+$=459.2; LCMS RT=2.49.

Example 74

Preparation of 4-amino-5-{4-[({[4-fluoro-3-(trifluoromethyl)phenyl]amino}carbonyl)amino]phenyl}-N-methylpyrrolo[2,1-f][1,2,4]triazine-6-carboxamide

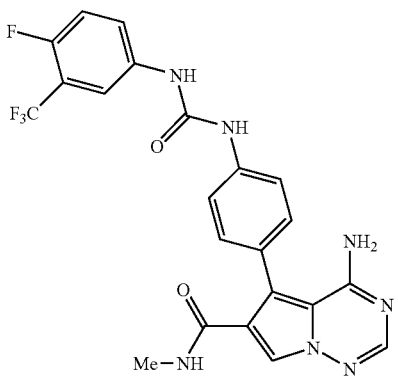

The procedure used for the preparation of Example 73 was used to prepare the title compound by substituting phenyl[4-fluoro-3-(trifluoromethyl)phenyl]carbamate for phenyl (4-tert-butylpyridin-2-yl)carbamate. $^1$H-NMR (CD$_3$OD) δ 7.97 (s, 1H), 7.91 (dd, J=6.4, 3.0 Hz, 1H), 7.83 (s, 1H), 7.68 to 7.62 (m, 1H), 7.59 (d, J=8.3 Hz, 2H), 7.40 (d, J=8.3 Hz, 2H), 7.27 (t, J=9.9 Hz, 1H), 2.76 (s, 3H); MS [M+H]$^+$=488.3; LCMS RT=2.31.

Example 75

Preparation of 4-amino-N-(tert-butyl)-5-{4-[({[2-fluoro-5-(trifluoromethyl)phenyl]amino}carbonyl)amino]phenyl}pyrrolo[2,1-f][1,2,4]triazine-6-carboxamide

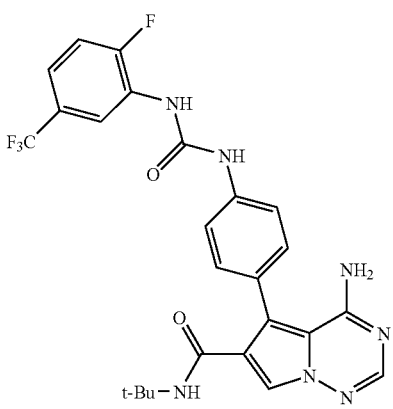

The procedure used for the preparation of Example 69 was used to prepare the title compound by substituting 2-methylpropan-2-amine for cyclopropanamine. $^1$H-NMR (DMSO-$d_6$) δ 9.35 (s, 1H), 8.95 (s, 1H), 8.61 (d, J=5 Hz, 1H), 8.02 (s, 1H), 7.88 (s, 1H), 7.98 to 7.92 (m, 1H), 7.57 (d, J=8 Hz, 2H), 7.45 to 7.44 (m, 1H), 7.41 to 7.36 (m, 1H), 7.34 (d, J=8 Hz, 2H), 6.62 (s, 1H), 1.15 (s, 9H); MS [M+H]$^+$=530.3; LCMS RT=2.94 min; TLC R$_f$=0.68 (3:2 v/v CH$_2$Cl$_2$-THF).

Example 76

Preparation of 4-amino-5-[4-({[(4-tert-butylpyridin-2-yl)amino]carbonyl}amino)phenyl]-N-cyclopropylpyrrolo[2,1-f][1,2,4]triazine-6-carboxamide

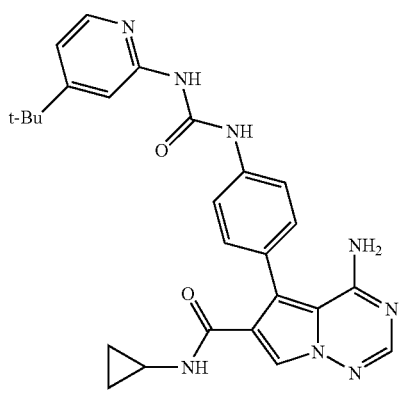

The procedure used for the preparation of Example 73 was used to prepare the title compound by substituting Intermediate W for Intermediate X. $^1$H-NMR (CD$_3$OD) δ 8.22 (d, J=6.3 Hz, 1H), 7.98 (s, 1H), 7.83 (s, 1H), 7.71 (d, J=8.6 Hz, 2H), 7.42 (d, J=8.6 Hz, 2H), 7.21 (s, 1H), 7.10 (dd, J=5.6, 1.7 Hz, 1H), 2.72 to 2.59 (m, 1H), 1.31 (s, 9H), 0.72 to 0.62 (m, 2H), 0.42 to 0.33 (m, 2H); MS [M+H]$^+$=485.3; LCMS RT=2.70.

Example 77

Preparation of 4-amino-5-{4-[({[3-fluoro-5-(trifluoromethyl)phenyl]amino}carbonyl)amino]phenyl}-N-methylpyrrolo[2,1-f][1,2,4]triazine-6-carboxamide

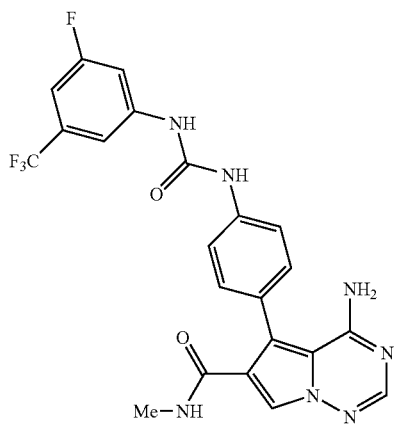

The procedure used for the preparation of Example 73 was used to prepare the title compound by substituting phenyl[3-fluoro-5-(trifluoromethyl)phenyl]carbamate for phenyl

127

(4-tert-butylpyridin-2-yl)carbamate. ¹H-NMR (DMSO-d₆) δ 8.04 (s, 1H), 7.88 (s, 1H), 7.70 (s, 1H), 7.61 (d, J=11.0 Hz, 1H), 7.52 (d, J=8.6 Hz, 2H), 7.29 (d, J=8.6 Hz, 2H), 7.21 (d, J=8.1 Hz, 1H), 3.11 to 3.08 (m, 1H), 2.62 (d, J=3.4 Hz, 3H); MS [M+H]⁺=488.2; LCMS RT=3.05.

Example 78

Preparation of 4-amino-N-cyclopropyl-5-{4-[({[4-fluoro-3-(trifluoromethyl)phenyl]amino}carbonyl)amino]phenyl}pyrrolo[2,1-f][1,2,4]triazine-6-carboxamide

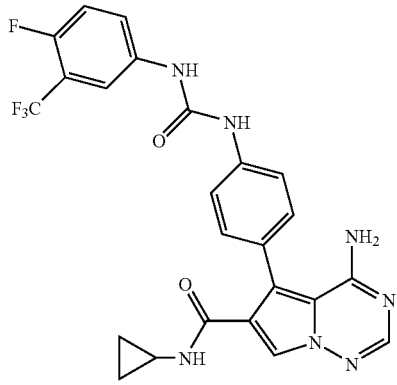

The procedure used for the preparation of Example 73 was used to prepare the title compound by substituting Intermediate W for Intermediate X and by substituting phenyl[4-fluoro-3-(trifluoromethyl)phenyl]carbamate for phenyl (4-tert-butylpyridin-2-yl)carbamate. ¹H-NMR (CD₃OD) δ 7.62 (s, 1H), 7.55 (dd, J=7.8, 2.8 Hz, 1H), 7.47 (s, 1H), 7.34 to 7.27 (m, 1H), 7.24 (d, J=8.4 Hz, 2H), 7.03 (d, J=8.4 Hz, 2H), 6.91 (t, J=9.8 Hz, 1H), 2.36 to 2.24 (m, 1H), 0.39 to 0.28 (m, 2H), 0.058 to −0.027 (m, 2H); MS [M+H]⁺=514.2; LCMS RT=3.11.

Example 79

Preparation of 4-amino-N-cyclopropyl-5-{4-[({[3-fluoro-5-(trifluoromethyl)phenyl]amino}carbonyl)amino]phenyl}pyrrolo[2,1-f][1,2,4]triazine-6-carboxamide

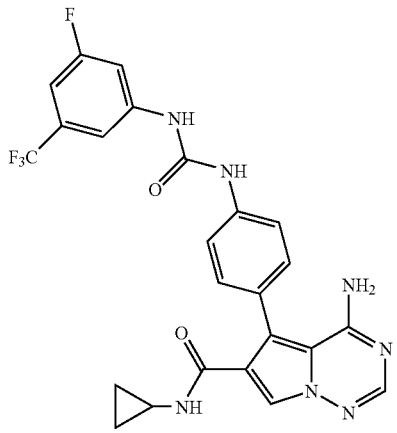

The procedure used for the preparation of Example 73 was used to prepare the title compound by substituting Intermediate W for Intermediate X and by substituting phenyl[3-fluoro-5-(trifluoromethyl)phenyl]carbamate for phenyl

128

(4-tert-butylpyridin-2-yl)carbamate. ¹H-NMR (Acetone-d₆) δ 7.67 (s, 1H), 7.51 (s, 1H), 7.33 (s, 1H), 7.24 (d, J=1.5 Hz, 1H), 7.15 (d, J=9.0 Hz, 2H), 6.92 (d, J=9.0 Hz, 2H), 6.84 (d, J=8.6 Hz, 1H), 2.74 to 2.69 (m, 1H), 2.29 to 2.21 (m, 1H), 0.24 to 0.15 (m, 2H), 0.045 to −0.021 (m, 2H); MS [M+H]⁺=514.3; LCMS RT=3.19.

Example 80

Preparation of 4-amino-N-cyclopropyl-5-[4-({[(2,2,4,4-tetrafluoro-4H-1,3-benzodioxin-6-yl)amino]carbonyl}amino)phenyl]pyrrolo[2,1-f][1,2,4]triazine-6-carboxamide

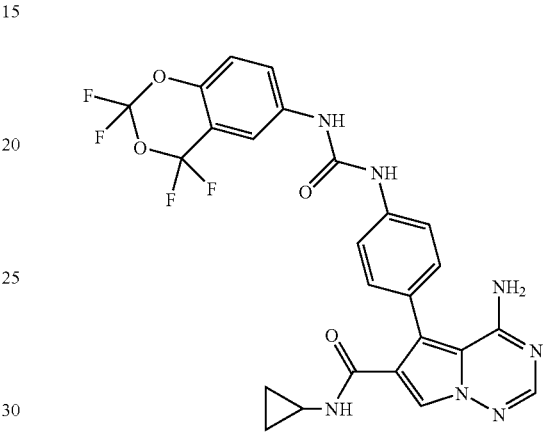

The procedure used for the preparation of Example 73 was used to prepare the title compound by substituting Intermediate W for Intermediate X and by substituting phenyl (2,2,4,4-tetrafluoro-4H-1,3-benzodioxin-6-yl)carbamate for phenyl (4-tert-butylpyridin-2-yl)carbamate. ¹H-NMR (CD₃OD) δ 8.02 (d, J=2.5 Hz, 1H), 7.98 (s, 1H), 7.84 (s, 1H), 7.67 (dd, J=9.1, 2.8 Hz, 1H), 7.61 (d, J=8.8 Hz, 2H), 7.40 (d, J=8.4 Hz, 2H), 7.25 (d, J=9.1 Hz, 1H), 2.72 to 2.63 (m, 1H), 0.73 to 0.65 (m, 2H), 0.42 to 0.35 (m, 2H); MS [M+H]⁺=558.2; LCMS RT=3.29.

Example 81

Preparation of 4-amino-N-cyclopropyl-5-{4-[({[3-(2,2,2-trifluoroethyl)phenyl]amino}carbonyl)amino]phenyl}pyrrolo[2,1-f][1,2,4]triazine-6-carboxamide

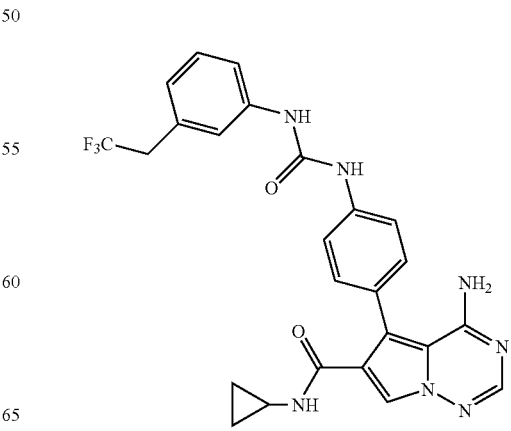

The procedure used for the preparation of Example 73 was used to prepare the title compound by substituting Intermediate W for Intermediate X and by substituting phenyl[3-(2,2,2-trifluoroethyl)phenyl]carbamate for phenyl (4-tert-butylpyridin-2-yl)carbamate. $^1$H-NMR (Acetone-d$_6$) δ 7.64 (s, 1H), 7.47 (s, 1H), 7.38 (d, J=4.0 Hz, 1H), 7.11 (d, J=8.7 Hz, 2H), 7.06 (d, J=8.7 Hz, 2H), 6.89 to 6.83 (m, 4H), 3.22 to 3.09 (m, 2H), 2.74 to 2.68 (m, 1H), 2.30 to 2.20 (m, 1H), 0.25 to 0.17 (m 2H), 0.040 to −0.027 (m, 2H); MS [M+H]$^+$=510.2; LCMS RT=3.01.

Example 82

Preparation of 4-amino-N-cyclopropyl-5-{4-[({[4-(trifluoromethyl)pyridin-2-yl]amino}carbonyl)amino]phenyl}pyrrolo[2,1-f][1,2,4]triazine-6-carboxamide

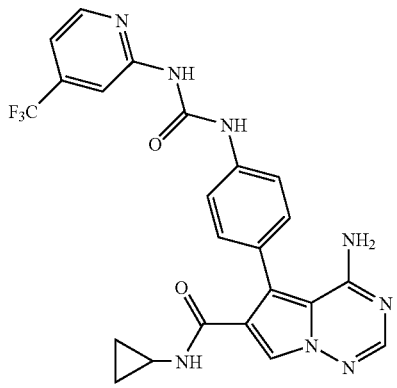

The procedure used for the preparation of Example 73 was used to prepare the title compound by substituting Intermediate W for Intermediate X and by substituting phenyl[4-(trifluoromethyl)pyridin-2-yl]carbamate for phenyl (4-tert-butylpyridin-2-yl)carbamate. $^1$H-NMR (DMSO-d$_6$) δ 8.52 (d, J=5.8 Hz, 1H), 8.06 (s, 1H), 8.04 (s, 1H), 7.87 (s, 1H), 7.56 (d, J=8.4 Hz, 2H), 7.34 (d, J=5.0 Hz, 1H), 7.30 (d, J=8.4 Hz, 2H), 3.12 to 3.09 (m, 1H), 2.68 to 2.60 (m, 1H), 0.62 to 0.55 (m 2H), 0.44 to 0.36 (m, 2H); MS [M+H]$^+$=497.2; LCMS RT=2.94.

Example 83

Preparation of 4-amino-5-{4-[({[4-chloro-3-(trifluoromethyl)phenyl]amino}carbonyl)amino]phenyl}-N-cyclopropylpyrrolo[2,1-f][1,2,4]triazine-6-carboxamide

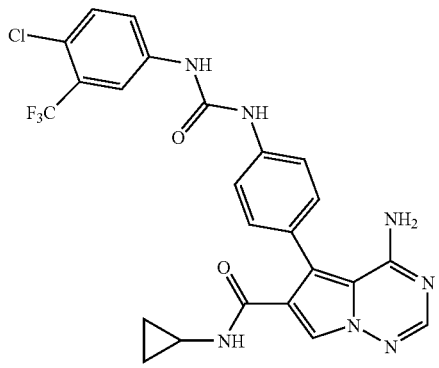

The procedure used for the preparation of Example 73 was used to prepare the title compound by substituting Intermediate W for Intermediate X and by substituting phenyl[4-chloro-3-(trifluoromethyl)phenyl]carbamate for phenyl (4-tert-butylpyridin-2-yl)carbamate. $^1$H-NMR (DMSO-d$_6$) δ 8.11 (d, J=2.4 Hz, 1H), 8.04 (s, 1H), 7.87 (s, 1H), 7.66 to 7.58 (m, 2H), 7.52 (d, J=8.4 Hz, 2H), 7.28 (d, J=8.4 Hz, 2H), 3.13 to 3.09 (m, 1H), 2.69 to 2.60 (m, 1H), 0.64 to 0.56 (m 2H), 0.43 to 0.37 (m, 2H); MS [M+H]$^+$=530.2; LCMS RT=3.25.

Example 84

Preparation of 4-amino-5-{4-[({[4-fluoro-3-(trifluoromethyl)phenyl]amino}carbonyl)amino]phenyl}-N-(2-methoxyethyl)-N-methylpyrrolo[2,1-f][1,2,4]triazine-6-carboxamide

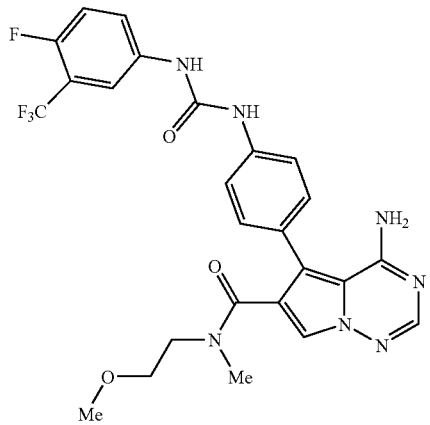

The procedure used for the preparation of Example 69 was used to prepare the title compound by substituting 2-methoxy-N-methylethanamine for cyclopropanamine. $^1$H-NMR (DMSO-d$_6$) δ 9.07 (s, 1H), 8.98 to 8.91 (m, 1H), 8.01 to 7.97 (m, 1H), 7.90 (s, 1H), 7.87 to 7.81 (m, 1H), 7.68 to 7.60 (m, 1H), 7.59 to 7.50 (m, 2H), 7.48 to 7.40 (m, 1H), 7.17 to 7.10 (m, 1H), 3.44 to 3.40 (m, 2H), 3.25 to 3.10 (m, 5H), 2.83 (s, 3H—rotamer A), 2.65 (s, 3H—rotamer b); MS [M+H]$^+$=546.2; LCMS RT=3.04 nm; TLC R$_f$=0.47 (55:40:5 v/v CH$_2$Cl$_2$-THF-EtOH).

Example 85

Preparation of N-[4-(4-amino-6-methylpyrrolo[2,1-f][1,2,4]triazin-5-yl)phenyl]-N'-[2-fluoro-5-(trifluoromethyl)phenyl]urea

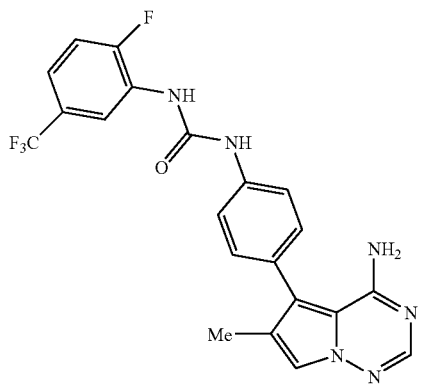

The procedure used for the preparation of Example 73 was used to prepare the title compound by substituting Intermediate T for Intermediate X and by substituting phenyl[2- fluoro-5-(trifluoromethyl)phenyl]carbamate for phenyl (4-tert-butylpyridin-2-yl)carbamate. ¹H-NMR (CD₃OD) δ 8.61 (d, J=2.6 Hz, 1H), 7.73 (s, 1H), 7.62 (d, J=8.7 Hz, 2H), 7.49 (s, 1H), 7.37 to 7.31 (m, 4H), 2.14 (s, 3H); MS [M+H]⁺=445.1; LCMS RT=2.80.

Example 86

Preparation of N-[4-(4-amino-6-methylpyrrolo[2,1-f][1,2,4]triazin-5-yl)phenyl]-N'-[4-chloro-3-(trifluoromethyl)phenyl]urea

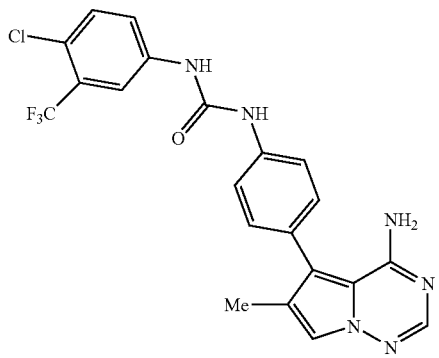

The procedure used for the preparation of Example 73 was used to prepare the title compound by substituting Intermediate T for Intermediate X and by substituting phenyl[4-chloro-3-(trifluoromethyl)phenyl]carbamate for phenyl (4-tert-butylpyridin-2-yl)carbamate. ¹H-NMR (CD₃OD) δ 8.05 (d, J=2.4 Hz, 1H), 7.73 (s, 1H), 7.67 to 7.58 (m, 3H), 7.50 (s, 1H), 7.48 (d, J=8.1 Hz, 1H), 7.33 (d, J=8.7 Hz, 2H), 2.18 (s, 3H); MS [M+H]⁺=461.1; LCMS RT=2.89.

Example 87

Preparation of 4-amino-5-{4-[({[4-chloro-3-(trifluoromethyl)phenyl]amino}carbonyl)amino]phenyl}-N-(2,2,2-trifluoroethyl)pyrrolo[2,1-f][1,2,4]triazine-6-carboxamide

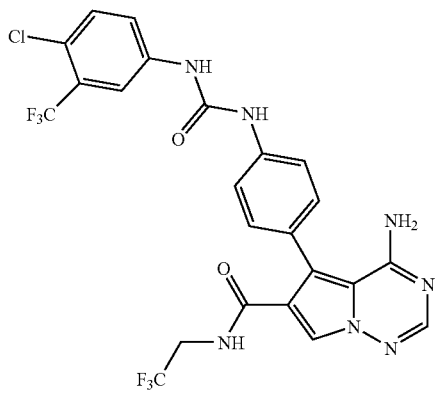

The procedure used for the preparation of Example 73 was used to prepare the title compound by substituting Intermediate M for Intermediate X and by substituting phenyl[4-chloro-3-(trifluoromethyl)phenyl]carbamate for phenyl (4-tert-butylpyridin-2-yl)carbamate. ¹H-NMR (CD₃OD) δ 8.04 (s, 1H), 8.00 (d, J=2.4 Hz, 1H), 7.84 (s, 1H), 7.64 (dd, J=8.4, 2.8 Hz, 1H), 7.59 (d, J=8.4 Hz, 2H), 7.49 (d, J=8.6 Hz, 1H), 7.38 (d, J=8.4 Hz, 2H), 3.94 (q, J=9.2 Hz, 2H); MS [M+H]⁺=572.1; LCMS RT=3.07.

Example 88

Preparation of 4-amino-5-{4-[({[4-fluoro-3-(trifluoromethyl)phenyl]amino}carbonyl)amino]phenyl}-N-(2,2,2-trifluoroethyl)pyrrolo[2,1-f][1,2,4]triazine-6-carboxamide

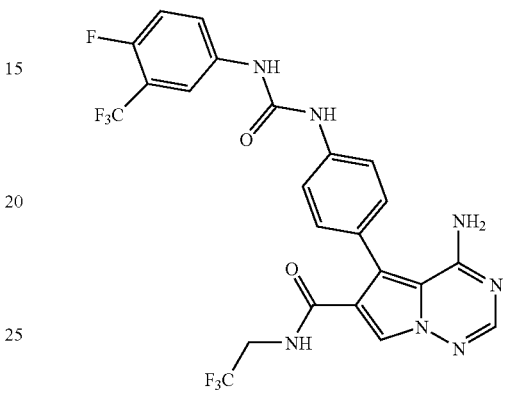

The procedure used for the preparation of Example 73 was used to prepare the title compound by substituting Intermediate M for Intermediate X and by substituting phenyl[4-fluoro-3-(trifluoromethyl)phenyl]carbamate for phenyl (4-tert-butylpyridin-2-yl)carbamate. ¹H-NMR (CD₃OD) δ 8.04 (s, 1H), 7.90 (dd, J=6.3, 2.7 Hz, 1H), 7.85 (s, 1H), 7.68 to 7.63 (m, 1H), 7.59 (d, J=8.6 Hz, 2H), 7.39 (d, J=8.7 Hz, 2H), 7.26 (t, J=9.8 Hz, 1H), 3.94 (q, J=9.2 Hz, 2H); MS [M+H]⁺=556.1; LCMS RT=2.94.

Example 89

Preparation of 4-amino-5-{4-[({[3-fluoro-5-(trifluoromethyl)phenyl]amino}carbonyl)amino]phenyl}-N-(2,2,2-trifluoroethyl)pyrrolo[2,1-f][1,2,4]triazine-6-carboxamide

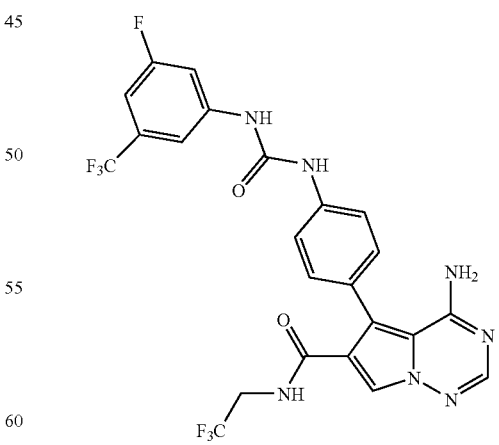

The procedure used for the preparation of Example 73 was used to prepare the title compound by substituting Intermediate M for Intermediate X and by substituting phenyl[3-fluoro-5-(trifluoromethyl)phenyl]carbamate for phenyl (4-tert-butylpyridin-2-yl)carbamate. ¹H-NMR (CD₃OD) δ

8.04 (s, 1H), 7.84 (s, 1H), 7.66 to 7.53 (m, 4H), 7.38 (d, J=8.7 Hz, 2H), 7.03 (d, J=8.2 Hz, 1H), 3.94 (q, J=9.2 Hz, 2H); MS [M+H]⁺=556.1; LCMS RT=3.02.

Example 90

Preparation of 4-amino-5-[4-({[(3,4-dichlorophenyl)amino]carbonyl}amino)phenyl]-N-(2,2,2-trifluoroethyl)pyrrolo[2,1-f][1,2,4]triazine-6-carboxamide

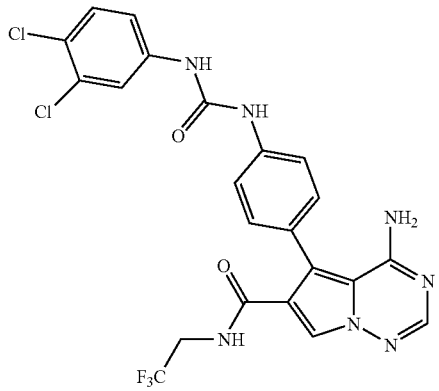

The procedure used for the preparation of Example 73 was used to prepare the title compound by substituting Intermediate M for Intermediate X and by substituting phenyl (3,4-dichlorophenyl)carbamate for phenyl (4-tert-butylpyridin-2-yl)carbamate. ¹H-NMR (CD₃OD) δ 8.04 (s, 1H), 7.85 (s, 1H), 7.81 (d, J=2.4 Hz, 1H), 7.58 (d, J=8.8 Hz, 2H), 7.43 to 7.37 (m, 3H), 7.31 (dd, J=8.9, 2.5 Hz, 1H), 3.94 (q, J=9.2 Hz, 2H); MS [M+H]⁺=538.1; LCMS RT=2.97.

Example 91

Preparation of 4-amino-5-[4-({[(2,2,4,4-tetrafluoro-4H-1,3-benzodioxin-6-yl)amino]carbonyl}amino)phenyl]-N-(2,2,2-trifluoroethyl)pyrrolo[2,1-f][1,2,4]triazine-6-carboxamide

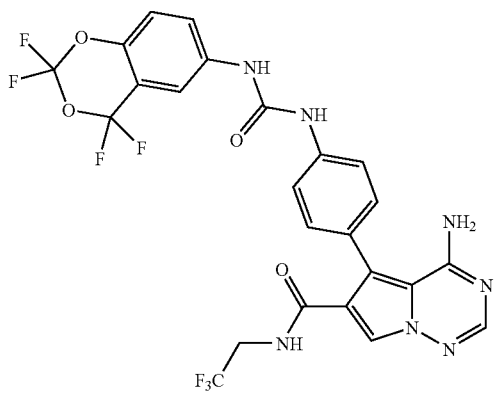

The procedure used for the preparation of Example 73 was used to prepare the title compound by substituting Intermediate M for Intermediate X and by substituting phenyl (2,2,4,4-tetrafluoro-4H-1,3-benzodioxin-6-yl)carbamate for phenyl (4-tert-butylpyridin-2-yl)carbamate. ¹H-NMR (CD₃OD)

δ 8.04 (s, 1H), 8.01 (d, J=2.3 Hz, 1H), 7.84 (s, 1H), 7.66 (dd, J=9.2, 2.8 Hz, 1H), 7.60 (d, J=8.3 Hz, 2H), 7.39 (d, J=8.3 Hz, 2H), 7.23 (d, J=9.3 Hz, 1H), 3.94 (q, J=9.2 Hz, 2H); MS [M+H]⁺=600.0; LCMS RT=3.11.

Example 92

Preparation of 4-amino-N-(2,2,2-trifluoroethyl)-5-{4-[({[3-(2,2,2-trifluoroethyl)phenyl]amino}carbonyl)amino]phenyl}pyrrolo[2,1-f][1,2,4]triazine-6-carboxamide

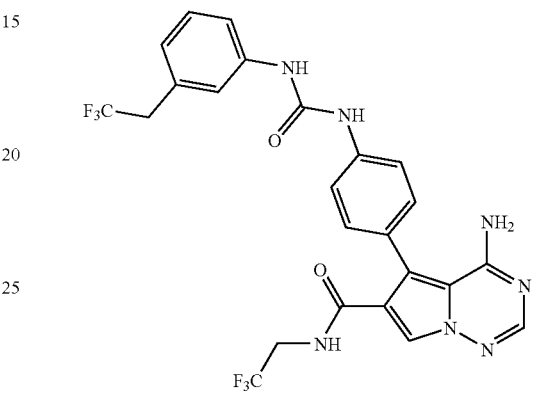

The procedure used for the preparation of Example 73 was used to prepare the title compound by substituting Intermediate M for Intermediate X and by substituting phenyl[3-(2,2,2-trifluoroethyl)phenyl]carbamate for phenyl (4-tert-butylpyridin-2-yl)carbamate. ¹H-NMR (CD₃OD) δ 8.04 (s, 1H), 7.85 (s, 1H), 7.59 (d, J=8.6 Hz, 2H), 7.46 (d, J=8.6 Hz, 2H), 7.38 (d, J=8.5 Hz, 2H), 7.26 (d, J=8.5 Hz, 2H), 3.94 (q, J=9.2 Hz, 2H), 3.42 (q, J=10.2 Hz, 2H); MS [M+H]⁺=552.1; LCMS RT=2.84.

Example 93

Preparation of 4-amino-N-(2,2,2-trifluoroethyl)-5-{4-[({[4-(trifluoromethyl)pyridin-2-yl]amino}carbonyl)amino]phenyl}pyrrolo[2,1-f][1,2,4]triazine-6-carboxamide

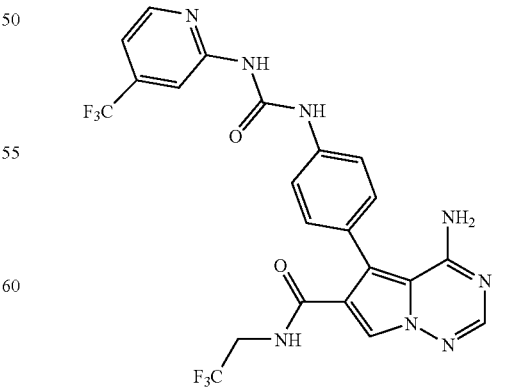

The procedure used for the preparation of Example 73 was used to prepare the title compound by substituting Intermediate M for Intermediate X and by substituting phenyl[4-(trifluoromethyl)pyridin-2-yl]carbamate for phenyl (4-tert-butylpyridin-2-yl)carbamate. ¹H-NMR (CD₃OD) δ 8.54 (d, J=5.1 Hz, 1H), 8.19 (s, 1H), 8.06 (br s, 1H), 7.91 (s, 1H), 7.60 (d, J=8.7 Hz, 2H), 7.35 (d, J=5.6 Hz, 2H), 7.31 (d, J=8.9 Hz, 2H), 3.94 (q, J=9.2 Hz, 2H); MS [M+H]⁺=539.0; LCMS RT=2.77.

Example 94

Preparation of 4-amino-5-[4-({[(3-tert-butyl-1-methyl-1H-pyrazol-5-yl)amino]carbonyl}amino)phenyl]-N-(2,2,2-trifluoroethyl)pyrrolo[2,1-f][1,2,4]triazine-6-carboxamide

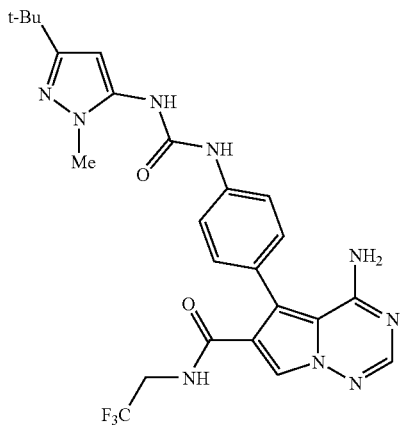

The procedure used for the preparation of Example 73 was used to prepare the title compound by substituting Intermediate M for Intermediate X and by substituting phenyl (3-tert-butyl-1-methyl-1H-pyrazol-5-yl)carbamate for phenyl (4-tert-butylpyridin-2-yl)carbamate. ¹H-NMR (CD₃OD) δ 8.04 (s, 1H), 7.85 (s, 1H), 7.59 (d, J=8.5 Hz, 2H), 7.39 (d, J=8.7 Hz, 2H), 6.13 (s, 1H), 3.94 (q, J=9.2 Hz, 2H), 3.70 (s, 3H), 1.28 (s, 9H); MS [M+H]⁺=530.1; LCMS RT=2.45.

Example 95

Preparation of ethyl 4-amino-5-(4-{[({3-[2-(diethylamino)ethoxy]-4-methoxyphenyl}amino)carbonyl]amino}phenyl)pyrrolo[2,1-f][1,2,4]triazine-6-carboxylate

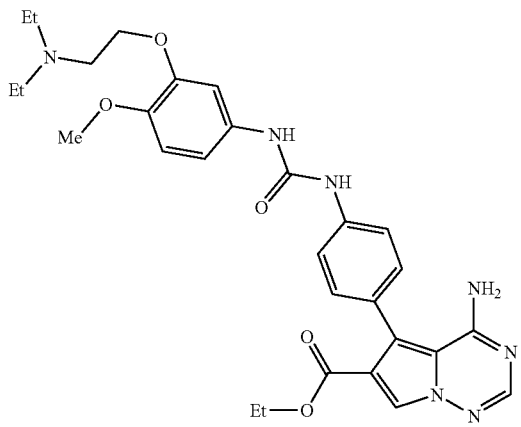

The procedure used for the preparation of Example 3 was used to prepare the title compound by substituting 3-[2-(diethylamino)ethoxy]-4-methoxyaniline for 4-fluoro-3-(trifluoromethyl)aniline. ¹H-NMR (CD₃OD) δ 8.07 (s, 1H), 7.83 (s, 1H), 7.56 (d, J=8.8 Hz, 2H), 7.33 (d, J=8.9 Hz, 2H), 7.26 (s, 1H), 6.91 (d, J=1.1 Hz, 2H), 4.20 to 4.10 (m, 4H), 3.81 (s, 3H), 3.18 to 2.99 (m, 2H), 2.86 to 2.74 (m, 4H), 1.18 to 1.10 (m, 9H); MS [M+H]⁺=562.4; LCMS RT=2.57.

Example 96

Preparation of ethyl 4-amino-5-{4-[({[4-methoxy-3-(morpholin-4-ylmethyl)phenyl]amino}carbonyl)amino]phenyl}pyrrolo[2,1-f][1,2,4]triazine-6-carboxylate

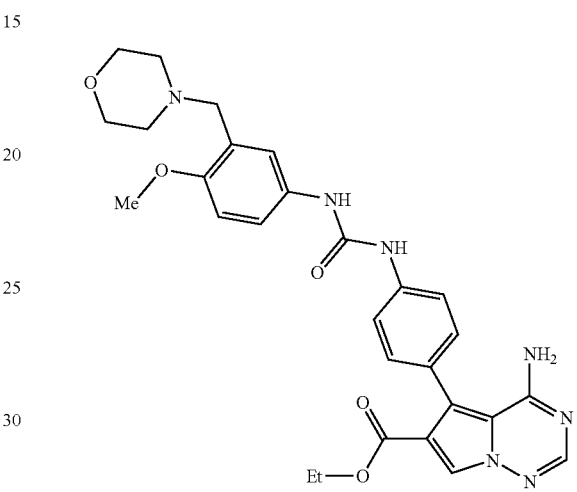

The procedure used for the preparation of Example 3 was used to prepare the title compound by substituting 4-methoxy-3-(morpholin-4-ylmethyl)aniline for 4-fluoro-3-(trifluoromethyl)aniline. ¹H-NMR (CD₃OD) δ 8.11 (s, 1H), 7.91 (s, 1H), 7.50 (d, J=8.5 Hz, 2H), 7.36 to 7.32 (m, 2H), 7.27 (d, J=8.5 Hz, 2H), 6.89 (d, J=9.6, 1H), 4.08 (q, J=7.3 Hz, 2H), 3.71 (s, 2H), 3.59 to 3.53 (m, 4H), 3.28 (s, 3H), 2.39 to 2.33 (m, 4H), 1.08 (t, J=7.2 Hz, 3H); MS [M+H]⁺=546.2; LCMS RT=2.47.

Example 97

Preparation of ethyl 4-amino-5-{4-[({[4-(pyrrolidin-1-ylmethyl)phenyl]amino}carbonyl)amino]phenyl}pyrrolo[2,1-f][1,2,4]triazine-6-carboxylate

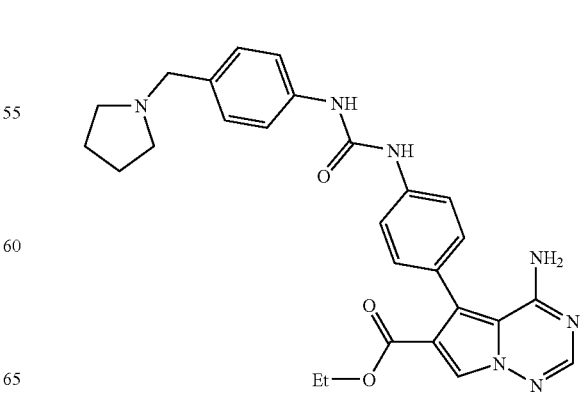

The procedure used for the preparation of Example 3 was used to prepare the title compound by substituting 4-(pyrrolidin-1-ylmethyl)aniline for 4-fluoro-3-(trifluoromethyl)aniline. ¹H-NMR (CD₃OD) δ 8.07 (s, 1H), 7.83 (s, 1H), 7.56 (d, J=8.5 Hz, 2H), 7.47 (d, J=8.5 Hz, 2H), 7.33 (t, J=8.9 Hz, 4H), 4.13 (q, J=7.3 Hz, 2H), 3.78 (s, 2H), 2.79 to 2.70 (m, 4H), 1.91 to 1.84 (m, 4H), 1.15 (t, J=7.2 Hz, 3H); MS [M+H]⁺=500.2; LCMS RT=2.46.

Example 98

Preparation of ethyl 4-amino-5-(4-{[({3-[2-(diethylamino)ethoxy]phenyl}amino)carbonyl]amino}phenyl)pyrrolo[2,1-f][1,2,4]triazine-6-carboxylate

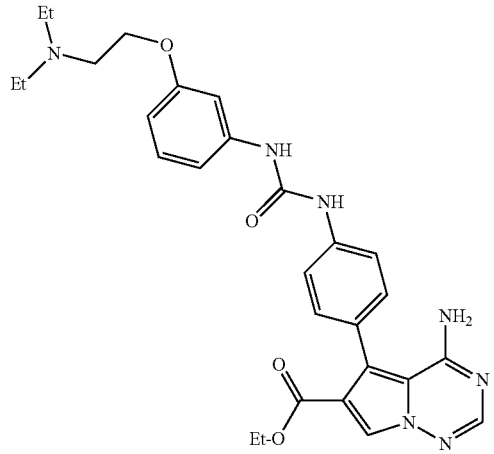

The procedure used for the preparation of Example 3 was used to prepare the title compound by substituting 3-[2-(diethylamino)ethoxy]aniline for 4-fluoro-3-(trifluoromethyl)aniline and purifying via HPLC (10-90% ACN/H₂O). ¹H-NMR (CD₃OD) δ 8.05 (s, 1H), 7.82 (s, 1H), 7.57 (d, J=8.4 Hz, 2H), 7.35 to 7.30 (m, 3H), 7.20 (t, J=8.0 Hz, 1H), 6.94 (dd, J=7.9, 2.0 Hz, 1H), 6.63 (dd, J=8.4, 1.9 Hz, 1H), 4.17 to 4.03 (m, 4H), 3.29 to 3.25 (m, 2H), 3.10 to 2.97 (m, 4H), 1.28 to 1.19 (m, 9H); MS [M+H]⁺=532.4; LCMS RT=2.57.

Example 99

Preparation of N-[4-(4-amino-6-cyanopyrrolo[2,1-f][1,2,4]triazin-5-yl)phenyl]-N'-[2-fluoro-5-(trifluoromethyl)phenyl]urea

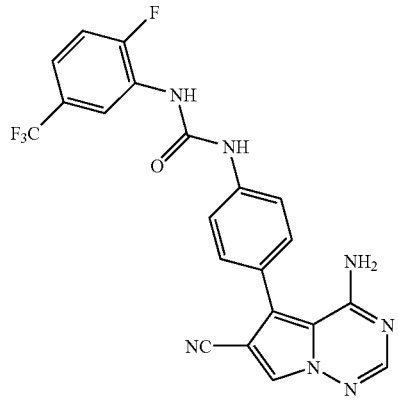

The procedure used for the preparation of Example 73 was used to prepare the title compound by substituting Intermediate P for Intermediate X and by substituting phenyl[2-fluoro-5-(trifluoromethyl)phenyl]carbamate for phenyl (4-tert-butylpyridin-2-yl)carbamate. ¹H-NMR (CD₃OD) δ 8.62 (d, J=7.0 Hz, 1H), 8.19 (s, 1H), 7.91 (s, 1H), 7.69 (d, J=8.6 Hz, 2H), 7.50 (d, J=8.6 Hz, 2H), 7.34 (d, J=8.7 Hz, 2H); MS [M+H]⁺=456.1; LCMS RT=3.10.

Example 100

Preparation of N-{4-[4-amino-6-(methoxymethyl)pyrrolo[2,1-f][1,2,4]triazin-5-yl]phenyl}-N'-[2-fluoro-5-(trifluoromethyl)phenyl]urea

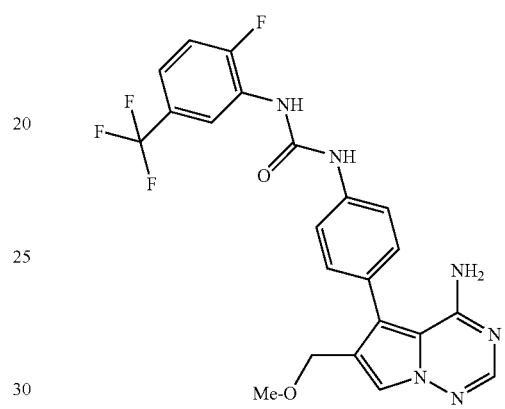

The procedure used for the preparation of Example 73 was used to prepare the title compound by substituting Intermediate U for Intermediate X and by substituting phenyl[2-fluoro-5-(trifluoromethyl)phenyl]carbamate for phenyl (4-tert-butylpyridin-2-yl)carbamate. ¹H-NMR (CD₃OD) δ 8.61 (d, J=7.6 Hz, 1H), 7.78 (s, 1H), 7.68 (s, 1H), 7.62 (d, J=8.7 Hz, 2H), 7.40 (d, J=8.6 Hz, 2H), 7.33 (d, J=8.7 Hz, 2H), 4.35 (s, 2H), 3.30 (s, 3H); MS [M+H]⁺=475.2; LCMS RT=2.81.

Example 101

Preparation of N-{4-[4-amino-6-(methoxymethyl)pyrrolo[2,1-f][1,2,4]triazin-5-yl]phenyl}-N'-[4-(trifluoromethyl)pyridin-2-yl]urea

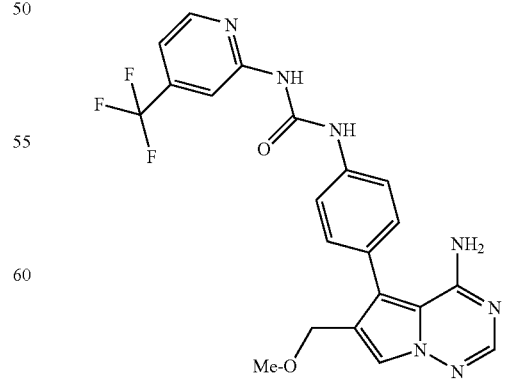

The procedure used for the preparation of Example 73 was used to prepare the title compound by substituting Intermediate U for Intermediate X and by substituting phenyl[4-(trifluoromethyl)pyridin-2-yl]carbamate for phenyl (4-tert-butylpyridin-2-yl)carbamate. ¹H-NMR (CD₃OD) δ 8.52 (d, J=5.4 Hz, 1H), 7.79 (s, 1H), 7.76 (s, 1H), 7.71 to 7.67 (m, 3H), 7.43 (d, J=8.6 Hz, 2H), 7.28 (d, J=5.3 Hz, 1H), 4.36 (s, 2H), 3.29 (s, 3H); MS [M+H]⁺=458.1; LCMS RT=2.66.

Example 102

Preparation of N-{4-[4-amino-6-(methoxymethyl)pyrrolo[2,1-f][1,2,4]triazin-5-yl]phenyl}-N'-[3-fluoro-5-(trifluoromethyl)phenyl]urea

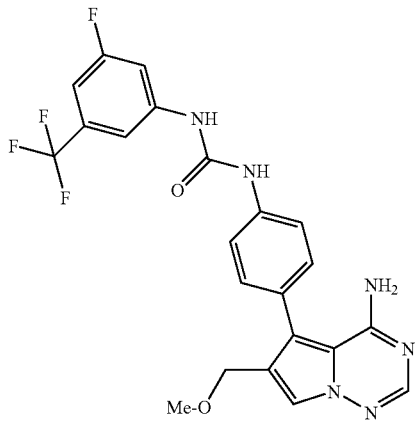

The procedure used for the preparation of Example 76 was used to prepare the title compound by substituting Intermediate U for Intermediate X and by substituting phenyl[3-fluoro-5-(trifluoromethyl)phenyl]carbamate for phenyl (4-tert-butylpyridin-2-yl)carbamate. ¹H-NMR (CD₃OD) δ 7.77 (s, 1H), 7.67 (s, 1H), 7.66 to 7.60 (m, 4H), 7.39 (d, J=8.5 Hz, 2H), 7.03 (d, J=8.9 Hz, 1H), 4.34 (s, 2H), 3.20 (s, 3H); MS [M+H]⁺=475.2; LCMS RT=2.88.

Example 103

Preparation of N-[4-(4-amino-6-cyanopyrrolo[2,1-f][1,2,4]triazin-5-yl)phenyl]-N'-[3-fluoro-5-(trifluoromethyl)phenyl]urea

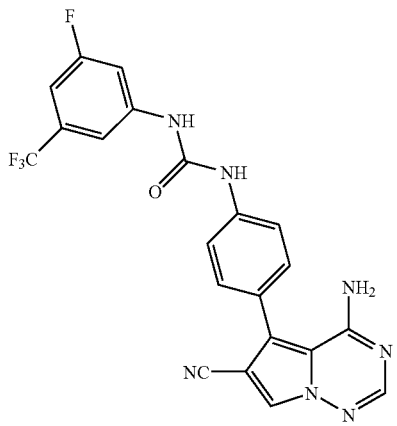

The procedure used for the preparation of Example 73 was used to prepare the title compound by substituting Intermediate P for Intermediate X and by substituting phenyl[3-fluoro-5-(trifluoromethyl)phenyl]carbamate for phenyl (4-tert-butylpyridin-2-yl)carbamate. ¹H-NMR (CD₃OD) δ 8.18 (s, 1H), 7.90 (s, 1H), 7.70 to 7.62 (m, 3H), 7.59 (s, 1H), 7.49 (d, J=8.9 Hz, 2H), 7.06 (d, J=8.9 Hz, 1H); MS [M+H]⁺=456.4; LCMS RT=3.26.

Example 104

Preparation of 4-amino-5-{4-[({[2-fluoro-5-(trifluoromethyl)phenyl]amino}carbonyl)amino]phenyl}pyrrolo[2,1-f][1,2,4]triazine-6-carboxamide

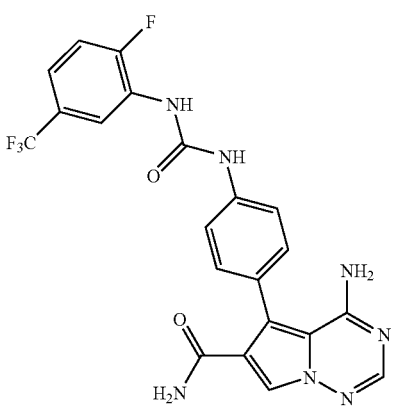

The procedure used for the preparation of Example 73 was used to prepare the title compound by substituting Intermediate Q for Intermediate X and by substituting phenyl[2-fluoro-5-(trifluoromethyl)phenyl]carbamate for phenyl (4-tert-butylpyridin-2-yl)carbamate. ¹H-NMR (CD₃OD) δ 8.61 (d, J=7.9 Hz, 1H), 8.23 (s, 1H), 7.99 (s, 1H), 7.66 (d, J=8.7 Hz, 2H), 7.46 (d, J=8.7 Hz, 2H), 7.35 (d, J=8.7 Hz, 2H); MS [M+H]⁺=474.3; LCMS RT=2.89.

Example 105

Preparation of ethyl 4-amino-5-{4-[({[2-chloro-5-(trifluoromethyl)phenyl]amino}carbonyl)amino]phenyl}pyrrolo[2,1-f][1,2,4]triazine-6-carboxylate

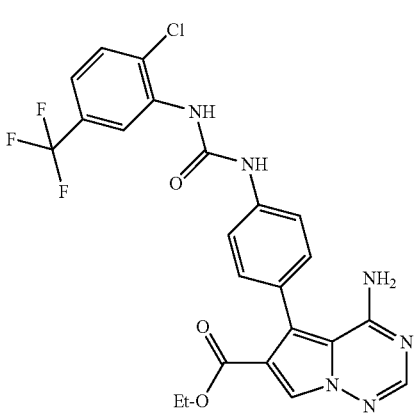

To a solution of DCE (5 mL) was added Intermediate B (300 mg, 1.01 mmol) followed by 2-chloro-1-isocyanato-4-(trifluoromethyl)benzene (0.32 mL, 2.12 mmol). The reaction was stirred under N₂ at rt for 1 h, and then aq 2N HCl (0.50 mL, 1.01 mmol) was added to the reaction followed by DMF (5 mL). The solution was heated for an additional 1 h. Upon cooling to rt the solution was diluted with EtOAc, transferred to a separatory funnel, and washed with aq saturated NaHCO₃. The aq layer was back extracted with EtOAc. The combined organic layers were collected, dried, concentrated, and purified by column chromatography (95:5 v/v CH₂Cl₂-MeOH). The resulting fractions containing product were concentrated and triturated using CH₂Cl₂ and hexanes. The product was filtered and dried in vacuo to afford 408 mg of the above compound as a white solid (0.79 mmol, yield 78%). $^1$H-NMR (DMSO-d₆) δ 9.72 (s, 1H), 8.67 (s, 1H), 8.64 (s, 1H), 8.13 (s, 1H), 8.08 (br s, 1H), 7.93 (s, 1H), 7.72 (d, J=8.5 Hz, 1H), 7.56 (d, J=8.8 Hz, 2H), 7.39 to 7.36 (m, 1H), 7.34 (d, J=8.6 Hz, 2H), 5.10 (br s, 1H), 4.09 (q, J=7.0 Hz, 2H), 1.12 (t, J=7.1 Hz, 3H); MS [M+H]⁺=519; LCMS RT=3.58 min; TLC R$_f$=0.26 (95:5 v/v CH₂Cl₂-MeOH).

Example 106

Preparation of 4-amino-N-(tert-butyl)-5-{4-[({[2-chloro-5-(trifluoromethyl)phenyl]amino}carbonyl)amino]phenyl}pyrrolo[2,1-f][1,2,4]triazine-6-carboxamide

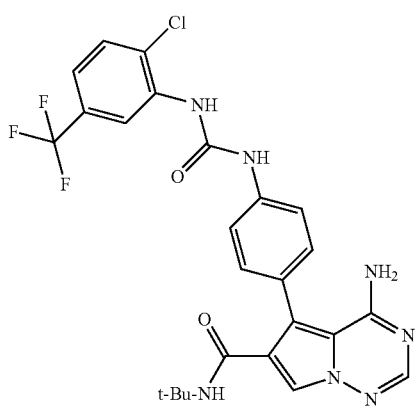

The procedure used for the preparation of Example 105 was used to prepare the title compound by substituting Intermediate L for Intermediate B. $^1$H-NMR (DMSO-d₆) δ 9.74 (s, 1H), 8.67 (s, 1H), 8.64 (d, J=2.4 Hz, 1H), 8.03 (s, 1H), 7.89 (s, 1H), 7.72 (d, J=7.5 Hz, 1H), 7.59 (d, J=8.6 Hz, 2H), 7.39 (s, 1H), 7.36 (d, J=8.7 Hz, 2H), 6.64 (s, 1H), 1.19 (s, 9H); MS [M+H]⁺=546; LCMS RT=3.09 min; TLC R$_f$=0.47 (9:1 v/v CH₂Cl₂-MeOH).

Example 107

Preparation of 4-amino-5-[4-({[(2-fluorophenyl)amino]carbonyl}amino)phenyl]-N-(2-methoxyethyl)pyrrolo[2,1-f][1,2,4]triazine-6-carboxamide

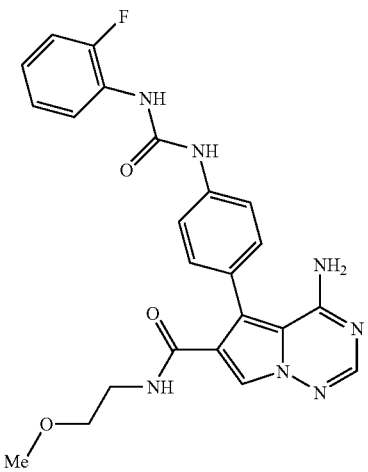

To an EPA vial charged with Intermediate N (50 mg, 0.11 mmol) was added CH₂Cl₂ (2 mL). 1-fluoro-2-isocyanatobenzene (15 mg, 0.11 mmol) was added and stirred at room temperature for 20 min. Then the reaction was heated to 42° C. and shaken at this temperature overnight. A TLC was run 3:7 v/v EtOAc-hexanes and showed that the reaction had consumed nearly all the SM. To the vial was added TFA (100 μL). It was stirred overnight at room temperature. LCMS showed desired product had formed. The sample was concentrated down by GeneVac and DMSO (2 mL) was added. The sample was purified by Prep LCMS to afford 27.3 mg of the above compound (0.059 mmol, yield 58%). $^1$H-NMR (DMSO-d₆) δ 3.2 (s, 3H) 7.0 (m, 1H) 7.2 (t, J=7.3 Hz, 1H) 7.2 (s, 1H) 7.3 (d, J=7.3 Hz, 2H) 7.6 (d, J=7.8 Hz, 3H) 7.6 (s, 2H) 7.9 (s, 1H) 8.2 (m, 3H) 8.6 (s, 1H) 9.2 (s, 1H). MS [M+H]⁺=464; LCMS RT=2.86 min.

Example 108

Preparation of 4-amino-5-[4-({[(3-fluorophenyl)amino]carbonyl}amino)phenyl]-N-(2-methoxyethyl)pyrrolo[2,1-f][1,2,4]triazine-6-carboxamide

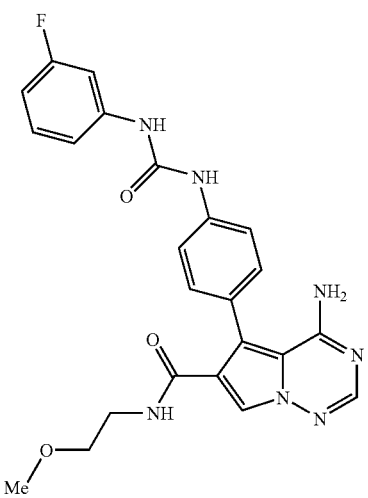

The procedure used for the preparation of Example 107 was used to prepare the title compound by substituting 1-fluoro-3-isocyanatobenzene for 1-fluoro-2-isocyanatobenzene. $^{1}$H-NMR (DMSO-$d_6$) δ 3.2 (d, J=11.2 Hz, 2H) 3.3 (d, J=11.7 Hz, 2H) 3.3 (s, 1H) 6.8 (m, 1H) 7.1 (d, J=7.8 Hz, 1H) 7.3 (d, J=8.8 Hz, 1H) 7.5 (m, 4H) 7.6 (s, 2H) 7.9 (s, 1H) 8.1 (s, 2H) 9.0 (d, J=19.6 Hz, 3H); MS [M+H]$^+$=464; LCMS RT=2.90 min.

Example 109

Preparation of 4-amino-N-(2-methoxyethyl)-5-[4-({[(3-methoxyphenyl)amino]carbonyl}amino)phenyl]pyrrolo[2,1-f][1,2,4]triazine-6-carboxamide

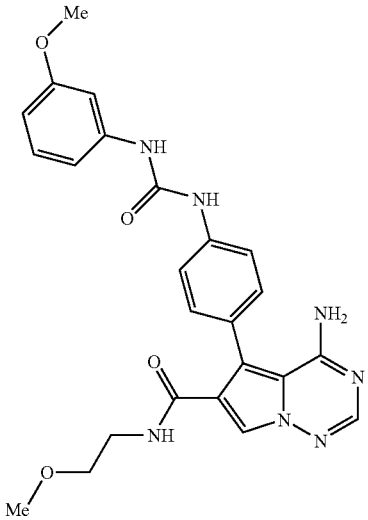

The procedure used for the preparation of Example 107 was used to prepare the title compound by substituting 1-isocyanato-3-methoxybenzene for 1-fluoro-2-isocyanatobenzene. $^{1}$H-NMR (DMSO-$d_6$) δ 3.2 (s, 3H) 3.3 (m, 5H) 6.6 (d, J=7.8 Hz, 1H) 7.0 (d, J=8.3 Hz, 1H) 7.2 (m, 3H) 7.3 (d, J=7.8 Hz, 2H) 7.6 (d, J=7.8 Hz, 3H) 7.6 (s, 1H) 7.9 (s, 1H) 8.1 (s, 2H) 8.8 (s, 1H) 8.9 (s, 1H); MS [M+H]$^+$=476; LCMS RT=2.84 min.

Example 110

Preparation of 4-amino-5-[4-({[(3,4-dichlorophenyl)amino]carbonyl}amino)phenyl]-N-(2-methoxyethyl)pyrrolo[2,1-f][1,2,4]triazine-6-carboxamide

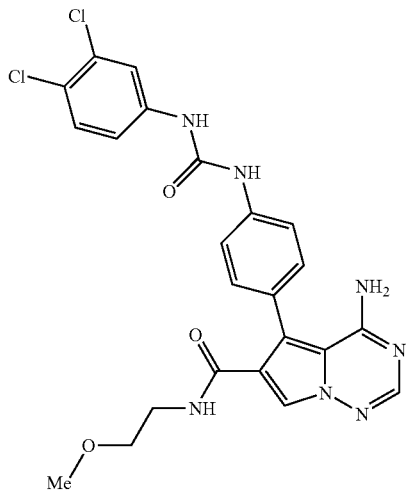

The procedure used for the preparation of Example 107 was used to prepare the title compound by substituting 1,2-dichloro-4-isocyanatobenzene for 1-fluoro-2-isocyanatobenzene. $^{1}$H-NMR (DMSO-$d_6$) δ 3.2 (s, 2H) 3.3 (d, J=11.7 Hz, 2H) 3.3 (s, 1H) 7.3 (m, 4H) 7.5 (t, J=8.3 Hz, 4H) 7.6 (s, 2H) 7.9 (d, J=13.7 Hz, 1H) 8.1 (s, 2H) 9.0 (s, 1H) 9.1 (s, 1H); MS [M+H]$^+$=514; LCMS RT=3.17 min.

Example 111

Preparation of 4-amino-5-[4-({[(3-chlorophenyl)amino]carbonyl}amino)phenyl]-N-(2-methoxyethyl)pyrrolo[2,1-f][1,2,4]triazine-6-carboxamide

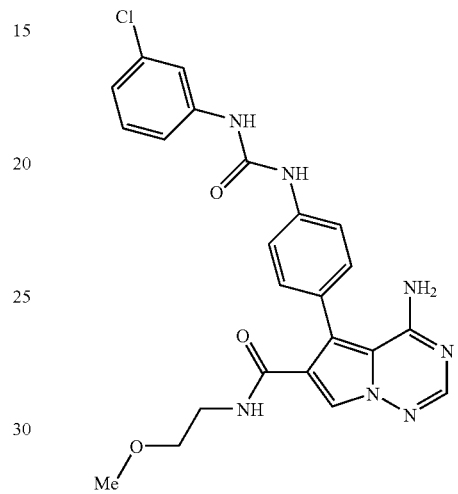

The procedure used for the preparation of Example 107 was used to prepare the title compound by substituting 1-chloro-3-isocyanatobenzene for 1-fluoro-2-isocyanatobenzene. $^{1}$H-NMR (DMSO-$d_6$) δ 3.2 (s, 2H) 3.3 (d, J=11.2 Hz, 3H) 3.3 (s, 2H) 7.0 (d, J=6.4 Hz, 1H) 7.3 (m, 2H) 7.6 (d, J=7.8 Hz, 3H) 7.6 (s, 2H) 7.7 (s, 1H) 7.9 (s, 1H) 8.1 (s, 2H) 9.0 (d, J=4.9 Hz, 3H); MS [M+H]$^+$=480; LCMS RT=3.02 min.

Example 112

Preparation of 4-amino-5-[4-({[(2,3-dichlorophenyl)amino]carbonyl}amino)phenyl]-N-(2-methoxyethyl)pyrrolo[2,1-f][1,2,4]triazine-6-carboxamide

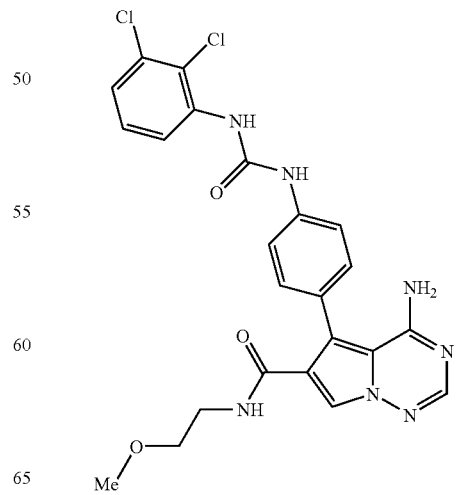

The procedure used for the preparation of Example 107 was used to prepare the title compound by substituting 1,2-dichloro-3-isocyanatobenzene for 1-fluoro-2-isocyanatobenzene. ¹H-NMR (DMSO-d$_6$) δ 3.2 (s, 1H) 3.3 (d, J=5.9 Hz, 2H) 7.3 (s, 2H) 7.3 (d, J=7.8 Hz, 4H) 7.6 (d, J=8.3 Hz, 3H) 7.6 (s, 2H) 7.9 (s, 1H) 8.1 (s, 1H) 8.2 (d, J=8.3 Hz, 1H) 8.5 (s, 1H) 9.7 (s, 1H); MS [M+H]$^+$=514; LCMS RT=3.12 min.

Example 113

Preparation of 4-amino-5-[4-({[(3-bromophenyl)amino]carbonyl}amino)phenyl]-N-(2-methoxyethyl)pyrrolo[2,1-f][1,2,4]triazine-6-carboxamide

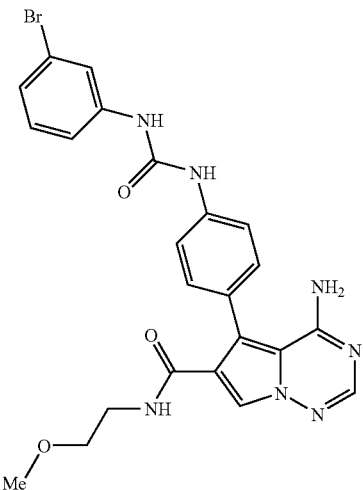

The procedure used for the preparation of Example 107 was used to prepare the title compound by substituting 1-bromo-3-isocyanatobenzene for 1-fluoro-2-isocyanatobenzene. ¹H-NMR (DMSO-d$_6$) δ 3.2 (s, 3H) 3.3 (m, 2H) 7.2 (d, J=7.3 Hz, 1H) 7.3 (t, J=7.8 Hz, 2H) 7.3 (d, J=7.3 Hz, 4H) 7.6 (d, J=8.3 Hz, 3H) 7.6 (s, 1H) 7.9 (s, 1H) 7.9 (s, 1H) 8.1 (s, 1H) 9.0 (s, 3H); MS [M+H]$^+$=524; LCMS RT=3.04 min.

Example 114

Preparation of 4-amino-5-[4-({[(4-fluoro-3-nitrophenyl)amino]carbonyl}amino)phenyl]-N-(2-methoxyethyl)pyrrolo[2,1-f][1,2,4]triazine-6-carboxamide

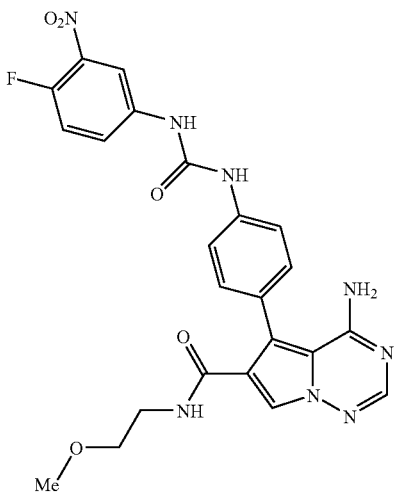

The procedure used for the preparation of Example 107 was used to prepare the title compound by substituting 1-fluoro-4-isocyanato-2-nitrobenzene for 1-fluoro-2-isocyanatobenzene. ¹H-NMR (DMSO-d$_6$) δ 3.2 (s, 3H) 3.3 (m, 2H) 7.3 (d, J=8.3 Hz, 3H) 7.5 (m, 4H) 7.7 (s, 1H) 7.7 (s, 1H) 7.9 (s, 1H) 8.1 (s, 1H) 8.5 (s, 1H) 9.1 (s, 1H) 9.3 (s, 1H); MS [M+H]$^+$=509; LCMS RT=2.93 min.

Example 115

Preparation of 4-amino-N-(2-methoxyethyl)-5-[4-({[(3-nitrophenyl)amino]carbonyl}amino)phenyl]pyrrolo[2,1-f][1,2,4]triazine-6-carboxamide

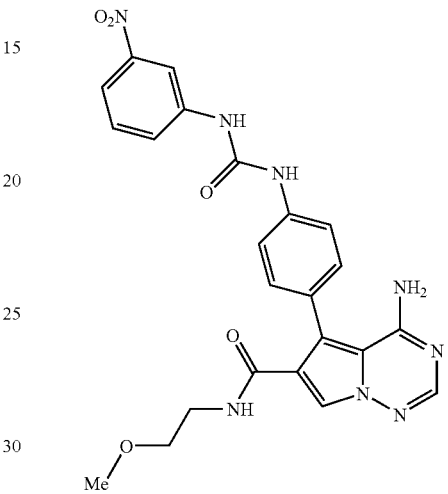

The procedure used for the preparation of Example 107 was used to prepare the title compound by substituting 1-isocyanato-3-nitrobenzene for 1-fluoro-2-isocyanatobenzene. ¹H-NMR (DMSO-d$_6$) δ 3.2 (s, 1H) 3.3 (d, J=4.4 Hz, 1H) 3.3 (s, 1H) 7.3 (d, J=7.8 Hz, 3H) 7.6 (d, J=7.3 Hz, 5H) 7.7 (s, 2H) 7.7 (d, J=7.8 Hz, 2H) 7.8 (d, J=8.3 Hz, 2H) 8.0 (s, 1H) 8.1 (s, 1H) 8.6 (m, 1H) 9.1 (s, 1H) 9.3 (s, 1H); MS [M+H]$^+$=491; LCMS RT=2.92 min.

Example 116

Preparation of 4-amino-5-{4-[({[2-chloro-5-(trifluoromethyl)phenyl]amino}carbonyl)amino]phenyl}-N-(2-methoxyethyl)pyrrolo[2,1-f][1,2,4]triazine-6-carboxamide

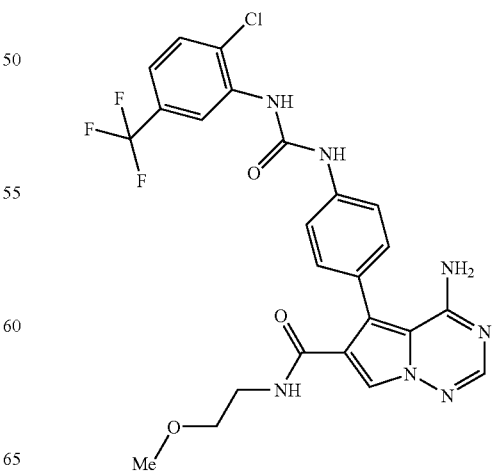

The procedure used for the preparation of Example 107 was used to prepare the title compound by substituting 1-chloro-2-isocyanato-4-(trifluoromethyl)benzene for 1-fluoro-2-isocyanatobenzene. $^1$H-NMR (DMSO-d$_6$) δ 3.2 (s, 2H) 3.3 (d, J=11.7 Hz, 2H) 3.3 (s, 1H) 7.4 (dd, J=16.9, 8.6 Hz, 3H) 7.6 (d, J=7.8 Hz, 3H) 7.7 (s, 2H) 7.7 (d, J=8.3 Hz, 2H) 8.0 (s, 1H) 8.1 (s, 2H) 8.7 (d, J=12.2 Hz, 3H) 9.7 (s, 1H); MS [M+H]$^+$=548; LCMS RT=3.24 min.

Example 117

Preparation of 4-amino-5-{4-[({[4-chloro-3-(trifluoromethyl)phenyl]amino}carbonyl)amino]phenyl}-N-(2-methoxyethyl)pyrrolo[2,1-f][1,2,4]triazine-6-carboxamide

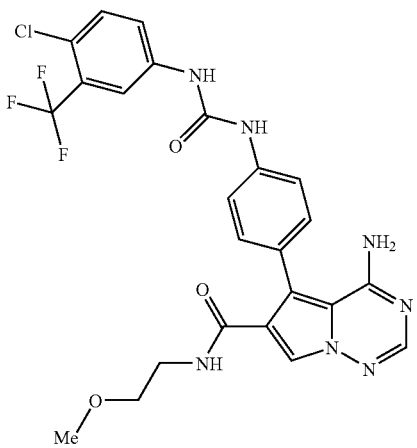

The procedure used for the preparation of Example 107 was used to prepare the title compound by substituting 1-chloro-4-isocyanato-2-(trifluoromethyl)benzene for 1-fluoro-2-isocyanatobenzene. $^1$H-NMR (DMSO-d$_6$) δ 3.2 (s, 1H) 3.3 (m, 2H) 7.3 (d, J=7.3 Hz, 3H) 7.6 (d, J=7.3 Hz, 3H) 7.6 (m, 4H) 7.9 (s, 1H) 8.1 (s, 3H) 9.1 (s, 1H) 9.3 (s, 2H); MS [M+H]$^+$=548; LCMS RT=3.26 min.

Example 118

Preparation of 4-amino-5-[4-({[(2,5-difluorophenyl)amino]carbonyl}amino)phenyl]-N-(2-methoxyethyl)pyrrolo[2,1-f][1,2,4]triazine-6-carboxamide

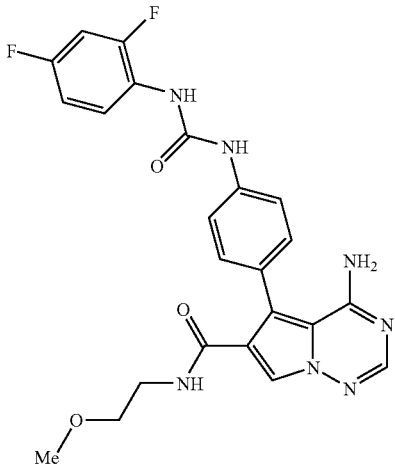

The procedure used for the preparation of Example 107 was used to prepare the title compound by substituting 2,4-difluoro-1-isocyanatobenzene for 1-fluoro-2-isocyanatobenzene. $^1$H-NMR (DMSO-d$_6$) δ H) 6.8 (s, 1H) 7.3 (d, J=7.8 Hz, 3H) 7.6 (d, J=7.8 Hz, 2H) 7.6 (s, 1H) 7.9 (s, 1H) 8.1 (s, 2H) 8.8 (s, 1H) 9.3 (s, 1H); MS [M+H]$^+$=482; LCMS RT=2.97 min.

Example 119

Preparation of 4-amino-5-[4-({[(3,5-dichlorophenyl)amino]carbonyl}amino)phenyl]-N-(2-methoxyethyl)pyrrolo[2,1-f][1,2,4]triazine-6-carboxamide

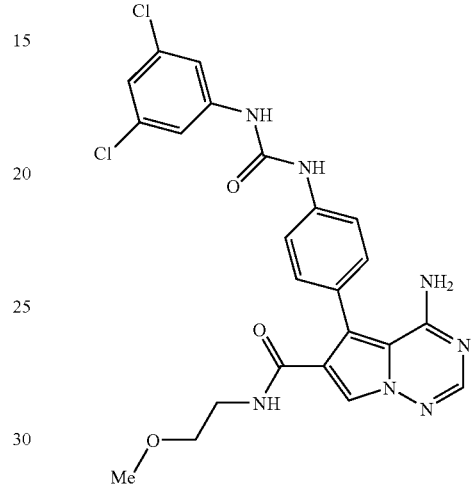

The procedure used for the preparation of Example 107 was used to prepare the title compound by substituting 1,3-dichloro-5-isocyanatobenzene for 1-fluoro-2-isocyanatobenzene. $^1$H-NMR (DMSO-d$_6$) δ 3.2 (s, 3H) 3.3 (d, J=17.1 Hz, 3H) 7.2 (s, 1H) 7.3 (d, J=7.8 Hz, 3H) 7.6 (s, 6H) 7.6 (s, 2H) 8.1 (s, 2H) 9.1 (s, 1H) 9.1 (s, 1H); MS [M+H]$^+$=514; LCMS RT=3.23 min.

Example 120

Preparation of 5-[4-({[(3-acetylphenyl)amino]carbonyl}amino)phenyl]-4-amino-N-(2-methoxyethyl)pyrrolo[2,1-f][1,2,4]triazine-6-carboxamide

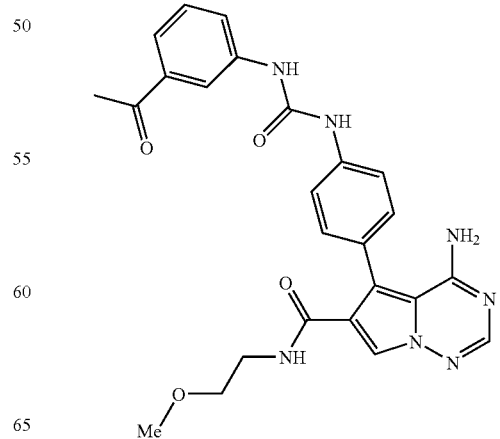

The procedure used for the preparation of Example 107 was used to prepare the title compound by substituting 1-(3-isocyanatophenyl)ethanone for 1-fluoro-2-isocyanatobenzene. ¹H-NMR (DMSO-d₆) δ 3.2 (s, 1H) 3.3 (s, 1H) 3.3 (s, 1H) 7.3 (d, J=7.8 Hz, 3H) 7.5 (t, J=7.6 Hz, 2H) 7.6 (m, 7H) 7.7 (d, J=7.3 Hz, 2H) 8.0 (s, 1H) 8.1 (d, J=15.7 Hz, 3H) 8.9 (s, 2H) 9.0 (s, 1H); MS [M+H]⁺=488; LCMS RT=2.78 min.

Example 121

Preparation of 4-amino-5-{4-[({[2-fluoro-3-(trifluoromethyl)phenyl]amino}carbonyl)amino]phenyl}-N-(2-methoxyethyl)pyrrolo[2,1-f][1,2,4]triazine-6-carboxamide

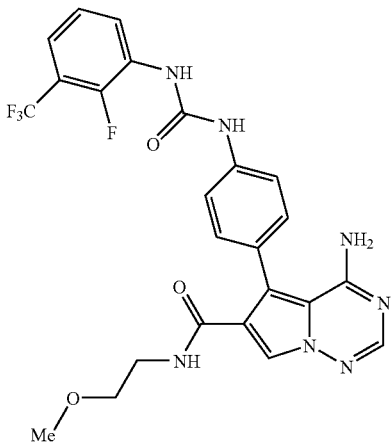

The procedure used for the preparation of Example 107 was used to prepare the title compound by substituting 2-fluoro-1-isocyanato-3-(trifluoromethyl)benzene for 1-fluoro-2-isocyanatobenzene. ¹H-NMR (DMSO-d₆) δ 3.2 (s, 3H) 3.3 (d, J=16.6 Hz, 3H) 7.4 (m, 5H) 7.4 (s, 2H) 7.6 (d, J=7.3 Hz, 4H) 7.6 (s, 2H) 7.9 (s, 1H) 8.1 (s, 2H) 8.5 (s, 2H) 8.9 (s, 1H) 9.3 (s, 2H); MS [M+H]⁺=532; LCMS RT=3.14 min.

Example 122

Preparation of 4-amino-5-{4-[({[4-fluoro-3-(trifluoromethyl)phenyl]amino}carbonyl)amino]phenyl}-N-(2-methoxyethyl)pyrrolo[2,1-f][1,2,4]triazine-6-carboxamide

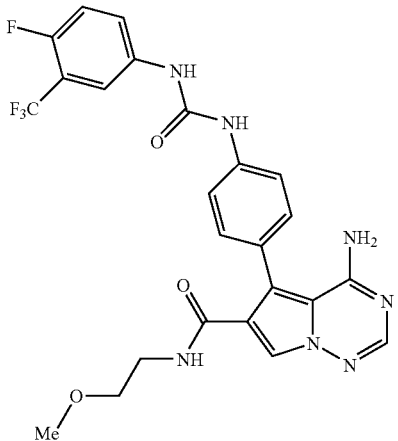

The procedure used for the preparation of Example 107 was used to prepare the title compound by substituting 1-fluoro-4-isocyanato-2-(trifluoromethyl)benzene for 1-fluoro-2-isocyanatobenzene. ¹H-NMR (DMSO-d₆) δ 2.5 (m, 5H) 3.4 (s, 2H) 7.3 (d, J=7.8 Hz, 2H) 7.5 (t, J=9.5 Hz, 1H) 7.6 (d, J=7.8 Hz, 2H) 7.6 (d, J=4.9 Hz, 3H) 7.9 (s, 1H) 8.0 (d, J=4.9 Hz, 1H) 8.1 (s, 1H) 9.0 (s, 1H) 9.1 (s, 1H); MS [M+H]⁺=532; LCMS RT=3.16 min.

Example 123

Preparation of 4-amino-N-(2-methoxyethyl)-5-(4-{[(2-naphthylamino)carbonyl]amino}phenyl)pyrrolo[2,1-f][1,2,4]triazine-6-carboxamide

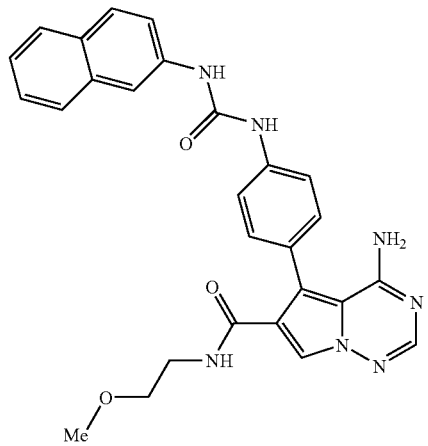

The procedure used for the preparation of Example 107 was used to prepare the title compound by substituting 2-isocyanatonaphthalene for 1-fluoro-2-isocyanatobenzene. ¹H-NMR (DMSO-d₆) δ 3.2 (s, 2H) 3.3 (d, J=14.7 Hz, 2H) 7.4 (m, 4H) 7.5 (t, J=7.3 Hz, 2H) 7.5 (d, J=8.8 Hz, 2H) 7.6 (d, J=8.3 Hz, 5H) 7.8 (m, 4H) 8.1 (s, 3H) 9.0 (s, 3H); MS [M+H]⁺=496; LCMS RT=3.07 min.

Example 124

Preparation of 4-amino-5-[4-({[(3,5-dimethoxyphenyl)amino]carbonyl}amino)phenyl]-N-(2-methoxyethyl)pyrrolo[2,1-f][1,2,4]triazine-6-carboxamide

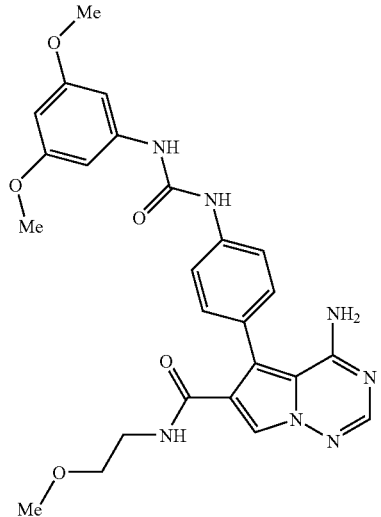

The procedure used for the preparation of Example 107 was used to prepare the title compound by substituting 1-isocyanato-3,5-dimethoxybenzene for 1-fluoro-2-isocyanatobenzene. ¹H-NMR (DMSO-d₆) δ 3.0 (s, 1H) 3.2 (s, 3H) 3.3 (m, 3H) 3.7 (s, 4H) 6.7 (s, 3H) 7.3 (d, J=7.8 Hz, 3H) 7.5 (d, J=7.8 Hz, 3H) 7.6 (s, 2H) 8.1 (s, 2H) 8.7 (s, 2H) 8.8 (s, 1H); MS [M+H]⁺=506; LCMS RT=2.88 min.

Example 125

Preparation of 4-amino-5-[4-({[(3-chloro-2-methylphenyl)amino]carbonyl}amino)phenyl]-N-(2-methoxyethyl)pyrrolo[2,1-f][1,2,4]triazine-6-carboxamide

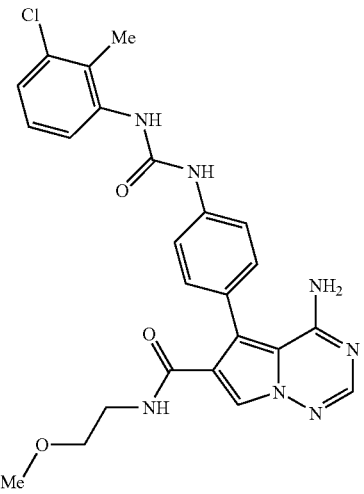

The procedure used for the preparation of Example 107 was used to prepare the title compound by substituting 1-chloro-3-isocyanato-2-methylbenzene for 1-fluoro-2-isocyanatobenzene. ¹H-NMR (DMSO-d₆) δ 2.3 (s, 3H) 2.5 (d, J=16.6 Hz, 9H) 3.5 (s, 1H) 5.2 (s, 1H) 7.2 (m, 2H) 7.3 (d, J=7.3 Hz, 2H) 7.6 (d, J=7.8 Hz, 2H) 7.6 (s, 1H) 7.8 (d, J=6.4 Hz, 1H) 7.9 (s, 1H) 8.1 (s, 1H) 8.2 (s, 1H) 9.2 (s, 1H); MS [M+H]⁺=494; LCMS RT=3.00 min.

Example 126

Preparation of 4-amino-5-[4-({[(2-fluoro-5-nitrophenyl)amino]carbonyl}amino)phenyl]-N-(2-methoxyethyl)pyrrolo[2,1-f][1,2,4]triazine-6-carboxamide

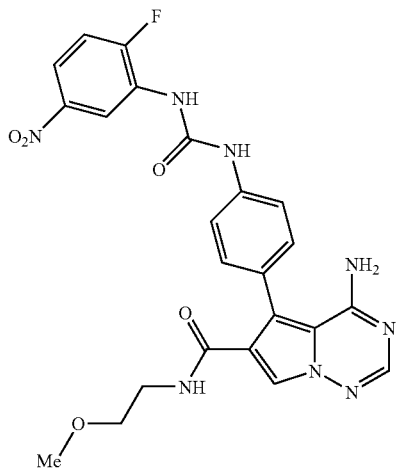

The procedure used for the preparation of Example 107 was used to prepare the title compound by substituting 1-fluoro-2-isocyanato-4-nitrobenzene for 1-fluoro-2-isocyanatobenzene. ¹H-NMR (DMSO-d₆) δ 3.2 (s, 2H) 3.3 (d, J=5.4 Hz, 1H) 3.3 (s, 1H) 7.4 (d, J=8.3 Hz, 3H) 7.6 (t, J=9.0 Hz, 5H) 7.7 (s, 2H) 7.9 (d, J=11.2 Hz, 2H) 8.1 (s, 2H) 9.1 (s, 1H) 9.2 (s, 1H) 9.4 (s, 1H); MS [M+H]⁺=509; LCMS RT=2.95 min.

Example 127

Preparation of 4-amino-5-[4-({[(3,4-difluorophenyl)amino]carbonyl}amino)phenyl]-N-(2-methoxyethyl)pyrrolo[2,1-f][1,2,4]triazine-6-carboxamide

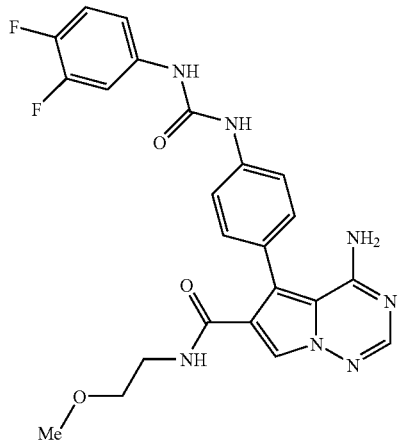

The procedure used for the preparation of Example 107 was used to prepare the title compound by substituting 1,2-difluoro-4-isocyanatobenzene for 1-fluoro-2-isocyanatobenzene. ¹H-NMR (DMSO-d₆) δ 3.2 (s, 3H) 3.3 (m, 3H) 7.1 (d, J=7.8 Hz, 1H) 7.3 (m, 4H) 7.6 (d, J=8.3 Hz, 3H) 7.6 (s, 3H) 7.9 (s, 1H) 8.1 (s, 1H) 9.0 (d, J=11.2 Hz, 3H); MS [M+H]⁺=482; LCMS RT=2.95 min.

Example 128

Preparation of 4-amino-5-[4-({[(3-iodophenyl)amino]carbonyl}amino)phenyl]-N-(2-methoxyethyl)pyrrolo[2,1-f][1,2,4]triazine-6-carboxamide

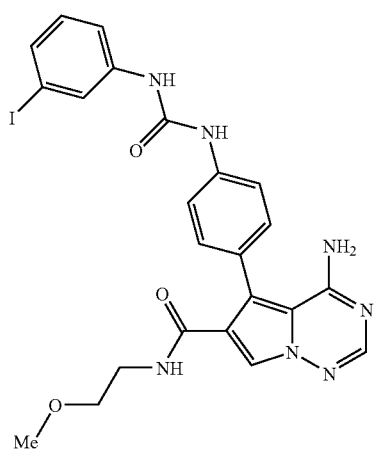

The procedure used for the preparation of Example 107 was used to prepare the title compound by substituting 1-iodo-3-isocyanatobenzene for 1-fluoro-2-isocyanatobenzene. ¹H-NMR (DMSO-d₆) δ 3.2 (s, 4H) 3.3 (m, 1H) 7.1 (t, J=7.6 Hz, 1H) 7.3 (m, 5H) 7.5 (m, 3H) 7.6 (s, 1H) 7.9 (s, 1H) 8.0 (s, 1H) 8.1 (s, 2H) 8.9 (d, J=18.6 Hz, 3H); MS [M+H]⁺=572; LCMS RT=3.09 min.

Example 129

Preparation of 4-amino-N-(2-methoxyethyl)-5-{4-[({[3-(methylthio)phenyl]amino}carbonyl)amino]phenyl}pyrrolo[2,1-f][1,2,4]triazine-6-carboxamide

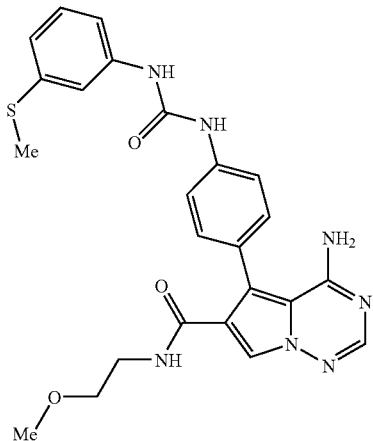

The procedure used for the preparation of Example 107 was used to prepare the title compound by substituting 1-isocyanato-3-(methylthio)benzene for 1-fluoro-2-isocyanatobenzene. ¹H-NMR (DMSO-d₆) δ 3.2 (s, 3H) 3.3 (m, 3H) 6.9 (d, J=7.3 Hz, 1H) 7.2 (m, 3H) 7.3 (d, J=7.3 Hz, 3H) 7.5 (s, 2H) 7.6 (d, J=7.8 Hz, 3H) 7.6 (s, 2H) 7.9 (s, 1H) 8.1 (s, 2H) 8.8 (s, 1H) 8.9 (s, 2H); MS [M+H]⁺=492; LCMS RT=2.97 min.

Example 130

Preparation of methyl 3-[({[4-(4-amino-6-{[(2-methoxyethyl)amino]carbonyl}pyrrolo[2,1-f][1,2,4]triazin-5-yl)phenyl]amino}carbonyl)amino]benzoate

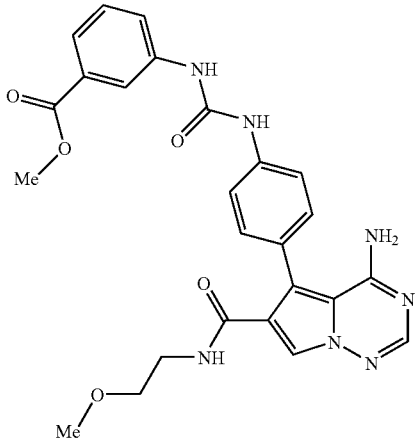

The procedure used for the preparation of Example 107 was used to prepare the title compound by substituting methyl 3-isocyanatobenzoate for 1-fluoro-2-isocyanatobenzene. ¹H-NMR (DMSO-d₆) δ 3.2 (s, 3H) 3.3 (m, 2H) 3.9 (s, 2H) 7.3 (d, J=7.8 Hz, 3H) 7.4 (t, J=7.6 Hz, 1H) 7.6 (d, J=7.8 Hz, 4H) 7.6 (m, 3H) 7.9 (s, 1H) 8.1 (s, 2H) 8.2 (s, 1H) 8.9 (s, 1H) 9.0 (s, 1H); MS [M+H]⁺=504; LCMS RT=2.87 min.

Example 131

Preparation of 4-amino-N-(2-methoxyethyl)-5-(4-{[({3-[(trifluoromethyl)thio]phenyl}amino)carbonyl]amino}phenyl)pyrrolo[2,1-f][1,2,4]triazine-6-carboxamide

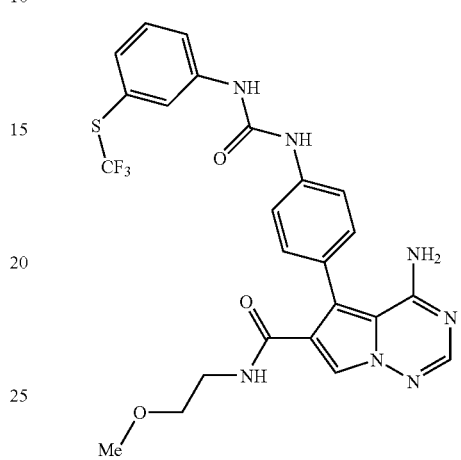

The procedure used for the preparation of Example 107 was used to prepare the title compound by substituting 1-isocyanato-3-[(trifluoromethyl)thio]benzene for 1-fluoro-2-isocyanatobenzene. ¹H-NMR (DMSO-d₆) δ 2.5 (d, J=16.1 Hz, 9H) 5.2 (s, 1H) 7.3 (d, J=7.3 Hz, 3H) 7.5 (t, J=7.6 Hz, 1H) 7.6 (d, J=6.4 Hz, 3H) 7.6 (s, 1H) 7.9 (s, 1H) 8.0 (s, 1H) 8.1 (s, 1H) 9.0 (s, 1H) 9.1 (s, 1H); MS [M+H]⁺=546; LCMS RT=3.26 min.

Example 132

Preparation of 4-amino-5-{4-[({[3-fluoro-5-(trifluoromethyl)phenyl]amino}carbonyl)amino]phenyl}-N-(2-methoxyethyl)pyrrolo[2,1-f][1,2,4]triazine-6-carboxamide

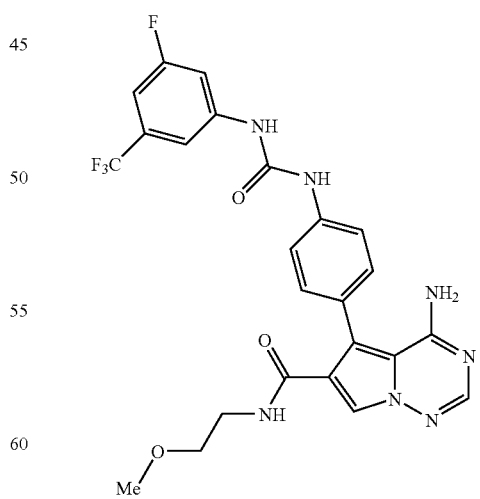

The procedure used for the preparation of Example 107 was used to prepare the title compound by substituting 1-fluoro-3-isocyanato-5-(trifluoromethyl)benzene for 1-fluoro-2-isocyanatobenzene. ¹H-NMR (DMSO-d₆) δ 3.5

(s, 3H) 7.2 (s, 2H) 7.3 (d, J=8.3 Hz, 4H) 7.6 (s, 2H) 7.6 (s, 4H) 7.7 (s, 2H) 8.1 (s, 2H) 9.1 (s, 2H) 9.3 (s, 2H); MS [M+H]$^+$=532; LCMS RT=3.22 min.

Example 133

Preparation of 4-amino-N-(2-methoxyethyl)-5-[4-({[(3-phenoxyphenyl)amino]carbonyl}amino)phenyl]pyrrolo[2,1-f][1,2,4]triazine-6-carboxamide

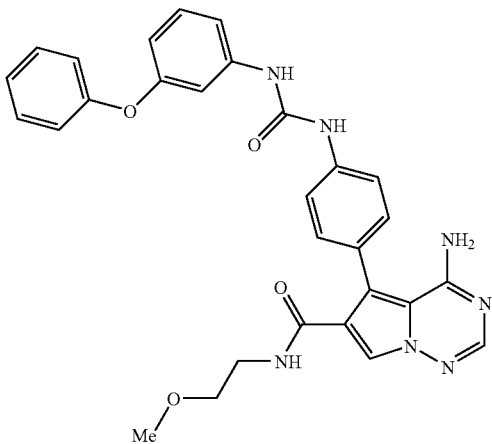

The procedure used for the preparation of Example 107 was used to prepare the title compound by substituting 1-isocyanato-3-phenoxybenzene for 1-fluoro-2-isocyanatobenzene. $^1$H-NMR (DMSO-d$_6$) δ 3.2 (s, 2H) 3.5 (s 2H) 6.6 (s, 1H) 7.0 (d, J=7.8 Hz, 2H) 7.2 (s, 3H) 7.3 (s, 2H) 7.3 (d, J=7.8 Hz, 5H) 7.4 (s, 3H) 7.5 (s, 1H) 7.6 (s, 1H) 7.9 (s, 1H) 8.1 (s, 1H) 8.8 (d, J=15.7 Hz, 3H); MS [M+H]$^+$=538; LCMS RT=3.22 min.

Example 134

Preparation of 4-amino-5-(4-{[(1,3-benzodioxol-5-ylamino)carbonyl]amino}phenyl)-N-(2-methoxyethyl)pyrrolo[2,1-f][1,2,4]triazine-6-carboxamide

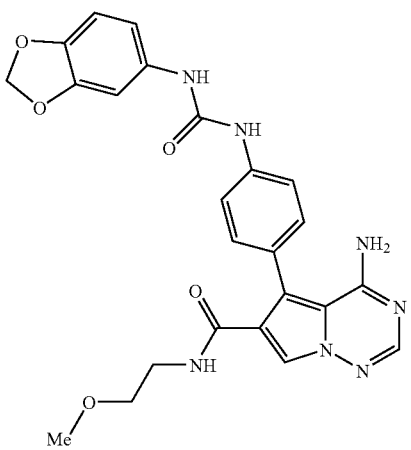

The procedure used for the preparation of Example 107 was used to prepare the title compound by substituting 5-isocyanato-1,3-benzodioxole for 1-fluoro-2-isocyanatobenzene. $^1$H-NMR (DMSO-d$_6$) δ 3.2 (s, 2H) 6.0 (s, 5H) 6.8 (s, 2H) 7.2 (s, 2H) 7.3 (d, J=7.3 Hz, 5H) 7.5 (s, 2H) 8.1 (s, 2H) 8.6 (s, 2H) 8.8 (s, 2H); MS [M+H]$^+$=490; LCMS RT=2.78 min.

Example 135

Preparation of 4-amino-5-[4-({[(3-fluorobenzyl)amino]carbonyl}amino)phenyl]-N-(2-methoxyethyl)pyrrolo[2,1-f][1,2,4]triazine-6-carboxamide

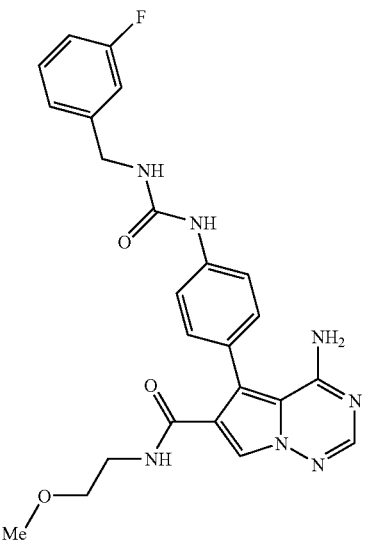

The procedure used for the preparation of Example 107 was used to prepare the title compound by substituting 1-fluoro-3-(isocyanatomethyl)benzene for 1-fluoro-2-isocyanatobenzene. $^1$H-NMR (DMSO-d$_6$) δ 4.3 (s, 3H) 6.8 (s, 2H) 7.1 (s, 1H) 7.1 (s, 4H) 7.3 (s, 4H) 7.4 (s, 1H) 7.5 (s, 4H) 7.9 (s, 1H) 8.1 (s, 2H) 8.8 (s, 2H); MS [M+H]$^+$=478; LCMS RT=2.82 min.

Example 136

Preparation of 4-amino-5-(4-{[(2,3-dihydro-1,4-benzodioxin-6-ylamino)carbonyl]amino}phenyl)-N-(2-methoxyethyl)pyrrolo[2,1-f][1,2,4]triazine-6-carboxamide

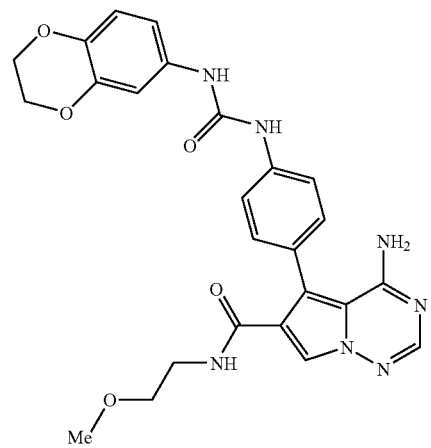

The procedure used for the preparation of Example 107 was used to prepare the title compound by substituting 6-isocyanato-2,3-dihydro-1,4-benzodioxine for 1-fluoro-2-isocyanatobenzene. ¹H-NMR (DMSO-d₆) δ 3.0 (s, 3H) 3.2 (s, 2H) 3.5 (s, 2H) 6.8 (s, 2H) 7.1 (s, 1H) 7.3 (d, J=7.3 Hz, 4H) 7.5 (s, 4H) 7.9 (s, 1H) 8.1 (s, 2H) 8.5 (s, 2H) 8.8 (s, 2H); MS [M+H]⁺=504; LCMS RT=2.78 min.

Example 137

Preparation of 4-amino-N-(2-methoxyethyl)-5-(4-{[(3-thienylamino)carbonyl]amino}phenyl)pyrrolo[2,1-f][1,2,4]triazine-6-carboxamide

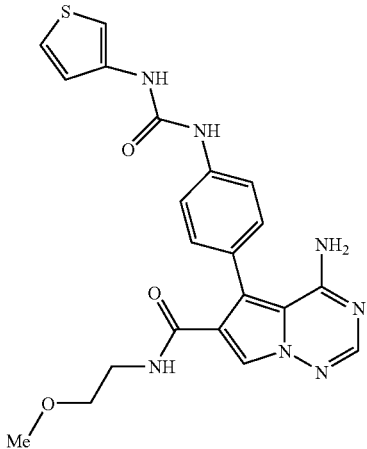

The procedure used for the preparation of Example 107 was used to prepare the title compound by substituting 3-isocyanatothiophene for 1-fluoro-2-isocyanatobenzene. ¹H-NMR (DMSO-d₆) δ 3.0 (s, 4H) 7.3 (s, 5H) 7.6 (s, 3H) 7.9 (s, 2H) 8.1 (s, 3H) 8.8 (s, 2H) 9.0 (s, 2H); MS [M+H]⁺=452; LCMS RT=2.77 min.

Example 138

Preparation of 4-amino-5-[4-({[(2-fluorobenzyl)amino]carbonyl}amino)phenyl]-N-(2-methoxyethyl)pyrrolo[2,1-f][1,2,4]triazine-6-carboxamide

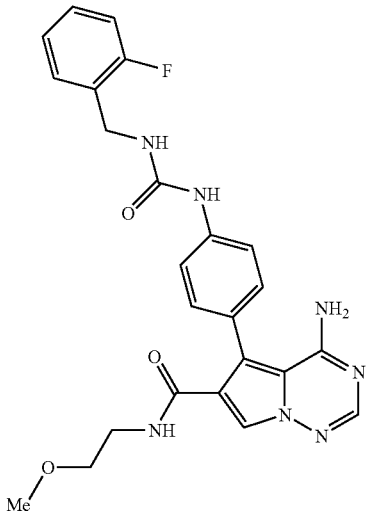

The procedure used for the preparation of Example 107 was used to prepare the title compound by substituting 1-fluoro-2-(isocyanatomethyl)benzene for 1-fluoro-2-isocyanatobenzene. ¹H-NMR (DMSO-d₆) δ 3.5 (s, 4H) 4.4 (s, 3H) 7.3 (d, J=7.8 Hz, 9H) 7.4 (s, 2H) 7.5 (s, 1H) 8.1 (s, 1H) 8.8 (s, 2H); MS [M+H]⁺=478; LCMS RT=2.82 min.

Example 139

Preparation of 4-amino-N-(2,2,2-trifluoroethyl)-5-{4-[({[6-(trifluoromethyl)pyridin-2-yl]amino}carbonyl)amino]phenyl}pyrrolo[2,1-f][1,2,4]triazine-6-carboxamide

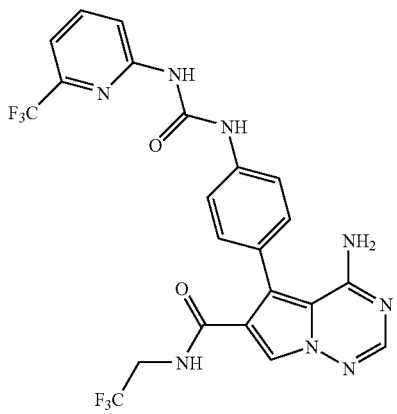

The procedure used for the preparation of Example 73 was used to prepare the title compound by substituting Intermediate M for Intermediate X and by substituting phenyl[6-(trifluoromethyl)pyridin-2-yl]carbamate for phenyl (4-tert-butylpyridin-2-yl)carbamate. ¹H-NMR (CD₃OD) δ 8.05 (s, 1H), 7.97 (s, 1H), 7.85 (s, 1H), 7.67 (d, J=8.7 Hz, 2H), 7.56 (d, J=8.7 Hz, 1H), 7.46 to 7.41 (m, 3H), 3.94 (q, J=8.9 Hz, 2H); MS [M+H]⁺=539.0; LCMS RT=2.71.

Example 140

Preparation of 4-amino-N-(2,2,2-trifluoroethyl)-5-{4-[({[2-(trifluoromethyl)pyridin-4-yl]amino}carbonyl)amino]phenyl}pyrrolo[2,1-f][1,2,4]triazine-6-carboxamide

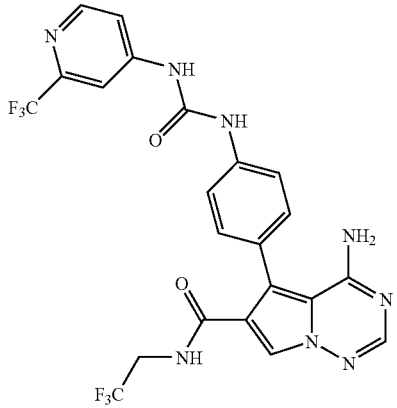

The procedure used for the preparation of Example 73 was used to prepare the title compound by substituting Intermediate M for Intermediate X and by substituting phenyl[2-(trifluoromethyl)pyridin-4-yl]carbamate for phenyl (4-tert-butylpyridin-2-yl)carbamate. ¹H-NMR (CD₃OD) δ 8.47 (d, J=5.9 Hz, 1H), 8.04 (s, 1H), 8.03 (d, J=2.9 Hz, 1H), 7.85 (s, 1H), 7.66 (dd, J=5.4, 1.9 Hz, 1H), 7.62 (d, J=8.9 Hz, 2H), 7.41 (d, J=8.8 Hz, 2H), 3.94 (q, J=9.2 Hz, 2H); MS [M+H]⁺=539.0; LCMS RT=2.56.

Example 141

Preparation of 4-amino-N-(tert-butyl)-5-{4-[({[3-fluoro-5-(trifluoromethyl)phenyl]amino}carbonyl)amino]phenyl}pyrrolo[2,1-f][1,2,4]triazine-6-carboxamide

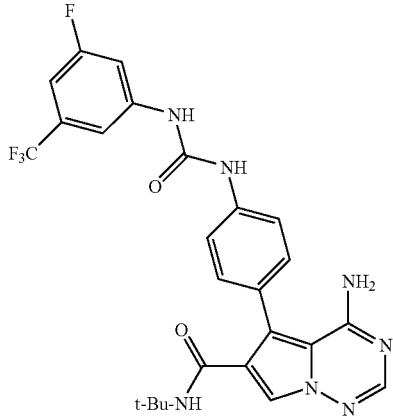

The procedure used for the preparation of Example 105 was used to prepare the title compound by substituting Intermediate L for Intermediate B and by substituting 1-fluoro-3-isocyanato-5-(trifluoromethyl)benzene for 1-chloro-2-isocyanato-4-(trifluoromethyl)benzene. ¹H-NMR (DMSO-d₆) δ 9.34 (s, 1H), 9.14 (s, 1H), 8.03 (s, 1H), 7.88 (s, 1H), 7.72 to 7.70 (m, 1H), 7.65 to 7.62 (m, 1H), 7.61 to 7.57 (m, 2H), 7.35 to 7.34 (m, 2H), 7.24 to 7.22 (m, 1H), 6.61 (m, 1H), 1.18 (s, 9H); MS [M+H]⁺=530; LCMS RT=3.09 min; TLC R$_f$=0.54 (5:4:1 v/v/v CH₂Cl₂-EtOAc-MeOH).

Example 142

Preparation of 4-amino-N-(tert-butyl)-5-{4-[({[4-(trifluoromethyl)pyridin-2-yl]amino}carbonyl)amino]phenyl}pyrrolo[2,1-f][1,2,4]triazine-6-carboxamide

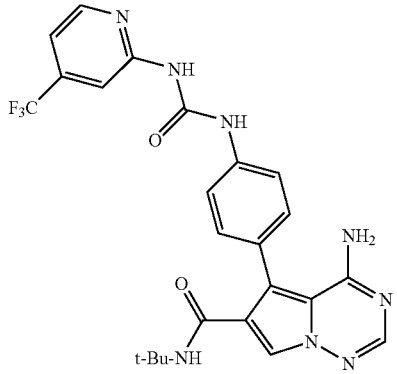

The procedure used for the preparation of Example 73 was used to prepare the title compound by substituting Intermediate L for Intermediate X and by substituting phenyl[4-(trifluoromethyl)pyridin-2-yl]carbamate for phenyl (4-tert-butylpyridin-2-yl)carbamate. ¹H-NMR (DMSO-d₆) δ 9.91 (s, 1H), 9.76 (s, 1H), 8.54 to 8.53 (d, J=5.1 Hz, 1H), 8.06 (s, 1H), 8.03 (s, 1H), 7.89 (s, 1H), 7.64 to 7.62 (d, J=8.6 Hz, 2H), 7.37 to 7.35 (d, J=8.6 Hz, 2H), 6.67 (s, 1H), 1.19 (s, 9H); MS [M+H]⁺=513; LCMS RT=2.84 min; TLC R$_f$=0.37 (5:4:1 v/v/v CH₂Cl₂-EtOAc-MeOH).

Example 143

Preparation of 4-amino-5-{4-[({[2-chloro-5-(trifluoromethyl)phenyl]amino}carbonyl)amino]phenyl}-N-(2-hydroxy-1,1-dimethylethyl)pyrrolo[2,1-f][1,2,4]triazine-6-carboxamide

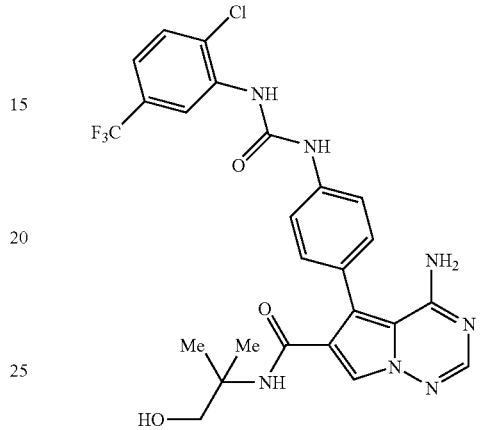

To a solution of DMF (2 mL) was added Intermediate J (50 mg, 0.10 mmol) followed by benzotriazol-1-yloxytris(dimethylamino)phosphonium hexafluorophosphate (45 mg, 0.10 mol), 4-methylmorpholine (0.01 mL, 0.10 mmol), and 2-amino-2-methylpropan-1-ol (0.01 mL, 0.10 mmol). The solution was stirred under N₂ at rt for 17 h. The reaction mixture was evaporated by rotary evaporation and then purified via column chromatography (5:4:1 v/v/v CH₂Cl₂-EtOAc-MeOH) to afford 38 mg of the above compound (0.068 mmol, yield 67%) ¹H-NMR (DMSO-d₆) δ 9.73 (s, 1H), 8.67 (s, 1H), 8.64 (d, J=2.2 Hz, 1H), 8.03 (s, 1H), 7.89 (s, 1H), 7.72 (d, J=8.5 Hz, 1H), 7.59 (d, J=8.6 Hz, 2H), 7.39 to 7.38 (m, 1H), 7.36 (d, J=8.5 Hz, 2H), 6.52 (s, 1H), 4.77 (t, J=5.8 Hz, 1H), 3.29 (d, J=5.9 Hz, 2H), 1.12 (s, 6H); MS [M+H]⁺=562; LCMS RT=3.16 min; TLC R$_f$=0.32 (5:4:1 v/v/v CH₂Cl₂-EtOAc-MeOH).

Example 144

Preparation of ethyl 4-amino-5-{4-[({[6-(trifluoromethyl)pyridin-2-yl]amino}carbonyl)amino]phenyl}pyrrolo[2,1-f][1,2,4]triazine-6-carboxylate

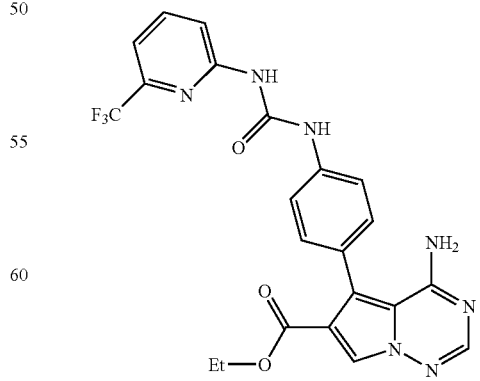

The procedure used for the preparation of Example 73 was used to prepare the title compound by substituting Intermediate B for Intermediate X and by substituting phenyl[6-(trifluoromethyl)pyridin-2-yl]carbamate for phenyl (4-tert-butylpyridin-2-yl)carbamate. ¹H-NMR (DMSO-d₆) δ 9.89 (s, 1H), 9.74 (s, 1H), 8.13 (s, 1H), 8.02 to 7.97 (m, 2H), 7.92 (s, 1H), 7.55 (d, J=9 Hz, 2H), 7.53 to 7.50 (m, 1H), 7.35 (d, J=9 Hz, 2H), 5.12 (bs, 1H), 4.07 (q, J=7 Hz, 2H), 1.09 (t, J=7 Hz, 3H); MS [M+H]⁺=486.0; LCMS RT=2.92 min; TLC R_f=0.38 (3:1 v/v CH₂Cl₂-THF).

Example 145

Preparation of 4-amino-N-(2-fluoro-1,1-dimethylethyl)-5-{4-[({[2-fluoro-5-(trifluoromethyl)phenyl]amino}carbonyl)amino]phenyl}pyrrolo[2,1-f][1,2,4]triazine-6-carboxamide

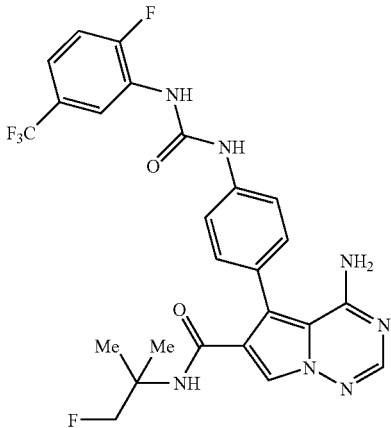

The procedure used for the preparation of Example 69 was used to prepare the title compound by substituting 1-fluoro-2-methylpropan-2-amine for cyclopropanamine. ¹H-NMR (DMSO-d₆) σ 9.20 (bs, 1H), 8.60 (d, J=7 Hz, 1H), 8.07 (s, 1H), 7.89 (s, 1H), 7.57 (d, J=8 Hz, 2H), 7.45 to 7.41 (m, 1H), 7.40 to 7.30 (m, 1H), 7.35 (d, J=8 Hz, 2H), 6.86 (s, 1H), 5.02 (bs, 1H) 4.39 (d, J=24 Hz, 2H), 1.15 (s, 9H); MS [M+H]⁺=548.4; LCMS RT=3.35 min; TLC R_f=0.58 (3:2 v/v CH₂Cl₂-THF).

Example 146

Preparation of 4-amino-5-{4-[({[2-fluoro-5-(trifluoromethyl)phenyl]amino}carbonyl)amino]phenyl}-N-(tetrahydrofuran-2-ylmethyl)pyrrolo[2,1-f][1,2,4]triazine-6-carboxamide

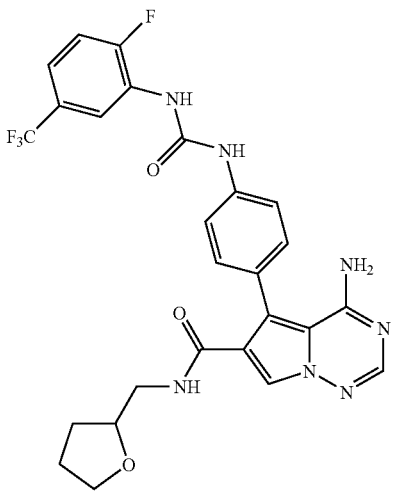

The procedure used for the preparation of Example 69 was used to prepare the title compound by substituting 1-(tetrahydrofuran-2-yl)methanamine for cyclopropanamine. ¹H-NMR (DMSO-d₆) δ 9.32 (s, 1H), 8.94 (d, J=3 Hz, 1H), 8.63 to 8.59 (m. 1H), 8.08 (s, 1H), 7.89 (s, 1H), 7.60 to 7.55 (m, 1H), 7.54 (d, J=8 Hz, 2H), 7.50 to 7.45 (m, 1H), 7.41 to 7.34 (m, 1H), 7.32 (d, J=8 Hz, 2H), 5.01 (bs, 1H), 3.80 to 3.72 (m, 1H) 3.76 to 3.60 (m, 1H), 3.58 to 3.50 (m, 1H), 3.20 to 3.12 (m, 1H), 1.80 to 1.69 (m, 1H); MS [M+H]⁺=558.3; LCMS RT=3.13 min; TLC R_f=0.29 (3:2 v/v CH₂Cl₂-THF).

Example 147

Preparation of 4-amino-5-{4-[({[2-chloro-5-(trifluoromethyl)phenyl]amino}carbonyl)amino]phenyl}-N-(2,2,2-trifluoroethyl)pyrrolo[2,1-f][1,2,4]triazine-6-carboxamide

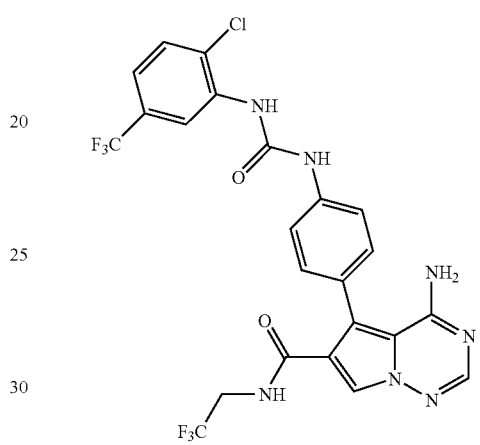

The procedure used for the preparation of Example 143 was used to prepare the title compound by substituting 2,2,2-trifluoroethanamine for 2-amino-2-methylpropan-1-ol. ¹H-NMR (DMSO-d₆) δ 9.70 (s, 1H), 8.67 (s, 1H), 8.64 (s, 1H), 8.52 (t, J=6.2 Hz, 1H), 8.19 (s, 1H), 7.92 (s, 1H), 7.72 (d, J=8.3 Hz, 1H), 7.54 (d, J=8.7 Hz, 2H), 7.39 to 7.36 (m, 1H), 7.30 (d, J=8.5 Hz, 2H), 3.98 to 3.91 (m, 2H); MS [M+H]⁺=573; LCMS RT=3.11 min; TLC R_f=0.43 (5:4:1 v/v/v CH₂Cl₂-EtOAc-MeOH).

Example 148

Preparation of 4-amino-N-(2,2-dimethylpropyl)-5-{4-[({[2-fluoro-5-(trifluoromethyl)phenyl]amino}carbonyl)amino]phenyl}pyrrolo[2,1-f][1,2,4]triazine-6-carboxamide

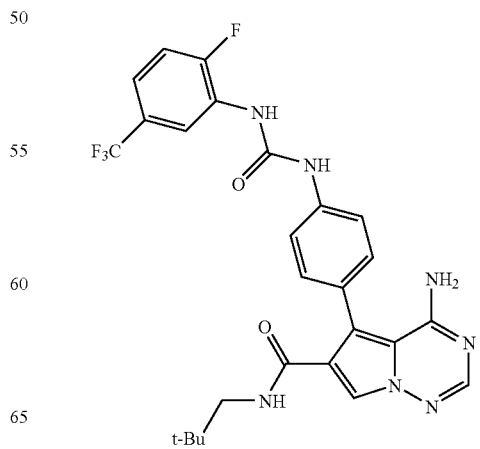

The procedure used for the preparation of Example 69 was used to prepare the title compound by substituting 2,2-dimethylpropan-1-amine for cyclopropanamine. ¹H-NMR (DMSO-d₆) δ 9.33 (s, 1H), 8.94 (d, J=3 Hz, 1H), 8.61 (dd, J=7, 2 Hz, 1H), 8.06 (s, 1H), 7.89 (s, 1H), 7.57 (d, J=9 Hz, 2H), 7.50 to 7.45 (m, 1H), 7.41 to 7.36 (m, 1H), 7.35 (d, J=9 Hz, 2H) 7.26 (t, J=6 Hz, 1H), 5.00 (bs, 1H), 2.91 (d, J=6 Hz, 1H), 0.72 (s, 9H); MS [M+H]⁺=544.5; LCMS RT=3.13 min; TLC R$_f$=0.51 (3:2 v/v CH₂Cl₂-THF).

Example 149

Preparation of 4-amino-5-{4-[({[2-chloro-5-(trifluoromethyl)phenyl]amino}carbonyl)amino]phenyl}-N-(1,1-dimethyl-2-morpholin-4-ylethyl)pyrrolo[2,1-f][1,2,4]triazine-6-carboxamide

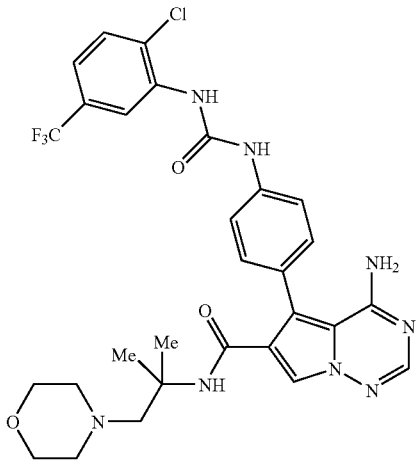

The procedure used for the preparation of Example 66 was used to prepare the title compound by substituting Intermediate AC for Intermediate I. ¹H-NMR (CD₃OD) δ 8.66 (d, J=1.7 Hz, 1H), 7.95 (s, 1H), 7.83 (s, 1H), 7.72 (d, J=8.8 Hz, 2H), 7.62 (d, J=8.7 Hz, 1H), 7.47 (d, J=8.8 Hz, 2H), 7.31 (dd, J=8.5, 2.1 Hz, 1H), 3.62 to 3.53 (m, 4H), 2.44 (s, 2H), 2.42 to 2.34 (m, 4H), 1.18 (s, 6H); MS [M+H]⁺=631.2; LCMS RT=2.84.

Example 150

Preparation of 4-amino-5-{4-[({[2-chloro-5-(trifluoromethyl)phenyl]amino}carbonyl)amino]phenyl}-N-[2-(dimethylamino)-1,1-dimethylethyl]pyrrolo[2,1-f][1,2,4]triazine-6-carboxamide

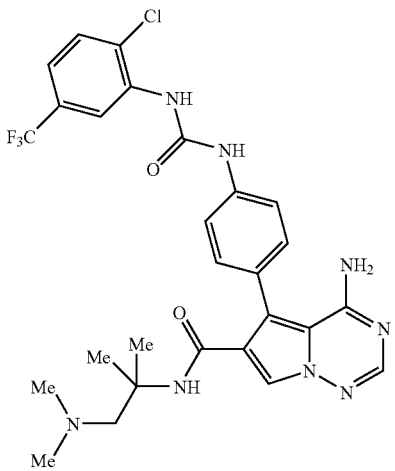

The procedure used for the preparation of Example 66 was used to prepare the title compound by substituting Intermediate AC for Intermediate I and by substituting N-methylmethanamine for morpholine. ¹H-NMR (CD₃OD) δ 8.66 (s, 1H), 8.00 (s, 1H), 7.84 (s, 1H), 7.71 (d, J=8.4 Hz, 2H), 7.63 (d, J=8.7 Hz, 1H), 7.46 (d, J=8.4 Hz, 2H), 7.32 (d, J=8.9 Hz, 1H), 2.27 (s, 2H), 2.04 (s, 6H), 1.13 (s, 6H); MS [M+H]⁺=456.1; MS [M+H]⁺=589.4; LCMS RT=2.50.

Example 151

Preparation of N-[4-(4-amino-6-cyanopyrrolo[2,1-f][1,2,4]triazin-5-yl)phenyl]-N'-[4-fluoro-3-(trifluoromethyl)phenyl]urea

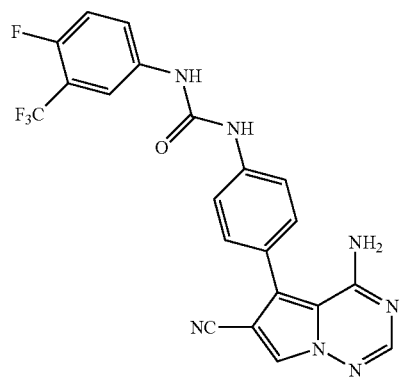

The procedure used for the preparation of Example 73 was used to prepare the title compound by substituting Intermediate P for Intermediate X and by substituting phenyl[4-fluoro-3-(trifluoromethyl)phenyl]carbamate for phenyl (4-tert-butylpyridin-2-yl)carbamate. ¹H-NMR (CD₃OD) δ 8.18 (s, 1H), 7.94 to 7.89 (m, 2H), 7.69 to 7.64 (m, 3H), 7.48 (d, J=8.1 Hz, 2H), 7.26 (t, J=9.9 Hz, 1H); MS [M+H]⁺=456.1; LCMS RT=3.09.

Example 152

Preparation of N-[4-(4-amino-6-cyanopyrrolo[2,1-f][1,2,4]triazin-5-yl)phenyl]-N'-[3-(trifluoromethoxy)phenyl]urea

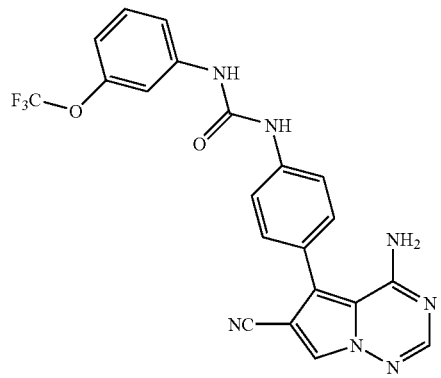

The procedure used for the preparation of Example 73 was used to prepare the title compound by substituting Intermediate P for Intermediate X and by substituting phenyl[3-(trifluoromethoxy)phenyl]carbamate for phenyl (4-tert-butylpyridin-2-yl)carbamate. $^1$H-NMR (CD$_3$OD) δ 8.17 (s, 1H), 7.90 (s, 1H), 7.68 to 7.61 (m, 3H), 7.48 (d, J=8.1 Hz, 2H), 7.40 to 7.29 (m, 2H), 6.91 (d, J=8.0 Hz, 1H); MS [M+H]$^+$=454.1; LCMS RT=3.11.

Example 153

Preparation of N-[4-(4-amino-6-cyanopyrrolo[2,1-f][1,2,4]triazin-5-yl)phenyl]-N'-[2-(trifluoromethyl)pyridin-4-yl]urea

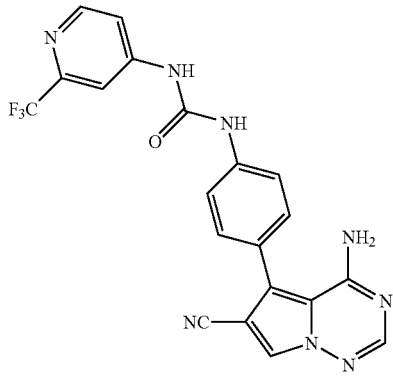

The procedure used for the preparation of Example 73 was used to prepare the title compound by substituting Intermediate P for Intermediate X and by substituting phenyl[2-(trifluoromethyl)pyridin-4-yl]carbamate for phenyl (4-tert-butylpyridin-2-yl)carbamate. $^1$H-NMR (CD$_3$OD) δ 8.47 (d, J=6.1 Hz, 1H), 8.18 (s, 1H), 8.05 (d, J=2.2 Hz, 1H), 7.09 (s, 1H), 7.71 to 7.64 (m, 3H), 7.50 (d, J=8.1 Hz, 2H); MS [M+H]$^+$=439.0; LCMS RT=2.72.

Example 154

Preparation of N-[4-(4-amino-6-cyanopyrrolo[2,1-f][1,2,4]triazin-5-yl)phenyl]-N'-(3-tert-butyl-1-methyl-1H-pyrazol-5-yl)urea

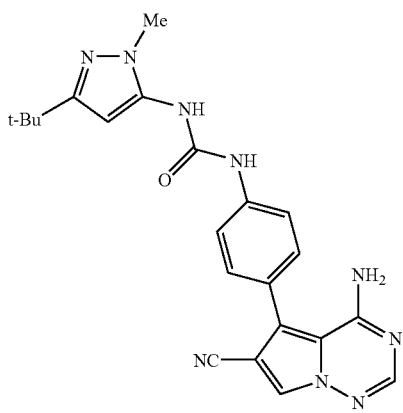

The procedure used for the preparation of Example 73 was used to prepare the title compound by substituting Intermediate P for Intermediate X and by substituting phenyl (3-tert-butyl-1-methyl-1H-pyrazol-5-yl)carbamate for phenyl (4-tert-butylpyridin-2-yl)carbamate. $^1$H-NMR (CD$_3$OD) δ 8.18 (s, 1H), 7.90 (s, 1H), 7.65 (d, J=8.0 Hz, 2H), 7.47 (d, J=8.0 Hz, 2H), 7.17 (m 1H), 7.11 (m, 1H), 6.13 (s, 1H), 3.71 (s, 3H), 1.28 (s, 9H); MS [M+H]$^+$=430.1; LCMS RT=2.56.

Example 155

Preparation of N-{4-[4-amino-6-(1,3-oxazol-5-yl)pyrrolo[2,1-f][1,2,4]triazin-5-yl]phenyl}-N'-[2-fluoro-5-(trifluoromethyl)phenyl]urea

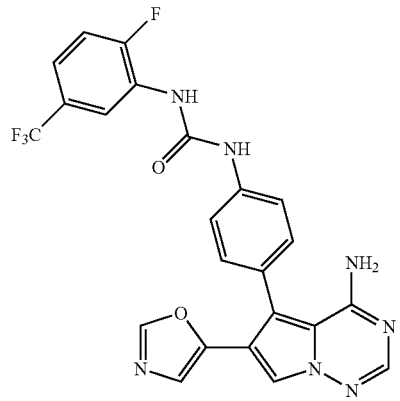

The procedure used for the preparation of Example 73 was used to prepare the title compound by substituting Intermediate AB for Intermediate X and by substituting phenyl[2-fluoro-5-(trifluoromethyl)phenyl]carbamate for phenyl (4-tert-butylpyridin-2-yl)carbamate. $^1$H-NMR (CD$_3$OD) δ 8.63 (d, J=6.8 Hz, 1H), 8.13 (s, 1H), 7.98 (s, 1H), 7.83 (s, 1H), 7.69 (d, J=8.5 Hz, 2H), 7.42 (d, J=8.4 Hz, 2H), 7.35 (d, J=8.3 Hz, 2H), 6.49 (s, 1H); MS [M+H]$^+$=498.1; LCMS RT=2.82.

Example 156

Preparation of N-{4-[4-amino-6-(1,3-oxazol-5-yl)pyrrolo[2,1-f][1,2,4]triazin-5-yl]phenyl}-N'-[4-(trifluoromethyl)pyridin-2-yl]urea

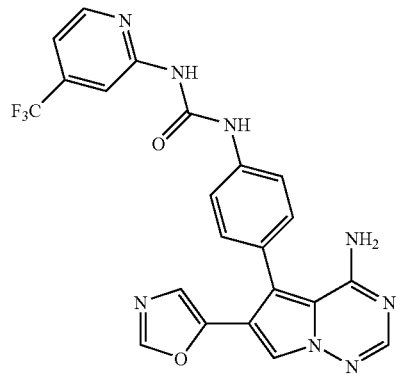

The procedure used for the preparation of Example 73 was used to prepare the title compound by substituting Intermediate AB for Intermediate X and by substituting phenyl[4-(trifluoromethyl)pyridin-2-yl]carbamate for phenyl (4-tert-butylpyridin-2-yl)carbamate. $^1$H-NMR (CD$_3$OD) δ 8.50 (d, J=5.3 Hz, 1H), 8.12 (s, 1H), 7.98 (s, 1H), 7.84 (s, 1H), 7.77 (s, 1H), 7.76 (d, J=8.1 Hz, 2H), 7.45 (d, J=8.0 Hz, 2H), 7.29 (d, J=6.3 Hz, 1H), 6.51 (s, 1H); MS [M+H]$^+$=481.0; LCMS RT=2.70.

Example 157

Preparation of N-(4-{4-amino-6-[(2-methoxyethoxy)methyl]pyrrolo[2,1-f][1,2,4]triazin-5-yl}phenyl)-N'-[2-fluoro-5-(trifluoromethyl)phenyl]urea

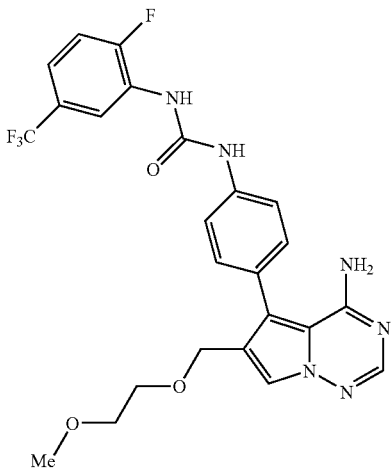

The procedure used for the preparation of Example 73 was used to prepare the title compound by substituting Intermediate Z for Intermediate X and by substituting phenyl[2-fluoro-5-(trifluoromethyl)phenyl]carbamate for phenyl (4-tert-butylpyridin-2-yl)carbamate. $^1$H-NMR (CD$_3$OD) δ 8.62 (d, J=8.0 Hz, 1H), 7.79 (s, 1H), 7.71 (s, 1H), 7.62 (d, J=8.1, 2H), 7.44 (d, J=8.2 Hz, 2H), 7.34 (d, J=9.0 Hz, 2H), 4.45 (s, 2H), 3.59 to 3.48 (m, 4H), 3.33 (s, 3H); MS [M+H]$^+$=519.2; LCMS RT=3.13.

Example 158

Preparation of N-(4-{4-amino-6-[(2,2,2-trifluoroethoxy)methyl]pyrrolo[2,1-f][1,2,4]triazin-5-yl}phenyl)-N'-[2-fluoro-5-(trifluoromethyl)phenyl]urea

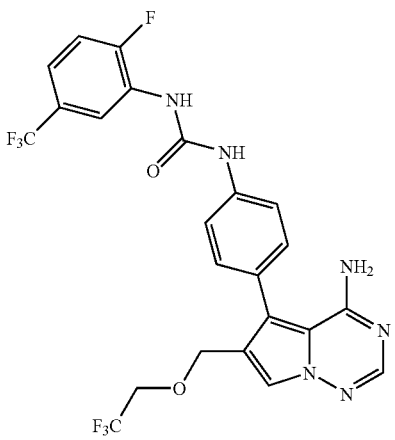

The procedure used for the preparation of Example 73 was used to prepare the title compound by substituting Intermediate AA for Intermediate X and by substituting phenyl[2-fluoro-5-(trifluoromethyl)phenyl]carbamate for phenyl (4-tert-butylpyridin-2-yl)carbamate. $^1$H-NMR (CD$_3$OD) δ 8.53 (d, J=6.7 Hz, 1H), 7.70 (s, 1H), 7.63 (s, 1H), 7.52 (d, J=8.3, 2H), 7.33 (d, J=8.3 Hz, 2H), 7.24 (d, J=8.3 Hz, 2H), 4.47 (s, 2H), 4.00 (q, J=7.9 Hz, 2H); MS [M+H]$^+$=543.3; LCMS RT=3.10.

Example 159

Preparation of N-{4-[4-amino-6-(1,3-oxazol-5-yl)pyrrolo[2,1-f][1,2,4]triazin-5-yl]phenyl}-N'-[3-fluoro-5-(trifluoromethyl)phenyl]urea

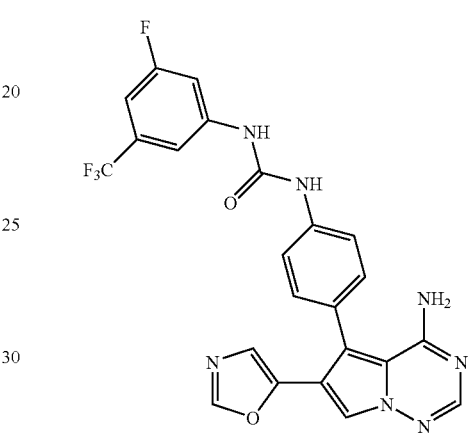

The procedure used for the preparation of Example 73 was used to prepare the title compound by substituting Intermediate AB for Intermediate X and by substituting phenyl[3-fluoro-5-(trifluoromethyl)phenyl]carbamate for phenyl (4-tert-butylpyridin-2-yl)carbamate. $^1$H-NMR (CD$_3$OD) δ 8.12 (s, 1H), 7.97 (s, 1H), 7.83 (s, 1H), 7.71 to 7.60 (m, 4H), 7.42 (d, J=8.2 Hz, 2H), 7.05 (d, J=8.1 Hz, 1H), 6.49 (s, 1H); MS [M+H]$^+$=498.2; LCMS RT=2.90.

Example 160

Preparation of N-(4-{4-amino-6-[(2,2,2-trifluoroethoxy)methyl]pyrrolo[2,1-f][1,2,4]triazin-5-yl}phenyl)-N'-[4-(trifluoromethyl)pyridin-2-yl]urea

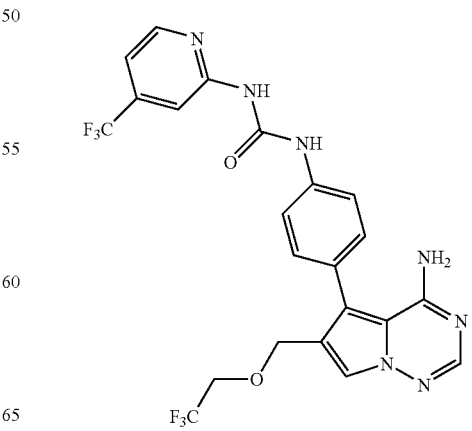

The procedure used for the preparation of Example 73 was used to prepare the title compound by substituting Intermediate AA for Intermediate X and by substituting phenyl[4-(trifluoromethyl)pyridin-2-yl]carbamate for phenyl (4-tert-butylpyridin-2-yl)carbamate. $^1$H-NMR (DMSO-d$_6$) δ 9.90 (s, 1H), 9.75 (s, 1H), 8.53 (d, J=4.7 Hz, 1H), 8.05 (s, 1H), 7.85 (s, 1H), 7.82 (s, 1H), 7.62 (d, J=8.6 Hz, 2H), 7.39 to 7.32 (m, J=8.0 Hz, 3H), 4.49 (s, 2H), 3.97 (q, J=9.1 Hz, 2H); MS [M+H]$^+$=526.0; LCMS RT=2.90.

Example 161

Preparation of N-[4-(4-amino-6-cyanopyrrolo[2,1-f][1,2,4]triazin-5-yl)phenyl]-N'-(3-tert-butylisoxazol-5-yl)urea

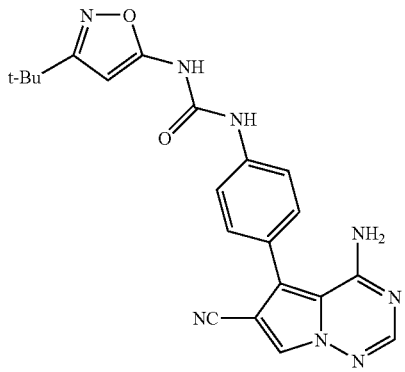

The procedure used for the preparation of Example 73 was used to prepare the title compound by substituting Intermediate P for Intermediate X and by substituting phenyl (3-tert-butylisoxazol-5-yl)carbamate for phenyl (4-tert-butylpyridin-2-yl)carbamate. $^1$H-NMR (CD$_3$OD) δ 8.17 (s, 1H), 7.90 (s, 1H), 7.68 (d, J=7.8 Hz, 2H), 7.48 (d, J=7.8 Hz, 2H), 6.13 (s, 1H), 1.31 (s, 9H); MS [M+H]$^+$=417.1; LCMS RT=2.87.

Example 162

Preparation of N-{4-[4-amino-6-(1,3-oxazol-5-yl)pyrrolo[2,1-f][1,2,4]triazin-5-yl]phenyl}-N'-[4-fluoro-3-(trifluoromethyl)phenyl]urea

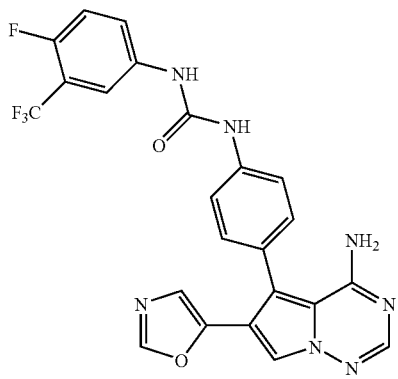

The procedure used for the preparation of Example 73 was used to prepare the title compound by substituting Intermediate AB for Intermediate X and by substituting phenyl[4-fluoro-3-(trifluoromethyl)phenyl]carbamate for phenyl (4-tert-butylpyridin-2-yl)carbamate. $^1$H-NMR (CD$_3$OD) δ 8.12 (s, 1H), 7.97 (s, 1H), 7.92 (dd, J=2.7, 6.2 Hz, 1H), 7.83 (s, 1H), 7.70 to 7.62 (m, 3H), 7.41 (d, J=8.0 Hz, 2H), 7.28 (t, J=9.5 Hz, 1H), 6.49 (s, 1H); MS [M+H]$^+$=498.2; LCMS RT=3.14.

Example 163

Preparation of N-{4-[4-amino-6-(1,3,4-oxadiazol-2-yl)pyrrolo[2,1-f][1,2,4]triazin-5-yl]phenyl}-N'-[2-fluoro-5-(trifluoromethyl)phenyl]urea

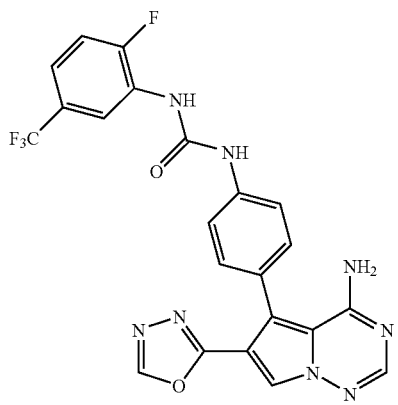

The procedure used for the preparation of Example 73 was used to prepare the title compound by substituting Intermediate AD for Intermediate X and by substituting phenyl[2-fluoro-5-(trifluoromethyl)phenyl]carbamate for phenyl (4-tert-butylpyridin-2-yl)carbamate. $^1$H-NMR (CD$_3$OD) δ 8.80 (s, 1H), 8.62 (d, J=6.7 Hz, 1H), 8.28 (s, 1H), 7.89 (s, 1H), 7.64 (d, J=8.2 Hz, 2H), 7.45 (d, J=8.2 Hz, 2H), 7.34 (d, J=8.9 Hz, 2H); MS [M+H]$^+$=499.2; LCMS RT=2.82.

Example 164

Preparation of 4-amino-N-(tert-butyl)-5-{4-[({[6-(trifluoromethyl)pyridin-2-yl]amino}carbonyl)amino]phenyl}pyrrolo[2,1-f][1,2,4]triazine-6-carboxamide

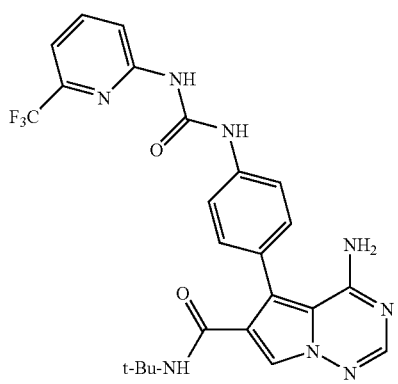

The procedure used for the preparation of Example 73 was used to prepare the title compound by substituting Intermediate L for Intermediate X and by substituting phenyl[6-(trifluoromethyl)pyridin-2-yl]carbamate for phenyl (4-tert-butylpyridin-2-yl)carbamate. $^1$H-NMR (DMSO-$d_6$) δ 9.88 (s, 1H), 9.73 (s, 1H), 8.05 to 7.99 (m, 1H), 8.04 (d, J=8 Hz, h H), 7.88 (s, 1H), 7.55 (d, J=8 Hz, 2H), 7.50 to 7.46 (m, 1H), 7.36 (d, J=8 Hz, 2H), 6.66 (s, 1H), 5.00 (bs, 1H), 1.16 (s, 9H); MS [M+H]$^+$=513.1; LCMS RT=2.84 min; TLC $R_f$=0.64 (3:2 v/v $CH_2Cl_2$-THF).

Example 165

Preparation of 4-amino-N-(2,2-dimethylpropyl)-5-{4-[({[6-(trifluoromethyl)pyridin-2-yl]amino}carbonyl)amino]phenyl}pyrrolo[2,1-f][1,2,4]triazine-6-carboxamide

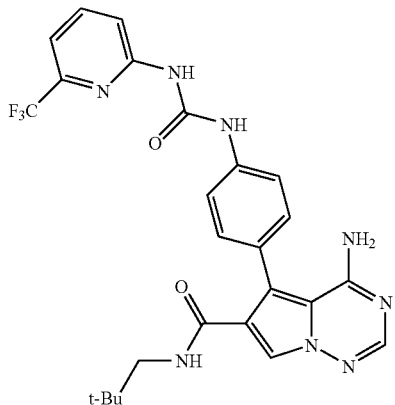

The procedure used for the preparation of Example 73 was used to prepare the title compound by substituting Intermediate AE for Intermediate X and by substituting phenyl[6-(trifluoromethyl)pyridin-2-yl]carbamate for phenyl (4-tert-butylpyridin-2-yl)carbamate. $^1$H-NMR (DMSO-$d_6$) δ 9.87 (s, 1H), 9.77 (s, 1H), 8.07 (s, 1H), 8.06 to 7.81 (m, 3H), 7.89 (s, 1H), 7.54 (d, J=8 Hz, 2H), 7.55 to 7.50 (m, 1H), 7.36 (d, J=8 Hz, 2H), 7.28 to 7.20 (m, 1H), 4.95 (bs, 1H), 2.91 (d, J=6 Hz, 2H), 0.72 (s, 9H); MS [M+H]$^+$=527.1; LCMS RT=2.89 min; TLC $R_f$=0.64 (3:2 v/v $CH_2Cl_2$-THF).

Example 166

Preparation of 1-[4-(4-Amino-6-imidazol-1-ylmethyl-pyrrolo[2,1-f][1,2,4]triazin-5-yl)-phenyl]-3-(2-fluoro-5-trifluoromethyl-phenyl)-urea

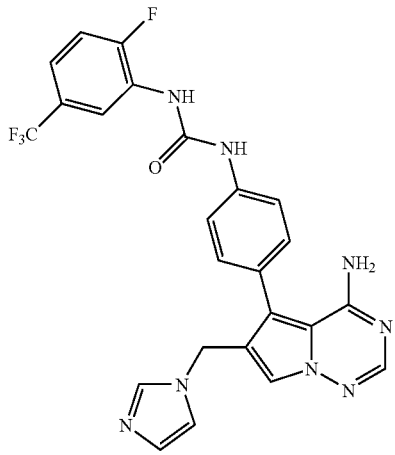

The procedure used for the preparation of Example 73 was used to prepare the title compound by substituting Intermediate AE for Intermediate X and by substituting phenyl[2-fluoro-5-(trifluoromethyl)phenyl]carbamate for phenyl (4-tert-butylpyridin-2-yl)carbamate $^1$H-NMR (CD$_3$OD) δ 8.61 (d, J=7.5 Hz, 1H), 7.80 (s, 1H), 7.72 (s, 1H), 7.61 (d, J=8.6 Hz, 2H), 7.46 (s, 1H), 7.34 (d, J=8.6 Hz, 2H), 7.24 (d, J=8.4 Hz, 2H), 6.93 (d, J=5.1 Hz, 2H), 5.17 (s, 2H); MS [M+H]$^+$=511.3; LCMS RT=2.63 min.

Example 167

Preparation of 4-amino-5-{4-[({[2-fluoro-5-(trifluoromethyl)phenyl]amino}carbonyl)amino]phenyl}-N-(2-methoxyethyl)pyrrolo[2,1-f][1,2,4]triazine-6-carboxamide

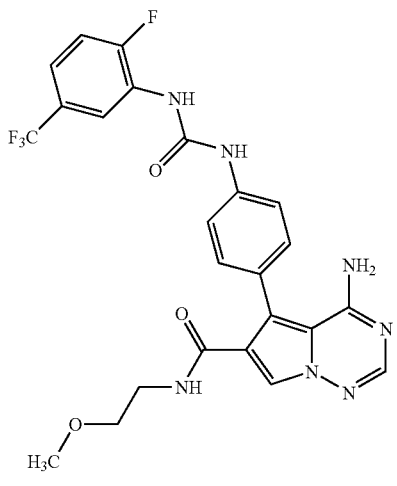

The procedure used for the preparation of Example 69 was used to prepare the title compound by substituting 2-methoxyethanamine for cyclopropanamine. $^1$H-NMR (CD$_3$OD) δ 8.62 (d, J=7.5 Hz, 1H), 8.03 (s, 1H), 7.84 (s, 1H), 7.69 (d, J=9.0 Hz, 2H), 7.45 (d, J=9.0, 2H), 7.35 (d, J=8.8 Hz, 2H), 3.39 to 3.34 (m, 4H), 3.24 (s, 3H); MS [M+H]$^+$=532.1; LCMS RT=3.05 min.

Example 168

Preparation of N-[4-(4-amino-6-cyanopyrrolo[2,1-f][1,2,4]triazin-5-yl)phenyl]-N'-[6-(trifluoromethyl)pyridin-2-yl]urea

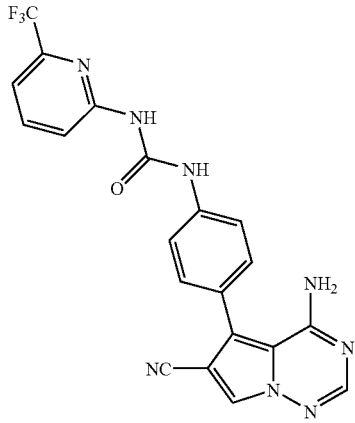

The procedure used for the preparation of Example 73 was used to prepare the title compound by substituting Intermediate P for Intermediate X and by substituting phenyl[6-(trifluoromethyl)pyridin-2-yl]carbamate for phenyl (4-tert-butylpyridin-2-yl)carbamate. $^1$H-NMR (DMSO-d$_6$) δ 9.89 (s, 1H), 9.75 (s, 1H), 8.51 (s, 1H), 8.03 to 7.99 (m, 3H), 7.63 (d, J=8.4, 2H), 7.51 to 7.44 (m, 3H); MS [M+H]$^+$=439; LCMS RT=2.62 min.

Example 169

Preparation of ethyl 3-(4-amino-5-{4-[({[6-(trifluoromethyl)pyridin-2-yl]amino}carbonyl)amino]phenyl}pyrrolo[2,1-f][1,2,4]triazin-6-yl)propanoate

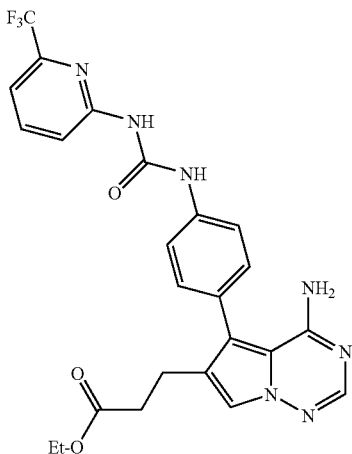

The procedure used for the preparation of Intermediate I was used to prepare the title compound by substituting phenyl [6-(trifluoromethyl)pyridin-2-yl]carbamate for phenyl[2-fluoro-5-(trifluoromethyl)phenyl]carbamate. $^1$H-NMR (DMSO-d$_6$) δ 9.88 (s 1H), 9.73 (s, 1H), 8.05 to 7.98 (m, 3H), 7.79 (s, 1H), 7.61 to 7.57 (m, 3H), 7.51 to 7.49 (m, 1H), 7.33 (d, J=8.7, 2H), 4.03 to 3.97 (m, 2H), 2.74 to 2.70 (m, 2H), 2.55 to 2.51 (m, 2H), 1.15 to 1.11 (m, 3H); MS [M+H]$^+$=514; LCMS RT=2.65 min.

Example 170

Preparation of N-{4-[4-amino-6-(1H-imidazol-1-ylmethyl)pyrrolo[2,1-f][1,2,4]triazin-5-yl]phenyl}-N'-[3-fluoro-5-(trifluoromethyl)phenyl]urea

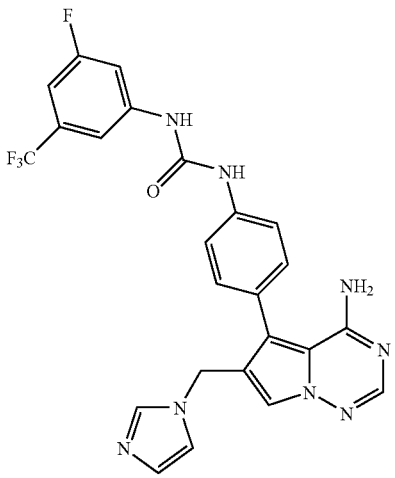

The procedure used for the preparation of Example 166 was used to prepare the title compound by substituting phenyl [3-fluoro-5-(trifluoromethyl)phenyl]carbamate for phenyl[2-fluoro-5-(trifluoromethyl)phenyl]carbamate. $^1$H-NMR (CD$_3$OD) δ 8.55 to 8.58 (m, 1H), 7.98 (s, 1H), 7.97 (s, 1H), 7.65 to 7.80 (m, 2H), 7.63 (d, J=9 Hz, 2H), 7.41 to 7.43 (m, 1H), 7.2 to 7.4 (m, 1H), 7.25 (d, J=9 Hz, 2H), 7.00 to 7.1 (m, 1H), 5.46 (s, 2H), 4.89 (bs, 4H); MS [M+H]$^+$=511.0; LCMS RT=2.29 min.

Example 171

Preparation of ethyl 4-amino-5-[4-({[(3-phenoxyphenyl)amino]carbonyl}amino)phenyl]pyrrolo[2,1-f][1,2,4]triazine-6-carboxylate

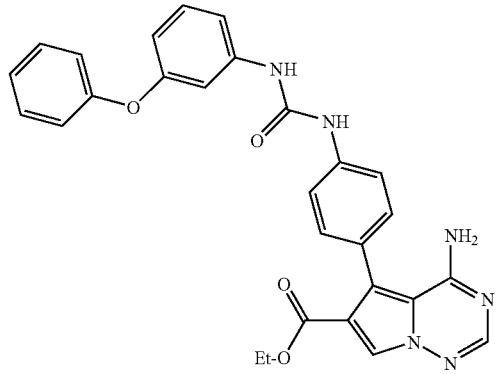

The procedure used for the preparation of Example 1 was used to prepare the title compound by substituting 3-phenoxyphenyl isocyanate for 1-fluoro-2-isocyanato-4-(trifluoromethyl)benzene. $^1$H-NMR (DMSO-d$_6$) δ 8.60 (s, 1H), 8.82 (s, 1H), 8.11 (s, 1H), 7.91 (s, 1H), 7.50 to 7.48 (m, 2H), 7.41 to 7.37 (m, 2H), 7.29 to 7.25 (m, 4H), 7.15 to 7.11 (m, 2H), 7.04 to 7.01 (m, 2H), 4.10 to 4.04 (m, 2H), 1.12 to 1.08 (m, 3H); MS [M+H]$^+$=509.1; LCMS RT=3.48 min.

Example 172

Preparation of tert-butyl (3-{[(4-amino-5-{4-[({[6-(trifluoromethyl)pyridin-2-yl]amino}carbonyl)amino]phenyl}pyrrolo[2,1-f][1,2,4]triazin-6-yl)carbonyl]amino}propyl)carbamate

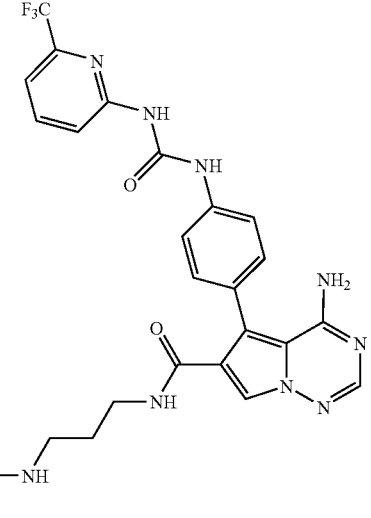

The procedure used for the preparation of Example 55 was used to prepare the title compound by substituting tert-butyl (3-aminopropyl)carbamate for N,N-dimethylpropane-1,3-diamine and phenyl[6-(trifluoromethyl)pyridin-2-yl]carbamate for phenyl[2-fluoro-5-(trifluoromethyl)phenyl]carbamate. $^1$H-NMR (DMSO-$d_6$) δ 9.88 (s, 1H), 9.72 (s, 1H), 8.06 to 7.97 (m, 3H), 7.89 (s, 1H), 7.78 to 7.75 (m, 1H), 7.53 to 7.48 (m, 3H), 7.33 to 7.31 (m, 2H), 6.75 to 6.72 (m, 1H), 3.11 to 3.06 (m, 2H), 2.91 to 2.86 (m, 2H), 1.52 to 1.48 (m, 2H), 1.35 (s, 9H); MS [M+H]$^+$=614.2; LCMS RT=2.55 min.

Example 173

Preparation of 4-amino-N-(3-aminopropyl)-5-{4-[({[2-fluoro-5-(trifluoromethyl)phenyl]amino}carbonyl)amino]phenyl}pyrrolo[2,1-f][1,2,4]triazine-6-carboxamide

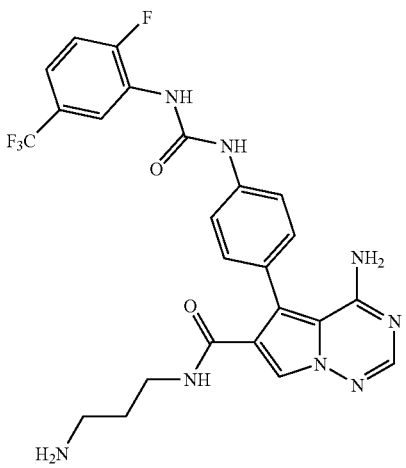

To a solution of DMF (5 mL) was added Intermediate G (100 mg, 0.21 mmol) and BOP (93 mg, 0.21 mmol) followed by NMM (23 μL, 0.21 mmol), and tert-butyl (3-aminopropyl) carbamate (37 mg, 0.21 mmol). The reaction was allowed to stir under N$_2$ at rt for 2 h. The solution was then diluted with EtOAc (20 mL) and aq NaHCO$_3$ (20 mL), transferred to separatory funnel, and separated. The aqueous layer was back extracted with EtOAc (2×20 ml). The organic layers were combined, dried (MgSO$_4$), filtered, and concentrated in vacuo. The crude material was purified by flash chromatography (9:1 v/v CH$_2$Cl$_2$/MeOH). The isolated product, tert-butyl (3-{[(4-amino-5-{4-[({[2-fluoro-5-(trifluoromethyl)phenyl]amino}carbonyl)amino]phenyl}pyrrolo[2,1-f][1,2,4]triazin-6-yl)carbonyl]amino}propyl)carbamate, was treated with CH$_2$Cl$_2$ (5 mL) and TFA (5 mL) and was left stirring under N$_2$ at rt for 17 h. The reaction mixture was then concentrated in vacuo and purified by preparative HPLC (10-90% ACN/H$_2$O with 0.1% TFA). The resulting purified fractions were diluted in EtOAc (20 mL) and aq NaHCO$_3$ (20 mL) and separated. The organic layer was washed with H$_2$O, isolated, dried (MgSO4), filtered, and concentrated to dryness producing 29 mg of the above compound as a white solid (0.055 mmol, yield 26%). $^1$H-NMR (DMSO-$d_6$) δ 9.59 to 9.55 (br s, 1H), 8.58 to 8.56 (d, J=9.7 Hz, 1H), 8.05 (s, 1H), 7.89 (s, 1H), 7.76 to 7.74 (m, 1H), 7.57 to 7.55 (d, J=8.5 Hz, 2H), 7.50 to 7.45 (m, 1H), 7.39 to 7.35 (m, 1H), 7.32 to 7.29 (d, J=8.6 Hz, 2H), 3.19 to 3.14 (m, 2H), 2.57 to 2.54 (m, 2H), 1.57 to 1.50 (m, 2H); MS [M+H]$^+$=531.3; LCMS RT=2.52 min.

Example 174

Preparation of 4-amino-N-(3-aminopropyl)-5-{4-[({[6-(trifluoromethyl)pyridin-2-yl]amino}carbonyl)amino]phenyl}pyrrolo[2,1-f][1,2,4]triazine-6-carboxamide

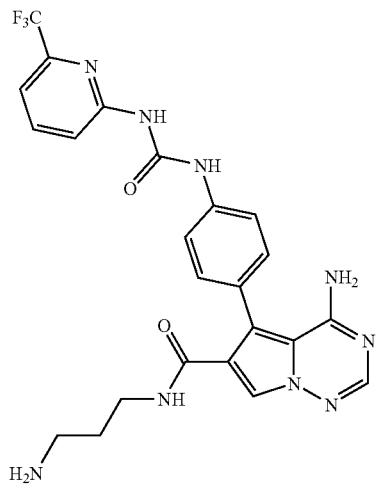

The procedure used for the preparation of Example 173 was used to prepare the title compound by substituting Example 250 for Intermediate G. $^1$H-NMR (CD$_3$OD) δ 7.99 (s, 1H), 7.98 to 7.94 (m, 1H), 7.84 (s, 1H), 7.68 to 7.65 (m, 2H), 7.52 (d, J=8.5, 1H), 7.47 to 7.43 (m, 3H), 3.35 (m, 2H), 2.83 to 2.80 (m, 2H), 1.82 to 1.75 (m, 2H); MS [M+H]$^+$=514.1; LCMS RT=1.85 min.

Example 175

Preparation of 4-amino-N-methyl-5-{4-[({[6-(trifluoromethyl)pyridin-2-yl]amino}carbonyl)amino]phenyl}pyrrolo[2,1-f][1,2,4]triazine-6-carboxamide

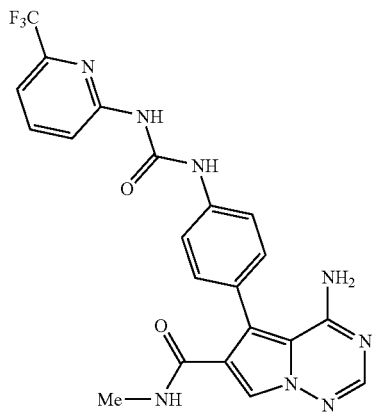

A solution of Intermediate AH (40 mg, 1 eq) and HATU (50 mg, 1.5 eq) in 1 ml anhydrous DMF were stirred at RT for 0.5 h. Then the above mixture was added into a 0.2 ml anhydrous DMF solution of the amine (1.5 eq). Triethylamine (26.5 mg, 3 eq) was added into the reaction and the reaction was stirred at the RT for overnight. The reaction mixture was purified without work-up on Prep LC-MS using gradient Water and Acetonitrile with 0.1% TFA as modifier. MS [M+H]$^+$=471.14; LCMS RT=2.97 min.

Example 176

Preparation of 4-amino-N-ethyl-5-{4-[({[6-(trifluoromethyl)pyridin-2-yl]amino}carbonyl)amino]phenyl}pyrrolo[2,1-f][1,2,4]triazine-6-carboxamide

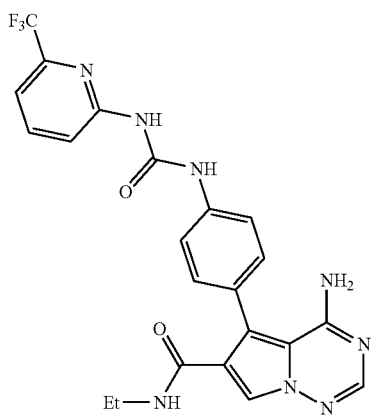

The procedure used for the preparation of Example 175 was used to prepare the title compound by substituting ethylamine for methylamine. MS [M+H]$^+$=485.16; LCMS RT=2.91 min.

Example 177

Preparation of 4-amino-N-cyclopropyl-5-{4-[({[6-(trifluoromethyl)pyridin-2-yl]amino}carbonyl)amino]phenyl}pyrrolo[2,1-f][1,2,4]triazine-6-carboxamide

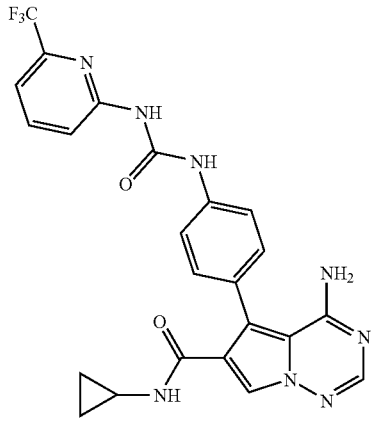

The procedure used for the preparation of Example 175 was used to prepare the title compound by substituting cyclopropylamine for methylamine. MS [M+H]$^+$=497.16; LCMS RT=2.94 min.

Example 178

Preparation of 4-amino-N-(2-pyrrolidin-1-ylethyl)-5-{4-[({[6-(trifluoromethyl)pyridin-2-yl]amino}carbonyl)amino]phenyl}pyrrolo[2,1-f][1,2,4]triazine-6-carboxamide

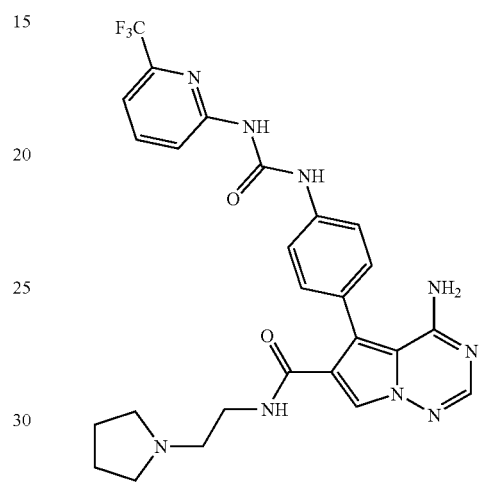

The procedure used for the preparation of Example 175 was used to prepare the title compound by substituting N-(2-aminoethyl)-pyrrolidine for methylamine. MS [M+H]$^+$=554.22; LCMS RT=2.6 min.

Example 179

Preparation of 4-amino-N-[2-(dimethylamino)ethyl]-5-{4-[({[6-(trifluoromethyl)pyridin-2-yl]amino}carbonyl)amino]phenyl}pyrrolo[2,1-f][1,2,4]triazine-6-carboxamide

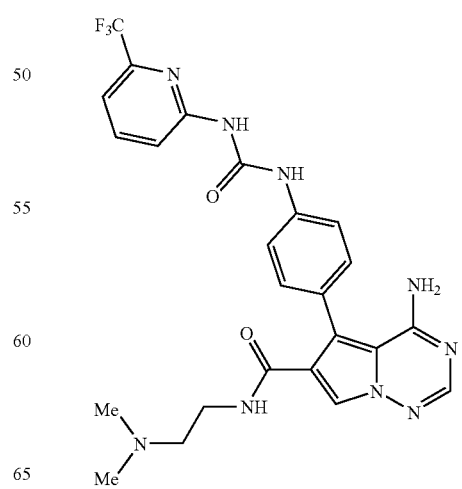

The procedure used for the preparation of Example 175 was used to prepare the title compound by substituting N,N-dimethylethylenediamine for methylamine. MS [M+H]⁺=528.2; LCMS RT=2.6 min.

Example 180

Preparation of 4-amino-N-(3-methoxypropyl)-5-{4-[({[6-(trifluoromethyl)pyridin-2-yl]amino}carbonyl)amino]phenyl}pyrrolo[2,1-f][1,2,4]triazine-6-carboxamide

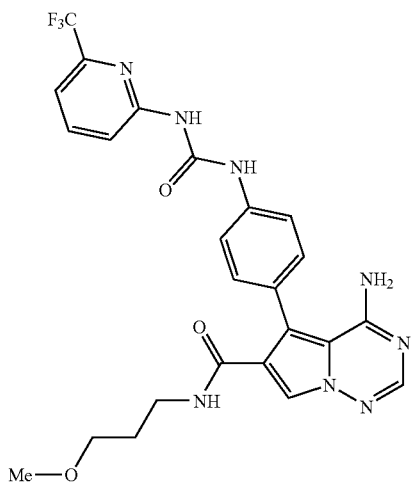

The procedure used for the preparation of Example 175 was used to prepare the title compound by substituting 3-methoxypropylamine for methylamine. MS [M+H]⁺=528.18; LCMS RT=2.9 min.

Example 181

Preparation of 4-amino-N-(2-ethoxyethyl)-5-{4-[({[6-(trifluoromethyl)pyridin-2-yl]amino}carbonyl)amino]phenyl}pyrrolo[2,1-f][1,2,4]triazine-6-carboxamide

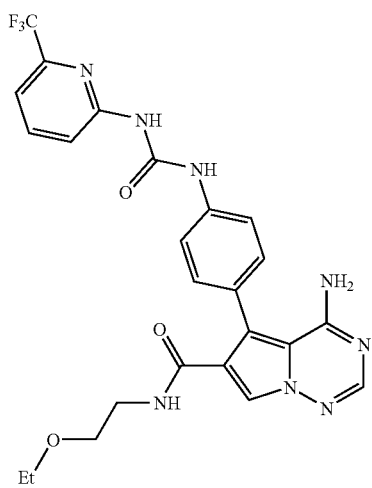

The procedure used for the preparation of Example 175 was used to prepare the title compound by substituting 2-ethoxyethylamine for methylamine. MS [M+H]⁺=529.18; LCMS RT=2.96 min.

Example 182

Preparation of N-{4-[4-amino-6-(morpholin-4-ylcarbonyl)pyrrolo[2,1-f][1,2,4]triazin-5-yl]phenyl}-N'-[6-(trifluoromethyl)pyridin-2-yl]urea

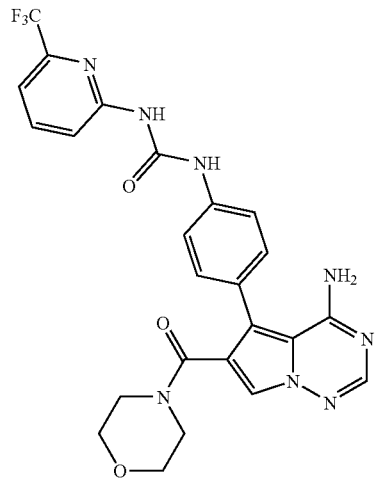

The procedure used for the preparation of Example 175 was used to prepare the title compound by substituting morpholine for methylamine. MS [M+H]⁺=527.17; LCMS RT=2.84 min.

Example 183

Preparation of 4-amino-N-(2-morpholin-4-ylethyl)-5-{4-[({[6-(trifluoromethyl)pyridin-2-yl]amino}carbonyl)amino]phenyl}pyrrolo[2,1-f][1,2,4]triazine-6-carboxamide

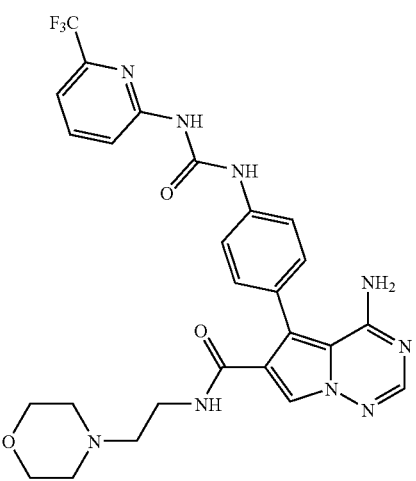

The procedure used for the preparation of Example 175 was used to prepare the title compound by substituting 4-(2- aminoethyl)morpholine for methylamine. MS [M+H]⁺=570.21; LCMS RT=2.58 min.

Example 184

Preparation of N-(4-{4-amino-6-[(4-methylpiperazin-1-yl)carbonyl]pyrrolo[2,1-f][1,2,4]triazin-5-yl}phenyl)-N'-[6-(trifluoromethyl)pyridin-2-yl]urea

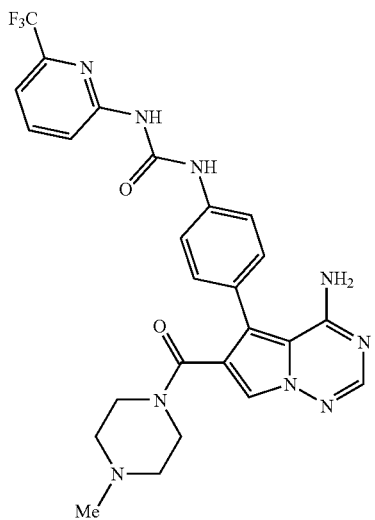

The procedure used for the preparation of Example 175 was used to prepare the title compound by substituting 1-methylpiperazine for methylamine. MS [M+H]⁺=540.2; LCMS RT=2.55 min.

Example 185

Preparation of 4-amino-N-[3-(4-methylpiperazin-1-yl)propyl]-5-{4-[({[6-(trifluoromethyl)pyridin-2-yl]amino}carbonyl)amino]phenyl}pyrrolo[2,1-f][1,2,4]triazine-6-carboxamide

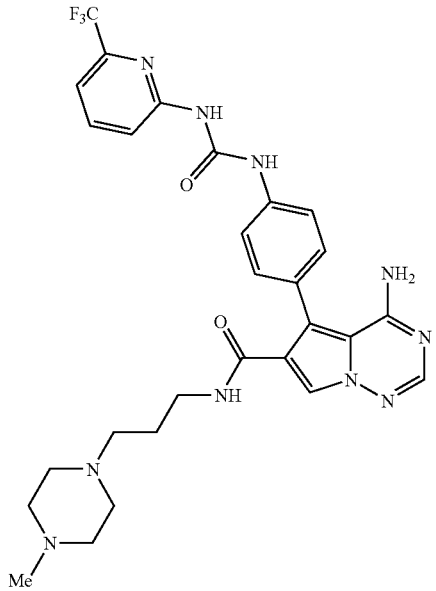

The procedure used for the preparation of Example 175 was used to prepare the title compound by substituting 1-(3-aminopropyl)-4-methylpiperazine for methylamine. MS [M+H]⁺=597.26; LCMS RT=2.5 min.

Example 186

Preparation of 4-amino-N-[3-(2-oxopyrrolidin-1-yl)propyl]-5-{4-[({[6-(trifluoromethyl)pyridin-2-yl]amino}carbonyl)amino]phenyl}pyrrolo[2,1-f][1,2,4]triazine-6-carboxamide

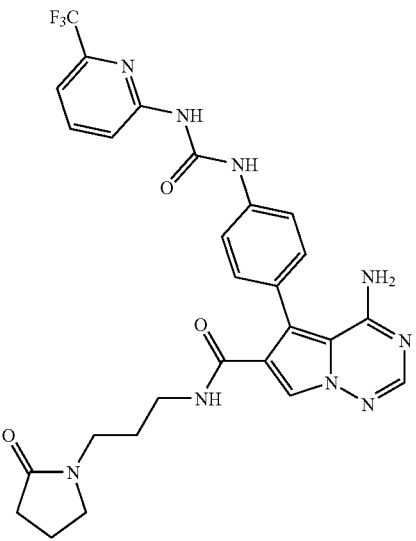

The procedure used for the preparation of Example 175 was used to prepare the title compound by substituting 1-(3-aminopropyl)-2-pyrrolidinone for methylamine. MS [M+H]⁺=582.21; LCMS RT=2.81 min.

Example 187

Preparation of 4-amino-N-[4-(dimethylamino)-3,3-dimethylbutyl]-5-{4-[({[6-(trifluoromethyl)pyridin-2-yl]amino}carbonyl)amino]phenyl}pyrrolo[2,1-f][1,2,4]triazine-6-carboxamide

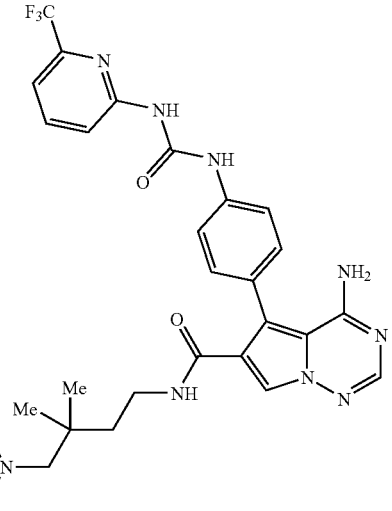

The procedure used for the preparation of Example 175 was used to prepare the title compound by substituting 2,2,N*1*,N*1*-tetramethyl-butane-1,4-diamine for methylamine. MS [M+H]⁺=570.25; LCMS RT=2.65 min.

Example 188

Preparation of 4-amino-N-[3-(dimethylamino)propyl]-N-methyl-5-{4-[({[6-(trifluoromethyl)pyridin-2-yl]amino}carbonyl)amino]phenyl}pyrrolo[2,1-f][1,2,4]triazine-6-carboxamide

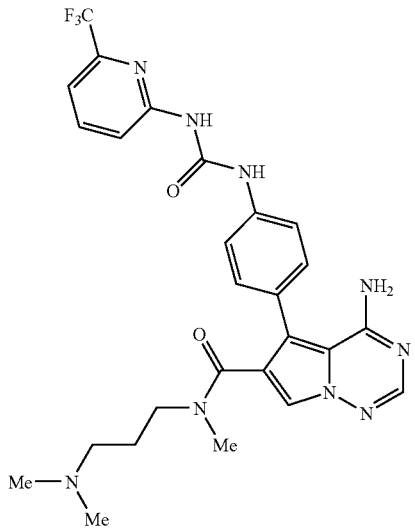

The procedure used for the preparation of Example 175 was used to prepare the title compound by substituting N,N,N'-trimethyl-1,3-propanediamine for methylamine. MS [M+H]⁺=556.23; LCMS RT=2.57 min.

Example 189

Preparation of 4-amino-N-(3-morpholin-4-ylpropyl)-5-{4-[({[6-(trifluoromethyl)pyridin-2-yl]amino}carbonyl)amino]phenyl}pyrrolo[2,1-f][1,2,4]triazine-6-carboxamide

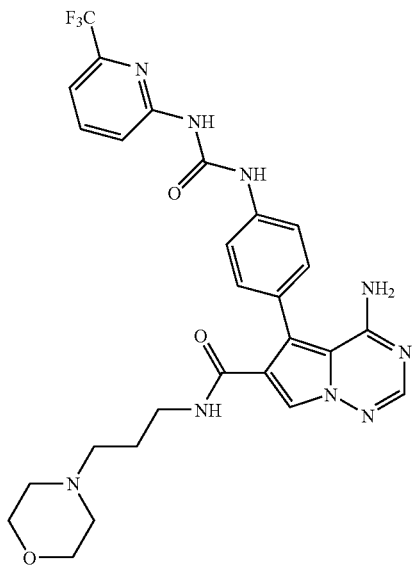

The procedure used for the preparation of Example 175 was used to prepare the title compound by substituting 4-(3-aminopropyl) morpholine for methylamine. MS [M+H]⁺=584.23; LCMS RT=2.6 min.

Example 190

Preparation of 4-amino-N-(4-pyrrolidin-1-ylbutyl)-5-{4-[({[6-(trifluoromethyl)pyridin-2-yl]amino}carbonyl)amino]phenyl}pyrrolo[2,1-f][1,2,4]triazine-6-carboxamide

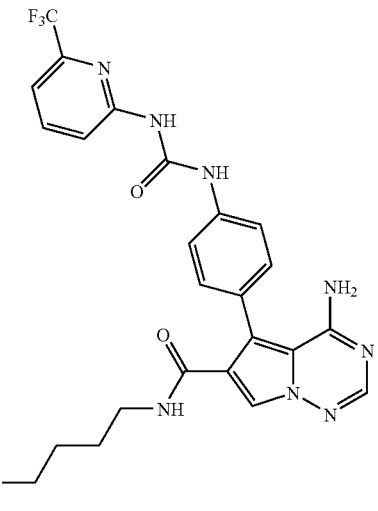

The procedure used for the preparation of Example 175 was used to prepare the title compound by substituting 4-(1-pyrrolidino) butylamine for methylamine. MS [M+H]⁺=582.25; LCMS RT=2.6 min.

Example 191

Preparation of 4-amino-N-[2-(1-methylpyrrolidin-2-yl)ethyl]-5-{4-[({[6-(trifluoromethyl)pyridin-2-yl]amino}carbonyl)amino]phenyl}pyrrolo[2,1-f][1,2,4]triazine-6-carboxamide

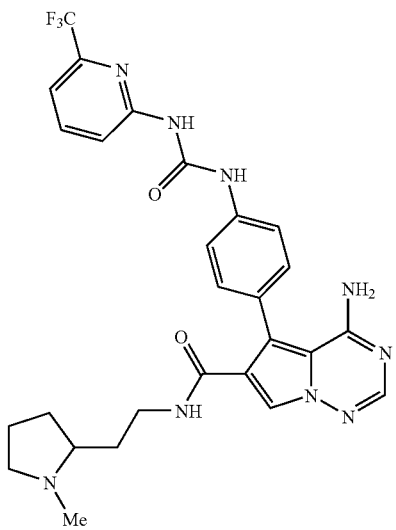

The procedure used for the preparation of Example 175 was used to prepare the title compound by substituting 2-(2-aminoethyl)-1-methylpyrrolidine for methylamine. MS [M+H]⁺=568.23; LCMS RT=2.6 min.

Example 192

Preparation of 4-amino-N-[4-(dimethylamino)butyl]-5-{4-[({[6-(trifluoromethyl)pyridin-2-yl]amino}carbonyl)amino]phenyl}pyrrolo[2,1-f][1,2,4]triazine-6-carboxamide

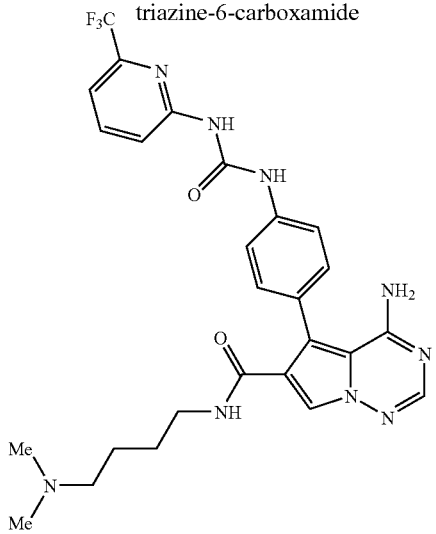

The procedure used for the preparation of Example 175 was used to prepare the title compound by substituting 4-dimethylaminobutylamine for methylamine. MS [M+H]⁺=556.23; LCMS RT=2.6 min.

Example 193

Preparation of N-{4-[4-amino-6-({4-[3-(dimethylamino)propyl]piperazin-1-yl}carbonyl)pyrrolo[2,1-f][1,2,4]triazin-5-yl]phenyl}-N'-[6-(trifluoromethyl)pyridin-2-yl]urea

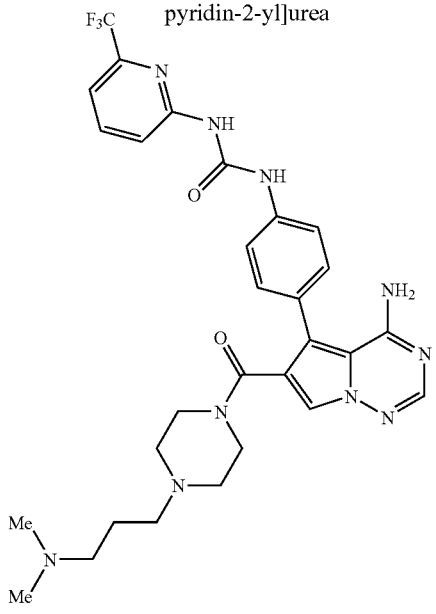

The procedure used for the preparation of Example 175 was used to prepare the title compound by substituting 1-(3-dimethylaminopropyl)-piperazine for methylamine. MS [M+H]⁺=611.27; LCMS RT=2.45 min.

Example 194

Preparation of N-{4-[4-amino-6-({4-[2-(dimethylamino)ethyl]piperazin-1-yl}carbonyl)pyrrolo[2,1-f][1,2,4]triazin-5-yl]phenyl}-N'-[6-(trifluoromethyl)pyridin-2-yl]urea

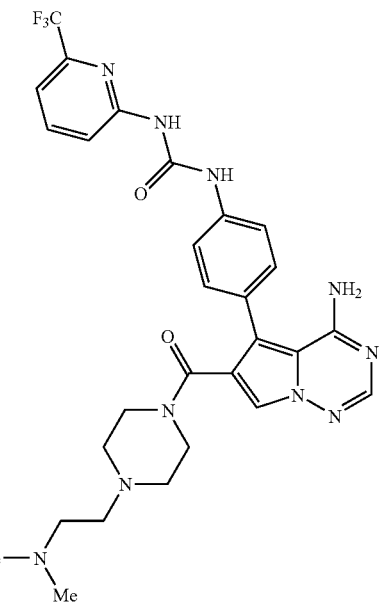

The procedure used for the preparation of Example 175 was used to prepare the title compound by substituting 1-(2-dimethylaminoethyl)-piperazine for methylamine. MS [M+H]⁺=597.26; LCMS RT=2.52 min.

Example 195

Preparation of 4-amino-N-[3-(dimethylamino)propyl]-5-{4-[({[6-(trifluoromethyl)pyridin-2-yl]amino}carbonyl)amino]phenyl}pyrrolo[2,1-f][1,2,4]triazine-6-carboxamide

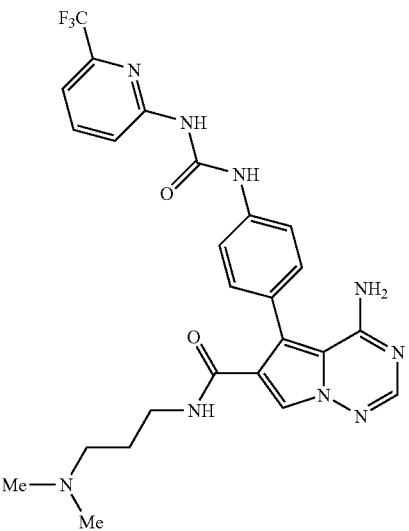

The procedure used for the preparation of Example 175 was used to prepare the title compound by substituting 3-(dimethylamino)propylamine for methylamine. MS [M+H]+=542.22; LCMS RT=2.6 min.

Example 196

Preparation of 4-amino-N-[4-(diethylamino)butyl]-5-{4-[({[6-(trifluoromethyl)pyridin-2-yl]amino}carbonyl)amino]phenyl}pyrrolo[2,1-f][1,2,4]triazine-6-carboxamide

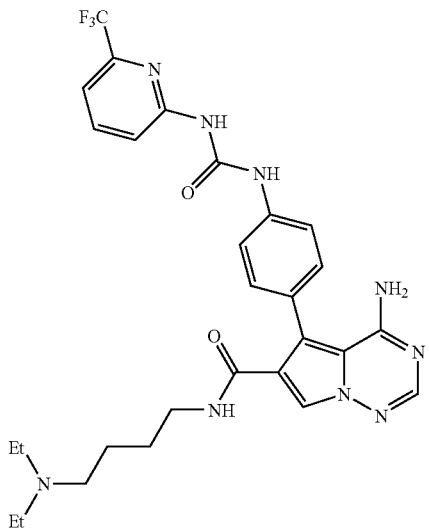

The procedure used for the preparation of Example 175 was used to prepare the title compound by substituting 4-diethylaminobutylamine for methylamine. MS [M+H]+=598.28; LCMS RT=2.67 min.

Example 197

Preparation of 4-amino-N,N-bis(2-methoxyethyl)-5-{4-[({[6-(trifluoromethyl)pyridin-2-yl]amino}carbonyl)amino]phenyl}pyrrolo[2,1-f][1,2,4]triazine-6-carboxamide

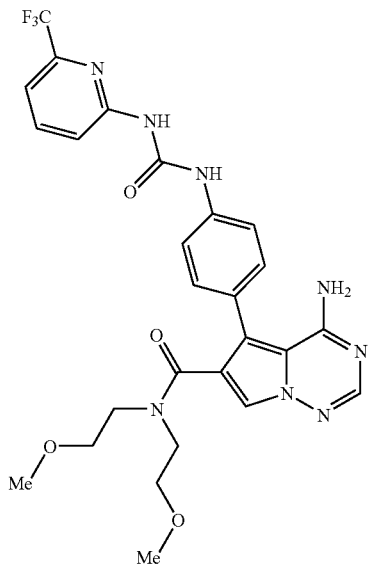

The procedure used for the preparation of Example 175 was used to prepare the title compound by substituting bis(2-methoxyethyl)amine for methylamine. MS [M+H]+=573.21; LCMS RT=2.93 min.

Example 198

Preparation of N-{4-[4-amino-6-(1,4-dioxa-8-azaspiro[4.5]dec-8-ylcarbonyl)pyrrolo[2,1-f][1,2,4]triazin-5-yl]phenyl}-N'-[6-(trifluoromethyl)pyridin-2-yl]urea

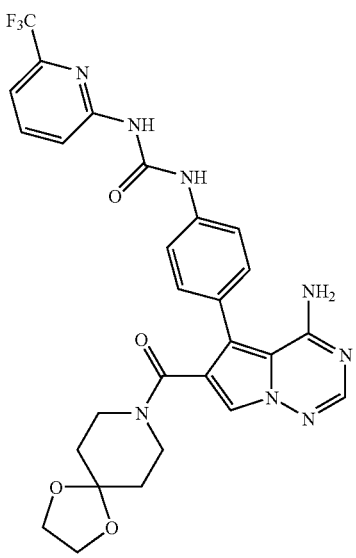

The procedure used for the preparation of Example 175 was used to prepare the title compound by substituting 1,4-dioxa-8-azaspiro[4.5]decane for methylamine. MS [M+H]+=583.2; LCMS RT=2.93 min.

Example 199

Preparation of 4-amino-N-(cyclohexylmethyl)-5-{4-[({[6-(trifluoromethyl)pyridin-2-yl]amino}carbonyl)amino]phenyl}pyrrolo[2,1-f][1,2,4]triazine-6-carboxamide

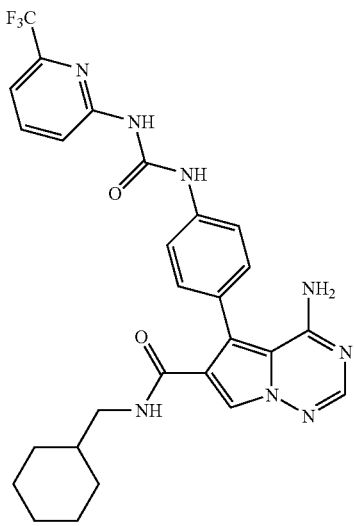

The procedure used for the preparation of Example 175 was used to prepare the title compound by substituting cyclohexanemethylamine for methylamine. MS [M+H]$^+$=553.22; LCMS RT=3.31 min.

Example 200

Preparation of 4-amino-N-cyclopentyl-5-{4-[({[6-(trifluoromethyl)pyridin-2-yl]amino}carbonyl)amino]phenyl}pyrrolo[2,1-f][1,2,4]triazine-6-carboxamide

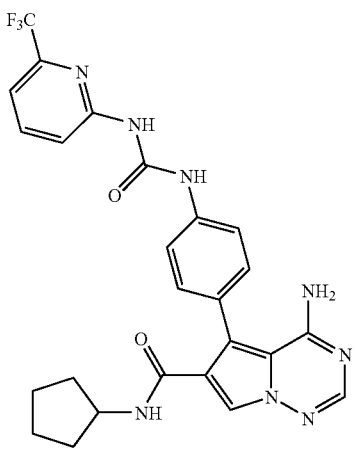

The procedure used for the preparation of Example 175 was used to prepare the title compound by substituting cyclopentylamine for methylamine. MS [M+H]$^+$=525.19; LCMS RT=3.1 min.

Example 201

Preparation of 4-amino-N-(2-isopropoxyethyl)-5-{4-[({[6-(trifluoromethyl)pyridin-2-yl]amino}carbonyl)amino]phenyl}pyrrolo[2,1-f][1,2,4]triazine-6-carboxamide

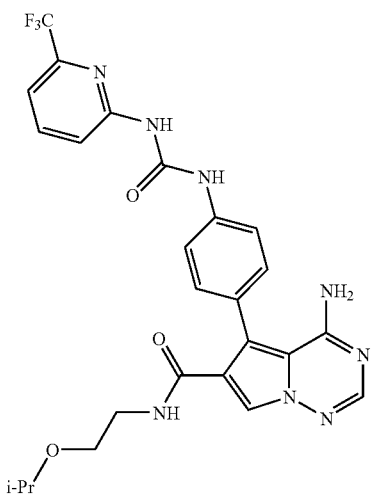

The procedure used for the preparation of Example 175 was used to prepare the title compound by substituting 2-aminoethyl isopropyl ether for methylamine. MS [M+H]$^+$=543.2; LCMS RT=3.05 min.

Example 202

Preparation of 4-amino-N-[3-(diethylamino)propyl]-5-{4-[({[6-(trifluoromethyl)pyridin-2-yl]amino}carbonyl)amino]phenyl}pyrrolo[2,1-f][1,2,4]triazine-6-carboxamide

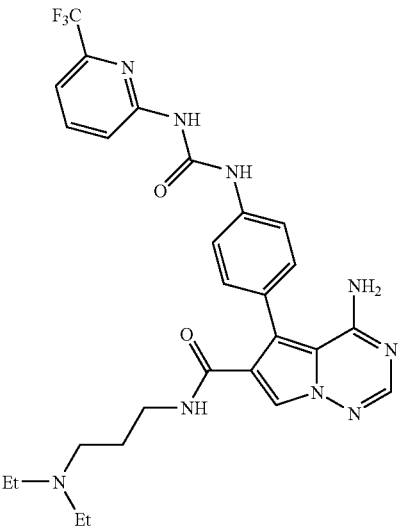

The procedure used for the preparation of Example 175 was used to prepare the title compound by substituting N,N-diethyl-1,3-propanediamine for methylamine. MS [M+H]$^+$=570.25; LCMS RT=2.62 min.

Example 203

Preparation of 4-amino-N-(cyclopropylmethyl)-5-{4-[({[6-(trifluoromethyl)pyridin-2-yl]amino}carbonyl)amino]phenyl}pyrrolo[2,1-f][1,2,4]triazine-6-carboxamide

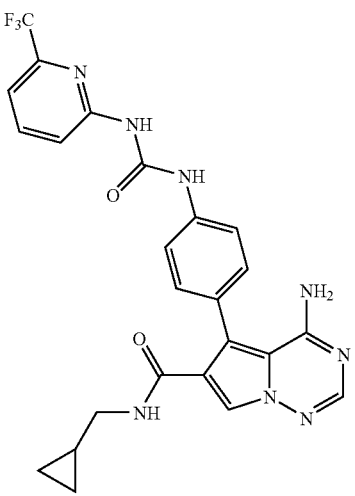

The procedure used for the preparation of Example 175 was used to prepare the title compound by substituting cyclopropanemethylamine for methylamine. MS [M+H]⁺=511.17; LCMS RT=3.04 min.

Example 204

Preparation of 4-amino-N-[3-(methylthio)propyl]-5-{4-[({[6-(trifluoromethyl)pyridin-2-yl]amino}carbonyl)amino]phenyl}pyrrolo[2,1-f][1,2,4]triazine-6-carboxamide

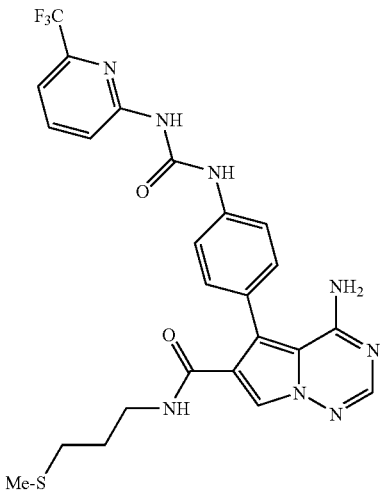

The procedure used for the preparation of Example 175 was used to prepare the title compound by substituting 3-(methylthio)propylamine for methylamine. MS [M+H]⁺=545.16; LCMS RT=3.06 min.

Example 205

Preparation of 4-amino-N-(3-isopropoxypropyl)-5-{4-[({[6-(trifluoromethyl)pyridin-2-yl]amino}carbonyl)amino]phenyl}pyrrolo[2,1-f][1,2,4]triazine-6-carboxamide

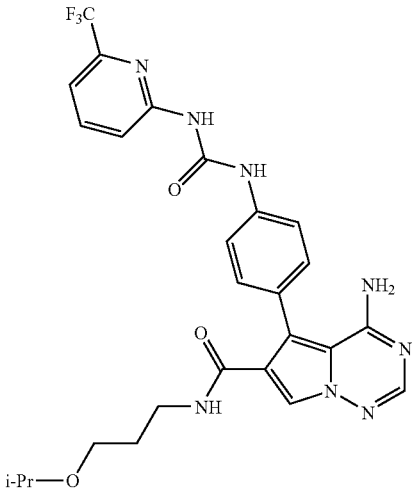

The procedure used for the preparation of Example 175 was used to prepare the title compound by substituting 3-isopropoxypropylamine for methylamine. MS [M+H]⁺=557.22; LCMS RT=3.05 min.

Example 206

Preparation of N-(4-{4-amino-6-[(4-cyclohexylpiperazin-1-yl)carbonyl]pyrrolo[2,1-f][1,2,4]triazin-5-yl}phenyl)-N'-[6-(trifluoromethyl)pyridin-2-yl]urea

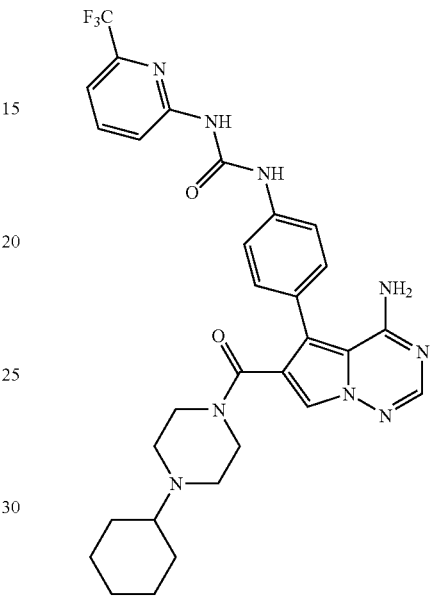

The procedure used for the preparation of Example 175 was used to prepare the title compound by substituting 1-cyclohexylpiperazine for methylamine. MS [M+H]⁺=608.26; LCMS RT=2.63 min.

Example 207

Preparation of 4-amino-N-[(1-ethylpyrrolidin-2-yl)methyl]-5-{4-[({[6-(trifluoromethyl)pyridin-2-yl]amino}carbonyl)amino]phenyl}pyrrolo[2,1-f][1,2,4]triazine-6-carboxamide

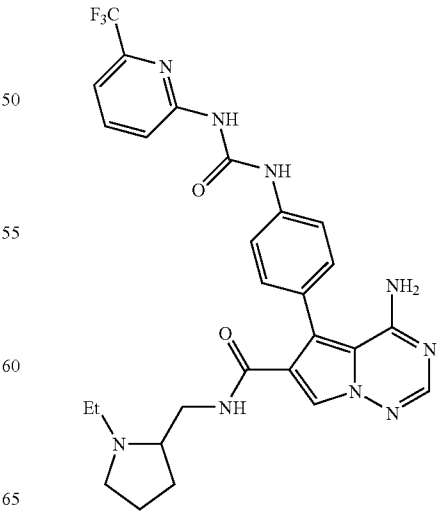

The procedure used for the preparation of Example 175 was used to prepare the title compound by substituting 2-(aminomethyl)-1-ethylpyrrolidine for methylamine. MS [M+H]⁺=568.23; LCMS RT=2.64 min.

Example 208

Preparation of N-[4-(4-amino-6-{[3-(dimethylamino)pyrrolidin-1-yl]carbonyl}pyrrolo[2,1-f][1,2,4]triazin-5-yl)phenyl]-N'-[6-(trifluoromethyl)pyridin-2-yl]urea

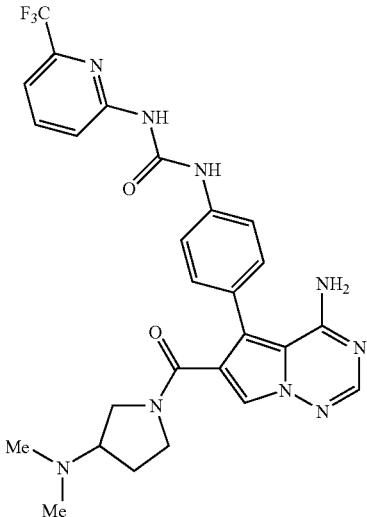

The procedure used for the preparation of Example 175 was used to prepare the title compound by substituting 3-(dimethylamino)pyrrolidine for methylamine. MS [M+H]⁺=554.22; LCMS RT=2.54 min.

Example 209

Preparation of N-(4-{4-amino-6-[(4-ethylpiperidin-1-yl)carbonyl]pyrrolo[2,1-f][1,2,4]triazin-5-yl}phenyl)-N'-[6-(trifluoromethyl)pyridin-2-yl]urea

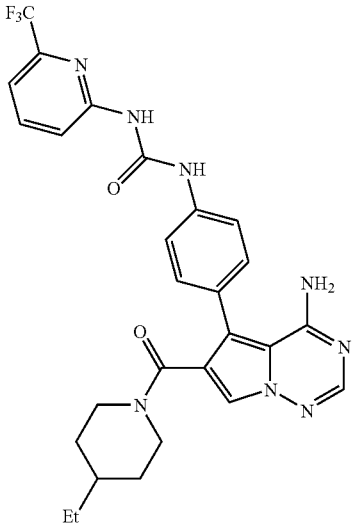

The procedure used for the preparation of Example 175 was used to prepare the title compound by substituting 4-ethylpiperidine for methylamine. MS [M+H]⁺=553.22; LCMS RT=3.25 min.

Example 210

Preparation of 4-amino-N-isobutyl-5-{4-[({[6-(trifluoromethyl)pyridin-2-yl]amino}carbonyl)amino]phenyl}pyrrolo[2,1-f][1,2,4]triazine-6-carboxamide

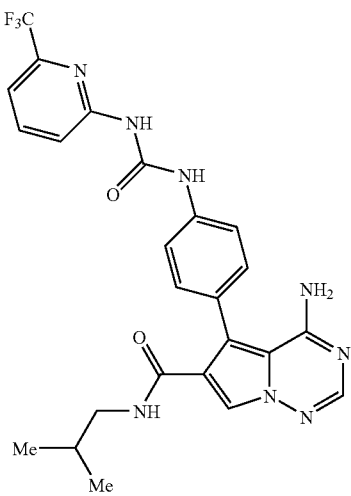

The procedure used for the preparation of Example 175 was used to prepare the title compound by substituting isobutylamine for methylamine. MS [M+H]⁺=513.19; LCMS RT=3.11 min.

Example 211

Preparation of 4-amino-N-butyl-5-{4-[({[6-(trifluoromethyl)pyridin-2-yl]amino}carbonyl)amino]phenyl}pyrrolo[2,1-f][1,2,4]triazine-6-carboxamide

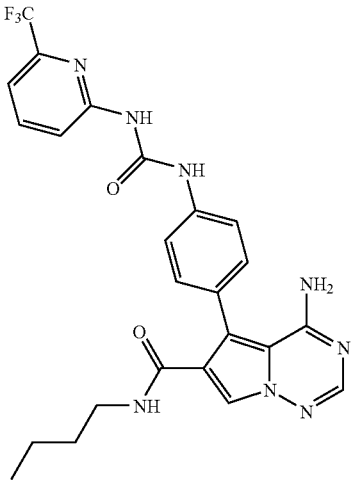

The procedure used for the preparation of Example 175 was used to prepare the title compound by substituting N-butylamine for methylamine. MS [M+H]⁺=513.19; LCMS RT=3.14 min.

Example 212

Preparation of ethyl 4-amino-5-{4-[({[4-(trifluoromethyl)-1,3-thiazol-2-yl]amino}carbonyl)amino]phenyl}pyrrolo[2,1-f][1,2,4]triazine-6-carboxylate

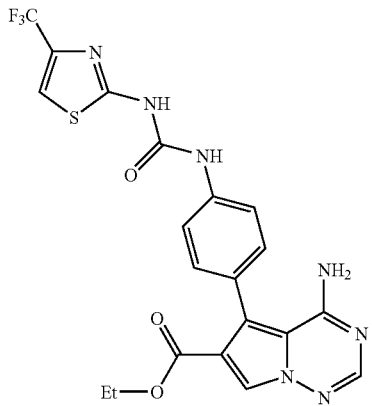

The procedure used for the preparation of Example 24 was used to prepare the title compound by substituting 4-(trifluoromethyl)-1,3-thiazol-2-amine for 2-isopropylaniline. $^1$H-NMR (DMSO-d$_6$) δ 11.0 (s, 1H), 9.15 (s, 1H), 8.13 (s, 1H), 7.93 (s, 1H), 7.87 (s, 1H), 7.57 to 7.55 (m, 2H), 7.35 to 3.33 (m, 2H), 1.12 to 1.09 (m, 3H); MS [M+H]⁺=492; LCMS RT=2.73 min.

Example 213

Preparation of ethyl 4-amino-5-{4-[({[4-(trifluoromethyl)-1,3-thiazol-2-yl]amino}carbonyl)amino]phenyl}pyrrolo[2,1-f][1,2,4]triazine-6-carboxylic acid

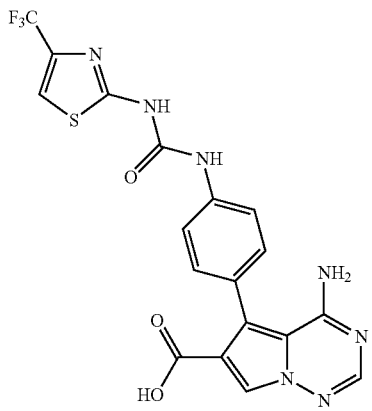

The procedure used for Step 2 in the preparation of Intermediate J was used to prepare the title compound by substituting phenyl[4-(trifluoromethyl)-1,3-thiazol-2-yl]carbamate for phenyl[2-chloro-5-(trifluoromethyl)phenyl] carbamate. $^1$H-NMR (DMSO-d$_6$) δ 12.3 to 12.2 (br s, 1H), 11.2 to 11.1 (br s, 1H), 9.41 to 9.18 (br s, 1H), 8.30 (s, 1H), 8.29 to 8.1 (br s, 1H), 7.90 (s, 1H), 7.82 (s, 1H), 7.65 to 7.58 (m, 2H), 7.55 to 7.30 (m, 2H), 5.27 to 4.71 (br s, 1H); MS [M+H]⁺=464; LCMS RT=2.28 min.

Example 214

Preparation of 4-amino-N-(2,2,2-trifluoroethyl)-5-{4-[({[4-(trifluoromethyl)-1,3-thiazol-2-yl]amino}carbonyl)amino]phenyl}pyrrolo[2,1-f][1,2,4]triazine-6-carboxamide

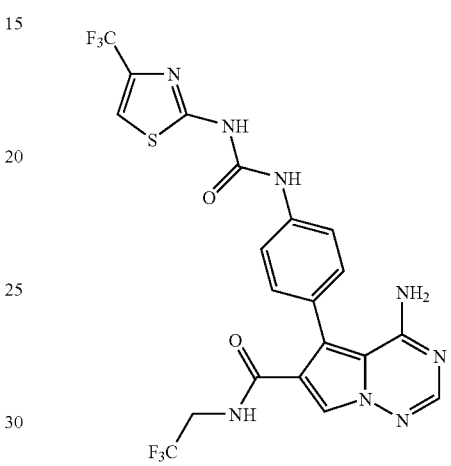

The procedure used for the preparation of Example 69 was used to prepare the title compound by substituting Example 213 for Intermediate G and substituting 2,2,2-trifluoroethanamine for cyclopropanamine. $^1$H-NMR (DMSO-d$_6$) δ 11.0 (s, 1H), 9.13 (s, 1H), 8.55 to 8.52 (m, 1H), 8.19 (s, 1H), 7.91 (s, 1H), 7.85 (s, 1H), 7.55 to 7.52 (m, 2H), 7.32 to 7.30 (m, 2H), 3.97 to 3.93 (m, 2H); MS [M+H]⁺=544.9; LCMS RT=2.52 min.

Example 215

Preparation of ethyl 4-amino-5-{4-[({[2-fluoro-3-(trifluoromethyl)phenyl]amino}carbonyl)amino]phenyl}pyrrolo[2,1-f][1,2,4]triazine-6-carboxylate

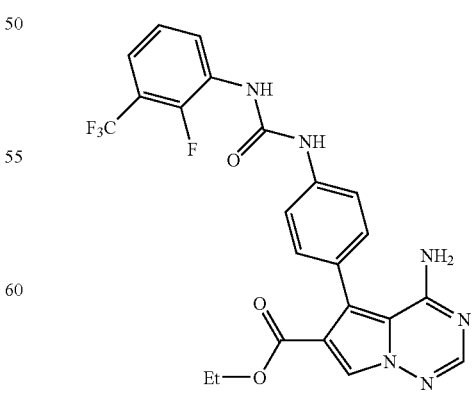

The procedure used for the preparation of Example 24 was used to prepare the title compound by substituting 2-fluoro- 3-(trifluoromethyl)phenylamine for 2-isopropylaniline. $^1$H-NMR (DMSO-d$_6$) δ 9.33 (s, 1H), 8.92 (s, 1H), 8.52 to 8.45 (m, 1H), 8.16 (s, 1H), 8.10 (bs, 1H), 7.96 (s, 1H), 7.57 (d, J=9.0 Hz, 2H), 7.40 to 7.34 (m, 4H), 5.14 (bs, 1H), 4.10 (q, J=8.0 Hz, 2H), 1.12 (q, J=7.8 Hz, 3H); MS [M+H]$^+$=503.2; LCMS RT=3.14 min.

Example 216

Preparation of ethyl N-{4-[4-amino-6-(methoxymethyl)pyrrolo[2,1-f][1,2,4]triazin-5-yl]phenyl}-N'-[3-(trifluoromethoxy)phenyl]urea

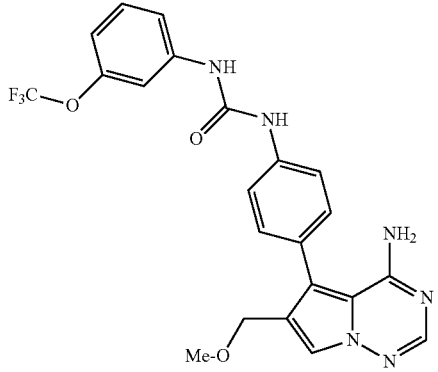

The procedure used for the preparation of Example 24 was used to prepare the title compound by substituting 3-methoxyaniline for 2-isopropylaniline and Intermediate U for intermediate B. $^1$H-NMR (DMSO-d$_6$) δ 7.81 (s, 1H), 7.73 (s, 1H), 7.65 to 7.71 (m, 2H), 7.61 (d, J=9 Hz, 2H), 7.40 ((d, J=9 Hz, 2H), 7.37 (m, 1H), 7.33 to 7.36 (m, 2H), 6.90 to 6.95 (m, 1H), 4.36 (s, 2H), 3.30 (s, 3H); MS [M+H]$^+$=473.1; LCMS RT=2.69 min.

Example 217

Preparation of N-{4-[4-amino-6-(methoxymethyl) pyrrolo[2,1-f][1,2,4]triazin-5-yl]phenyl}-N'-[3-tert-butyl-1-(4-fluorophenyl)-1H-pyrazol-5-yl]urea

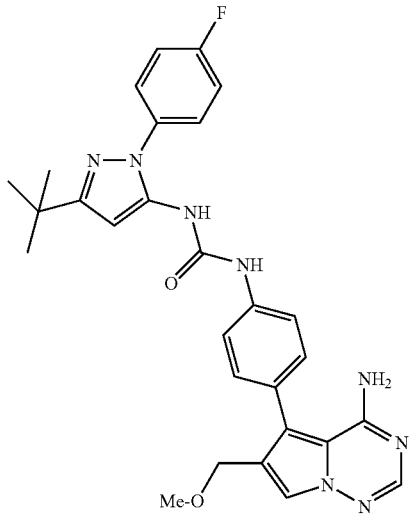

The procedure used for the preparation of Example 24 was used to prepare the title compound by substituting 3-tert-butyl-1-(4-fluorophenyl)-1H-pyrazol-5-amine for 2-isopropylaniline. $^1$H-NMR (CD$_3$OD) δ 7.78 (s, 1H), 7.68 (s, 1H), 7.52 to 7.58 (m, 2H), 7.52 (d, J=9 Hz, 2H) 7.37 (d, J=9 Hz, 2H), 7.28 to 7.31 (m, 2H), 6.44 (s, 1H), 4.34 (s, 2H), 3.30 (s, 3H), 1.26 (s, 9H); MS [M+H]$^+$=529.2; LCMS RT=3.04 min.

Example 218

Preparation of N-{4-[4-amino-6-(ethoxymethyl)pyrrolo[2,1-f][1,2,4]triazin-5-yl]phenyl}-N'-[4-(trifluoromethyl)pyridin-2-yl]urea

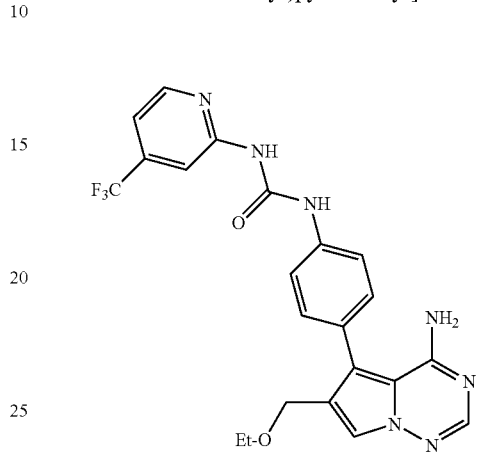

The procedure used for the preparation of Example 246 was used to prepare the title compound by substituting phenyl [4-(trifluoromethyl)pyridin-2-yl]carbamate for 1-fluoro-2-isocyanato-4-(trifluoromethyl)benzene. $^1$H-NMR (DMSO-d$_6$) δ 9.99 (s, 1H), 9.82 (s, 1H), 8.56 (d, J=5 Hz, 1H), 8.10 (s, 1H), 7.87 (s, 1H), 7.77 (s, 1H), 7.65 (d, J=9 Hz, 2H), 7.62 to 7.65 (m, 1H), 7.30 to 7.42 (m, 4H), 4.32 (s, 2H), 3.40 (q, J=7 Hz, 2H), 1.09 (t, J=7 Hz, 3H); MS [M+H]$^+$=472.1; LCMS RT=2.73 min.

Example 219

Preparation of N-{4-[4-amino-6-(hydroxymethyl) pyrrolo[2,1-f][1,2,4]triazin-5-yl]phenyl}-N'-[6-(trifluoromethyl)pyridin-2-yl]urea

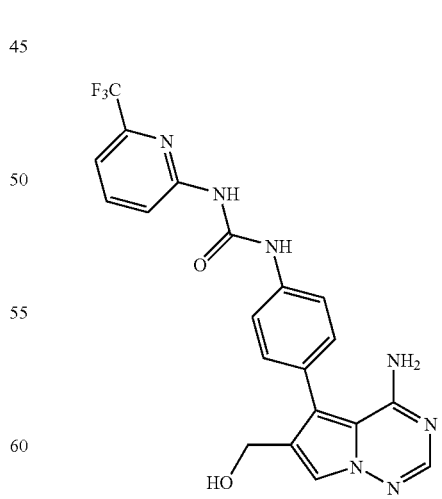

The procedure used in Step 1 of the preparation of Intermediate F was used to prepare the title compound by substituting Example 144 for Intermediate E. $^1$H-NMR (DMSO-d$_6$) δ 9.87 (s, 1H), 9.71 (s, 1H), 8.03 to 7.99 (m, 3H), 7.82 (s, 1H), 7.65 (s, 1H), 7.57 to 7.55 (m, 3H), 7.50 to 7.47 (m, 1H), 7.37 (d, J=8.5 Hz, 2H), 4.97 to 4.94 (m, 1H), 4.36 (d, J=5.2 Hz, 2H); MS [M+H]$^+$=444.0; LCMS RT=2.24 min.

Example 220

Preparation of ethyl N-[(4-amino-5-{4-[({[2-fluoro-5-(trifluoromethyl)phenyl]amino}carbonyl)amino]phenyl}pyrrolo[2,1-f][1,2,4]triazin-6-yl)carbonyl]serinate

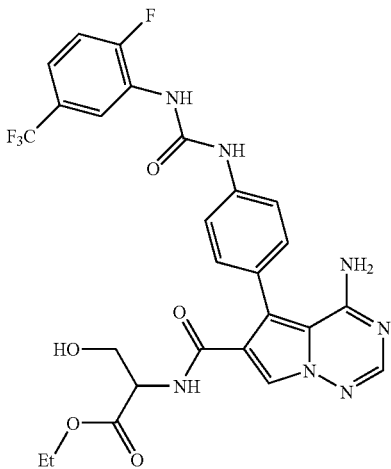

The procedure used for the preparation of Example 143 was used to prepare the title compound by substituting methyl serinate hydrochloride for 2-amino-2-methylpropan-1-ol and Intermediate G for Intermediate J. $^1$H-NMR (DMSO-d$_6$) δ 9.33 (s, 1H), 8.95 (d, J=2.5 Hz, 1H), 8.62 to 8.60 (d, J=8.8 Hz, 1H), 8.20 (s, 1H), 7.91 (s, 1H), 7.78 to 7.76 (d, J=7.8 Hz, 1H), 7.55 to 7.53 (d, J=8.7 Hz, 2H), 7.50 to 7.47 (m, 1H), 7.40 to 7.37 (m, 1H), 7.34 to 7.32 (d, J=8.4 Hz, 2H), 4.98 to 4.95 (t, J=5.9 Hz, 1H), 4.38 to 4.34 (m, 1H), 4.08 to 4.03 (q, J=7.2 Hz, 2H), 3.70 to 3.61 (m, 2H), 1.18 to 1.15 (t, J=7.1 Hz, 3H); MS [M+H]$^+$=590.0; LCMS RT=2.69 min.

Example 221

Preparation of ethyl N-[(4-amino-5-{4-[({[4-(trifluoromethyl)pyridin-2-yl]amino}carbonyl)amino]phenyl}pyrrolo[2,1-f][1,2,4]triazin-6-yl)carbonyl]serinate

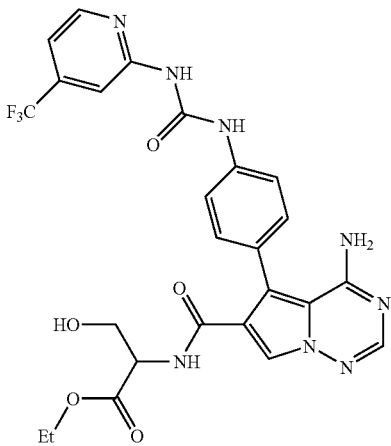

The procedure used for the preparation of Example 143 was used to prepare the title compound by substituting methyl serinate hydrochloride for 2-amino-2-methylpropan-1-ol and Example 250 for Intermediate J. $^1$H-NMR (DMSO-d$_6$) δ 9.87 (s, 1H), 9.74 (s, 1H), 8.54 to 8.53 (d, J=5.4 Hz, 1H), 8.20 (s, 1H), 8.06 (s, 1H), 7.91 (s, 1H), 7.79 to 7.77 (d, J=7.6 Hz, 1H), 7.59 to 7.57 (d, J=8.7 Hz, 2H), 7.37 to 7.33 (m, 3H), 4.98 to 4.95 (t, J=5.8 Hz, 1H), 4.39 to 4.34 (m, 1H), 4.08 to 4.03 (q, J=7.0 Hz, 2H), 3.72 to 3.61 (m, 2H), 1.18 to 1.14 (t, J=7.1 Hz, 3H); MS [M+H]$^+$=573.0; LCMS RT=2.55 min.

Example 222

Preparation of N-[4-(4-amino-6 vinylpyrrolo[2,1-f][1,2,4]triazin-5-yl)phenyl]-N'-[4-(trifluoromethyl)pyridin-2-yl]urea

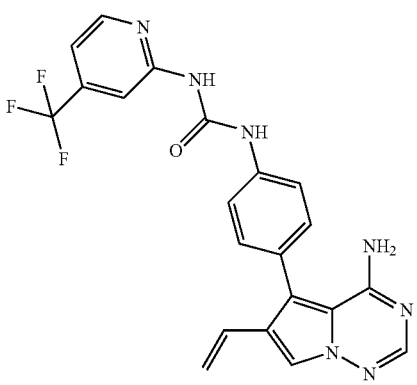

Potassium tert-butoxide (0.51 g, 4.53 mmol) was suspended in 1,4-dioxane (40 mL) and treated with methyl(triphenyl)phosphonium bromide (1.6 g, 4.53 mmol). The resulting yellow suspension was stirred at room temperature for 30 min. The mixture was then treated with Intermediate AG (1.0 g, 2.27 mmol). The mixture was stirred for 3 hours at room temperature. The mixture was then poured into water and stirred for 1 hour. The mixture was then filtered and rinsed with water and methanol. The remaining solid was dried under reduced pressure providing 0.62 g of product as an light brown solid (1.41 mmol, 62% yield). $^1$H-NMR (DMSO-d$_6$) δ 10.0 (bs, 1H), 9.86 (bs, 1H), 8.53 (d, J=5.1 Hz, 1H), 8.07 (s, 1H), 8.04 (s, 1H), 7.84 (s, 1H), 7.64 (d, J=8.5 Hz, 2H), 7.35 (d, J=5.2 Hz, H), 7.30 (d, J=8.4 Hz, 2H), 6.39 (q, J=11.0 Hz, 1H), 5.63 (dd, J=1.6 Hz, 1H), 5.11 (dd, J=1.6 Hz, 1H); MS [M+H]$^+$=440.0; LCMS RT=2.89 min.

Example 223

Preparation of N-[4-(6-acetyl-4-aminopyrrolo[2,1-f][1,2,4]triazin-5-yl)phenyl]-N'-[2-fluoro-5-(trifluoromethyl)phenyl]urea

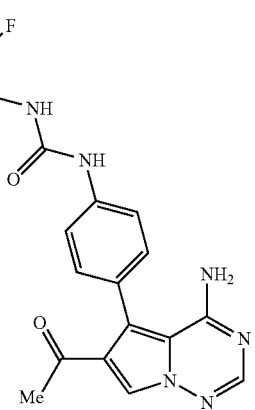

The procedure used for the preparation of Example 233 was used to prepare the title compound by substituting Example XXX for Example 269. ¹H-NMR (DMSO-d₆) δ 9.32 (s, 1H), 8.95 (d, J=2 Hz, 1H), 8.61 (dd, i=2, 5 Hz, 1H), 8.37 (s, 1H), 8.05 (bs, 1H), 7.92 (s, 1H), 7.54 (d, J=9 Hz, 2H), 7.46 to 7.52 (m, 1H), 7.36 to 7.40 (m, 1H), 7.31, d, J=9 Hz, 2H), 5.02 (bs, 1H), 2.30 (s, 3H); MS [M+H]⁺=473.3; LCMS RT=2.95 min.

Example 224

Preparation of 4-amino-5-{4-[({[2-fluoro-3-(trifluoromethyl)phenyl]amino}carbonyl)amino]phenyl}-N-(2,2,2-trifluoroethyl)pyrrolo[2,1-f][1,2,4]triazine-6-carboxamide

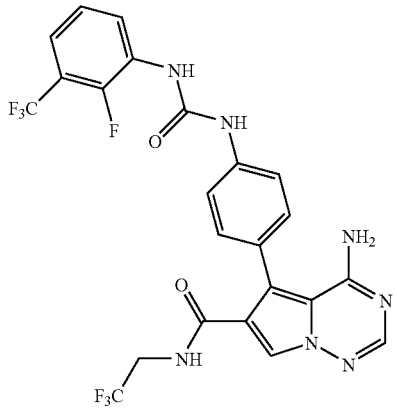

The procedure used for the preparation of Example 73 was used to prepare the title compound by substituting Intermediate M for intermediate X and by (2-Fluoro-3-trifluoromethyl-phenyl)-carbamic acid phenyl ester for phenyl (4-tert-butylpyridin-2-yl)carbamate. ¹H-NMR (DMSO-d₆) δ 9.34 (s, 1H), 8.94 (s, 1H), 8.58 to 8.48 (m, 2H), 8.23 (s, 1H), 7.98 (bs, 1H), 7.96 (s, 1H), 7.56 (d, J=7.5 Hz, 2H), 7.41 to 7.33 (m, 4H), 5.11 (bs, 1H), 4.10 (m, 2H); MS [M+H]⁺=556.1; LCMS RT=3.00 min.

Example 225

Preparation of N-{4-[4-amino-6-(morpholin-4-ylmethyl)pyrrolo[2,1-f][1,2,4]triazin-5-yl]phenyl}-N'-[4-(trifluoromethyl)pyridin-2-yl]urea

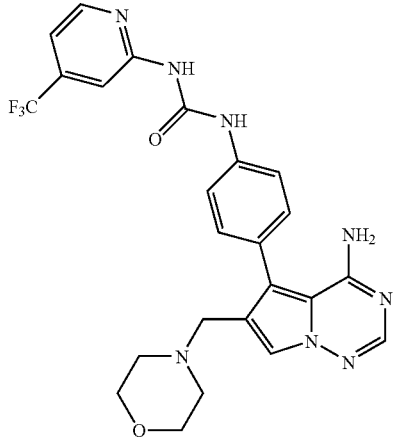

The procedure used for the preparation of Example 30 was used to prepare the title compound by substituting Intermediate AG for Intermediate F. ¹H-NMR (CD₃OD) δ 8.54 (s, 1H), 8.06 (s, 1H), 8.05 (s, 1H), 7.64 to 7.41 (m, 2H), 7.39 to 7.38 (m, 2H), 3.57 to 3.50 (m, 2H), 3.42 to 3.41 (m, 2H), 2.67 to 2.66 (m, 2H), 2.47 to 2.32 (m, 4H); MS [M+H]⁺=513.0; LCMS RT=1.92 min.

Example 226

Preparation of N-{4-[4-amino-6-(cyanomethyl)pyrrolo[2,1-f][1,2,4]triazin-5-yl]phenyl}-N'-[4-(trifluoromethyl)pyridin-2-yl]urea

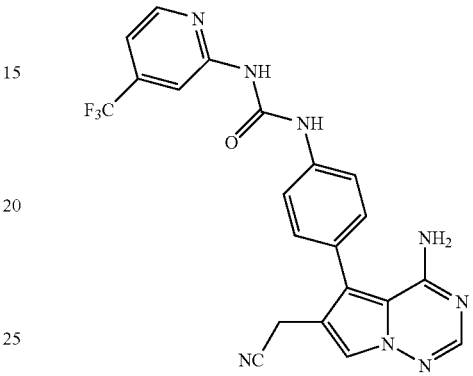

Step 1: Preparation of [4-amino-5-(4-nitrophenyl)pyrrolo[2,1-f][1,2,4]triazin-6-yl]acetonitrile

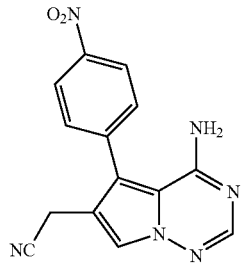

The procedure used for the preparation of Intermediate U Step 1 was used to prepare the title compound by substituting DMF for methanol and sodium cyanide for sodium hydride. MS [M+H]⁺=295.4; LCMS RT=2.11 min.

Step 2: Preparation of 4-amino-5-(4-aminophenyl)pyrrolo[2,1-f][1,2,4]triazin-6-yl]acetonitrile

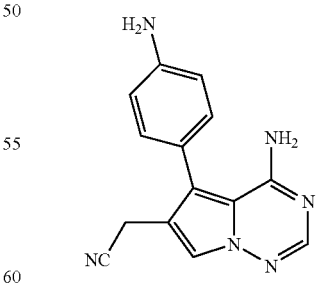

A solution of 4-amino-5-(4-aminophenyl)pyrrolo[2,1-f][1,2,4]triazin-6-yl]acetonitrile (250 mg, 0.85 mmol) and tin (II) chloride (1.61 g, 8.5 mmol) in 75 mL EtOH was heated at 80 C for 1 h. The reaction was then diluted with EtOAc and diluted with sat. NaHCO₃. After 15 min vigorous stirring the mixture was filtered thru a pad of celite, washing well with EtOAc. The organic layer was then separated, dried (Na₂SO₄) and evaporated to dryness. Trituration with Et₂O provided 210 mg of the title compound (93% yield). MS [M+H]⁺=265; LCMS RT=2.63 min.

Step 3: Preparation of [Preparation of N-{4-[4-amino-6-(cyanomethyl)pyrrolo[2,1-f][1,2,4]triazin-5-yl]phenyl}-N'-[4-(trifluoromethyl)pyridin-2-yl]urea

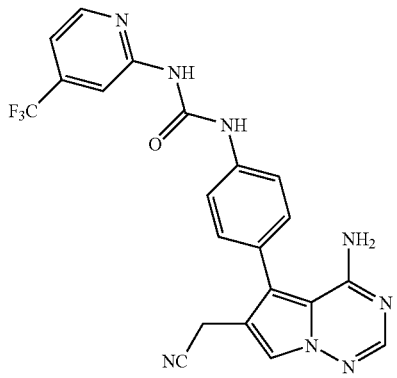

The procedure used for the preparation of Example 101 was used to prepare the title compound by substituting 4-amino-5-(4-aminophenyl)pyrrolo[2,1-f][1,2,4]triazin-6-yl]acetonitrile for intermediate U. ¹H-NMR (DMSO-d₆) δ 8.54 (d, J=5 Hz, 1H), 8.07 (s, 1H), 7.87 (s, 1H), 7.77 (s, 1H), 7.66 (d, J=9 Hz, 2H), 7.36 (d, J=9 Hz, 2H), 7.34 to 7.36 (m, 1H), 3.81 (s, 2H); MS [M+H]⁺=453.1; LCMS RT=2.67 min.

Example 227

Preparation of N-[4-(4-amino-6-{[(2,2,2-trifluoroethyl)amino]methyl}pyrrolo[2,1-f][1,2,4]triazin-5-yl)phenyl]-N'-[6-(trifluoromethyl)pyridin-2-yl]urea

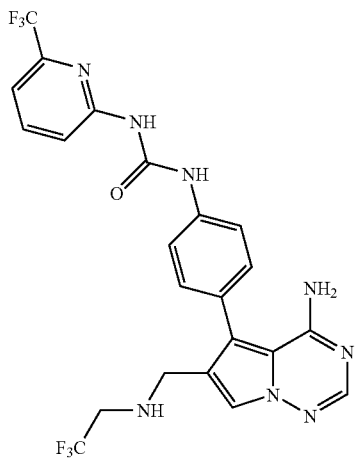

The procedure used for the preparation of Example 30 was used to prepare the title compound by substituting 2,2,2-trifluoroethanamine for morpholine and N-[4-(4-amino-6-formylpyrrolo[2,1-f][1,2,4]triazin-5-yl)phenyl]-N'-[6-(trifluoromethyl)pyridin-2-yl]urea for Intermediate F. ¹H-NMR (DMSO-d₆) δ 9.88 (s, 1H), 9.75 (s, 1H), 8.02 to 7.99 (m, 2H), 7.82 (s, 1H), 7.69 (s, 1H), 7.57 to 7.48 (m, 4H), 7.38 to 3.36 (m, 2H), 3.67 to 3.66 (s, 2H), 3.28 to 3.14 (m, 2H), 2.66 to 2.56 (m, 2H); MS [M+H]⁺=525.0; LCMS RT=2.10 min.

Example 228

Preparation of N-[4-(4-amino-6-{[(2,2,2-trifluoroethyl)amino]methyl}pyrrolo[2,1-f][1,2,4]triazin-5-yl)phenyl]-N'-[4-(trifluoromethyl)pyridin-2-yl]urea

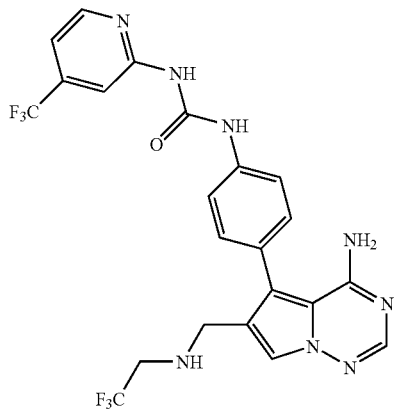

The procedure used for the preparation of Example 30 was used to prepare the title compound by substituting 2,2,2-trifluoroethanamine for morpholine and Intermediate AG for Intermediate F. ¹H-NMR (CD₃OD) δ 8.51 (d, J=5.3 Hz, 1H), 7.77 (s, 1H), 7.48 (br s, 1H), 7.70 to 7.68 (m, 3H), 7.44 to 7.42 (m, 2H), 7.29 to 7.27 (m, 2H), 3.81 (s, 2H), 3.18 to 3.11 (m, 2H); MS [M+H]⁺=525.1; LCMS RT=2.19 min.

Example 229

Preparation of N-[4-(4-amino-6-{[(2-methoxyethyl)amino]methyl}pyrrolo[2,1-f][1,2,4]triazin-5-yl)phenyl]-N'-[4-(trifluoromethyl)pyridin-2-yl]urea

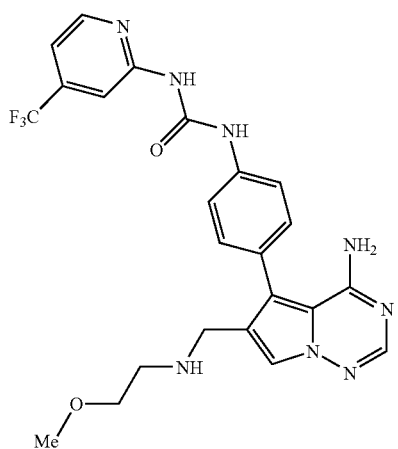

The procedure used for the preparation of Example 30 was used to prepare the title compound by substituting 2-methoxyethanamine for morpholine and Intermediate AG for Intermediate F. ¹H-NMR (CD₃OD) δ 8.51 (d, J=5.3 Hz, 1H), 7.80 (s, 1H), 7.78 (s, 1H), 7.75 to 7.72 (m, 3H), 7.43 to 7.41 (m, 2H), 7.28 (d, J=5.6 Hz, 1H), 3.97 (s, 2H), 3.48 to 3.45 (m, 2H), 2.89 to 2.86 (m, 2H); MS [M+H]⁺=501.0; LCMS RT=1.99 min.

Example 230

Preparation of ethyl 2-(4-amino-5-{4-[({[4-(trifluoromethyl)pyridin-2-yl]amino}carbonyl)amino]phenyl}pyrrolo[2,1-f][1,2,4]triazin-6-yl)-4,5-dihydro-1,3-oxazole-4-carboxylate

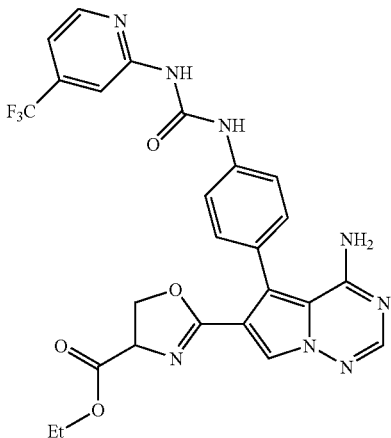

To a solution of THF (2 mL) was added ethyl N-[(4-amino-5-{4-[({[4-(trifluoromethyl)pyridin-2-yl]amino}carbonyl)amino]phenyl}pyrrolo[2,1-f][1,2,4]triazin-6-yl)carbonyl]serinate (Example 221) (50 mg, 0.09 mmol) which was cooled to −78° C. DAST (13 μL, 0.10 mmol) was added and the reaction proceeded for 1 h while stirring under N₂. Anhydrous K₂CO₃ was then added and the solution was allowed to warm to rt over the following 30 min. The reaction mixture was transferred to a separatory funnel, diluted with EtOAc (20 mL), washed with aq saturated NaHCO₃ (20 mL) and H₂O (20 mL). The organic was collected, dried (MgSO4), and evaporated in vacuo. The crude material was purified by preparative HPLC (10-90% ACN/H₂O with 0.1% TFA). The fractions were left overnight resulting in the partial formation of a new product. The two products were separated by column chromatography 5:4:1 v/v/v DCM/EtOAc/MeOH resulting in the isolation of 9 mg of the title compound (0.016 mmol, 18%). ¹H-NMR (DMSO-d₆) δ 9.91 (s, 1H), 9.78 (s, 1H), 8.54 to 8.53 (d, J=5.0 Hz, 1H), 8.08 (s, 1H), 8.05 (s, 1H), 7.91 (s, 1H), 7.58 to 7.56 (d, J=8.6 Hz, 2H), 7.37 to 7.36 (d, J=5.1 Hz, 1H), 7.34 to 7.32 (d, J=8.6 Hz, 2H), 4.75 to 4.71 (m, 1H), 4.38 to 4.29 (m, 2H), 4.13 to 4.08 (q, J=7.1 Hz, 2H), 1.21 to 1.18 (t, J=7.0 Hz, 3H); MS [M+H]⁺=555.1; LCMS RT=2.84 min.

Example 231

Preparation of 2-amino-3-ethoxy-3-oxopropyl 4-amino-5-{4-[({[4-(trifluoromethyl)pyridin-2-yl]amino}carbonyl)amino]phenyl}pyrrolo[2,1-f][1,2,4]triazine-6-carboxylate

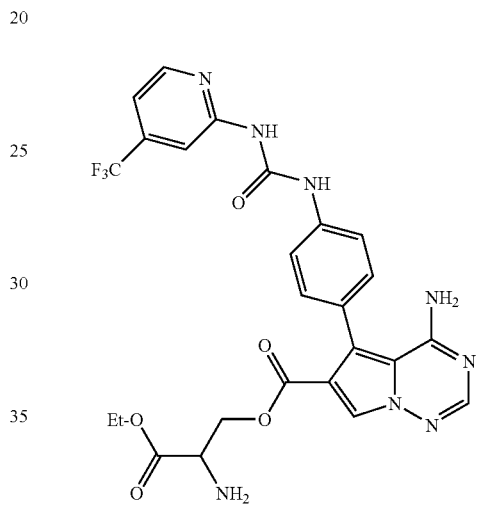

To a solution of THF (2 mL) was added ethyl N-[(4-amino-5-{4-[({[4-(trifluoromethyl)pyridin-2-yl]amino}carbonyl)amino]phenyl}pyrrolo[2,1-f][1,2,4]triazin-6-yl)carbonyl]serinate (Example 221) (50 mg, 0.09 mmol) which was cooled to −78° C. DAST (13 mL, 0.10 mmol) was added and the reaction proceeded for 1 h while stirring under N₂. Anhydrous K₂CO₃ was then added and the solution was allowed to warm to rt over the following 30 min. The reaction mixture was transferred to a separatory funnel, diluted with EtOAc (20 mL), washed with aq saturated NaHCO₃ (20 mL) and H₂O (20 mL). The organic was collected, dried (MgSO4), and evaporated in vacuo. The crude material was purified by preparative HPLC (10-90% ACN/H₂O with 0.1% TFA). The fractions were left overnight resulting in the partial formation of a new product. The two products were separated by column chromatography 5:4:1 v/v/v DCM/EtOAc/MeOH resulting in the isolation of 4 mg of the title compound (0.0075 mmol, 9%). ¹H-NMR (DMSO-d₆) δ 9.92 (s, 1H), 9.78 (s, 1H), 8.54 to 8.53 (d, J=5.4 Hz, 1H), 8.15 (s, 1H), 8.07 (s, 1H), 7.93 (s, 1H), 7.60 to 7.58 (d, J=8.8 Hz, 2H), 7.37 to 7.35 (d, J=6.4 Hz, 1H), 7.33 to 7.31 (d, J=8.6 Hz, 2H), 4.25 to 4.21 (m, 1H), 4.12 to 4.08 (m, 1H), 4.07 to 4.02 (q, J=7.0 Hz, 2H), 3.55 to 3.52 (t, J=4.9 Hz, 1H), 1.15 to 1.11 (t, J=7.2 Hz, 3H); MS [M+H]⁺=573.1; LCMS RT=2.38 min.

Example 232

Preparation of ethyl 2-(4-amino-5-{4-[({[4-(trifluoromethyl)pyridin-2-yl]amino}carbonyl)amino]phenyl}pyrrolo[2,1-f][1,2,4]triazin-6-yl)-1,3-oxazole-4-carboxylate

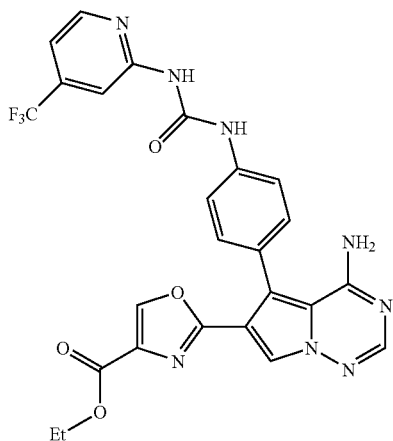

To a solution of THF (16 mL) was added ethyl N-[(4-amino-5-{4-[({[4-(trifluoromethyl)pyridin-2-yl]amino}carbonyl)amino]phenyl}pyrrolo[2,1-f][1,2,4]triazin-6-yl)carbonyl]serinate (Example 221) (437 mg, 0.76 mmol) which was cooled to −78° C. DAST (0.14 mL, 1.07 mmol) was added and the reaction proceeded for 1 h while stirring under N₂. Additional DAST (0.14 mL, 1.07 mmol) was added and the solution was stirred for 30 min. The acetone/dry ice cooling bath was replaced with an ice/water bath and DBU (0.41 mL, 2.75 mmol) and BrCCl₃ (0.27 mL, 2.75 mmol) were added and the solution was allowed to warm to rt over 17 h. Additional DBU (0.41 mL, 2.75 mmol) and BrCCl₃ (0.27 mL, 2.75 mmol) were added and the solution was allowed to stir for 6 h. The reaction mixture was transferred to a separatory funnel, diluted with EtOAc (50 mL), washed with aq saturated NaHCO₃ (50 mL) and H₂O (50 mL). The aqueous fraction was back extracted with DCM (3×30 mL). The combined organic layers were dried (MgSO4), evaporated in vacuo and flashed 5:4:1 v/v/v DCM/EtOAc/MeOH resulting in the isolation of 33 mg of the title compound (0.060 mmol, yield 8%). ¹H-NMR (DMSO-d₆) δ 9.93 (s, 1H), 9.77 (s, 1H), 8.70 (s, 1H), 8.55 to 8.54 (d, J=5.0 Hz, 1H), 8.30 (s, 1H), 8.06 (s, 1H), 7.95 (s, 1H), 7.64 to 7.61 (d, J=8.8 Hz, 2H), 7.42 to 7.40 (d, J=8.8 Hz, 2H), 7.38 to 7.36 (d, J=6.2 Hz, 1H), 4.28 to 4.23 (q, J=7.6 Hz, 2H), 1.28 to 1.25 (t, J=7.1 Hz, 3H); MS [M+H]⁺=553.1; LCMS RT=3.04 min.

Example 233

Preparation of N-[4-(6-acetyl-4-aminopyrrolo[2,1-f][1,2,4]triazin-5-yl)phenyl]-N'-[4-(trifluoromethyl)pyridin-2-yl]urea

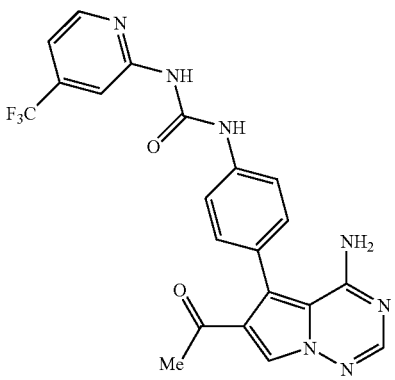

The procedure used for the preparation of Intermediate F step 2 was used to prepare the title compound by substituting Example 269 for N-{4-[4-amino-6-(hydroxymethyl)pyrrolo[2,1-f][1,2,4]triazin-5-yl]phenyl}-N'-[2-fluoro-5-(trifluoromethyl)phenyl]urea. ¹H-NMR (CD₃OD) δ 8.51 (d, J=5 Hz, 1H), 8.15 (s, 1H), 7.97 (s, 1H), 7.89 (s, 1H), 7.77 (d, J=9 Hz, 2H), 7.38 (d, J=9 Hz, 2H), 7.26 (d, J=5 Hz, 1H), 2.29 (s, 3H); MS [M+H]⁺=456.0; LCMS RT=2.71 min.

Example 234

Preparation of N-(4-{4-amino-6-[4-(hydroxymethyl)-1,3-oxazol-2-yl]pyrrolo[2,1-f][1,2,4]triazin-5-yl}phenyl)-N'-[4-(trifluoromethyl)pyridin-2-yl]urea

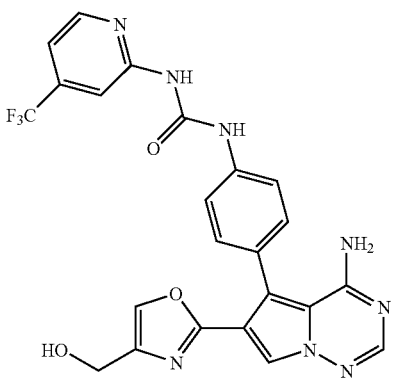

The procedure used for the preparation of Example 241 was used to prepare the title compound by substituting Example 232 for Example 237. ¹H-NMR (DMSO-d₆) δ 9.91 (s, 1H), 9.76 (s, 1H), 8.53 (d, J=5.4 Hz, 1H), 8.17 (s, 1H), 8.05 (s, 1H), 7.92 (s, 1H), 7.75 (s, 1H), 7.62 (s, 1H), 7.61 (d, J=8.6 Hz, 2H), 7.40 to 7.36 (m, 3H), 5.14 to 5.11 (m, 1H), 4.31 (d, J=5.7 Hz, 2H); MS [M+H]⁺=511.0; LCMS RT=2.33 min.

Example 235

Preparation of N-{4-[4-amino-6-(1,3-oxazol-2-yl)pyrrolo[2,1-f][1,2,4]triazin-5-yl]phenyl}-N'-[4-(trifluoromethyl)pyridin-2-yl]urea

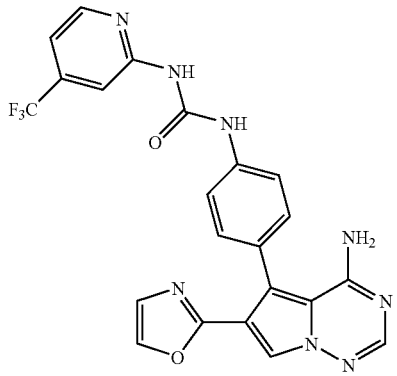

Step 1: Preparation of 5-(4-Nitro-phenyl)-6-oxazol-2-yl-pyrrolo[2,1-f][1,2,4]triazin-4-ylamine

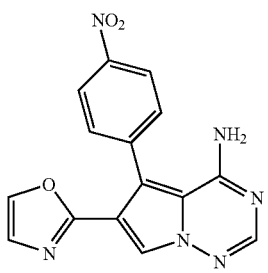

The procedure used for the preparation of the first step of intermediate M was used to prepare 4-Amino-5-(4-nitro-phenyl)-pyrrolo[2,1-f][1,2,4]triazine-6-carboxylic acid (2,2-dimethoxy-ethyl)-amide by substituting 2,2-Dimethoxyethylamine for 2,2,2-trifluoro-ethylamine hydrochloride salt. To a solution of methanesulfonic acid (1.5 ml) was added P₂O₅ (225.0 mg, 1.58 mmol) followed by the addition of 4-amino-5-(4-nitro-phenyl)-pyrrolo[2,1-f][1,2,4]triazine-6-carboxylic acid (2,2-dimethoxy-ethyl)-amide (150 mg, 0.388 mmol). The dark brown mixture was heated to 100° C. and allowed to stir for 18 hrs. The mixture was then poured over ice (15 g), stirred for fifteen minutes and enough saturated sodium carbonate solution was added to neutralize the reaction. A white precipitate was filtered and collected (35 mg, 27%). ¹H-NMR (DMSO-d₆) δ 8.33 (s, 1H), 8.31 (m, 2H), 8.03 (d, J=10 Hz, 2H), 7.73 (d, J=10 Hz, 2H), 7.28 (s, 1H). MS [M+H]⁺=323.2; LCMS RT=2.51 min.

Step 2: Preparation of 5-(4-Amino-phenyl)-6-oxazol-2-yl-pyrrolo[2,1-f][1,2,4]triazin-4-ylamine

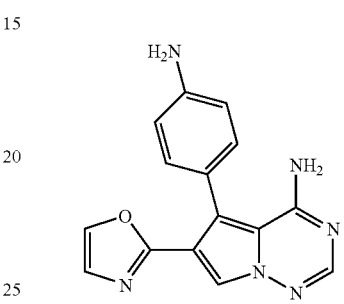

The procedure used for the preparation of intermediate B was used to prepare the title compound substituting 5-(4-Nitro-phenyl)-6-oxazol-2-yl-pyrrolo[2,1-f][1,2,4]triazin-4-ylamine for 4-amino-5-(4-aminophenyl)pyrrole[2,1-f][1,2,4]triazine-6-carboxylate. MS [M+H]⁺=293.3; LCMS RT=0.38 min.

Step 3: Preparation of N-{4-[4-amino-6-(1,3-oxazol-2-yl)pyrrolo[2,1-f][1,2,4]triazin-5-yl]phenyl}-N'-[4-(trifluoromethyl)pyridin-2-yl]urea

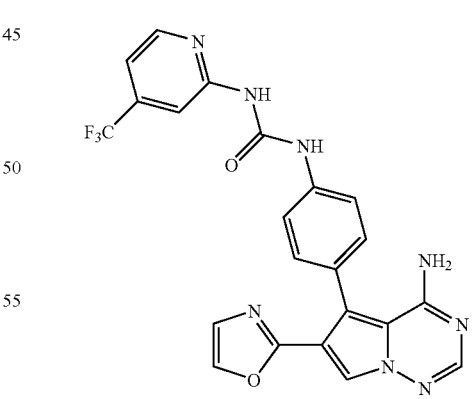

The procedure used for the preparation of Example 73 was used to prepare the title compound by substituting 5-(4-amino-phenyl)-6-oxazol-2-yl-pyrrolo[2,1-f][1,2,4]triazin-4-ylamine for intermediate X and phenyl[4-(trifluoromethyl)pyridin-2-yl]carbamate for phenyl (4-tertbutylpyridin-2-yl)carbamate. ¹H-NMR (DMSO-d₆) δ 9.94 (s, 1H), 9.79 (s, 1H), 8.55 (d, J=6.2 Hz, 1H), 8.23 (s, 1H), 8.07 (s, 1H), 8.00 (s, 1H), 7.94 (s, 1H), 7.61 (d, J=7.9 Hz, 2H), 7.40 (d, J=7.9 Hz, 2H), 7.36 (s, 1H), 7.18 (s, 1H); MS [M+H]⁺=481.1; LCMS RT=3.11 min.

Example 236

Preparation of ethyl 2-(4-amino-5-{4-[({[2-fluoro-5-(trifluoromethyl)phenyl]amino}carbonyl)amino]phenyl}pyrrolo[2,1-f][1,2,4]triazin-6-yl)-4,5-dihydro-1,3-oxazole-4-carboxylate

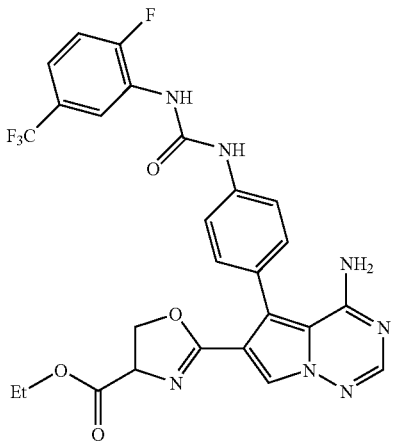

The procedure used for the preparation of Example 230 was used to prepare the title compound by substituting ethyl N-[(4-amino-5-{4-[({[2-fluoro-5-(trifluoromethyl)phenyl]amino}carbonyl)amino]phenyl}pyrrolo[2,1-f][1,2,4]triazin-6-yl)carbonyl]serinate (Example 220) for ethyl 2-(4-amino-5-{4-[({[4-(trifluoromethyl)pyridin-2-yl]amino}carbonyl)amino]phenyl}pyrrolo[2,1-f][1,2,4]triazin-6-yl)-4,5-dihydro-1,3-oxazole-4-carboxylate (Example 221). ¹H-NMR (DMSO-d₆) δ 9.31 (s, 1H), 8.96 to 8.95 (d, J=2.9 Hz, 1H), 8.63 to 8.61 (d, J=7.2 Hz, 1H), 8.08 (s, 1H), 7.91 (s, 1H), 7.54 to 7.52 (d, J=8.6 Hz, 2H), 7.50 to 7.48 (d, J=10.9 Hz, 1H), 7.41 to 7.38 (m, 1H), 7.33 to 7.31 (d, J=8.6 Hz, 2H), 4.76 to 4.71 (m, 1H), 4.38 to 4.29 (m, 2H), 4.13 to 4.08 (q, J=6.5 Hz, 2H), 1.21 to 1.18 (t, J=7.2 Hz, 3H); MS [M+H]⁺=572.2; LCMS RT=2.94 min.

Example 237

Preparation of ethyl 2-(4-amino-5-{4-[({[2-fluoro-5-(trifluoromethyl)phenyl]amino}carbonyl)amino]phenyl}pyrrolo[2,1-f][1,2,4]triazin-6-yl)-1,3-oxazole-4-carboxylate

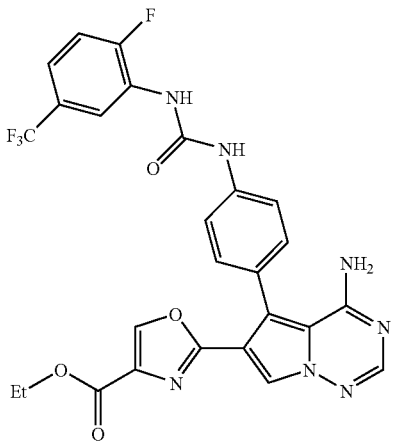

To a solution of THF (2 mL) and DCM (2 mL) cooled in an ice/water bath was added ethyl 2-(4-amino-5-{4-[({[2-fluoro-5-(trifluoromethyl)phenyl]amino}carbonyl)amino]phenyl}pyrrolo[2,1-f][1,2,4]triazin-6-yl)-4,5-dihydro-1,3-oxazole-4-carboxylate (Example 236) followed by DBU (24 µJ, 0.16 mmol) and BrCCl₃ (16 µL, 0.16 mmol). The solution was allowed to stir under N₂ for 1 h and then the solution was left to warm to rt while stirring for 17 h. The reaction mixture was evaporated in vacuo and then purified by flash chromatography 50:45:5 v/v/v DCM/EtOAc/MeOH resulting in the isolation of 16 mg of the title compound as a white solid (0.028 mmol, yield 65%). ¹H-NMR (DMSO-d₆) δ 9.35 (s, 1H), 8.96 (d, J=2.8 Hz, 1H), 8.69 (s, 1H), 8.62 to 8.60 (d, J=9.3 Hz, 1H), 8.29 (s, 1H), 7.94 (s, 1H), 7.58 to 7.56 (d, J=8.4 Hz, 2H), 7.52 to 7.47 (m, 1H), 7.40 to 7.37 (m, 3H), 4.27 to 4.23 (q, J=6.3 Hz, 2H), 1.28 to 1.24 (t, J=7.1 Hz, 3H); MS [M+H]⁺=570.1; LCMS RT=3.16 min.

Example 238

Preparation of N-[4-(4-amino-6-{[(1-methylpiperidin-4-yl)methoxy]methyl}pyrrolo[2,1-f][1,2,4]triazin-5-yl)phenyl]-N'-[2-fluoro-5-(trifluoromethyl)phenyl]urea

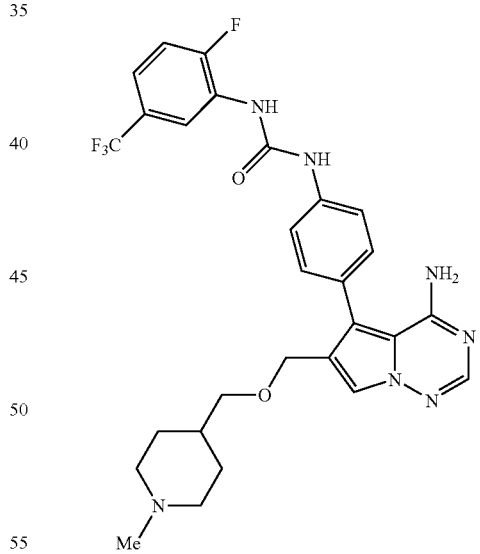

The procedure used for the preparation of Example 271 was used to prepare the title compound by substituting (1-methylpiperidin-4-yl)methanol for methanol and the product from Intermediate F (Step 1) for Example 262. ¹H-NMR (DMSO-d₆) δ 8.58 to 8.57 (m, 1H), 8.05 to 7.93 (m, 2H), 1.68 to 7.64 (m, 2H), 7.51 to 7.46 (m, 1H), 7.38 to 7.36 (m, 2H), 4.46 (s, 2H), 4.02 to 4.00 (m, 1H), 3.27 to 3.09 (m, 4H), 2.66 (s, 3H), 1.62 to 1.55 (m, 2H), 1.25 to 1.15 (m, 2H); MS [M+H]⁺=572.1; LCMS RT=2.06 min.

Example 239

Preparation of N-{4-[4-amino-6-(hydroxymethyl) pyrrolo[2,1-f][1,2,4]triazin-5-yl]phenyl}-N'-[3-tert-butyl-1-(4-fluorophenyl)-1H-pyrazol-5-yl]urea

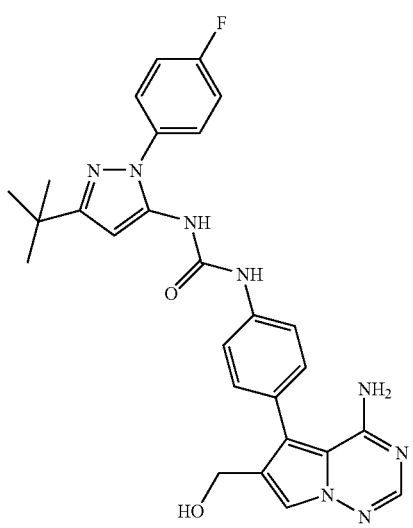

The procedure used for the preparation of Intermediate F step 1 was used to prepare the title compound by substituting Example 25 for Intermediate E. $^1$H-NMR (DMSO-d$_6$) δ 9.11 (s, 1H), 8.42 (s, 1H), 7.81 (s, 1H), 7.64 (s, 1H), 7.48 to 7.58 (m, 5H), 7.28 to 7.48 (m, 5H), 6.36 (s, 1H), 4.94 (t, J=5 Hz, 1H), 4.34 (d, J=5 Hz, 2H), 1.26 (s, 9H); MS [M+H]$^+$=515.2; LCMS RT=2.48 min.

Example 240

Preparation of N-{4-[4-amino-6-(cyanomethyl)pyrrolo[2,1-f][1,2,4]triazin-5-yl]phenyl}-N'-[2-fluoro-5-(trifluoromethyl)phenyl]urea

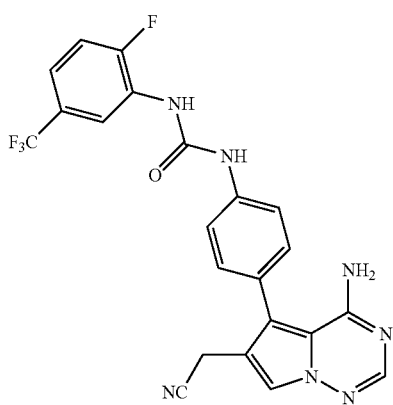

The procedure used for the preparation of Example 226 was used to prepare the title compound by substituting phenyl [2-fluoro-5-(trifluoromethyl)phenyl]carbamate for phenyl[2-fluoro-5-(trifluoromethyl)phenyl]carbamate. $^1$H-NMR (DMSO-d$_6$) δ 9.41 (s, 1H), 9.01 (d, J=3 Hz, 1H), 8.62 (d, J=3, 8 Hz, 1H), 7.81 (s, 1H), 7.77 (s, 1H), 7.61 (d, J=9 Hz, 2H), 7.47 to 7.54 (m, 1H), 7.38 to 7.42 (m, 1H), 7.35 (d, J=9 Hz, 2H), 5.35 (dd, J=2, 6 Hz), 3.82 (s, 2H); MS [M+H]$^+$=470.1; LCMS RT=2.80 nm.

Example 241

Preparation of N-(4-{4-amino-6-[4-(hydroxymethyl)-1,3-oxazol-2-yl]pyrrolo[2,1-f][1,2,4]triazin-5-yl}phenyl)-N'-[2-fluoro-5-(trifluoromethyl)phenyl]urea

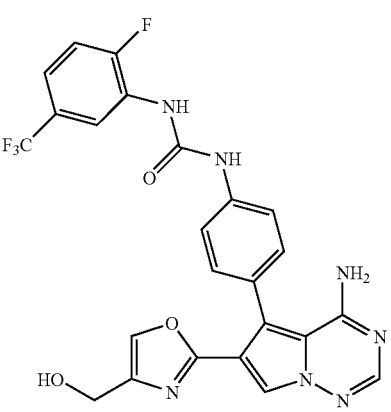

The procedure used for the preparation of Intermediate F Step 1 was used to prepare the title compound by substituting ethyl 2-(4-amino-5-{4-[({[2-fluoro-5-(trifluoromethyl)phenyl]amino}carbonyl)amino]phenyl}pyrrolo[2,1-f][1,2,4]triazin-6-yl)-1,3-oxazole-4-carboxylate (Example 232) for Intermediate E. $^1$H-NMR (DMSO-d$_6$) δ 9.35 (s, 1H), 8.97 to 8.96 (d, J=3.4 Hz, 1H), 8.63 to 8.61 (d, J=7.4 Hz, 1H), 8.17 (s, 1H), 7.93 (s, 1H), 7.75 (s, 1H), 7.58 to 7.56 (d, J=8.7 Hz, 2H), 7.53 to 7.48 (m, 1H), 7.41 to 7.36 (m, 3H), 5.16 to 5.13 (t, J=5.6 Hz, 1H), 4.32 to 4.31 (d, J=5.5 Hz, 2H); MS [M+H]$^+$=528.1; LCMS RT=2.68 min.

Example 242

Preparation of ethyl 4-amino-5-{3-fluoro-4-[({[4-(trifluoromethyl)pyridin-2-yl]amino}carbonyl)amino]phenyl}pyrrolo[2,1-f][1,2,4]triazine-6-carboxylate

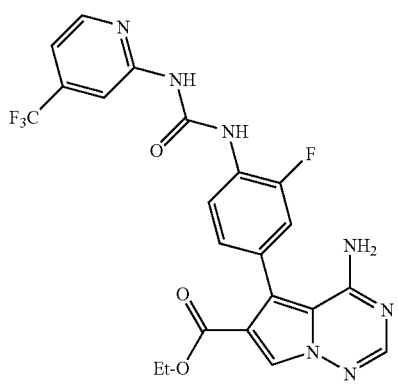

The procedure used for the preparation of Example 73 was used to prepare the title compound by substituting Intermediate AJ for Intermediate X and by substituting phenyl[4-(trifluoromethyl)pyridin-2-yl]carbamate for phenyl (4-tert-butylpyridin-2-yl)carbamate. $^1$H-NMR (DMSO-d$_6$) δ 10.14 (s, 1H), 10.11 to 10.04 (br s, 1H), 8.54 to 8.53 (d, J=5.3 Hz, 1H), 8.28 to 8.23 (t, J=8.4 Hz, 1H), 8.14 (s, 1H), 8.01 (s, 1H), 7.94 (s, 1H), 7.39 to 7.33 (m, 2H), 7.18 to 7.16 (d, J=10.0 Hz, 1H), 4.12 to 4.06 (q, J=8.3 Hz, 2H), 1.14 to 1.10 (t, J=7.1 Hz, 3H); MS [M+H]$^+$=504.1; LCMS RT=3.12 min.

Example 243

Preparation of N-{4-[4-amino-6-(hydroxymethyl)pyrrolo[2,1-f][1,2,4]triazin-5-yl]-2-fluorophenyl}-N'-[4-(trifluoromethyl)pyridin-2-yl]urea

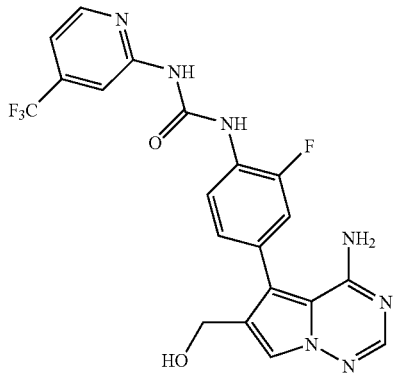

The procedure used for the preparation of Intermediate F Step 1 was used to prepare the title compound by substituting ethyl 4-amino-5-{3-fluoro-4-[({[4-(trifluoromethyl)pyridin-2-yl]amino}carbonyl)amino]phenyl}pyrrolo[2,1-f][1,2,4]triazine-6-carboxylate (Example 242) for Intermediate E. $^1$H-NMR (DMSO-d$_6$) δ 10.13 (s, 1H), 10.07 to 10.02 (br s, 1H), 8.54 to 8.53 (d, J=5.3 Hz, 1H), 8.29 to 8.24 (t, J=8.5 Hz, 1H), 8.03 (s, 1H), 7.84 (s, 1H), 7.67 (s, 1H), 7.39 (s, 1H), 7.38 to 7.35 (d, J=8.7 Hz, 1H), 7.21 to 7.19 (d, J=9.7 Hz, 1H), 5.02 to 5.00 (t, J=5.1 Hz, 1H), 4.39 to 4.37 (d, J=5.2 Hz, 2H); MS [M+H]$^+$=462.0; LCMS RT=2.44 min.

Example 244

Preparation of N-[4-(4-amino-6-cyanopyrrolo[2,1-f][1,2,4]triazin-5-yl)phenyl]-N'-[4-(trifluoromethyl)pyridin-2-yl]urea

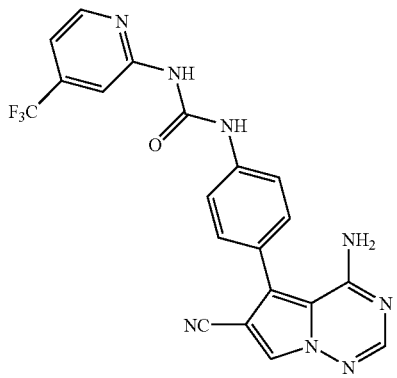

The procedure used for the preparation of Example 73 was used to prepare the title compound by substituting Intermediate P for Intermediate X and by substituting phenyl[2-fluoro-5-(trifluoromethyl)phenyl]carbamate for phenyl (4-tert-butylpyridin-2-yl)carbamate. $^1$H-NMR (DMSO-d$_6$) δ 9.96 (s, 1H), 9.78 (s, 1H), 8.55 (d, J=5 Hz, 1H), 8.52 (s, 1H), 8.07 (s, 1H), 7.99 (s, 1H), 7.69 (d, J=9 Hz, 2H), 7.45 (d, J=9 Hz, 2H), 7.36 (d, J=5 Hz, 1H); MS [M+H]$^+$=439.1; LCMS RT=3.01 min.

Example 245

Preparation of methyl 4-amino-5-{4-[({[3-tert-butyl-1-(4-fluorophenyl)-1H-pyrazol-5-yl]amino}carbonyl)amino]phenyl}pyrrolo[2,1-f][1,2,4]triazine-6-carboxylate

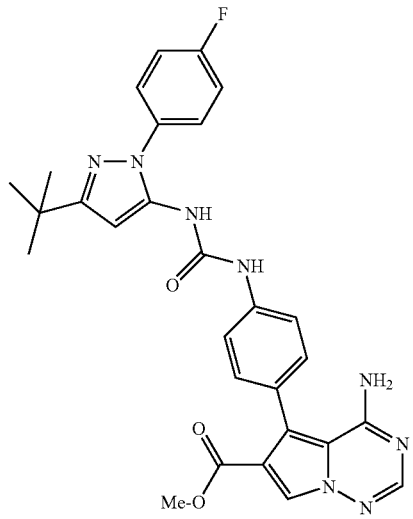

The procedure used for the preparation of Example 25 was used to prepare the title compound by substituting methyl 4-amino-5-(4-aminophenyl)pyrrolo[2,1f][1,2,4]triazine-6-carboxylate for Intermediate B. $^1$H-NMR (DMSO-d$_6$) δ 9.14 (s, 1H), 8.43 (s, 1H), 8.13 (s, 1H), 7.92 (s, 1H), 7.25 to 7.60 (m, 8H), 6.36 (s, 1H), 7.32 to 7.40 (m, 4H), 7.17 to 7.25 (m, 1H), 7.14 (bs, 1H), 6.34 (s, 1H), 3.61 (s, 1H); MS [M+Na]$^+$=565.2; LCMS RT=3.13 min.

Example 246

Preparation of N-{4-[4-amino-6-(ethoxymethyl)pyrrolo[2,1-f][1,2,4]triazin-5-yl]phenyl}-N'-[2-fluoro-5-(trifluoromethyl)phenyl]urea

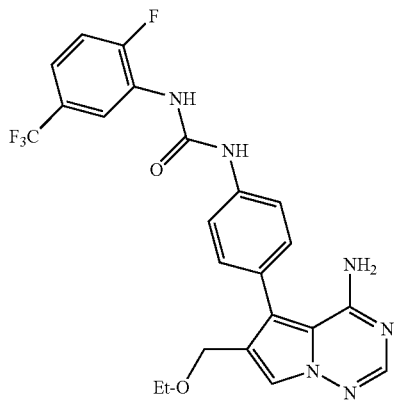

217

Step 1: Preparation of 6-(ethoxymethyl)-5-(4-nitrophenyl)pyrrolo[2,1-f][1,2,4]triazin-4-amine

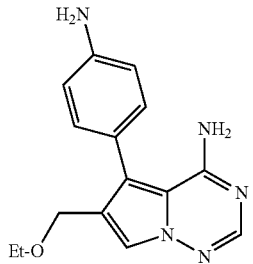

The method used in the preparation of Intermediate U was used to prepare the title compounds by substituting ethanol for methanol. MS [M+H]$^+$=284.1; LCMS RT=0.35 min.

Step 2: Preparation of N-{4-[4-amino-6-(ethoxymethyl)pyrrolo[2,1-f][1,2,4]triazin-5-yl]phenyl}-N'-[2-fluoro-5-(trifluoromethyl)phenyl]urea

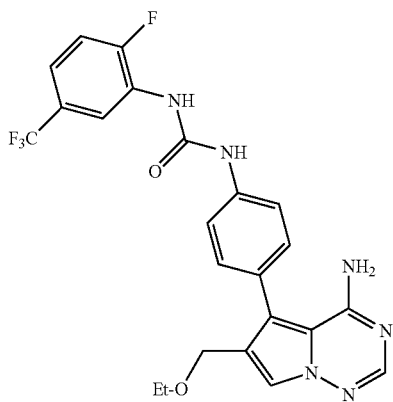

The procedure used for the preparation of Example 1 was used to prepare the title compound by substituting 6-(ethoxymethyl)-5-(4-aminophenyl)pyrrolo[2,1-f][1,2,4]triazin-4-amine in place of Intermediate B. $^1$H-NMR (DCM-d$_2$) δ 12.19 (s, 1H), 8.51 (d, J=7.5 Hz, 1H), 8.01 (s, 1H), 7.74 (s, 1H), 7.4-7.3 (bs, 1H), 7.29-7.14 (m, 5H), 6.8 (s, 1H), 4.34 (s, 2H), 3.40 (q, J=7.0 Hz, 2H), 0.80 (m, 3H); MS [M+H]$^+$=489.2; LCMS RT=3.92 min.

Example 247

Preparation of N-{4-[4-amino-6-(methoxymethyl)pyrrolo[2,1-f][1,2,4]triazin-5-yl]-2-fluorophenyl}-N'-[4-(trifluoromethyl)pyridin-2-yl]urea

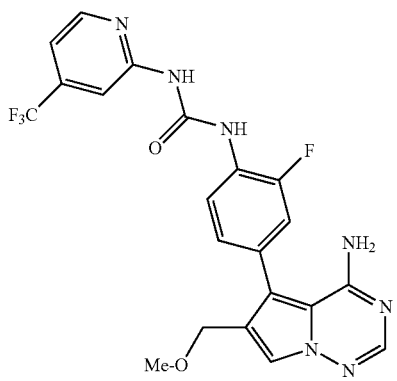

218

The procedure used for the preparation of Example 271 was used to prepare the title compound by substituting N-{4-[4-amino-6-(hydroxymethyl)pyrrolo[2,1-f][1,2,4]triazin-5-yl]-2-fluorophenyl}-N'-[4-(trifluoromethyl)pyridin-2-yl]urea (Example 243) for N-{4-[4-amino-6-(hydroxymethyl)pyrrolo[2,1-f][1,2,4]triazin-5-yl]phenyl}-N'-(4-methylpyridin-2-yl)urea (Example 262). $^1$H-NMR (DMSO-d$_6$) δ 10.14 (s, 1H), 10.09 to 10.04 (br s, 1H), 8.54 to 8.53 (d, J=5.5 Hz, 1H), 8.30 to 8.26 (t, J=8.5 Hz, 1H), 8.00 (s, 1H), 7.86 (s, 1H), 7.76 (s, 1H), 7.39 to 7.38 (d, J=5.2 Hz, 1H), 7.35 to 7.32 (d, J=12.0 Hz, 1H), 7.21 to 7.18 (d, J=10.2 Hz, 1H), 4.28 (s, 2H), 3.22 (s, 3H); MS [M+H]$^+$=476.1; LCMS RT=2.77 min.

Example 248

Preparation of N-(4-{4-amino-6-[(2-methoxyethoxy)methyl]pyrrolo[2,1-f][1,2,4]triazin-5-yl}phenyl)-N'-[3-tert-butyl-1-(4-fluorophenyl)-1H-pyrazol-5-yl]urea

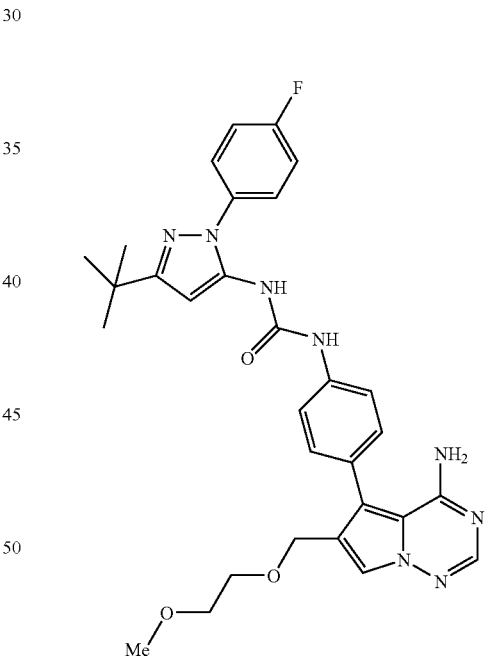

The procedure used for preparation of Example 73 was used to prepare the title compound by substituting Intermediate Z for Intermediate X and substituting phenyl (3-tert-butyl-1-(4-fluorophenyl)-1H-pyrazol-5-)-carbamate for phenyl (4-tert-butylpyridin-2-yl)carbamate. $^1$H-NMR (DMSO-d$_6$) δ 9.13 (s, 1H), 8.43 (s, 1H), 7.83 (s, 1H), 7.73 (s, 1H), 7.58-7.49 (m, 4H), 7.38 (d, J=9.4 Hz 2H), 7.31 (d, J=9.4 Hz, 2H), 6.37 (s, 1H), 4.30 (s, 2H), 3.46-3.43 (m, 2H), 3.40-3.37 (m, 2H), 3.20 (s, 3H), 1.26 (s, 9H); MS [M+H]$^+$=573.1; LCMS RT=2.71 min.

Example 249

Preparation of ethyl 4-amino-5-{3-fluoro-4-[({[2-fluoro-5-(trifluoromethyl)phenyl]amino}carbonyl)amino]phenyl}pyrrolo[2,1-f][1,2,4]triazine-6-carboxylate

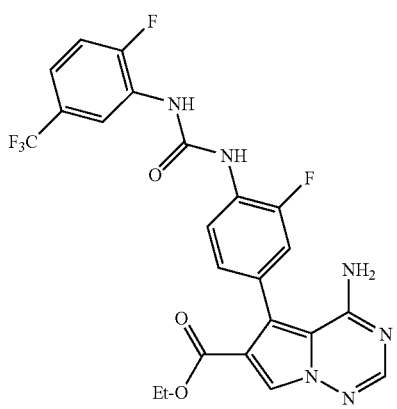

The procedure used for the preparation of Example 73 was used to prepare the title compound by substituting Intermediate AJ for Intermediate X and phenyl[2-fluoro-5-(trifluoromethyl)phenyl]carbamate for phenyl (4-tert-butylpyridin-2-yl)carbamate. $^1$H-NMR (DMSO-d$_6$) δ 9.42 (s, 1H), 9.28 (s, 1H), 8.65 to 8.63 (m, 1H), 8.27 to 8.22 (m, 1H), 8.13 (s, 1H), 7.93 (s, 1H), 4.11 to 4.06 (m, 2H), 1.14 to 1.10 (m, 3H); MS [M+H]$^+$=521.3; LCMS RT=2.98 min.

Example 250

Preparation of 4-amino-5-{4-[({[4-(trifluoromethyl)pyridin-2-yl]amino}carbonyl)amino]phenyl}pyrrolo[2,1-f][1,2,4]triazine-6-carboxylic acid

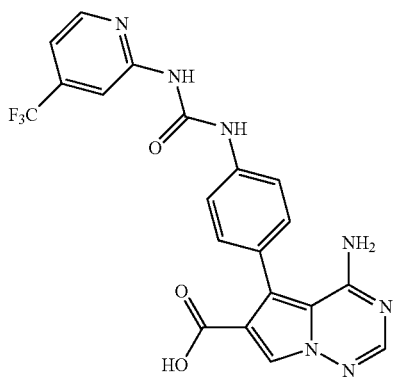

The procedure used for the preparation of Intermediate G was used to prepare the title compound by substituting Example 51 for Intermediate E. $^1$H-NMR (DMSO-d$_6$) δ 12.3 (s, 1H), 9.87 (s, 1H), 9.75 (s, 1H), 8.53 (d, J=5.3 Hz, 2H), 8.07 to 8.06 (m, 3H), 7.86 (s, 1H), 7.58 to 7.56 (m, 2H), 7.36 to 7.33 (m, 3H); MS [M+H]$^+$=458.0; LCMS RT=2.28 min.

Example 251

Preparation of N-{4-[4-amino-6-(hydroxymethyl)pyrrolo[2,1-f][1,2,4]triazin-5-yl]-2-fluorophenyl}-N'-[2-fluoro-5-(trifluoromethyl)phenyl]urea

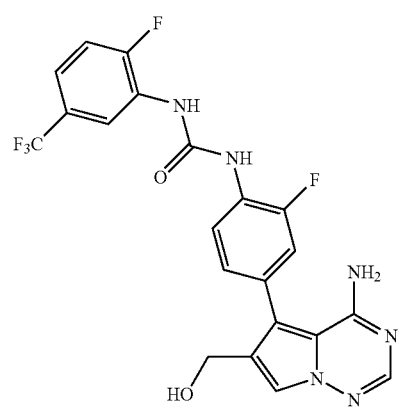

The procedure used for the preparation of Intermediate AF was used to prepare the title compound by substituting Example 249 for Example 51. $^1$H-NMR (DMSO-d$_6$) δ 9.41 (s, 1H), 9.40 (s, 1H), 9.26 to 8.63 (m, 1H), 8.28 to 8.24 (m, 1H), 7.83 (s, 1H), 7.66 (s, 1H), 7.53 to 7.48 (m, 1H), 7.41 to 7.33 (m, 2H), 7.18 (d, J=8.2 Hz, 1H), 5.01 to 4.98 (m, 1H), 4.37 (d, J=5.0 Hz, 2H); MS [M+H]$^+$=479.1; LCMS RT=2.49 min.

Example 252

Preparation of 4-amino-5-{3-fluoro-4-[({[2-fluoro-5-(trifluoromethyl)phenyl]amino}carbonyl)amino]phenyl}pyrrolo[2,1-f][1,2,4]triazine-6-carboxylic acid

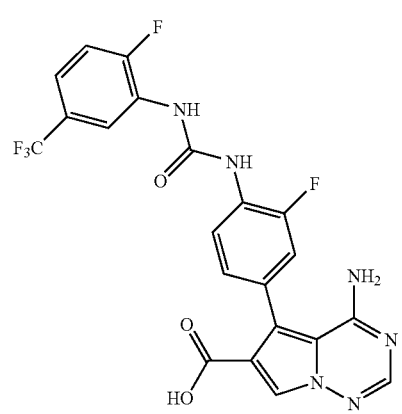

The procedure used for the preparation of Intermediate G was used to prepare the title compound by substituting Example 249 for Intermediate E. $^1$H-NMR (DMSO-d$_6$) δ

12.3 (s, 1H), 9.43 (s, 1H), 9.27 (s, 1H), 8.65 to 8.63 (m, 1H), 8.25 to 8.20 (m, 1H), 8.07 (s, 1H), 8.02 (s, 1H); MS [M+H]⁺=433.1; LCMS RT=2.58 min.

Example 253

Preparation of 4-amino-5-{4-[({[4-(trifluoromethyl) pyridin-2-yl]amino}carbonyl)amino]phenyl}pyrrolo[2,1-f][1,2,4]triazine-6-carboxamide

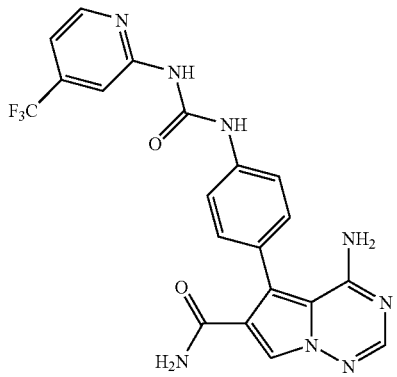

The procedure used for the preparation of Example 104 was used to prepare the title compound by substituting phenyl [4-(trifluoromethyl)pyridin-2-yl]carbamate for phenyl[3-fluoro-5-(trifluoromethyl)phenyl]carbamate. ¹H-NMR (CD₃OD) δ 8.52 (d, J=5 Hz, 1H), 8.06 (s, 1H), 7.84 (s, 1H), 7.71 (s, 1H), 7.70 (d, J=9 Hz, 2H), 7.46 (d, J=9 Hz, 2H), 7.28 (d, J=5 Hz, 1H); MS [M+H]⁺=457.0; LCMS RT=2.36 min.

Example 254

Preparation of N-{4-[4-amino-6-(methoxymethyl) pyrrolo[2,1-f][1,2,4]triazin-5-yl]-2-fluorophenyl}-N'-[2-fluoro-5-(trifluoromethyl)phenyl]urea

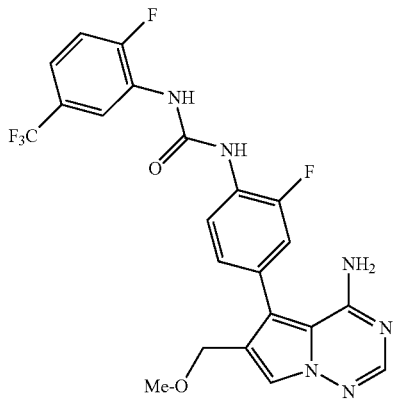

The procedure used for the preparation of Example 271 was used to prepare the title compound by Example 251 for Example 262. ¹H-NMR (CD₃OD) δ 8.65 (d, J=8.0 Hz, 1H), 8.31 to 8.27 (m, 1H), 7.80 (s, 1H), 7.70 (s, 1H), 7.35 to 7.23 (m, 4H), 4.37 (s, 2H), 3.33 (s, 3H); MS [M+H]⁺=493.1; LCMS RT=2.84 min.

Example 255

Preparation of N-{4-[4-amino-6-(cyanomethyl)pyrrolo[2,1-f][1,2,4]triazin-5-yl]-2-fluorophenyl}-N'-[4-(trifluoromethyl)pyridin-2-yl]urea

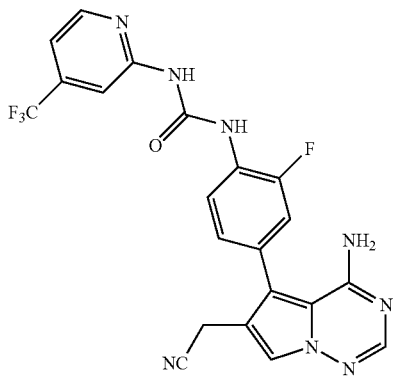

The procedure used for the preparation of Example 271 was used to prepare the title compound by substituting N-{4-[4-amino-6-(hydroxymethyl)pyrrolo[2,1-f][1,2,4]triazin-5-yl]-2-fluorophenyl}-N'-[4-(trifluoromethyl)pyridin-2-yl] urea (Example 243) for N-{4-[4-amino-6-(hydroxymethyl) pyrrolo[2,1-f][1,2,4]triazin-5-yl]phenyl}-N'-(4-methylpyridin-2-yl)urea (Example 262) and sodium cyanide for MeOH. ¹H-NMR (Acetone-d₆) δ 10.99 (s, 1H), 9.39 (s, 1H), 8.59 to 8.58 (d, J=5.1 Hz, 1H), 8.51 to 8.47 (t, J=8.5 Hz, 1H), 7.84 (s, 1H), 7.82 to 7.81 (d, J=6.4 Hz, 1H), 7.75 (s, 1H), 7.38 to 7.35 (m, 2H), 7.30 to 7.28 (d, J=8.4 Hz, 1H), 3.86 (s, 2H); MS [M+H]⁺=471.0; LCMS RT=2.75 min.

Example 256

Preparation of N-[4-(4-amino-6-cyanopyrrolo[2,1-f][1,2,4]triazin-5-yl)-2-fluorophenyl]-N'-[2-fluoro-5-(trifluoromethyl)phenyl]urea

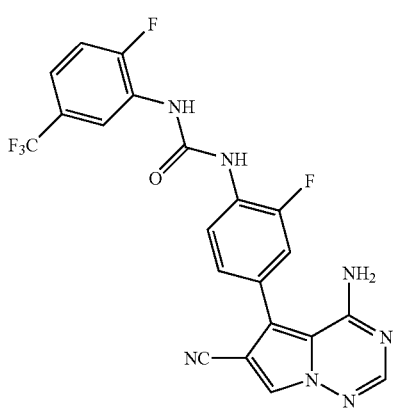

The procedure used for the preparation of Intermediate O was used to prepare the title compound by substituting Intermediate AN for Intermediate H. ¹H-NMR (CD₃OD) δ 8.66 to 8.64 (m, 1H), 8.41 to 8.37 (m, 1H), 8.20 (s, 1H), 7.92 (s, 1H), 7.40 to 7.31 (m, 4H); MS [M+H]⁺=474.1; LCMS RT=2.92 min.

Example 257

Preparation of N-(4-{4-amino-6-[4-(morpholin-4-ylmethyl)-1,3-oxazol-2-yl]pyrrolo[2,1-f][1,2,4]triazin-5-yl}phenyl)-N'-[2-fluoro-5-(trifluoromethyl)phenyl]urea

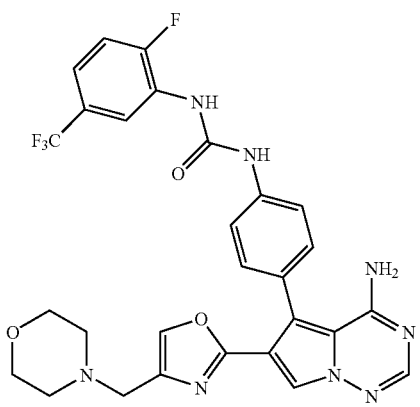

The procedure used for the preparation of Example 66 was used to prepare the title compound by substituting Intermediate AM for Intermediate I. ¹H-NMR (CD₃OD) δ 8.62 to 8.60 (d, J=7.6 Hz, 1H), 8.15 (s, 1H), 7.85 (s, 1H), 7.65 (s, 1H), 7.61 to 7.59 (d, J=8.7 Hz, 2H), 7.42 to 7.40 (d, J=8.5 Hz, 2H), 7.35 to 7.33 (m, 2H), 3.69 to 3.66 (t, J=4.7 Hz, 4H), 3.46 (s, 2H), 2.53 to 2.50 (t, J=4.6 Hz, 4H); MS [M+H]⁺=597.1; LCMS RT=2.44 min.

Example 258

Preparation of ethyl 4-amino-5-[4-({[(4-methylpyridin-2-yl)amino]carbonyl}amino)phenyl]pyrrolo[2,1-f][1,2,4]triazine-6-carboxylate

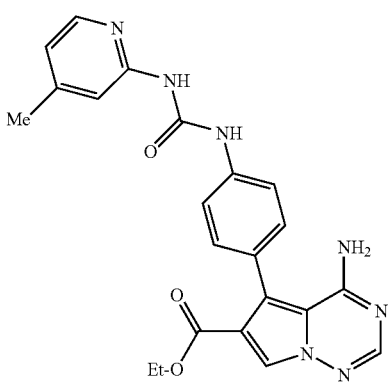

The procedure used for the preparation of Example 73 was used to prepare the title compound by substituting Intermediate B for Intermediate X and by substituting diphenyl (4-methylpyridin-2-yl)imidodicarbonate for phenyl (4-tert-butylpyridin-2-yl)carbamate. ¹H-NMR (DMSO-d₆) δ 10.83 (s, 1H), 9.45 (s, 1H), 8.15 to 8.13 (d, J=5.3 Hz, 1H), 8.13 (s, 1H), 7.93 (s, 1H), 7.62 to 7.60 (d, J=8.3 Hz, 2H), 7.34 to 7.32 (d, J=8.3 Hz, 2H), 7.28 (s, 1H), 6.87 to 6.86 (d, J=5.3 Hz, 1H), 4.11 to 4.06 (q, J=7.1 Hz, 2H), 2.30 (s, 3H) 1.13 to 1.10 (t, J=7.1 Hz, 3H); MS [M+H]⁺=432.1; LCMS RT=2.30 min.

Example 259

Preparation of N-{4-[4-amino-6-(ethoxymethyl)pyrrolo[2,1-f][1,2,4]triazin-5-yl]phenyl}-N'-[2-fluoro-3-(trifluoromethyl)phenyl]urea

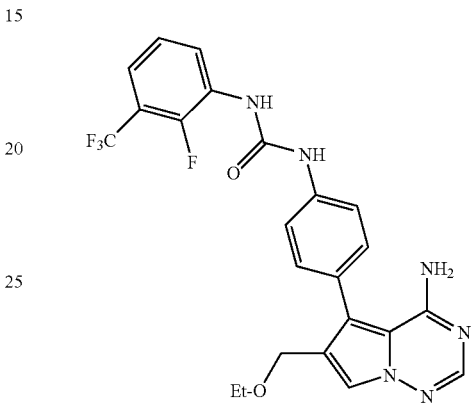

The procedure used for preparation of Example 1 was used to prepare the title compound by substituting 6-(ethoxymethyl)-5-(4-nitrophenyl)pyrrolo[2,1-f][1,2,4]triazin-4-amine for Intermediate B and substituting 2-fluoro-1-isocyanato-3-(trifluoromethyl)benzene for 1-fluoro-2-isocyanato-4-(trifluoromethyl)benzene. ¹H-NMR (DMSOD6) δ 9.28 (s, 1H), 8.89 (s, 1H), 8.48-8.42 (m, 1H), 7.83 (s, 1H), 7.73 (s, 1H), 7.59 (s, 1H), 7.56 (s, 1H), 7.36-7.32 (m, 4H), 4.28 (s, 2H), 3.37 (q, J=5.2 Hz, 2H), 1.06 (t, J=7 Hz, 3H); MS [M+H]⁺=489.1; LCMS RT=2.87.

Example 260

Preparation of 4-amino-5-[4-({[(4-methylpyridin-2-yl)amino]carbonyl}amino)phenyl]pyrrolo[2,1-f][1,2,4]triazine-6-carboxylic acid

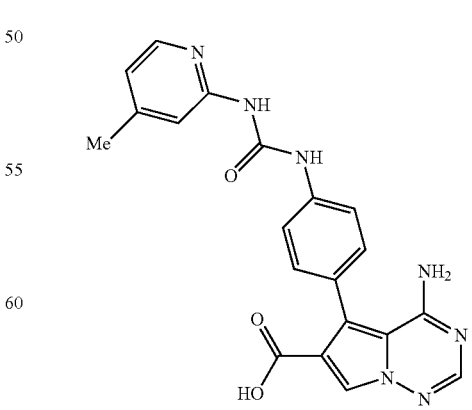

The procedure used for the preparation of Intermediate G was used to prepare the title compound by substituting ethyl 4-amino-5-[4-({[(4-methylpyridin-2-yl)amino]carbonyl}amino)phenyl]pyrrolo[2,1-f][1,2,4]triazine-6-carboxylate (Example 258) for Intermediate E. $^1$H-NMR (DMSO-$d_6$) δ 12.28 (s, 1H) 10.82 (s, 1H), 9.46 (s, 1H), 8.14 to 8.13 (d, J=5.4 Hz, 1H), 8.07 (s, 1H), 7.91 (s, 1H), 7.60 to 7.58 (d, J=8.6 Hz, 2H), 7.34 to 7.31 (d, J=8.6 Hz, 2H), 7.27 (s, 1H), 6.86 to 6.85 (d, J=5.9 Hz, 1H), 2.30 (s, 3H); MS [M+H]$^+$=404.2; LCMS RT=0.38 min.

Example 261

Preparation of 4-amino-N-(2-hydroxy-1-methylethyl)-5-{4-[({[4-(trifluoromethyl)pyridin-2-yl]amino}carbonyl)amino]phenyl}pyrrolo[2,1-f][1,2,4]triazine-6-carboxamide

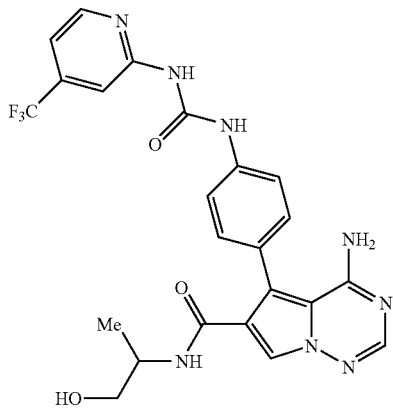

The procedure used for the preparation of Example 143 was used to prepare the title compound by substituting 1-aminopropan-2-ol for 2-amino-2-methylpropan-1-ol and Example 250 for Intermediate J. $^1$H-NMR (DMSO-$d_6$) δ 9.87 (s, 1H), 9.74 (s, 1H), 8.54 to 8.53 (d, J=5.0 Hz, 1H), 8.11 (s, 1H), 8.06 (s, 1H), 7.89 (s, 1H), 7.59 to 7.57 (d, J=8.6 Hz, 2H), 7.37 to 7.31 (m, 4H), 4.65 to 4.62 (t, J=5.8 Hz, 1H), 3.85 to 3.79 (m, 1H), 3.23 to 3.16 (m, 2H), 1.01 to 1.00 (d, J=6.7 Hz, 3H); MS [M+H]$^+$=515.0; LCMS RT=2.41 min.

Example 262

Preparation of N-{4-[4-amino-6-(hydroxymethyl)pyrrolo[2,1-f][1,2,4]triazin-5-yl]phenyl}-N'-(4-methylpyridin-2-yl)urea

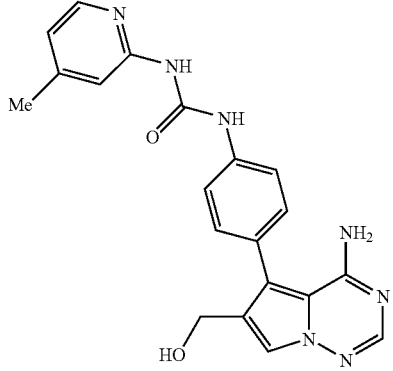

The procedure used for the preparation of Intermediate F Step 1 was used to prepare the title compound by substituting ethyl 4-amino-5-[4-({[(4-methylpyridin-2-yl)amino]carbonyl}amino)phenyl]pyrrolo[2,1-f][1,2,4]triazine-6-carboxylate (Example 258) for Intermediate E. $^1$H-NMR (DMSO-$d_6$) δ 10.84 (s, 1H), 9.45 (s, 1H), 8.14 to 8.13 (d, J=5.6 Hz, 1H), 7.82 (s; 1H), 7.65 (s, 1H), 7.64 to 7.62 (d, J=8.5 Hz, 2H), 7.37 to 7.35 (d, J=8.5 Hz, 2H), 7.27 (s, 1H), 6.86 to 6.85 (d, J=5.1 Hz, 1H), 4.97 to 4.95 (t, J=5.3 Hz, 1H), 4.38 to 4.37 (d, J=5.4 Hz, 2H), 2.30 (s, 3H); MS [M+H]$^+$=390.0; LCMS RT=1.51 min.

Example 263

Preparation of N-(4-{4-amino-6-[(2-methoxyethoxy)methyl]pyrrolo[2,1-f][1,2,4]triazin-5-yl}-2-fluorophenyl)-N'-[2-fluoro-5-(trifluoromethyl)phenyl]urea

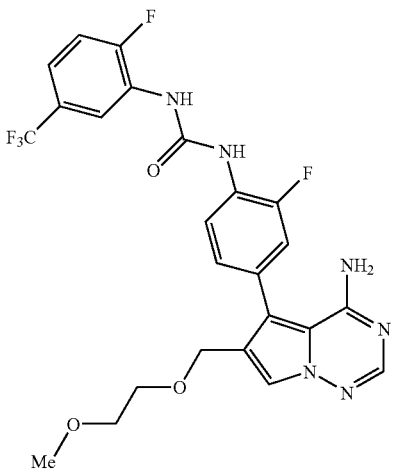

The procedure used for the preparation of Example 271 was used to prepare the title compound by substituting 3-methoxypropan-1-ol for methanol and Example 251 for Example 262. $^1$H-NMR (CD$_3$OD) δ 8.64 (d, J=6.9 Hz, 1H), 8.31 to 8.26 (m, 1H), 7.79 (s, 1H), 7.71 (s, 1H), 7.37 to 7.33 (m, 3H), 7.25 (d, J=8.4 Hz, 1H), 4.49 (s, 2H), 3.54 to 3.52 (m, 2H), 3.33 (s, 3H); MS [M+H]$^+$=537.1; LCMS RT=2.82 min.

Example 264

Preparation of 4-amino-5-[4-({[(4-methylpyridin-2-yl)amino]carbonyl}amino)phenyl]-N-(2,2,2-trifluoroethyl)pyrrolo[2,1-f][1,2,4]triazine-6-carboxamide

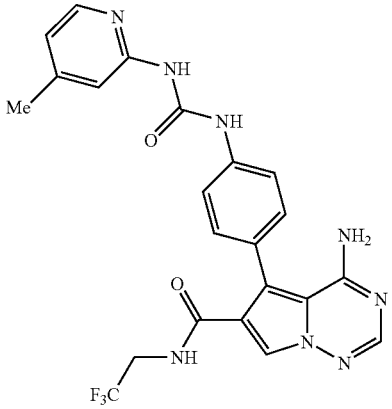

The procedure used for the preparation of Example 143 was used to prepare the title compound by substituting 2,2,2-trifluoroethanamine for 2-amino-2-methylpropan-1-ol and 4-amino-5-[4-({[(4-methylpyridin-2-yl)amino]

carbonyl}amino)phenyl]pyrrolo[2,1-f][1,2,4]triazine-6-carboxylic acid (Example 260) for Intermediate J. ¹H-NMR (DMSO-d₆) δ 10.80 (s, 1H), 9.44 (s, 1H), 8.52 to 8.49 (t, J=6.2 Hz, 1H), 8.18 (s, 1H), 8.14 to 8.13 (d, J=5.3 Hz, 1H), 7.91 (s, 1H), 7.59 to 7.57 (d, J=8.6 Hz, 2H), 7.31 to 7.28 (d, J=8.6 Hz, 2H), 7.28 (s, 1H), 6.86 to 6.85 (d, J=5.2 Hz, 1H), 3.97 to 3.93 (m, 2H), 2.30 (s, 3H); MS [M+H]⁺=485.1; LCMS RT=2.06 min.

Example 265

Preparation of 4-amino-N-methyl-5-[4-({[(4-methylpyridin-2-yl)amino]carbonyl}amino)phenyl]pyrrolo[2,1-f][1,2,4]triazine-6-carboxamide

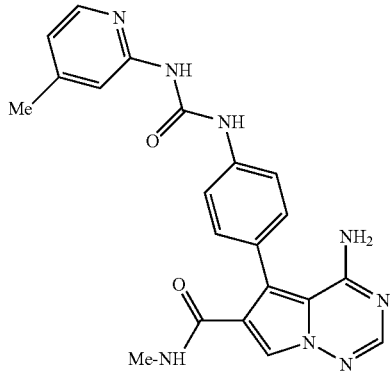

The procedure used for the preparation of Example 143 was used to prepare the title compound by substituting methanamine for 2-amino-2-methylpropan-1-ol and 4-amino-5-[4-({[(4-methylpyridin-2-yl)amino]carbonyl}amino)phenyl]pyrrolo[2,1-f][1,2,4]triazine-6-carboxylic acid (Example 260) for Intermediate J. ¹H-NMR (DMSO-d₆) δ 10.80 (s, 1H), 9.45 (s, 1H), 8.14 to 8.13 (d, J=5.4 Hz, 1H), 8.05 (s, 1H), 7.89 (s, 1H), 7.82 to 7.80 (m, 1H), 7.59 to 7.57 (d, J=8.6 Hz, 2H), 7.31 to 7.29 (d, J=8.4 Hz, 2H), 7.28 (s, 1H), 6.86 to 6.85 (d, J=5.1 Hz, 1H), 2.64 to 2.63 (d, J=4.7 Hz, 3H), 2.30 (s, 3H); MS [M+H]⁺=417.0; LCMS RT=1.54 min.

Example 266

Preparation of 4-amino-N-ethyl-5-[4-({[(4-methylpyridin-2-yl)amino]carbonyl}amino)phenyl]pyrrolo[2,1-f][1,2,4]triazine-6-carboxamide

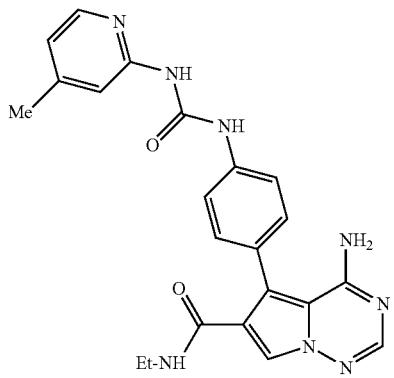

The procedure used for the preparation of Example 143 was used to prepare the title compound by substituting ethanamine for 2-amino-2-methylpropan-1-ol and 4-amino-5-[4-({[(4-methylpyridin-2-yl)amino]carbonyl}amino)phenyl]pyrrolo[2,1-f][1,2,4]triazine-6-carboxylic acid (Example 260) for Intermediate J. ¹H-NMR (DMSO-d₆) δ 10.80 (s, 1H), 9.45 (s, 1H), 8.14 to 8.13 (d, J=5.1 Hz, 1H), 8.06 (s, 1H), 7.89 (s, 1H), 7.76 to 7.73 (t, J=5.9 Hz, 1H), 7.59 to 7.57 (d, J=8.6 Hz, 2H), 7.32 to 7.30 (d, J=8.6 Hz, 2H), 7.28 (s, 1H), 6.86 to 6.85 (d, J=6.9 Hz, 1H), 3.16 to 3.09 (m, 2H), 2.30 (s, 3H) 1.03 to 1.00 (t, J=7.1 Hz, 3H); MS [M+H]⁺=431.1; LCMS RT=1.80 min.

Example 267

Preparation of 4-amino-N-(2-hydroxy-1-methylethyl)-5-[4-({[(4-methylpyridin-2-yl)amino]carbonyl}amino)phenyl]pyrrolo[2,1-f][1,2,4]triazine-6-carboxamide

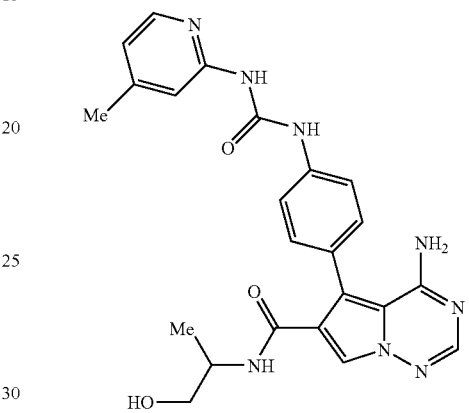

The procedure used for the preparation of Example 143 was used to prepare the title compound by substituting 2-aminopropan-1-ol for 2-amino-2-methylpropan-1-ol and 4-amino-5-[4-({[(4-methylpyridin-2-yl)amino]carbonyl}amino)phenyl]pyrrolo[2,1-f][1,2,4]triazine-6-carboxylic acid (Example 260) for Intermediate J. ¹H-NMR (DMSO-d₆) δ 10.82 (s, 1H), 9.45 (s, 1H), 8.14 to 8.13 (d, J=5.2 Hz, 1H), 8.10 (s, 1H), 7.89 (s, 1H), 7.61 to 7.59 (d, J=8.8 Hz, 2H), 7.33 to 7.31 (d, J=8.6 Hz, 2H), 7.30 to 7.28 (m, 2H), 6.87 to 6.85 (d, J=5.8 Hz, 1H), 4.65 to 4.62 (t, J=5.7 Hz, 1H), 3.84 to 3.78 (m, 1H), 3.22 to 3.16 (m, 2H), 2.30 (s, 3H), 1.01 to 0.99 (d, J=6.7 Hz, 3H)); MS [M+H]⁺=461.1; LCMS RT=1.62 min.

Example 268

Preparation of N-{4-[4-amino-6-(1-hydroxy-1-methylethyl)pyrrolo[2,1-f][1,2,4]triazin-5-yl]phenyl}-N'-[4-(trifluoromethyl)pyridin-2-yl]urea

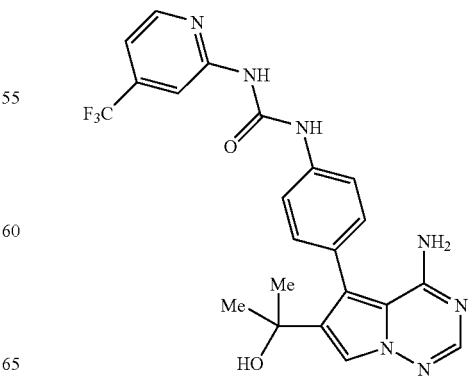

A solution of Example 51 (78 mg, 0.155 mmol) in 5 mL THF was treated with methylmagnesium bromide (0.78 mL, 2.3 mmol, 3N in Et$_2$O) and heated to 60 C for 4 h. The reaction was quenched with MeOH and diluted with EtOAc and washed with sat. NH$_4$Cl. The organic layer was dried with sodium sulfate and evaporated to dryness. The residue was titurated with Et$_2$O to provide 64 mg of the title product (87% yield). $^1$H-NMR (DMSO-d$_6$) δ 9.98 (s, 1H), 9.79 (s, 1H), 8.52 (d, J=5 Hz, 1H), 8.70 (s, 1H), 7.77 (s, 1H), 7.58 (d, J=9 Hz, 2H), 7.56 (s, 1H), 7.33 (d, J=9 Hz, 2H), 7.30 to 7.35 (m, 1H), 7.11 (bs, 2H), 4.91 (s, 1H), 1.24 (s, 6H); MS [M+H]$^+$=472.1; LCMS RT=2.48 min.

Example 269

Preparation of N-{4-[4-amino-6-(1-hydroxyethyl) pyrrolo[2,1-f][1,2,4]triazin-5-yl]phenyl}-N'-[4-(trifluoromethyl)pyridin-2-yl]urea

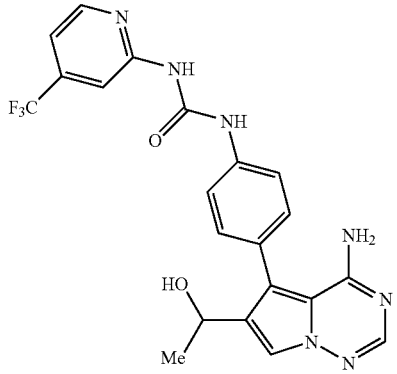

Step 1: Preparation of 4-amino-5-{4-[({[4-(trifluoromethyl)pyridin-2-yl]amino}carbonyl)amino]phenyl}pyrrolo[2,1-f][1,2,4]triazine-6-carboxylic acid

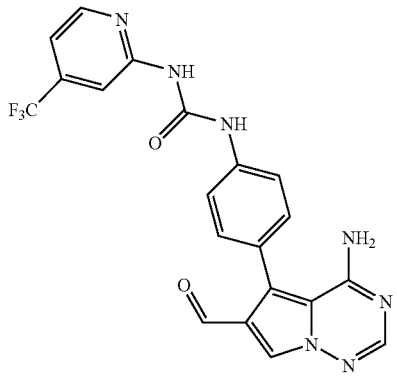

The procedure used for the preparation of Intermediate F was used to prepare the title compound by substituting Example 51 for Intermediate E. $^1$H-NMR (DMSO-d$_6$) δ 9.97 (s, 1H), 9.78 (s, 1H), 9.75 (s, 1H), 8.54 (d, J=5 Hz, 1H), 8.27 (s, 1H), 8.07 (s, 1H), 7.96 (s, 1H), 7.67 (d, J=9 Hz, 2H), 7.75 (d, J=9 Hz, 2H), 7.36 (d, J=5 Hz, 1H), 5.33 to 5.37 (m, 1H); MS [M+H]$^+$=422.0; LCMS RT=2.77 min.

Step 2: Preparation of Preparation N-{4-[4-amino-6-(1-hydroxyethyl)pyrrolo[2,1f][1,2,4]triazin-5-yl] phenyl}-N'-[4-(trifluoromethyl)pyridin-2-yl]urea

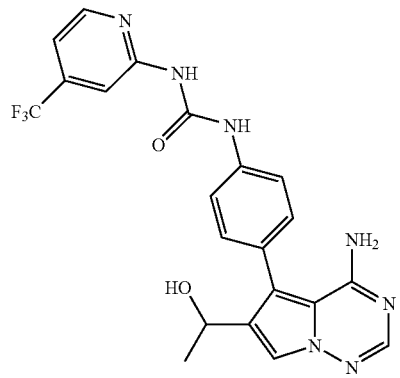

A solution of 4-amino-5-{4-[({[4-(trifluoromethyl)pyridin-2-yl]amino}carbonyl)amino]phenyl}pyrrolo[2,1-f][1,2,4]triazine-6-carboxylic acid (60 mg, 0.136 mmol) in 5 mL THF was treated with methylmagnesium bromide (0.68 mL, 2.1 mmol, 3 M in Et$_2$O) dropwise over 2 min. The reaction was allowed to stir for 15 min, then quenched with MeOH, diluted with EtOAc and washed with aq. NH$_4$Cl. The organic layer was dried with sodium sulfate and evaporated to dryness. The residue was triturated with Et$_2$O to provide 50.1 mg of the title compound (82% yield). $^1$H-NMR (DMSO-d$_6$) δ 10.05 (s, 1H), 9.82 (s, 1H), 8.52 (d, J=5 Hz, 1H), 8.09 (s, 1H), 7.81 (s, 1H), 7.64 (s, 1H), 7.61 (d, J=9 Hz, 2H), 7.34 (d, J=9 Hz, 2H), 4.96 (d, J=5 Hz, 1H), 4.63 (dq, J=5, 6 Hz, 1H), 1.24 (d, J=6 Hz, 3H); MS [M+H]$^+$=458.0; LCMS RT=2.41 min.

Example 270

Preparation of N-[4-(4-amino-6-propionylpyrrolo[2,1-f][1,2,4]triazin-5-yl)phenyl]-N'-[4-(trifluoromethyl)pyridin-2-yl]urea

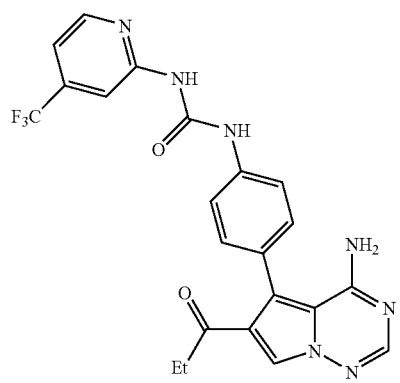

The procedure used for the preparation of Example 233 was used to prepare the title compound by substituting Example 274 for Example 269. $^1$H-NMR (DMSO-d$_6$) δ 9.98 (s, 1H), 9.85 (s, 1H), 8.53 (d, J=5 Hz, 1H), 8.37 (s, 1H), 8.07

(s, 1H), 8.00 to 8.10 (bs, 1H), 7.59 (d, J=9 Hz, 2H), 7.30 to 7.39 (m, 3H), 2.71 (d, J=7 Hz, 2H), 0.92 (t, J=7 Hz, 3H); MS [M+Na]⁺=492.0; LCMS RT=2.87 min.

Example 271

Preparation of N-{4-[4-amino-6-(methoxymethyl)pyrrolo[2,1-f][1,2,4]triazin-5-yl]phenyl}-N'-(4-methylpyridin-2-yl)urea

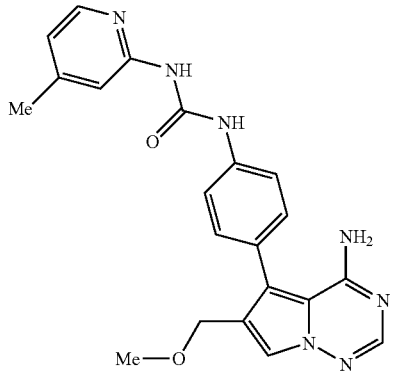

To a solution of DCM (5 mL) was added N-{4-[4-amino-6-(hydroxymethyl)pyrrolo[2,1-f][1,2,4]triazin-5-yl]phenyl}-N'-(4-methylpyridin-2-yl)urea (Example 262) (40 mg, 0.10 mmol) followed by 2M thionyl chloride in DCM (0.51 mL, 1.03 mmol). The solution was stirred at rt for 1 h and was then evaporated in vacuo. THF (5 mL) and MeOH (5 mL) were added to the crude reaction followed by triethylamine (43 µL, 0.31 mmol). The solution was heated to 50° C. for 3 d and then evaporated in vacuo and purified by MPLC (Isco) 0-5% MeOH/DCM. The resulting purified fractions were combined and evaporated producing 25 mg of the title compound (0.061 mmol, yield 60%). ¹H-NMR (DMSO-d₆) δ 10.86 (s, 1H), 9.46 (s, 1H), 8.14 to 8.13 (d, J=6.3 Hz, 1H), 7.84 (s, 1H), 7.75 (s, 1H), 7.65 to 7.63 (d, J=8.7 Hz, 2H), 7.36 to 7.34 (d, J=8.6 Hz, 2H), 7.27 (s, 1H), 6.87 to 6.86 (d, J=5.0 Hz, 1H), 4.27 (s, 2H), 3.20 (s, 3H), 2.30 (s, 3H); MS [M+H]⁺=404.0; LCMS RT=1.99 min.

Example 272

Preparation of N-(4-{4-amino-6-[(2-methoxyethoxy)methyl]pyrrolo[2,1-f][1,2,4]triazin-5-yl}phenyl)-N'-(4-methylpyridin-2-yl)urea

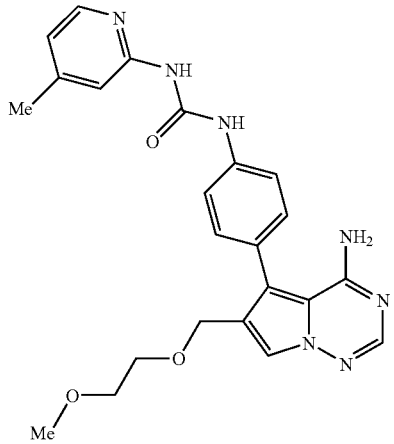

The procedure used for the preparation of Example 271 was used to prepare the title compound by substituting 2-methoxyethanol for MeOH. ¹H-NMR (DMSO-d₆) δ 10.85 (s, 1H), 9.46 (s, 1H), 8.14 to 8.13 (d, J=5.4 Hz, 1H), 7.84 (s, 1H), 7.75 (s, 1H), 7.65 to 7.62 (d, J=8.6 Hz, 2H), 7.38 to 7.36 (d, J=8.1 Hz, 2H), 7.26 (s, 1H), 6.87 to 6.85 (d, J=5.9 Hz, 1H), 4.33 (s, 2H), 3.49 to 3.46 (m, 2H), 3.43 to 3.40 (m, 2H), 3.22 (s, 2H), 2.30 (s, 3H); MS [M+H]⁺=448.0; LCMS RT=2.00 min.

Example 273

Preparation of 4-amino-N-cyclopropyl-5-[4-({[(4-methylpyridin-2-yl)amino]carbonyl}amino)phenyl]pyrrolo[2,1-f][1,2,4]triazine-6-carboxamide

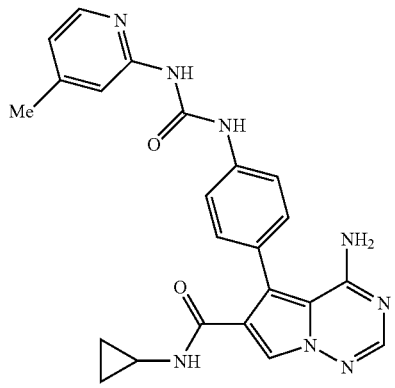

The procedure used for the preparation of Example 143 was used to prepare the title compound by substituting cyclopropanamine for 2-amino-2-methylpropan-1-ol and 4-amino-5-[4-({[(4-methylpyridin-2-yl)amino]carbonyl}amino)phenyl]pyrrolo[2,1-f][1,2,4]triazine-6-carboxylic acid (Example 260) for Intermediate J. ¹H-NMR (DMSO-d₆) δ 10.79 (s, 1H), 9.45 (s, 1H), 8.15 to 8.13 (d, J=5.6 Hz, 1H), 8.05 (s, 1H), 7.89 (s, 1H), 7.83 to 7.82 (d, J=3.6 Hz, 1H), 7.59 to 7.57 (d, J=8.7 Hz, 2H), 7.31 to 7.29 (m, 3H), 6.86 to 6.85 (d, J=5.1 Hz, 1H), 2.68 to 2.63 (m, 1H), 2.30 (s, 3H), 0.63 to 0.58 (m, 2H), 0.44 to 0.40 (m, 2H); MS [M+H]⁺=465.1; LCMS RT=1.86 min.

Example 274

Preparation of N-{4-[4-amino-6-(1-hydroxypropyl)pyrrolo[2,1-f][1,2,4]triazin-5-yl]phenyl}-N'-[4-(trifluoromethyl)pyridin-2-yl]urea

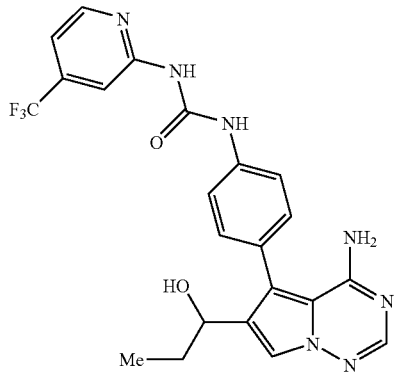

The procedure used for the preparation of Example 269 was used to prepare the title compound by substituting ethylmagnesium bromide for methylmagnesium bromide. $^1$H-NMR (DMSO-d$_6$) δ 9.95 (s, 1H), 9.77 (s, 1H), 8.53 (d, J=5 Hz, 1H), 8.04 (s, 1H), 0.1 to 8.2 (bs, 1H), 8.05 to 8.10 (m, 1H), 7.65 (d, J=9 Hz, 2H), 7.39 (d, J=9 Hz, 2H), 7.32 to 7.40 (m, 1H); MS [M+H]$^+$=472.0; LCMS RT=2.59 min.

Example 275

Preparation of N-(4-{4-amino-6-[cyclopropyl(hydroxy)methyl]pyrrolo[2,1-f][1,2,4]triazin-5-yl}phenyl)-N'-[4-(trifluoromethyl)pyridin-2-yl]urea

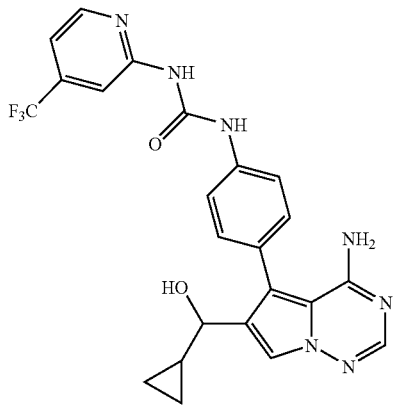

The procedure used for the preparation of Example 269 was used to prepare the title compound by substituting cyclopropylmagnesium bromide for methylmagnesium bromide. $^1$H-NMR (DMSO-d$_6$) δ 9.95 (s, 1H), 9.83 (s, 1H), 8.61 (d, J=5 Hz, 1H), 8.14 (s, 1H), 7.91 (s, 1H), 7.78 (s, 1H), 7.69 (d, J=9 Hz, 2H), 7.40 to 46 (m, 3H), 5.00 (d, J=5 Hz, 1H), 4.00-4.02 (m, 1H), 0.25 to 0.48 (m, 3H), 0.00 to 0.08 (m, 2H); MS [M+H]$^+$=484.0; LCMS RT=2.60 min.

Example 276

Preparation of N-{4-[4-amino-6-(1,3-oxazol-5-yl)pyrrolo[2,1-f][1,2,4]triazin-5-yl]-2-fluorophenyl}-N'-[4-(trifluoromethyl)pyridin-2-yl]urea

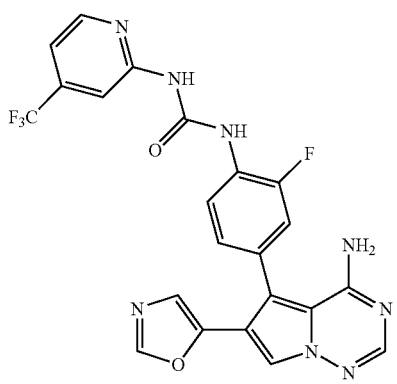

To a solution of THF (10 mL) and MeOH (10 mL) cooled in an ice/water bath was added 0.5 M sodium methoxide in MeOH (0.96 mL, 0.48 mmol) followed by TosMIC (93 mg, 0.48 mmol). The solution was allowed to stir for 5 min and then Intermediate AL (73 mg, 0.16 mmol) was added. The solution was heated to 60° C. for 17 h. The reaction mixture was allowed to cool and was transferred to a separatory funnel, diluted with EtOAc (20 mL), washed with aq saturated NaHCO$_3$ (20 mL) and H$_2$O (20 mL). The aqueous layer was back extracted with EtOAc (2×20 mL). The combined organic layers were dried (MgSO$_4$), filtered, evaporated in vacuo and purified by flash chromatography 5:4:1 v/v/v DCM/EtOAc/MeOH the resulting purified fractions were combined and evaporated providing 26 mg of the title compound as a white solid (0.052 mmol, yield 33%). $^1$H-NMR (DMSO-d$_6$) δ 10.18 (s, 1H), 10.16 to 10.12 (br s, 1H), 8.55 to 8.54 (d, J=5.4 Hz, 1H), 8.35 to 8.31 (t, J=8.3 Hz, 1H), 8.30 (s, 1H), 8.10 (s, 1H), 8.01 (s, 1H), 7.91 (s, 1H), 7.39 to 7.36 (m, 2H), 7.23 to 7.21 (d, J=10.4 Hz, 1H), 6.63 (s, 1H); MS [M+H]$^+$=499.0; LCMS RT=2.85 min.

Example 277

Preparation of N-{4-[4-amino-6-(1,3-oxazol-5-yl)pyrrolo[2,1-f][1,2,4]triazin-5-yl]phenyl}-N'-(4-methylpyridin-2-yl)urea

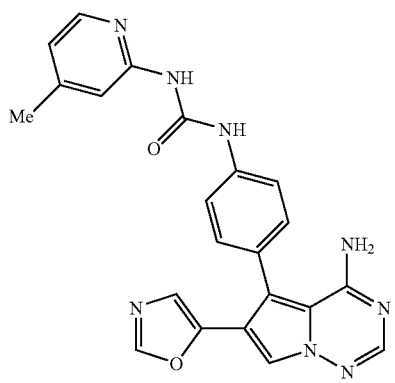

The procedure used for the preparation of Example 276 was used to prepare the title compound by Intermediate AK for Intermediate 5. $^1$H-NMR (DMSO-d$_6$) δ 10.92 (s, 1H), 9.50 (s, 1H), 8.29 (s, 1H), 8.15 to 8.14 (d, J=4.9 Hz, 1H), 8.09 (s, 1H), 7.90 (s, 1H), 7.69 to 7.67 (d, J=8.4 Hz, 2H), 7.38 to 7.36 (d, J=8.5 Hz, 2H), 7.27 (s, 1H), 6.87 to 6.86 (d, J=5.8 Hz, 1H), 6.57 (s, 1H), 2.30 (s, 3H); MS [M+H]$^+$=427.1; LCMS RT=2.09 min.

Example 278

Preparation of N-{4-[4-amino-6-(cyclopropylcarbonyl)pyrrolo[2,1-f][1,2,4]triazin-5-yl]phenyl}-N'-[4-(trifluoromethyl)pyridin-2-yl]urea

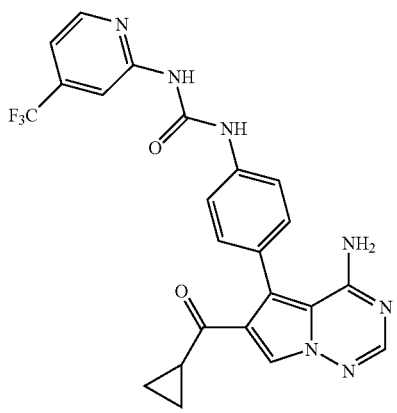

The procedure used for the preparation of Example 233 was used to prepare the title compound by substituting Example 275 for Example 269. ¹H-NMR (DMSO-d₆) δ 9.87 (s, 1H), 9.74 (s, 1H), 8.53 (d, J=5 Hz, 1H), 8.51 (s, 1H), 8.05 (s, 1H), 8.00 to 8.05 (bs, 1H), 7.57 (d, J=9 Hx, 2H), 7.30 to 7.40 (m, 3H), 2.40 (m, 1H), 0.76 to 0.9 (m, 4H); MS [M+H]⁺=482.0; LCMS RT=2.96 min.

Example 279

Preparation of 4-amino-N-(2-hydroxy-1,1-dimethylethyl)-5-{4-[({[4-(trifluoromethyl)pyridin-2-yl]amino}carbonyl)amino]phenyl}pyrrolo[2,1-f][1,2,4]triazine-6-carboxamide

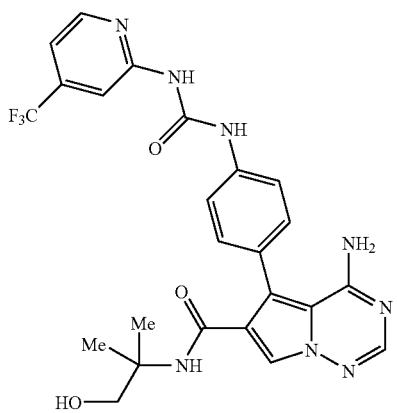

Step 1: Preparation of 4-amino-5-{4-[({[4-(trifluoromethyl)pyridin-2-yl]amino}carbonyl)amino]phenyl}pyrrolo[2,1-f][1,2,4]triazine-6-carboxylic acid

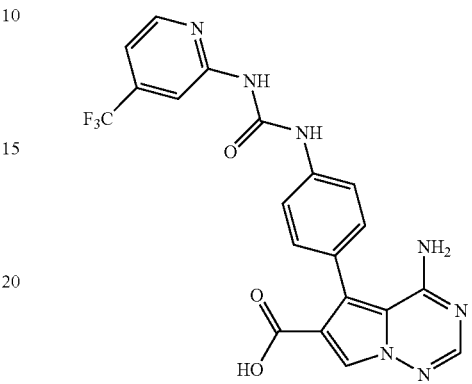

The procedure used for the preparation of Intermediate G was used to prepare the title compound by substituting Example 51 for Intermediate E. ¹H-NMR (DMSO-d₆) δ 12.28 (bs, 1H), 9.87 (s, 1H) 9.75 (s, 1H), 8.53 (d, J=5 Hz, 1H), 8.07 (s, 1H), 8.06 (s, 1H), 7.91 (s, 1H), 7.57 (d, J=9 Hz, 2H), 7.34 to 7.37 (m, 1H), 7.34 (d, J=9 Hz, 2H); MS [M+H]⁺=458.1; LCMS RT=2.53 min.

Step 2: Preparation 4-amino-N-(2-hydroxy-1,1-dimethylethyl)-5-{4-[({[4-(trifluoromethyl)pyridin-2-yl]amino}carbonyl)amino]phenyl}pyrrolo[2,1-f][1,2,4]triazine-6-carboxamide

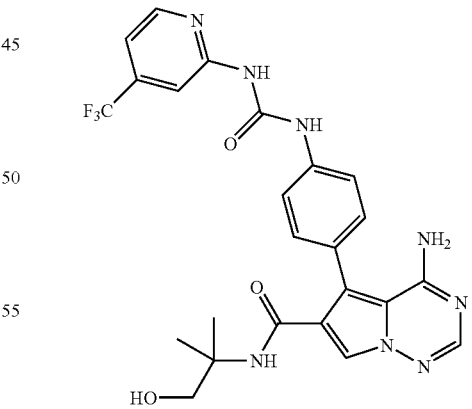

The procedure used for the preparation of Example 143 was used to prepare the title compound by substituting 4-amino-5-{4-[({[4-(trifluoromethyl)pyridin-2-yl]amino}carbonyl)amino]phenyl}pyrrolo[2,1-f][1,2,4]triazine-6-carboxylic acid for Intermediate J. ¹H-NMR (DMSO-d₆) δ 9.92 (s, 1H), 9.77 (s, 1H), 8.54 (d, J=5.0 Hz, 1H), 8.06 (s, 1H), 8.03 (s, 1H), 7.89 (s, 1H), 7.62 (d, J=8.8 Hz, 2H), 7.36

(d, J=8.8 Hz, 4-H), 6.53 (s, 1H), 4.75 (t, J=6.2 Hz, 2H), 3.27 (d, J=5.9 Hz, 2H), 1.09 (s, 6H); MS [M+H]⁺=529.0; LCMS RT=2.59 min.

Example 280

Preparation of N-{4-[4-amino-6-(4,4-dimethyl-4,5-dihydro-1,3-oxazol-2-yl)pyrrolo[2,1-f][1,2,4]triazin-5-yl]phenyl}-N'-[4-(trifluoromethyl)pyridin-2-yl]urea

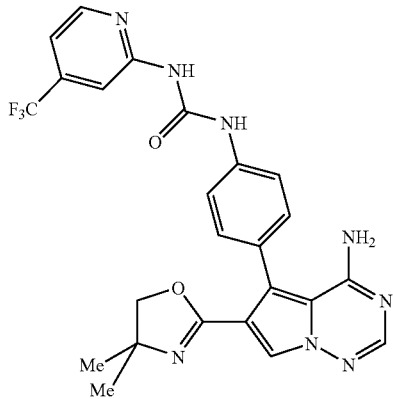

A solution of Example 279 (25 mg, 0.047 mmol) in 2 mL CH₂Cl₂ was treated with thionyl chloride (0.95 mmol, 11.2 mg) and allowed to stir for 15 min. The reaction was diluted with ethyl acetate and washed with sodium bicarbonate. The organic layer was dried (Na₂SO₄), filtered and concentrated to dryness. The residue was triturated with Et₂O/hexanes to give 19.4 mg of the above compound as a yellow solid (yield 81%). ¹H-NMR (DMSO-d₆) δ10.40 (s, 1H), 9.96 (s, 1H), 8.91 (s, 1H), 8.54 (d, J=6.2 Hz, 1H), 8.13 (s, 1H), 8.07 (s, 1H), 7.64 (d, J=8.8 Hz, 2H), 7.44 (d, J=8.8 Hz, 4H), 7.35 (d, J=5.3 Hz, 1H), 5.67 (bs, 1H), 4.54 (s, 2H), 1.47 (s, 6H); MS [M+H]⁺=511.0; LCMS RT=2.44 min.

Example 281

Preparation of N-{4-[4-amino-6-(4-methyl-4,5-dihydro-1,3-oxazol-2-yl)pyrrolo[2,1-f][1,2,4]triazin-5-yl]phenyl}-N'-[4-(trifluoromethyl)pyridin-2-yl]urea

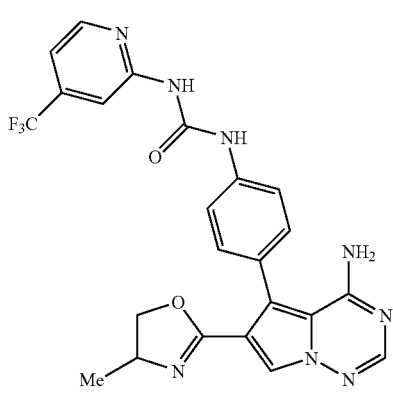

The procedure used for the preparation of Example 230 was used to prepare the title compound by substituting 4-amino-N-(2-hydroxy-1-methylethyl)-5-{4-[({[4-(trifluoromethyl)pyridin-2-yl]amino}carbonyl)amino]phenyl}pyrrolo[2,1-f][1,2,4]triazine-6-carboxamide (Example 261) for ethyl 2-(4-amino-5-{4-[({[4-(trifluoromethyl)pyridin-2-yl]amino}carbonyl)amino]phenyl}pyrrolo[2,1-f][1,2,4]triazin-6-yl)-4,5-dihydro-1,3-oxazole-4-carboxylate (Example 221). ¹H-NMR (DMSO-d₆) δ 9.89 (s, 1H), 9.77 (s, 1H), 8.54 to 8.53 (d, J=5.3 Hz, 1H), 8.05 (s, 1H), 8.01 (s, 1H), 7.90 (s, 1H), 7.58 to 7.56 (d, J=8.7 Hz, 2H), 7.37 to 7.36 (m, 1H), 7.35 to 7.33 (d, J=8.6 Hz, 2H), 4.28 to 4.24 (t, J=8.6 Hz, 2H), 4.15 to 4.06 (m, 1H), 3.71 to 3.67 (t, J=7.9 Hz, 2H, 1.13 to 1.11 (d, J=6.6 Hz, 3H); MS [M+H]⁺=497.0; LCMS RT=2.43 min.

Example 282

Preparation of N-[4-(4-amino-6-{[(2-methoxyethyl)amino]methyl}pyrrolo[2,1-f][1,2,4]triazin-5-yl)phenyl]-N'-(4-methylpyridin-2-yl)urea

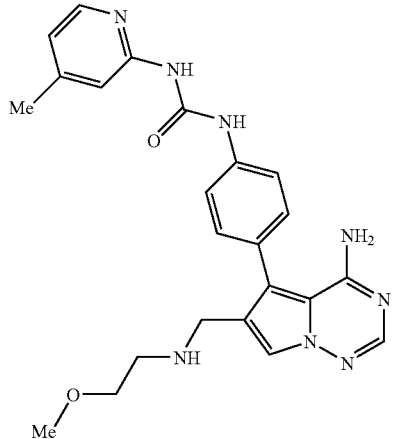

The procedure used for the preparation of Example 66 was used to prepare the title compound by substituting Intermediate AK for Intermediate I and 2-methoxyethanamine for morpholine. ¹H-NMR (CD₃OD) δ 8.15 to 8.14 (d, J=5.3 Hz, 1H), 7.81 (s, 1H), 7.80 (s, 1H), 7.74 to 7.72 (d, J=8.7 Hz, 2H), 7.42 to 7.40 (d, J=8.6 Hz, 2H), 7.00 (s, 1H), 6.90 to 6.89 (d, J=5.3 Hz, 1H), 4.04 (s, 2H), 3.49 to 3.46 (t, J=5.1 Hz, 2H), 2.95 to 2.92 (t, J=5.1 Hz, 2H), 2.37 (s, 3H), 1.93 (s, 3H); MS [M+H]⁺=446.9; LCMS RT=1.25 min.

Example 283

Preparation of N-{4-[4-amino-6-(morpholin-4-ylmethyl)pyrrolo[2,1-f][1,2,4]triazin-5-yl]phenyl}-N'-(4-methylpyridin-2-yl)urea

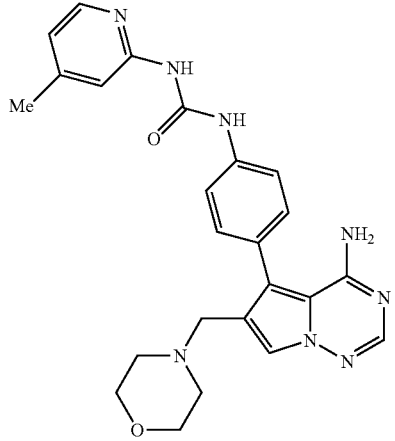

The procedure used for the preparation of Example 66 was used to prepare the title compound by substituting Intermediate AK for Intermediate I. $^1$H-NMR (DMSO-$d_6$) δ 10.90 to 10.87 (br s, 1H), 9.48 (s, 1H), 8.14 to 8.13 (d, J=5.1 Hz, 1H), 7.82 (s, 1H), 7.64 (s, 1H), 7.64 to 7.62 (d, J=8.5 Hz, 2H), 7.40 to 7.38 (d, J=8.5 Hz, 2H), 7.26 (s, 1H), 6.87 to 6.85 (d, J=5.6 Hz, 1H), 3.55 to 3.50 (m, 4H), 3.34 to 3.33 (br s, 2H), 2.32 to 2.28 (m, 4H), 2.30 (s, 3H); MS [M+H]$^+$=459.0; LCMS RT=1.16 min.

Example 284

Preparation of N-{4-[4-amino-6-(hydroxymethyl)pyrrolo[2,1-f][1,2,4]triazin-5-yl]phenyl}-N'-(3-tert-butylisoxazol-5-yl)urea

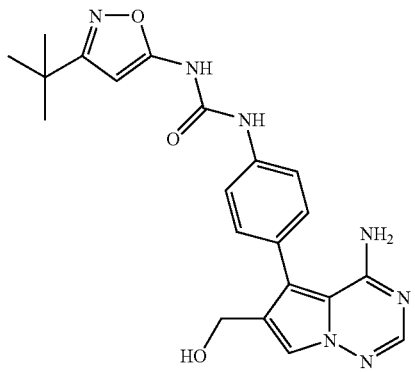

The procedure used for the preparation of Intermediate F was used to prepare the title compound by substituting Example 52 for Intermediate E. $^1$H-NMR (DMSO-$d_6$) δ 10.13 (s, 1H), 8.96 (s, 1H), 7.82 (s, 1H), 7.65 (s, 1H), 7.56 (d, J=9 Hz, 2H), 7.35 (d, J=9 Hz, 2H), 6.05 (s, 1H), 4.94 (t, J=5 Hz, 1H), 4.35 (d, J=5 Hz, 2H), 1.24 (s, 9H); MS [M+H]$^+$=422.1; LCMS RT=2.26 min.

Example 285

Preparation of N-{4-[4-amino-6-(1-hydroxyethyl)pyrrolo[2,1-f][1,2,4]triazin-5-yl]phenyl}-N'-(3-tert-butylisoxazol-5-yl)urea

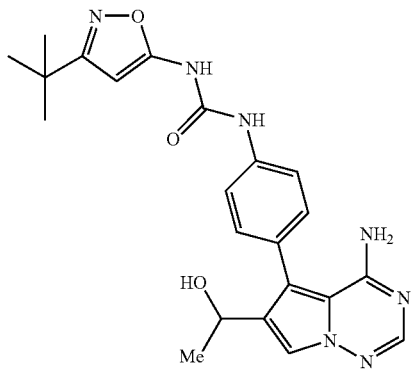

The procedure used for the preparation of Example 269 was used to prepare the title compound by substituting Example 52 for Example 51. $^1$H-NMR (DMSO-$d_6$) δ 10.19 (s, 1H), 9.07 (s, 1H), 8.81 (s, 1H), 7.64 (s, 1H), 7.56 (d, J=8 Hz, 2H), 7.30 to 7.40 (m, 2H), 6.05 (s, 1H), 4.95 (m, 1), 4.60 to 4.64 (m, 1H), 1.36 (m, 2H), 1.23 (s, 9H); MS [M+H]$^+$=436.1; LCMS RT=2.41 min.

Example 286

Preparation of N-(4-{4-amino-6-[cyclopropyl(hydroxy)methyl]pyrrolo[2,1-f][1,2,4]triazin-5-yl}phenyl)-N'-(3-tert-butylisoxazol-5-yl)urea

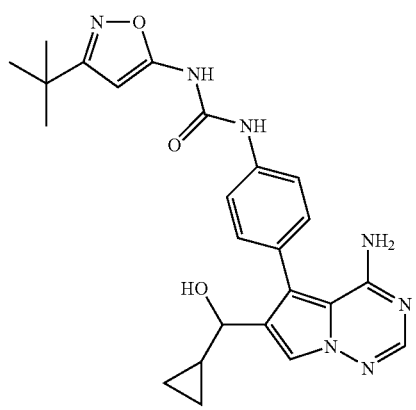

The procedure used for the preparation of Example 269 was used to prepare the title compound by substituting Example 52 for Example 51 and by substituting cyclopropylmagnesium bromide for methylmagnesium bromide. $^1$H-NMR (DMSO-$d_6$) δ 10.24 (s, 1H), 9.07 (s, 1H), 8.81 (s, 1H), 7.64 (s, 1H), 7.56 (d, J=8 Hz, 2H), 7.30 to 7.40 (m, 2H), 6.05 (s, 1H) 4.98 (d, J=5 Hz, 1H), 3.97 to 4.01 (m, 1H), 1.28 (s, 9H), 0.25 to 0.48 (m, 3H), 0.00 to 0.08 (m, 2H); MS [M+H]$^+$=434.1; LCMS RT=2.63 min.

Example 287

Preparation of N-[4-(6-acetyl-4-aminopyrrolo[2,1-f][1,2,4]triazin-5-yl)phenyl]-N'-(3-tert-butylisoxazol-5-yl)urea

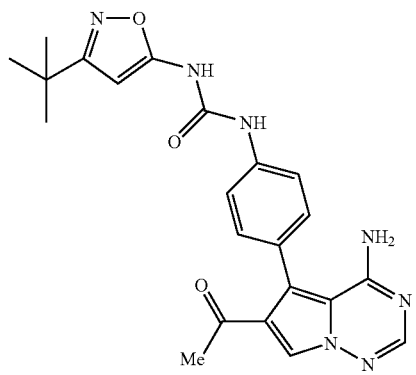

The procedure used for the preparation of Example 233 was used to prepare the title compound by substituting Example 285 for Example 269. $^1$H-NMR (DMSO-$d_6$) δ 10.15

(s, 1H), 8.98 (s, 1H), 8.37 (s, 1H), (8.01 (bs, 1H), 7.92 (s, 1H), 7.53 (d, J=9 Hz, 2H), 7.30 (d, J=9 Hz, 2H), 6.05 (s, 1H), 2.27 (s, 3H); MS [M+H]$^+$=434.1; LCMS RT=2.63 min.

Example 288

Preparation of N-{4-[4-amino-6-(cyclopropylcarbonyl)pyrrolo[2,1-f][1,2,4]triazin-5-yl]phenyl}-N'-(3-tert-butylisoxazol-5-yl)urea

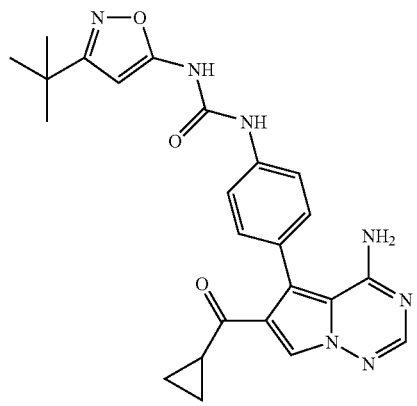

The procedure used for the preparation of Example 233 was used to prepare the title compound by substituting Example 286 for Example 269. $^1$H-NMR (DMSO-d$_6$) δ δ 10.15 (s, 1H), 8.98 (s, 1H), 8.37 (s, 1H), (8.01 (bs, 1H), 7.92 (s, 1H), 7.53 (d, J=9 Hz, 2H), 7.30 (d, J=9 Hz, 2H), 6.05 (s, 1H); MS [M+H]$^+$=460.1; LCMS RT=2.81 min.

Example 289

Preparation of 4-amino-5-[4-({[(3-tert-butylisoxazol-5-yl)amino]carbonyl}amino)phenyl]pyrrolo[2,1-f][1,2,4]triazine-6-carboxylic acid

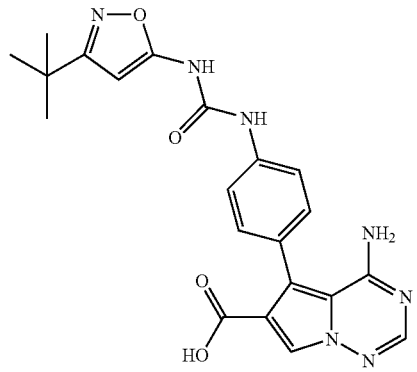

The procedure used for the preparation of Intermediate G was used to prepare the title compound by substituting Example 52 for intermediate E. $^1$H-NMR (DMSO-d$_6$) δ 10.18 (s, 1H), 9.04 (s, 1H), 8.07 (s, 1H), 7.19 (s, 1H), 7.52 (d, J=8.2 Hz, 1H), 7.31 (d, J=8.2 Hz, 2H), 6.05 (s, 1H), 5.73 (s, 1H), 1.24 (s, 9H); MS [M+H]$^+$=436.1; LCMS RT=2.43 min.

Example 290

Preparation of N-{4-[4-amino-6-(isopropoxymethyl)pyrrolo[2,1-f][1,2,4]triazin-5-yl]phenyl}-N'-[2-fluoro-5-(trifluoromethyl)phenyl]urea

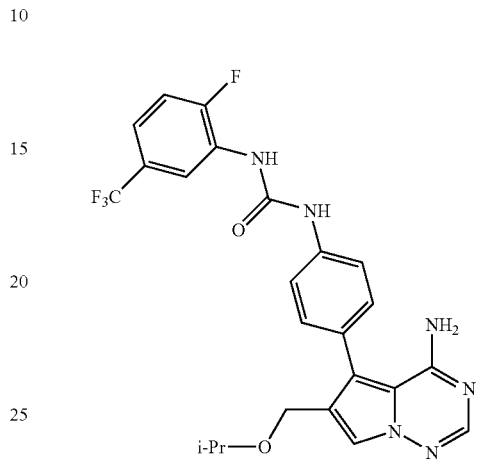

The procedure used for the preparation of Example 246 was used to prepare the title compound by substituting isopropyl alcohol for ethanol. $^1$H-NMR (DMSO-d$_6$) δ 12.25 (s, 1H), 8.48 (d, J=6.8 Hz, 1H), 8.27 (s, 1H), 8.04 (s, 1H), 7.61-7.51 (m, 3H), 7.18 (d, J=8.2 Hz, 2H), 6.70 (d, J=8.2 Hz, 2H), 4.33 (s, 2H), 3.55 (m, 1H), 1.04 (d, J=6.2 Hz, 6H); MS [M+H]$^+$=503.1; LCMS RT=3.70 min.

Example 291

Preparation of 4-amino-5-[4-({[(3-tert-butylisoxazol-5-yl)amino]carbonyl}amino)phenyl]-N-(2-hydroxy-1,1-dimethylethyl)pyrrolo[2,1-f][1,2,4]triazine-6-carboxamide

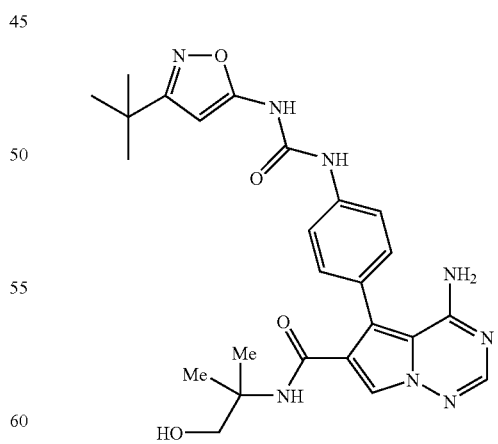

The procedure used for the preparation of Example 143 was used to prepare the title compound by substituting Example 289 for Intermediate J. $^1$H-NMR (DMSO-d$_6$) δ 10.14 (s, 1H), 9.00 (s, 1H), 8.03 (s, 1H), 7.89 (s, 1H), 7.56 (d, J=8.8 Hz, 2H), 7.34 (d, J=8.8 Hz, 4H), 6.51 (s, 1H), 6.06 (s, 1H), 5.74 (s, 1H), 4.75 (t, J=3.8 Hz, 1H), 3.27 (bs, 2) 1.24 (s, 9H), 1.09 (s, 6H); MS [M+H]⁺=507.1; LCMS RT=2.46 min.

Example 292

Preparation of N-{4-[4-amino-6-(4,4-dimethyl-4,5-dihydro-1,3-oxazol-2-yl)pyrrolo[2,1-f][1,2,4]triazin-5-yl]phenyl}-N'-(3-tert-butylisoxazol-5-yl)urea

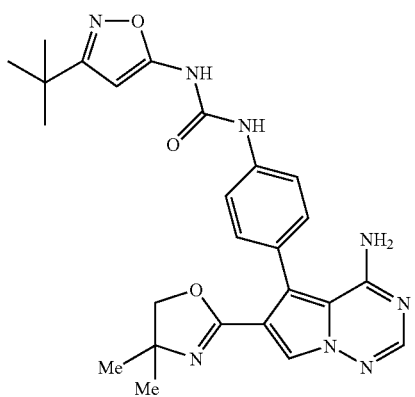

The procedure used for the preparation of Example 280 was used to prepare the title compound by substituting Example 291 for Example 279. ¹H-NMR (DMSO-d₆) δ 10.19 (s, 1H), 9.43 (s, 1H), 8.61 (s, 1H), 8.41 (bs, 1H), 8.01 (s, 1H), 7.56 (d, J=8.8 Hz, 2H), 7.40 (d, J=8.8 Hz, 2H), 6.12 (s, 1H), 5.41 (bs, 1H), 4.45 (s, 2H), 1.41 (s, 6H), 1.24 (s, 9H); MS [M+H]⁺=489.1; LCMS RT=2.36 min.

Example 293

Preparation of N-{4-[4-amino-6-(1,3-oxazol-5-yl)pyrrolo[2,1-f][1,2,4]triazin-5-yl]phenyl}-N'-(4-tert-butylpyridin-2-yl)urea

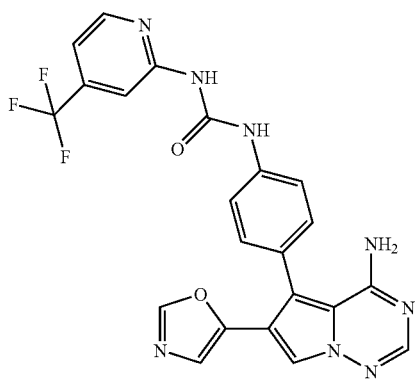

The procedure used for the preparation of Example 73 was used to prepare the title compound by substituting Intermediate AB for Intermediate X. ¹H-NMR (DMSO-d₆) δ 10.96 to 10.93 (br s, 1H), 9.48 (s, 1H), 8.30 (s, 1H), 8.20 to 8.18 (d, J=6.1 Hz, 1H), 8.09 (s, 1H), 7.90 (s, 1H), 7.70 to 7.68 (d, J=8.6 Hz, 2H), 7.50 (s, 1H), 7.38 to 7.36 (d, J=8.5 Hz, 2H), 7.08 to 7.06 (d, J=5.4 Hz, 1H), 6.57 (s, 1H), 1.28 (s, 9H); MS [M+H]⁺=469.1; LCMS RT=2.44 min.

Example 294

Preparation of N-{4-[4-amino-6-(1,3-oxazol-5-yl)pyrrolo[2,1-f][1,2,4]triazin-5-yl]phenyl}-N'-[3-tert-butyl-1-(4-fluorophenyl)-1H-pyrazol-5-yl]urea

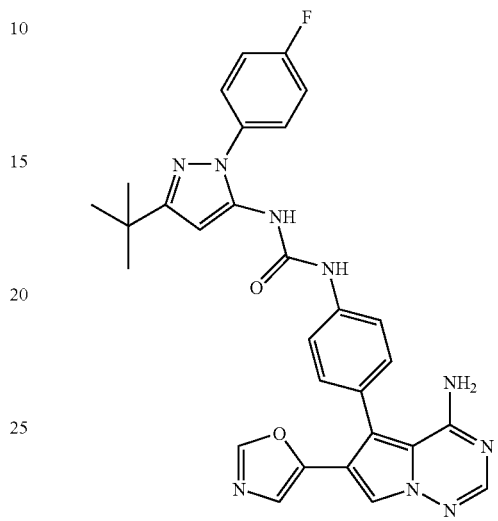

The procedure used for the preparation of Example 73 was used to prepare the title compound by substituting Intermediate AB for Intermediate X and by substituting phenyl[3-tert-butyl-1-(4-fluorophenyl)-1H-pyrazol-5-yl]carbamate for phenyl (4-tert-butylpyridin-2-yl)carbamate. ¹H-NMR (DMSO-d₆) δ 9.19 (s, 1H), 8.45 (s, 1H), 8.28 (s, 1H), 8.07 (s, 1H), 7.89 (s, 1H), 7.58 to 7.54 (m, 4H), 7.39 to 7.31 (m, 4H), 6.53 (s, 1H), 6.36 (s, 1H), 1.28 (s, 9H); MS [M+H]⁺=552.1; LCMS RT=2.88 min.

Example 295

Preparation of N-{4-[4-amino-6-(1,3-oxazol-5-yl)pyrrolo[2,1-f][1,2,4]triazin-5-yl]phenyl}-N'-(3-tert-butyl-1-methyl-1H-pyrazol-5-yl)urea

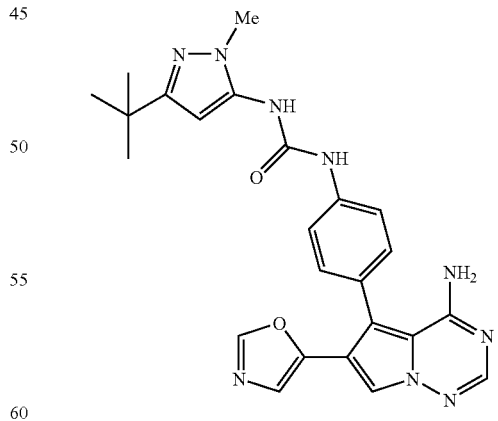

The procedure used for the preparation of Example 73 was used to prepare the title compound by substituting Intermediate AB for Intermediate X and by substituting phenyl (3-tert-butyl-1-methyl-1H-pyrazol-5-yl)carbamate for phenyl (4-tert-butylpyridin-2-yl)carbamate. ¹H-NMR (DMSO-d₆) δ 9.10 (s, 1H), 8.54 (s, 1H), 8.29 (s, 1H), 8.08 (s, 1H), 7.90

(s, 1H), 7.62 to 7.59 (d, J=8.6 Hz, 2H), 7.35 to 7.33 (d, J=8.6 Hz, 2H), 6.54 (s, 1H), 6.05 (s, 1H), 3.61 (s, 3H), 1.22 (s, 9H); MS [M+H]+=472.2; LCMS RT=2.43 min.

Example 296

Preparation of N-{4-[4-amino-6-(1,3-oxazol-5-yl)pyrrolo[2,1-f][1,2,4]triazin-5-yl]phenyl}-N'-(3-tert-butylisoxazol-5-yl)urea

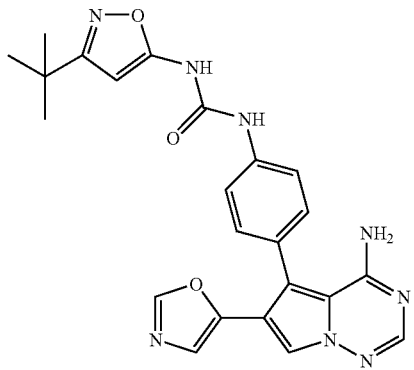

The procedure used for the preparation of Example 73 was used to prepare the title compound by substituting Intermediate AB for intermediate X and by substituting phenyl (3-tert-butylisoxazol-5-yl)carbamate for phenyl (4-tert-butylpyridin-2-yl)carbamate. $^1$H-NMR (DMSO-$d_6$) δ 10.21 (s, 1H), 9.07 (s, 1H), 8.29 (s, 1H), 8.09 (s, 1H), 7.90 (s, 1H), 7.62 to 7.60 (d, J=8.6 Hz, 2H), 7.38 to 7.35 (d, J=8.5 Hz, 2H), 6.55 (s, 1H), 6.07 (s, 1H), 1.26 (s, 9H); MS [M+H]+=459.1; LCMS RT=2.65 min.

Example 297

Preparation of N-{4-[4-amino-6-(1,3-oxazol-5-yl)pyrrolo[2,1-f][1,2,4]triazin-5-yl]phenyl}-N'-[3-(trifluoromethoxy)phenyl]urea

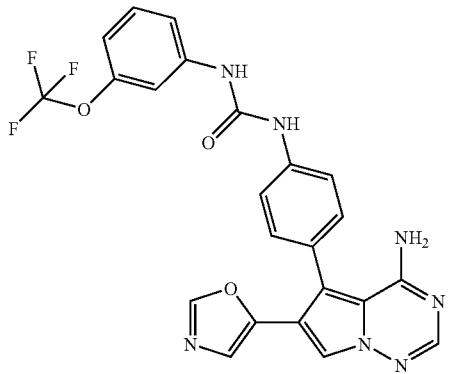

The procedure used for the preparation of Example 73 was used to prepare the title compound by substituting Intermediate AB for intermediate X and by substituting phenyl[3-(trifluoromethoxy)phenyl]carbamate for phenyl (4-tert-butylpyridin-2-yl)carbamate. $^1$H-NMR (DMSO-$d_6$) δ 9.11 (s, 1H), 9.02 (s, 1H), 8.30 (s, 1H), 8.08 (s, 1H), 7.90 (s, 1H), 7.71 (s, 1H), 7.62 to 7.60 (d, J=8.4 Hz, 2H), 7.42 to 7.38 (t, J=8.1 Hz, 1H), 7.36 to 7.34 (d, J=8.7 Hz, 2H), 7.32 to 7.29 (d, J=9.1 Hz, 1H), 6.96 to 6.93 (d, J=10.6, 1H), 6.55 (s, 1H); MS [M+H]+=496.1; LCMS RT=2.89 min.

Example 298

Preparation of N-{4-[4-amino-6-(1,3-oxazol-5-yl)pyrrolo[2,1-f][1,2,4]triazin-5-yl]phenyl}-N'-[4-chloro-3-(trifluoromethyl)phenyl]urea

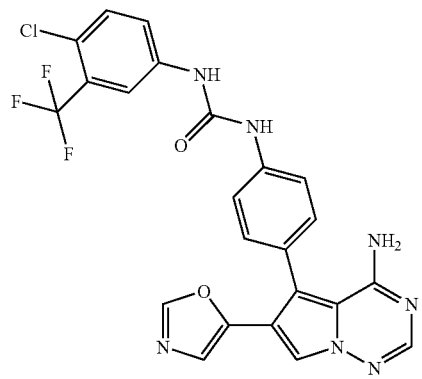

The procedure used for the preparation of Example 73 was used to prepare the title compound by substituting Intermediate AB for Intermediate X and by substituting phenyl[4-chloro-3-(trifluoromethyl)phenyl]carbamate for phenyl (4-tert-butylpyridin-2-yl)carbamate. $^1$H-NMR (DMSO-$d_6$) δ 9.26 (s, 1H), 9.08 (s, 1H), 8.30 (s, 1H), 8.12 (s, 1H), 8.09 (s, 1H), 7.90 (s, 1H), 7.64 to 7.61 (m, 4H), 7.37 to 7.35 (d, J=8.5 Hz, 2H), 6.55 (s, 1H); MS [M+H]+=514.1; LCMS RT=3.02 min.

Example 299

Preparation of N-{4-[4-amino-6-(2-thienylcarbonyl)pyrrolo[2,1-f][1,2,4]triazin-5-yl]phenyl}-N'-(3-tert-butylisoxazol-5-yl)urea

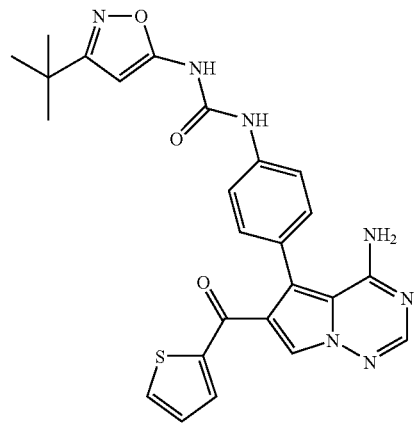

The procedure used for the preparation of Example 287 was used to prepare the title compound by substituting 2-thienylmagnesium bromide for methylmagnesium bromide.

$^1$H-NMR (DMSO-d$_6$) 8.26 (s, 1H), 7.98 (dd, J=1, 4 Hz, 1H), 7.96 (s, 1H), 7.75 (dd, J=1, 3 Hz), 7.53 (d, J=6 Hz, 2H), 7.30 (d, J=6 Hz, 2H), 7.19 (dd, J=3, 4 Hz, 1H), 6.05 (s, 1H) 1.25 (s, 9H); MS [M+H]$^+$=502.1; LCMS RT=2.98 min.

Example 300

Preparation of N-{4-[4-amino-6-(1-hydroxyethyl)pyrrolo[2,1-f][1,2,4]triazin-5-yl]phenyl}-N'-[2-fluoro-5-(trifluoromethyl)phenyl]urea

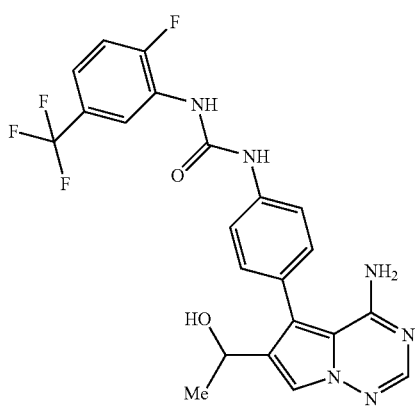

The procedure used for the preparation of Example 269 was used to prepare the title compound by substituting Example 1 for Example 51. $^1$H-NMR (DMSO-d$_6$) δ 9.41 (s, 1H), 9.01 (d, J=3 Hz, 1H), 8.62 (d, J=3, 8 Hz, 1H), 7.81 (s, 1H), 7.77 (s, 1H), 7.61 (d, J=9 Hz, 2H), 7.47 to 7.54 (m, 1H), 7.38 to 7.42 (m, 1H), 7.35 (d, J=9 Hz, 2H); MS [M+H]$^+$=475.1; LCMS RT=2.59 min.

Example 301

Preparation of N-{4-[4-amino-6-(1,2-dihydroxyethyl)pyrrolo[2,1-f][1,2,4]triazin-5-yl]phenyl}-N'-[4-(trifluoromethyl)pyridin-2-yl]urea

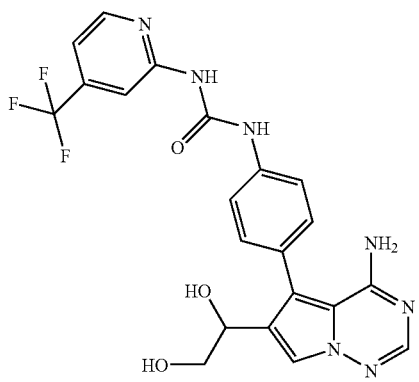

Methanesulfonamide (65 mg, 0.683 mmol) was dissolved in a 1:1 solution of tert-Butanol:water (5 mL) and treated with AD-mix β (1.0 g). The mixture was then treated with Example 222 (0.3 g, 0.683 mmol) and the reaction was stirred at room temperature overnight. After completion, the solution was treated with solid sodium sulfite (1.5 g) and stirred for 1 hour. The reaction was then transferred to a sep. funnel and the crude product was extracted with EtOAc. The organic layer was washed with water and saturated NaCl solution. The solution was then dried over MgSO$_4$, filtered and concentrated under reduced pressure. No purification was needed for the title compound isolated as 0.3 g of a tan solid (0.634 mmol, 93% yield). $^1$H-NMR (DMSO-d$_6$) δ 9.88 (bs, 1H), 9.76 (bs, 1H), 8.53 (d, J=5.7 Hz, 1H), 8.06 (s, 1H), 7.82 (s, 1H), 7.63 (s, 1H), 7.61 (d, J=8.8 Hz, 2H), 7.37-7.35 (m, 3H), 5.03 (d, J=4.6 Hz, 2H), 4.65 (t, J=5.8 Hz, 1H), 4.47-4.43 (m, 1H), 3.45-3.38 (m, 2H); MS [M+H]$^+$=474.0; LCMS RT=2.13 min.

Example 302

Preparation of 4-amino-N,N-dimethyl-5-{4-[({[6-(trifluoromethyl)pyridin-2-yl]amino}carbonyl)amino]phenyl}pyrrolo[2,1-f][1,2,4]triazine-6-carboxamide

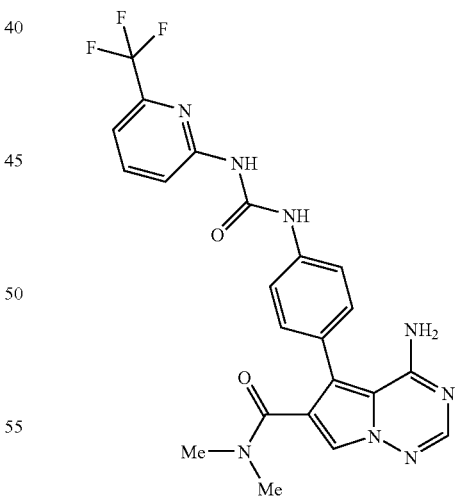

The procedure used for the preparation of Example 69 was used to prepare the title compound by substituting Intermediate AH for Intermediate G and dimethylamine for cyclopropylamine. The reaction was stirred for 16 h and was purified by HPLC (20-85% acetonitrile in water). $^1$H NMR (DMSO-d$_6$) δ 9.87 (s, 1H), 9.68 (s, 1H), 8.05 to 7.96 (m, 2H), 7.89 (s, 1H), 7.85 (s, 1H), 7.57 to 7.52 (m, 2H), 7.49 (dd, J=6.6, 1.6 Hz, 1H), 7.32 to 7.27 (m, 2H), 2.81 (s, 3H), 2.64 (s, 3H); MS [M+H]⁺=485.0; LCMS RT=2.43 min.

Example 303

Preparation of 4-amino-N-ethyl-N-methyl-5-{4-[({[6-(trifluoromethyl)pyridin-2-yl]amino}carbonyl)amino]phenyl}pyrrolo[2,1-f][1,2,4]triazine-6-carboxamide

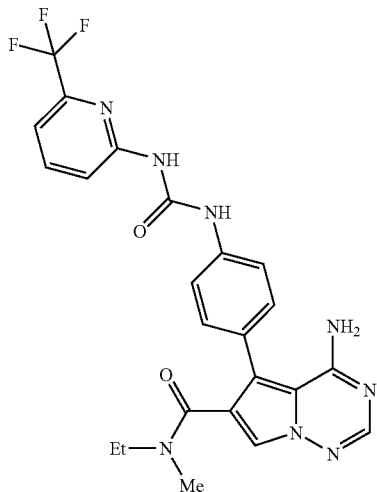

The procedure used for the preparation of Example 69 was used to prepare the title compound by substituting Intermediate AH for Intermediate G and N-ethyl-N-methylamine for cyclopropylamine. The reaction was stirred for 16 h and was purified by HPLC (20-85% acetonitrile in water). ¹H NMR (DMSO-d₆) δ 9.86 (s, 1H), 9.68 (s, 1H), 8.05 to 7.96 (m, 2H), 7.89 (s, 1H), 7.85 (s, 1H), 7.56 to 7.46 (m, 3H), 7.30 (d, J=8.1 Hz, 2H), 3.31 and 3.06 (diastereomeric quartets, 2H), 2.79 and 2.58 (diastereomeric singlets, 3H), 0.93 and 0.81 (diastereomeric triplets, 3H); MS [M+H]⁺=499.1; LCMS RT=2.55 min.

Example 304

Preparation of 4-amino-N,N-diethyl-5-{4-[({[6-(trifluoromethyl)pyridin-2-yl]amino}carbonyl)amino]phenyl}pyrrolo[2,1-f][1,2,4]triazine-6-carboxamide

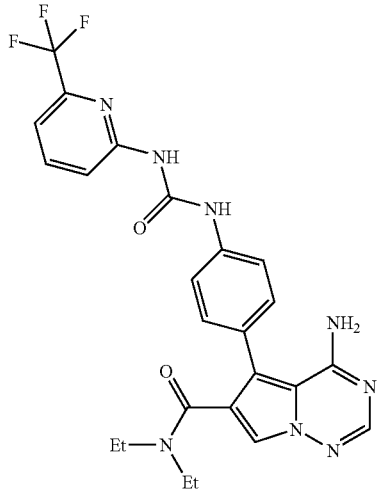

The procedure used for the preparation of Example 69 was used to prepare the title compound by substituting Intermediate AH for Intermediate G and diethylamine for cyclopropylamine. The reaction was stirred for 16 h and was purified by HPLC (20-85% acetonitrile in water). ¹H NMR (DMSO-d₆) δ 9.85 (s, 1H), 9.67 (s, 1H), 8.05 to 7.96 (m, 2H), 7.89 (s, 1H), 7.85 (s, 1H), 7.55 to 7.46 (m, 3H), 7.33 to 7.28 (m, 2H), 3.32 and 3.02 (diastereomeric quartets, 2H), 0.94 and 0.82 (diastereomeric triplets, 3H); MS [M+H]⁺=513.1; LCMS RT=2.64 min.

Example 305

Preparation of N-{4-[4-amino-6-(pyrrolidin-1-ylcarbonyl)pyrrolo[2,1-f][1,2,4]triazin-5-yl]phenyl}-N'-[6-(trifluoromethyl)pyridin-2-yl]urea

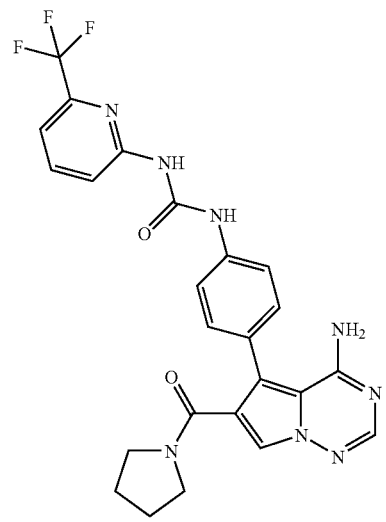

The procedure used for the preparation of Example 69 was used to prepare the title compound by substituting Intermediate AH for Intermediate G and pyrrolidine for cyclopropylamine. The reaction was stirred for 16 h and was purified by HPLC (20-85% acetonitrile in water). ¹H NMR (DMSO-d₆) δ 9.86 (s, 1H), 9.67 (s, 1H), 8.04 to 7.98 (m, 2H), 7.91 (s, 1H), 7.89 (s, 1H), 7.56 to 7.46 (m, 3H), 7.34 to 7.29 (m, 2H), 3.32 (t, J=6.4 Hz, 2H), 3.11 (t, J=6.4 Hz, 2H), 1.77 to 1.60 (m, 4H); MS [M+H]⁺=511.1; LCMS RT=2.53 min.

Example 306

Preparation of N-{4-[4-amino-6-(piperidin-1-ylcarbonyl)pyrrolo[2,1-f][1,2,4]triazin-5-yl]phenyl}-N'-[6-(trifluoromethyl)pyridin-2-yl]urea

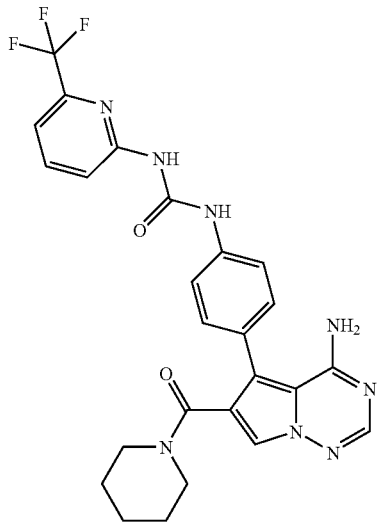

The procedure used for the preparation of Example 69 was used to prepare the title compound by substituting Intermediate AH for Intermediate G and piperidine for cyclopropylamine. The reaction was stirred for 16 h and was purified by HPLC (20-85% acetonitrile in water). $^1$H NMR (DMSO-$d_6$) δ 9.86 (s, 1H), 9.68 (s, 1H), 8.04 to 7.98 (m, 2H), 7.89 (s, 1H), 7.83 (s, 1H), 7.58 to 7.47 (m, 3H), 7.33 to 7.28 (m, 2H), 3.43 (br s, 2H), 3.04 (br s, 2H), 1.43 to 1.31 (m, 4H), 0.98 (br s, 2H); MS [M+H]$^+$=525.1; LCMS RT=2.73 min.

Example 307

Preparation of N-(4-{4-amino-6-[(2-methylpiperidin-1-yl)carbonyl]pyrrolo[2,1-f][1,2,4]triazin-5-yl}phenyl)-N'-[6-(trifluoromethyl)pyridin-2-yl]urea

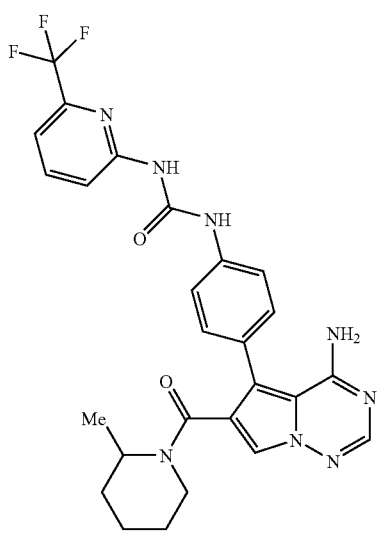

The procedure used for the preparation of Example 69 was used to prepare the title compound by substituting Intermediate AH for Intermediate G and piperidine for cyclopropylamine. The reaction was stirred for 16 h and was purified by HPLC (20-85% acetonitrile in water). $^1$H NMR (DMSO-$d_6$) δ 9.85 (s, 1H), 9.68 (s, 1H), 8.05 to 7.97 (m, 2H), 7.89 (s, 1H), 7.83 (s, 1H), 7.58 to 7.47 (m, 3H), 7.33 to 7.27 (m, 2H), 2.69 to 2.60 (m, 1H), 2.50 (br s, 2H), 1.50 to 1.31 (m, 4H), 0.99 to 0.90 (m, 5H); MS [M+H]$^+$=539.1; LCMS RT=2.81 min.

Example 308

Preparation of N-{4-[4-amino-6-(1,3-oxazol-5-yl)pyrrolo[2,1-f][1,2,4]triazin-5-yl]-2-fluorophenyl}-N'-[2-fluoro-5-(trifluoromethyl)phenyl]urea

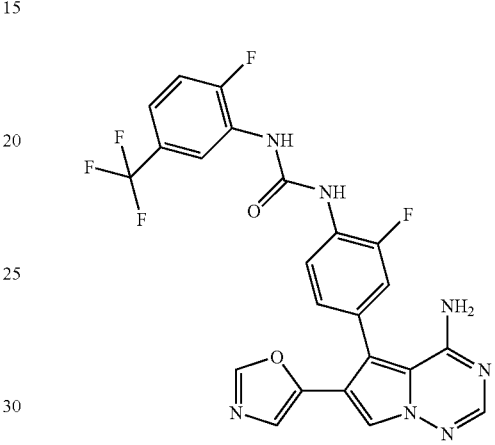

The procedure used for the preparation of Example 276 was used to prepare the title compound by Intermediate AL for Intermediate 7. $^1$H-NMR (DMSO-$d_6$) δ 9.46 (s, 1H), 9.32 (s, 1H), 8.65 to 8.64 (d, J=7.4 Hz, 1H), 8.35 to 8.30 (t, J=8.5 Hz, 1H), 8.30 (s, 1H), 8.09 (s, 1H), 7.90 (s, 1H), 7.53 to 7.48 (m, 1H), 7.42 to 7.39 (m, 1H), 7.37 to 7.34 (d, J=12.0 Hz, 1H), 7.21 to 7.19 (d, J=8.4 Hz, 1H), 6.62 (s, 1H); MS [M+H]$^+$=516.1; LCMS RT=3.01 min.

Example 309

Preparation of 4-amino-N-cyclopropyl-5-[4-({[(3-methoxyphenyl)amino]carbonyl}amino)phenyl]pyrrolo[2,1-f][1,2,4]triazine-6-carboxamide

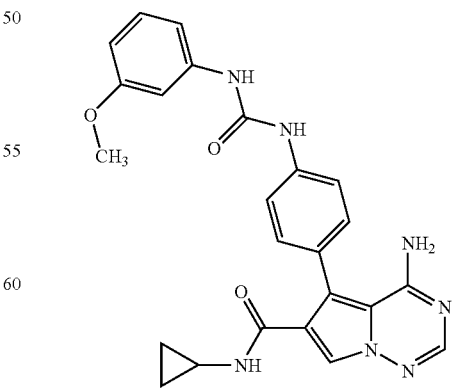

The procedure used for the preparation of Example 73 was used to prepare the title compound by substituting Intermediate W for Intermediate X and phenyl (3-methoxyphenyl) carbamate for phenyl (4-tert-butylpyridin-2-yl)carbamate. The reaction was heated at reflux overnight in THF. $^1$H NMR (DMSO-d$_6$) δ 8.81 (s, 1H), 8.75 (s, 1H), 8.04 (s, 1H), 7.92 (br s, 1H), 7.88 (s, 1H), 7.88 (d, J=4.3 Hz, 1H), 7.54 to 7.48 (m, 2H), 7.31 to 7.23 (m, 2H), 7.21 to 7.12 (m, 2H), 6.96 to 6.90 (m, 1H), 6.55 (ddd, J=8.1, 2.7, 0.7 Hz, 1H), 4.66 (br s, 1H), 3.73 (s, 3H), 2.70 to 2.62 (m, 1H), 0.64 to 0.58 (m, 2H), 0.44 to 0.38 (m, 2H); MS [M+H]$^+$=458.1; LCMS RT=2.38 min.

Example 310

Preparation of N-{4-[4-amino-6-(1,3-oxazol-5-yl)pyrrolo[2,1-f][1,2,4]triazin-5-yl]phenyl}-N'-[3-(trifluoromethyl)phenyl]urea

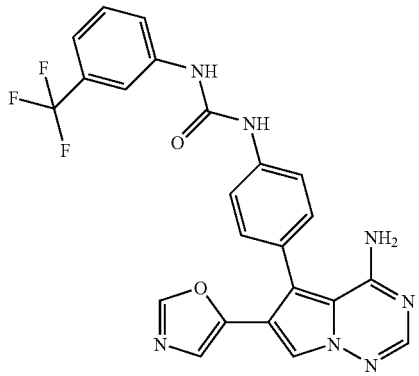

The procedure used for the preparation of Example 3 was used to prepare the title compound by substituting Intermediate AO for Intermediate C and 3-(trifluoromethyl)aniline for 4-fluoro-3-(trifluoromethyl)aniline. $^1$H-NMR (DMSO-d$_6$) δ 9.23 to 9.16 (br s, 2H), 8.28 (s, 1H), 8.07 (s, 1H), 7.89 (s, 1H), 7.72 (s, 1H), 7.63 to 7.61 (d, J=8.6 Hz, 2H), 7.34 to 7.28 (m, 4H), 7.01 to 6.99 (d, J=7.1 Hz, 1H), 6.55 (s, 1H); MS [M+H]$^+$=480.0; LCMS RT=2.84 min.

Example 311

Preparation of N-{4-[4-amino-6-(1,3-oxazol-5-yl)pyrrolo[2,1-f][1,2,4]triazin-5-yl]phenyl}-N'-(3-chlorophenyl)urea

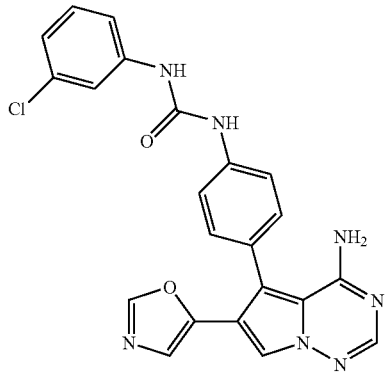

The procedure used for the preparation of Example 3 was used to prepare the title compound by substituting Intermediate AO for Intermediate C and 3-chloroaniline for 4-fluoro-3-(trifluoromethyl)aniline. $^1$H-NMR (DMSO-d$_6$) δ 8.29 (s, 1H), 8.08 (s, 1H), 8.04 (s, 1H), 7.90 (s, 1H), 7.68 to 7.66 (m, 3H), 7.51 to 7.47 (t, J=8.1 Hz, 1H), 7.34 to 7.32 (d, J=8.6 Hz, 2H), 7.30 to 7.28 (d, J=8.4 Hz, 1H), 6.56 (s, 1H); MS [M+H]$^+$=446.1; LCMS RT=2.72 min.

Example 312

Preparation of N-{4-[4-amino-6-(1,3-oxazol-5-yl)pyrrolo[2,1-f][1,2,4]triazin-5-yl]phenyl}-N'-(4-chlorophenyl)urea

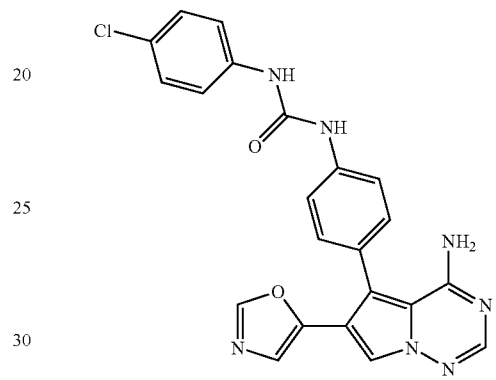

The procedure used for the preparation of Example 3 was used to prepare the title compound by substituting Intermediate AO for Intermediate C and 4-chloroaniline for 4-fluoro-3-(trifluoromethyl)aniline. $^1$H-NMR (DMSO-d$_6$) δ 8.93 (s, 1H), 8.90 (s, 1H), 8.29 (s, 1H), 8.08 (s, 1H), 7.90 (s, 1H), 7.61 to 7.59 (d, J=8.6 Hz, 2H), 7.50 to 7.48 (d, J=9.1 Hz, 2H), 7.35 to 7.32 (m, 4H), 6.55 (s, 1H); MS [M+H]$^+$=446.1; LCMS RT=2.65 min.

Example 313

Preparation of 4-amino-5-[4-({[(3-methoxyphenyl)amino]carbonyl}amino)phenyl]-N-(2,2,2-trifluoroethyl)pyrrolo[2,1-f][1,2,4]triazine-6-carboxamide

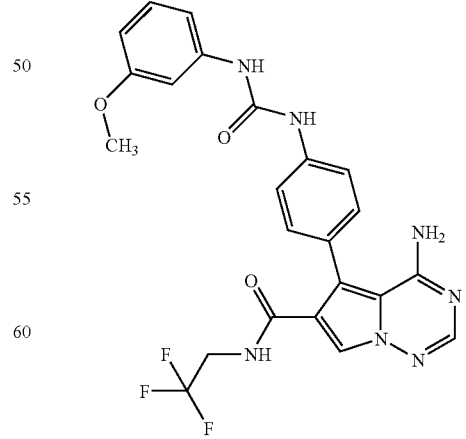

The procedure used for the preparation of Example 73 was used to prepare the title compound by substituting Intermediate M for Intermediate X and phenyl (3-methoxyphenyl) carbamate for phenyl (4-tert-butylpyridin-2-yl)carbamate. The reaction was heated at reflux overnight in THF. $^1$H NMR (DMSO-d$_6$) δ 8.79 (s, 1H), 8.72 (s, 1H), 8.48 (dd, J=6.4, 6.4 Hz, 1H), 8.17 (s, 1H), 8.00 (br s, 1H), 7.91 (s, 1H), 7.52 to 7.47 (m, 2H), 7.30 to 7.23 (m, 2H), 7.21 to 7.12 (m, 2H), 6.96 to 6.90 (m 1H), 6.54 (ddd, J=8.2, 2.6, 0.8 Hz, 1H), 5.08 (br s, 1H), 4.02 to 3.90 (m, 2H), 3.73 (s, 3H); MS [M+H]$^+$=500.2; LCMS RT=2.61 min.

The following further examples can be synthesized according to the synthetic procedures outlined above:

4-amino-5-[4-({[(3-phenoxyphenyl)amino]carbonyl}amino)phenyl]-N-(2,2,2-trifluoroethyl)pyrrolo[2,1-f][1,2,4]triazine-6-carboxamide

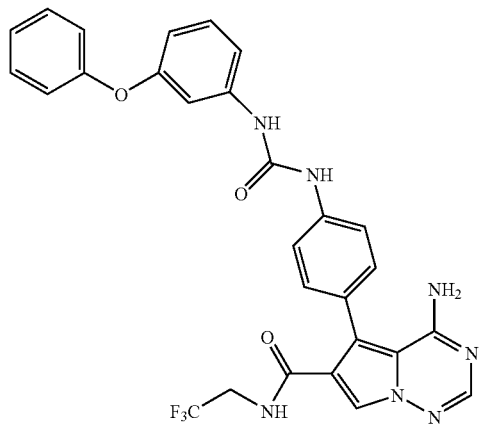

4-amino-N-cyclopropyl-5-[4-({[(3-phenoxyphenyl)amino]carbonyl}amino)phenyl]pyrrolo[2,1-f][1,2,4]triazine-6-carboxamide

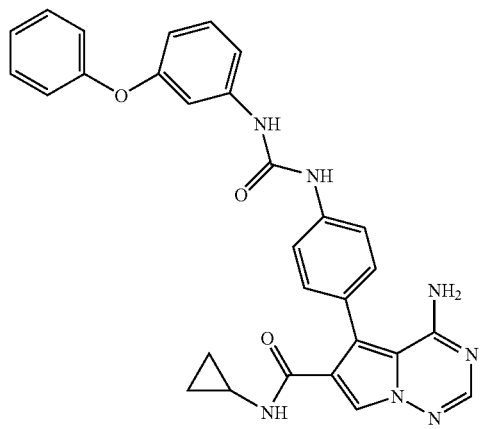

4-amino-N-(2,2,2-trifluoroethyl)-5-{4-[({[2-(trifluoromethyl)pyrimidin-4-yl]amino}carbonyl)amino]phenyl}pyrrolo[2,1-f][1,2,4]triazine-6-carboxamide

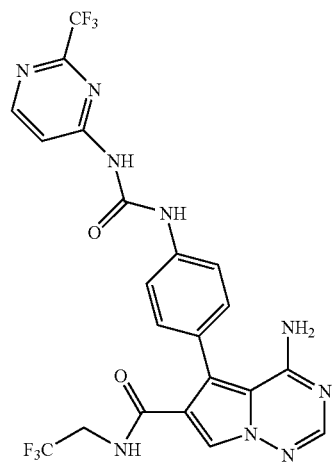

4-amino-N-cyclopropyl-5-{4-[({[2-(trifluoromethyl)pyrimidin-4-yl]amino}carbonyl)amino]phenyl}pyrrolo[2,1-f][1,2,4]triazine-6-carboxamide

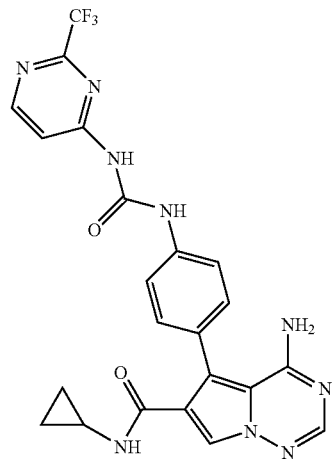

| 257 | 258 |
|---|---|
| 4-amino-N-(2,2,2-trifluoroethyl)-5-{4-[({[3-(trifluoromethoxy)phenyl]amino}carbonyl)amino]phenyl}pyrrolo[2,1-f][1,2,4]triazine-6-carboxamide | 4-amino-5-(4-{[(1,3-benzodioxol-5-ylamino)carbonyl]amino}phenyl)-N-(2,2,2-trifluoroethyl)pyrrolo[2,1-f][1,2,4]triazine-6-carboxamide |

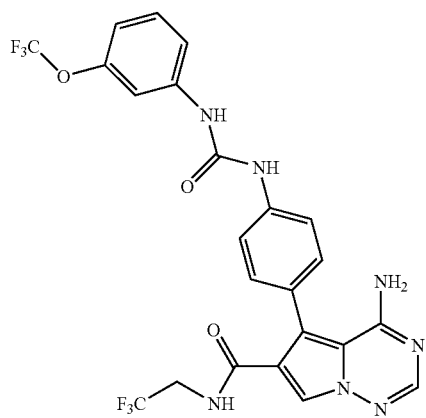

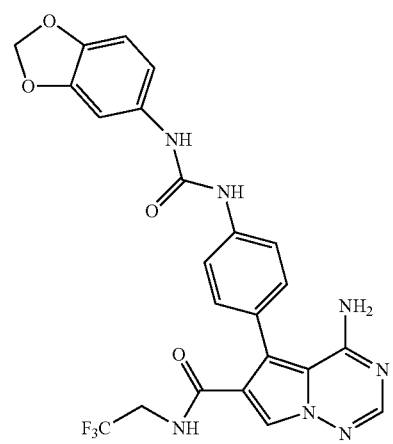

| | |
|---|---|
| 4-amino-N-cyclopropyl-5-{4-[({[3-(trifluoromethoxy)phenyl]amino}carbonyl)amino]phenyl}pyrrolo[2,1-f][1,2,4]triazine-6-carboxamide | 4-amino-5-(4-{[(1,3-benzodioxol-5-ylamino)carbonyl]amino}phenyl)-N-cyclopropylpyrrolo[2,1-f][1,2,4]triazine-6-carboxamide |

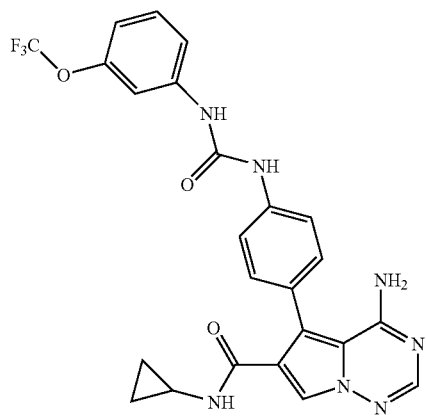

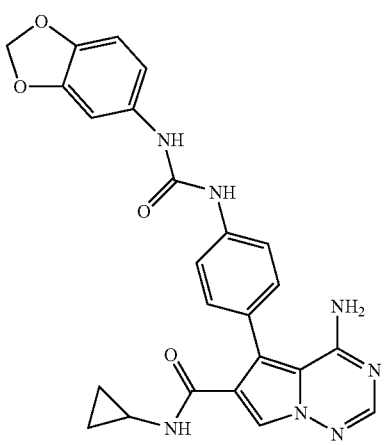

259

4-amino-5-[4-({[(6-methylpyridin-2-yl)amino]carbonyl}amino)phenyl]-N-(2,2,2-trifluoroethyl)pyrrolo[2,1-f][1,2,4]triazine-6-carboxamide

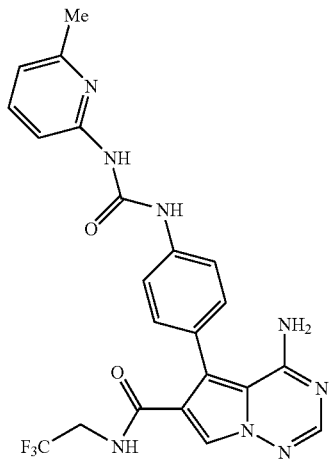

4-amino-N-cyclopropyl-5-[4-({[(6-methylpyridin-2-yl)amino]carbonyl}amino)phenyl]pyrrolo[2,1-f][1,2,4]triazine-6-carboxamide

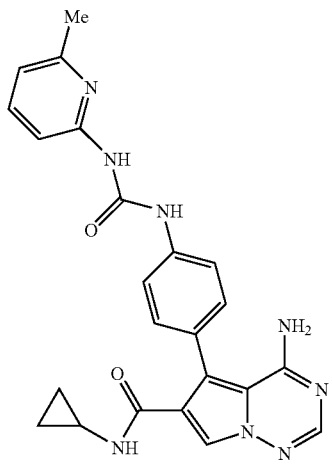

4-amino-5-{4-[({[3-(3-ethylphenoxy)phenyl]amino}carbonyl)amino]phenyl}-N-(2,2,2-trifluoroethyl)pyrrolo[2,1-f][1,2,4]triazine-6-carboxamide

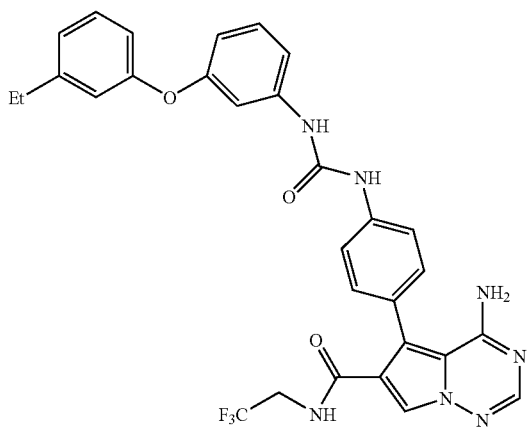

260

4-amino-5-{4-[({[3-(2-chlorophenoxy)phenyl]amino}carbonyl)amino]phenyl}-N-(2,2,2-trifluoroethyl)pyrrolo[2,1-f][1,2,4]triazine-6-carboxamide

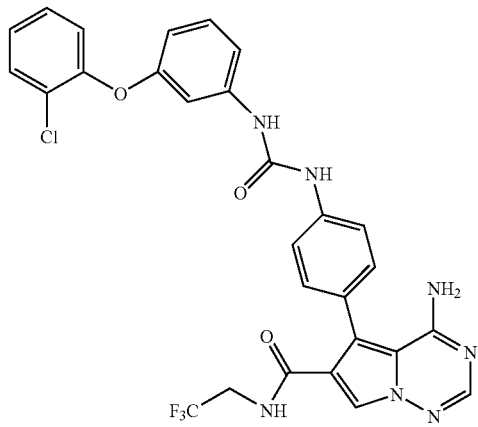

4-amino-N-(2,2,2-trifluoroethyl)-5-(4-{[({3-[4-(trifluoromethoxy)phenoxy]phenyl}amino)carbonyl]amino}phenyl)pyrrolo[2,1-f][1,2,4]triazine-6-carboxamide

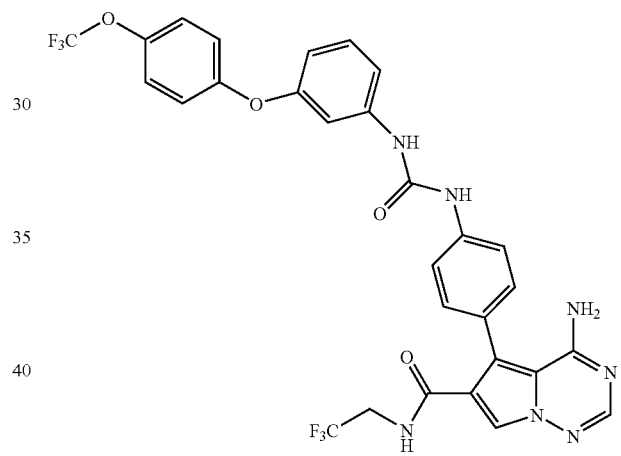

4-amino-N-cyclopropyl-5-{4-[({[3-(2-methylphenoxy)phenyl]amino}carbonyl)amino]phenyl}pyrrolo[2,1-f][1,2,4]triazine-6-carboxamide

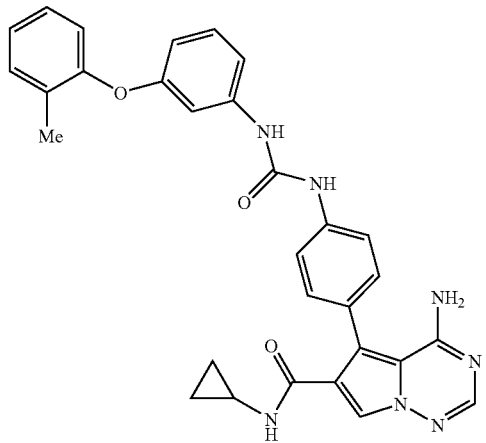

261

4-amino-N-cyclopropyl-5-{4-[({[3-(4-fluorophe-noxy)phenyl]amino}carbonyl)amino]phenyl}pyrrolo[2,1-f][1,2,4]triazine-6-carboxamide

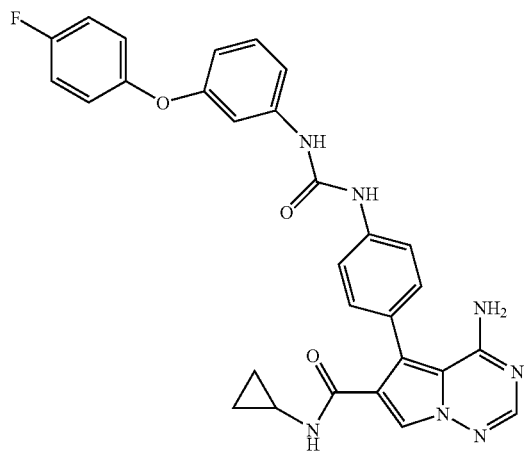

4-amino-N-cyclopropyl-5-{4-[({[3-(3-methoxyphe-noxy)phenyl]amino}carbonyl)amino]phenyl}pyrrolo[2,1-f][1,2,4]triazine-6-carboxamide

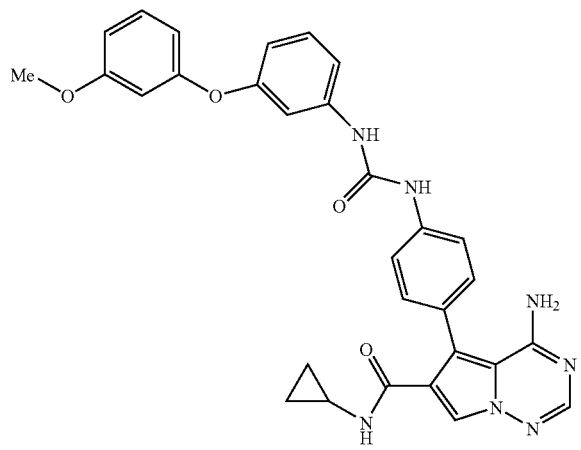

4-amino-N-(tert-butyl)-5-[4-({[(3-phenoxyphenyl)amino]carbonyl}amino)phenyl]pyrrolo[2,1-f][1,2,4]triazine-6-carboxamide

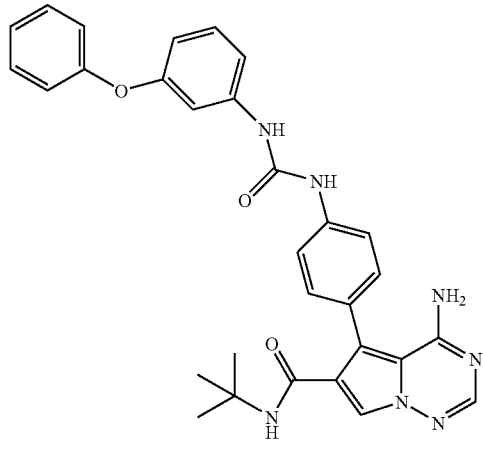

262

4-amino-N-(2,2,2-trifluoroethyl)-5-{-4-[({[4-(trifluo-romethyl)pyrimidin-2-yl]amino}carbonyl)amino]phenyl}pyrrolo[2,1-f][1,2,4]triazine-6-carboxamide

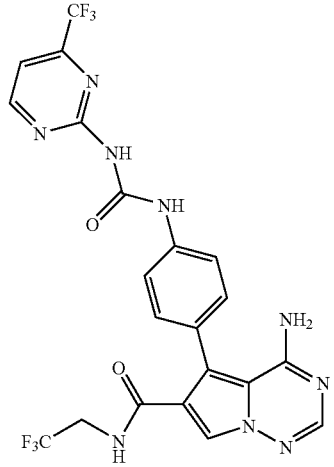

4-amino-N-cyclopropyl-5-{4-[({[4-(trifluoromethyl)pyrimidin-2-yl]amino}carbonyl)amino]phenyl}pyrrolo[2,1-f][1,2,4]triazine-6-carboxamide

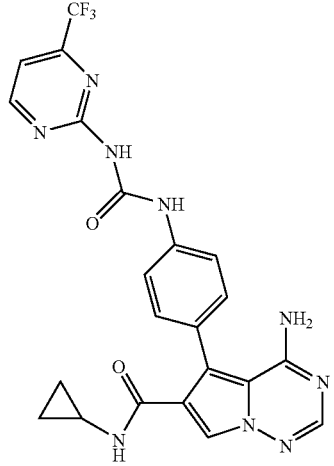

4-amino-5-{3-fluoro-4-[({[6-(trifluoromethyl)pyri-din-2-yl]amino}carbonyl)amino]phenyl}-N-(2,2,2-trifluoroethyl)pyrrolo[2,1-f][1,2,4]triazine-6-car-boxamide

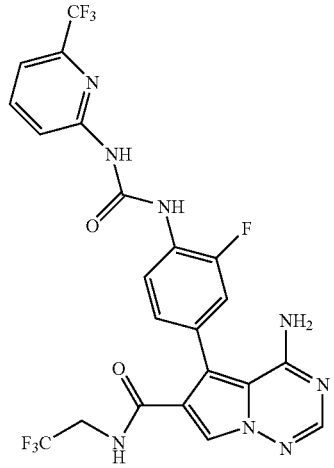

263

4-amino-5-{2-methyl-4-[({[6-(trifluoromethyl)pyridin-2-yl]amino}carbonyl)amino]phenyl}-N-(2,2,2-trifluoroethyl)pyrrolo[2,1-f][1,2,4]triazine-6-carboxamide

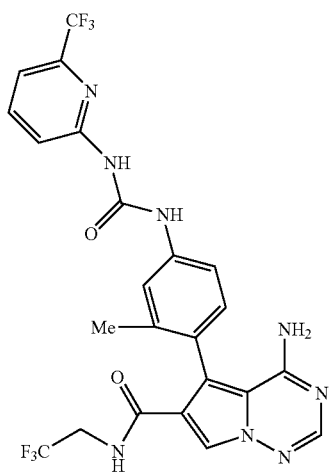

4-amino-5-{3-methoxy-4-[({[6-(trifluoromethyl)pyridin-2-yl]amino}carbonyl)amino]phenyl}-N-(2,2,2-trifluoroethyl)pyrrolo[2,1-f][1,2,4]triazine-6-carboxamide

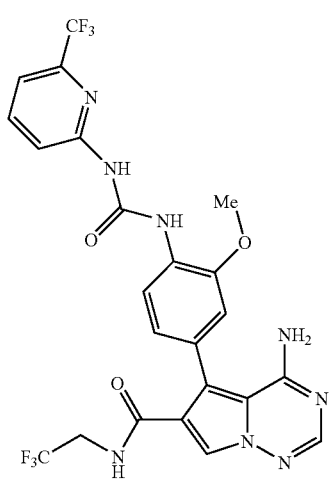

264

4-amino-N-cyclopropyl-5-{2-fluoro-4-[({[6-(trifluoromethyl)pyridin-2-yl]amino}carbonyl)amino]phenyl}pyrrolo[2,1-f][1,2,4]triazine-6-carboxamide

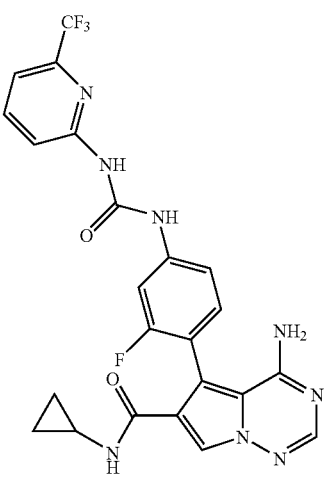

4-amino-N-cyclopropyl-5-{3-ethyl-4-[({[6-(trifluoromethyl)pyridin-2-yl]amino}carbonyl)amino]phenyl}pyrrolo[2,1-f][1,2,4]triazine-6-carboxamide

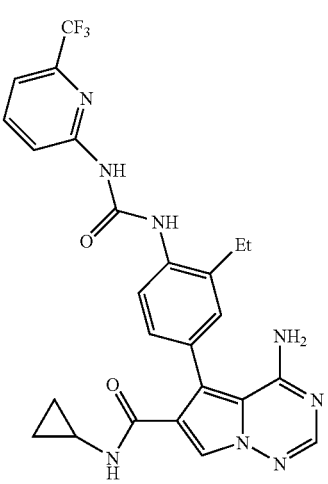

265

4-amino-N-cyclopropyl-5-{3-(trifluoromethoxy)-4-[({[6-(trifluoromethyl)pyridin-2-yl]amino}carbonyl)amino]phenyl}pyrrolo[2,1-f][1,2,4]triazine-6-carboxamide

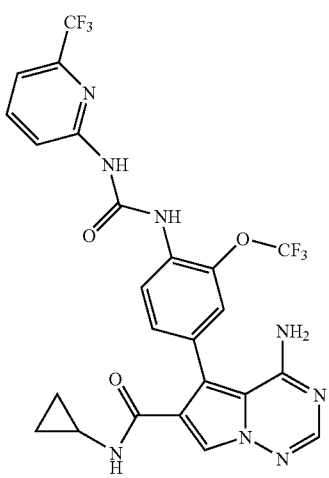

4-amino-N-(tert-butyl)-5-{3-fluoro-4-[({[6-(trifluoromethyl)pyridin-2-yl]amino}carbonyl)amino]phenyl}pyrrolo[2,1-f][1,2,4]triazine-6-carboxamide

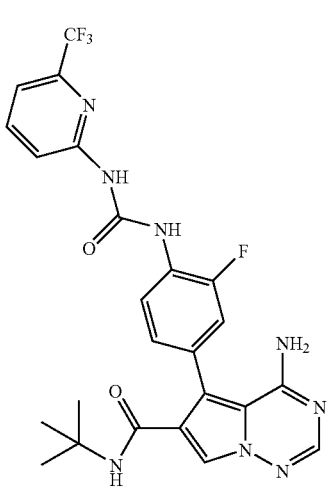

266

4-amino-N-(tert-butyl)-5-{2-methyl-4-[({[6-(trifluoromethyl)pyridin-2-yl]amino}carbonyl)amino]phenyl}pyrrolo[2,1-f][1,2,4]triazine-6-carboxamide

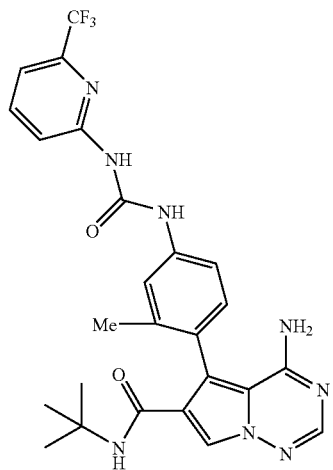

4-amino-N-(tert-butyl)-5-{3-methoxy-4-[({[6-(trifluoromethyl)pyridin-2-yl]amino}carbonyl)amino]phenyl}pyrrolo[2,1-f][1,2,4]triazine-6-carboxamide

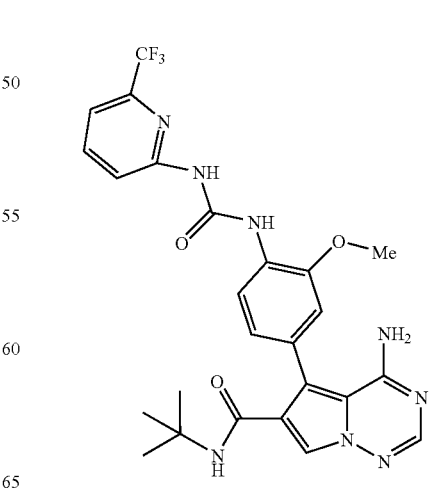

| 267 | 268 |
|---|---|
| 4-amino-N-(tert-butyl)-5-{4-[({[3-(2-methylphenoxy)phenyl]amino}carbonyl)amino]phenyl}pyrrolo[2,1-f][1,2,4]triazine-6-carboxamide | N-{4-[4-amino-6-(1,3-oxazol-5-yl)pyrrolo[2,1-f][1,2,4]triazin-5-yl]-2,6-difluorophenyl}-N'-[4-(trifluoromethyl)pyridin-2-yl]urea |

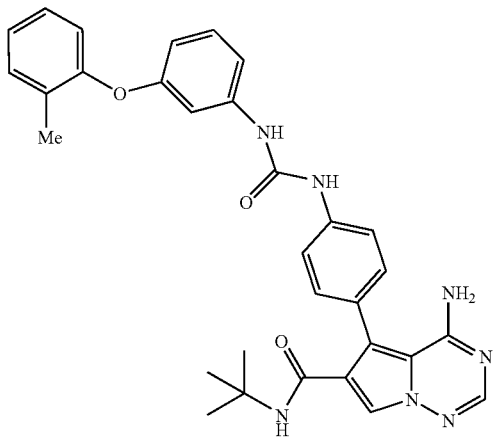
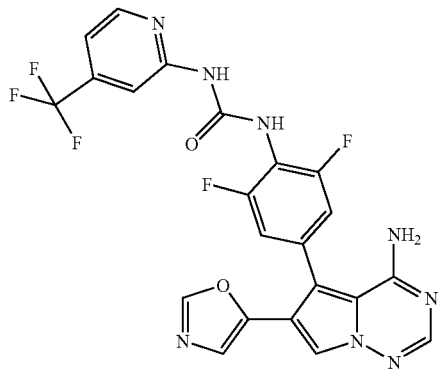

| | |
|---|---|
| 4-amino-N-(tert-butyl)-5-{4-[({[3-(4-fluorophenoxy)phenyl]amino}carbonyl)amino]phenyl}pyrrolo[2,1-f][1,2,4]triazine-6-carboxamide | N-{4-[4-amino-6-(1,3-oxazol-5-yl)pyrrolo[2,1-f][1,2,4]triazin-5-yl]-2,6-difluorophenyl}-N'-[2-fluoro-5-(trifluoromethyl)phenyl]urea |

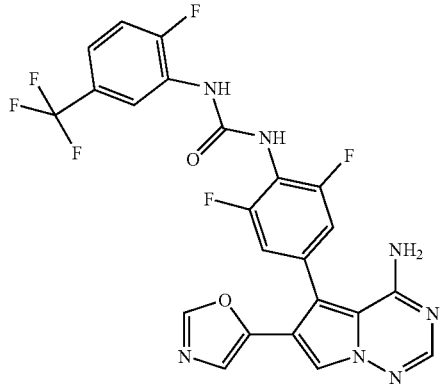

| | |
|---|---|
| 4-amino-N-(tert-butyl)-5-{4-[({[3-(3-methoxyphenoxy)phenyl]amino}carbonyl)amino]phenyl}pyrrolo[2,1-f][1,2,4]triazine-6-carboxamide | N-{4-[4-amino-6-(1,3-oxazol-5-yl)pyrrolo[2,1-f][1,2,4]triazin-5-yl]-2-chlorophenyl}-N'-[4-(trifluoromethyl)pyridin-2-yl]urea |

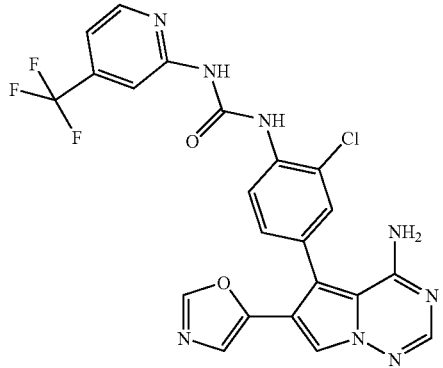

| 269 | 270 |
|---|---|
| N-{4-[4-amino-6-(1,3-oxazol-5-yl)pyrrolo[2,1-f][1,2,4]triazin-5-yl]-2-chlorophenyl}-N'-[2-fluoro-5-(trifluoromethyl)phenyl]urea | N-[4-(4-amino-6-glycoloylpyrrolo[2,1-f][1,2,4]triazin-5-yl)-2-fluorophenyl]-N'-[2-fluoro-5-(trifluoromethyl)phenyl]urea |

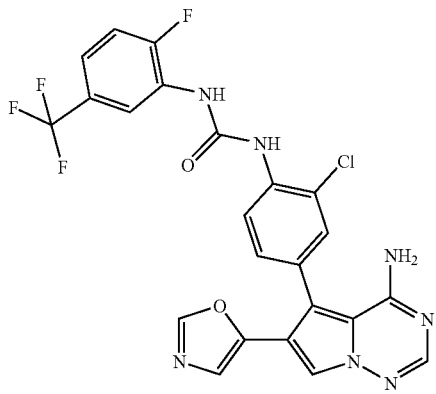 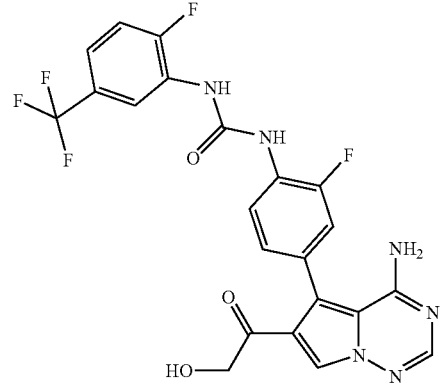

N-[4-(6-acetyl-4-aminopyrrolo[2,1-f][1,2,4]triazin-5-yl)-2-fluorophenyl]-N'-[2-fluoro-5-(trifluoromethyl)phenyl]urea N-{4-[4-amino-6-(1,3-thiazol-5-yl)pyrrolo[2,1-f][1,2,4]triazin-5-yl]phenyl}-N'-[4-(trifluoromethyl)pyridin-2-yl]urea

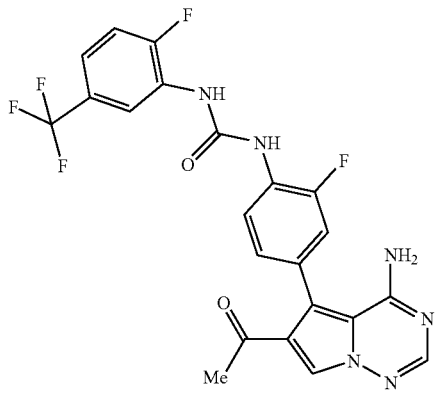 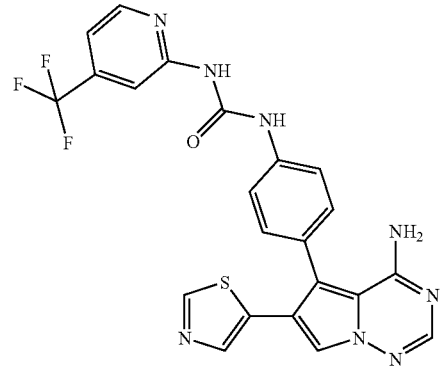

N-{4-[4-amino-6-(cyclopropylcarbonyl)pyrrolo[2,1-f][1,2,4]triazin-5-yl]-2-fluorophenyl}-N'-[2-fluoro-5-(trifluoromethyl)phenyl]urea N-{4-[4-amino-6-(4-methyl-1,3-thiazol-2-yl)pyrrolo[2,1-f][1,2,4]triazin-5-yl]phenyl}-N'-[4-(trifluoromethyl)pyridin-2-yl]urea

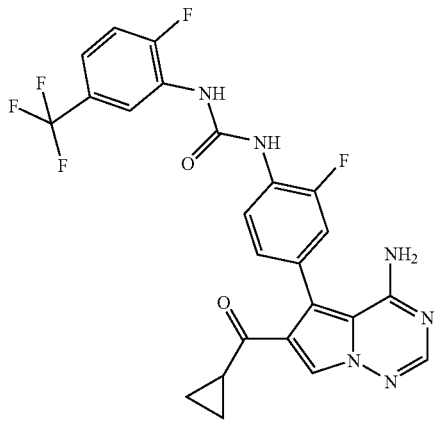 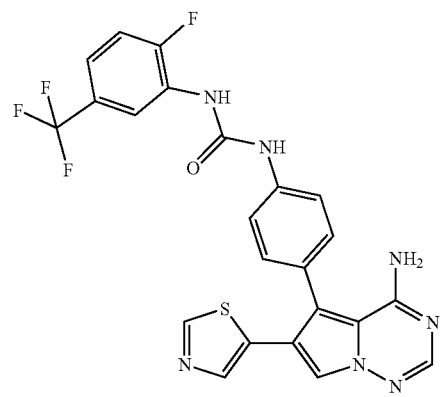

271

N-{4-[4-amino-6-(1,3-thiazol-5-yl)pyrrolo[2,1-f][1,2,4]triazin-5-yl]phenyl}-N'-[2-fluoro-5-(trifluoromethyl)phenyl]urea

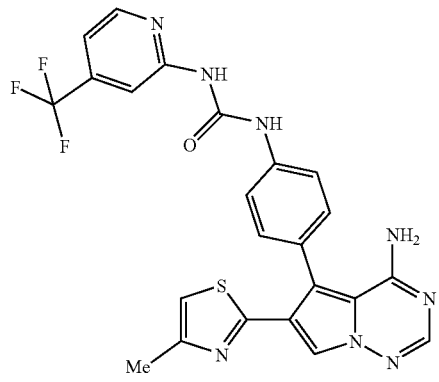

N-{4-[4-amino-6-(morpholin-4-ylacetyl)pyrrolo[2,1-f][1,2,4]triazin-5-yl]phenyl}-N'-[2-fluoro-5-(trifluoromethyl)phenyl]urea

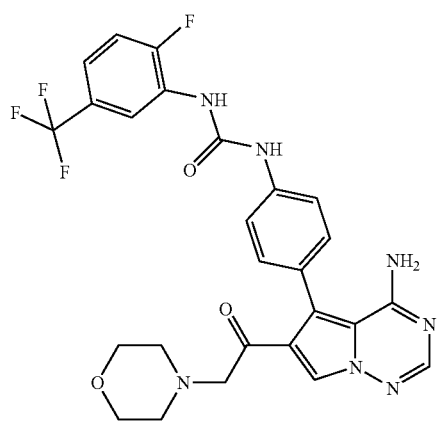

N-{4-[4-amino-6-(methoxyacetyl)pyrrolo[2,1-f][1,2,4]triazin-5-yl]phenyl}-N'-[2-fluoro-5-(trifluoromethyl)phenyl]urea

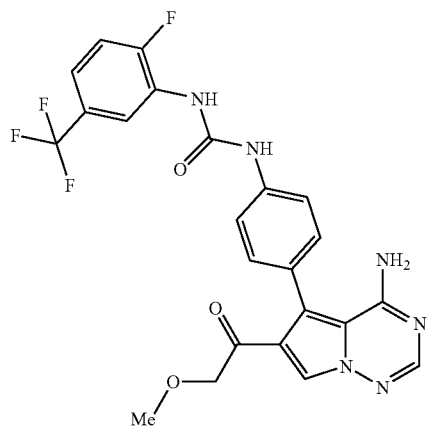

272

N-{4-[4-amino-6-(1,2,4-oxadiazol-5-yl)pyrrolo[2,1-f][1,2,4]triazin-5-yl]phenyl}-N'-[2-fluoro-5-(trifluoromethyl)phenyl]urea

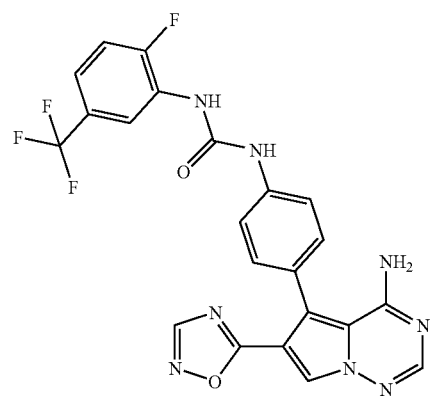

N-{4-[4-amino-6-(3-methyl-1,2,4-oxadiazol-5-yl)pyrrolo[2,1-f][1,2,4]triazin-5-yl]phenyl}-N'-[2-fluoro-5-(trifluoromethyl)phenyl]urea

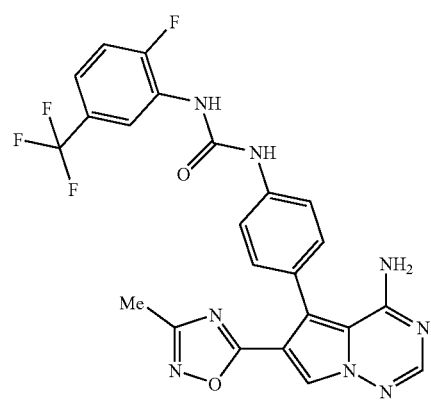

N-{4-[4-amino-6-(cyanomethyl)pyrrolo[2,1-f][1,2,4]triazin-5-yl]-2-fluorophenyl}-N'-[2-fluoro-5-(trifluoromethyl)phenyl]urea

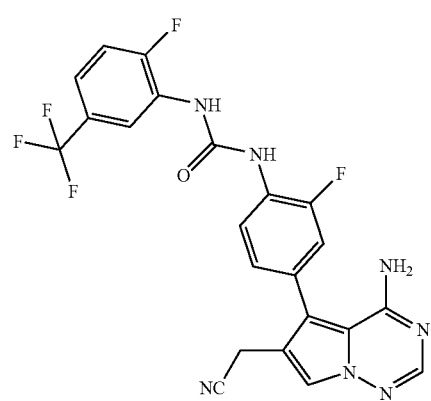

273

N-{4-[4-amino-6-(cyanomethyl)pyrrolo[2,1-f][1,2,4]triazin-5-yl]-2-fluorophenyl}-N'-[4-(trifluoromethyl)pyridin-2-yl]urea

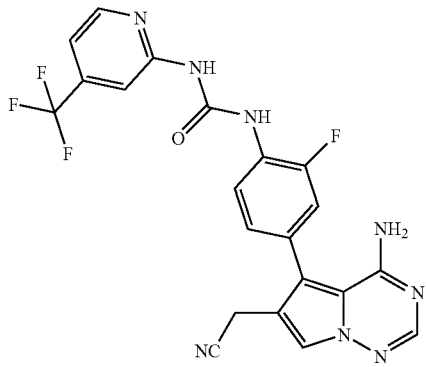

N-{4-[4-amino-6-(5-methylisoxazol-3-yl)pyrrolo[2,1-f][1,2,4]triazin-5-yl]phenyl}-N'-[2-fluoro-5-(trifluoromethyl)phenyl]urea

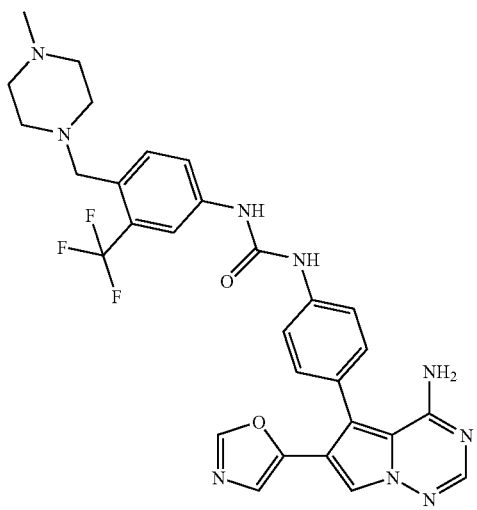

N-{4-[4-amino-6-(1,3-oxazol-5-yl)pyrrolo[2,1-f][1,2,4]triazin-5-yl]phenyl}-N'-[4-[(4-methylpiperazin-1-yl)methyl]-3-(trifluoromethyl)phenyl]urea

274

N-{4-[4-amino-6-(methoxymethyl)pyrrolo[2,1-f][1,2,4]triazin-5-yl]phenyl}-N'-[4-[(4-methylpiperazin-1-yl)methyl]-3-(trifluoromethyl)phenyl]urea

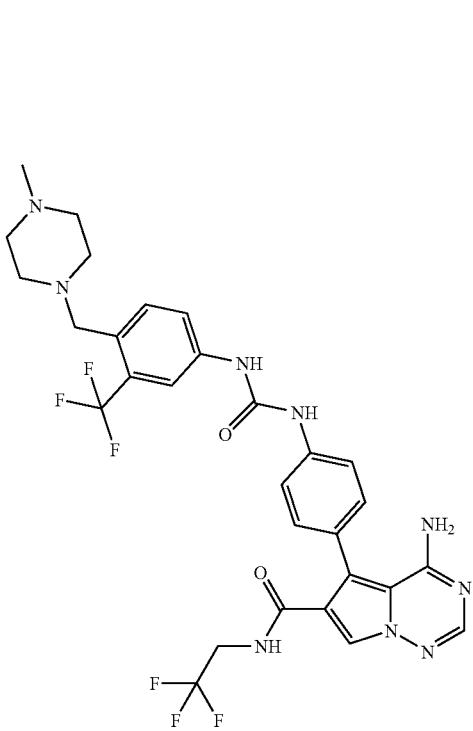

4-amino-5-{4-[({[4-[(4-methylpiperazin-1-yl)methyl]-3-(trifluoromethyl)phenyl]amino}carbonyl)amino]phenyl}-N-(2,2,2-trifluoroethyl)pyrrolo[2,1-f][1,2,4]triazine-6-carboxamide

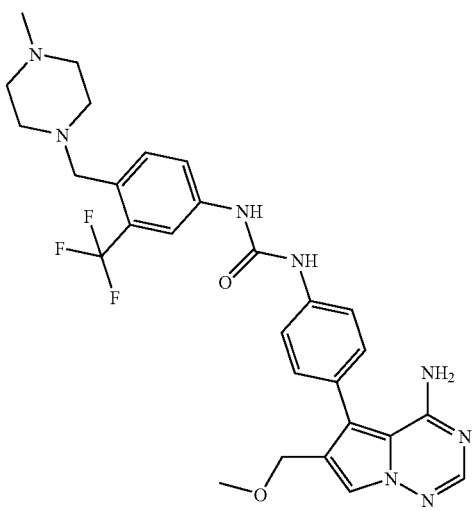

N-{4-[4-amino-6-(methoxymethyl)pyrrolo[2,1-f][1,2,4]triazin-5-yl]phenyl}-N'-[4-[(4-methylpiperazin-1-yl)methyl]-3-(trifluoromethyl)phenyl]urea

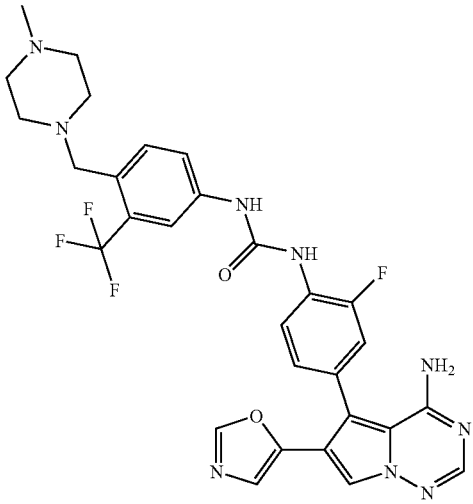

N-{4-[4-amino-6-(1,3-oxazol-5-yl)pyrrolo[2,1-f][1,2,4]triazin-5-yl]-2-fluorophenyl}-N'-[4-[(4-methylpiperazin-1-yl)methyl]-3-(trifluoromethyl)phenyl]urea

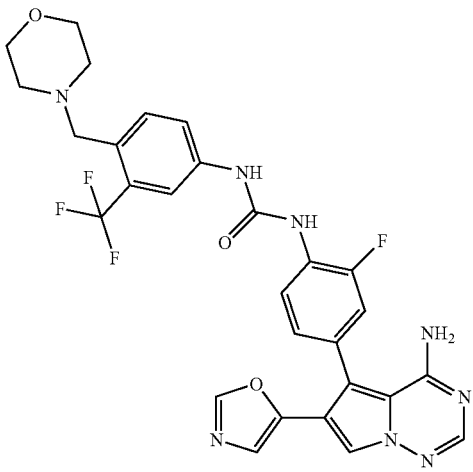

N-{4-[4-amino-6-(1,3-oxazol-5-yl)pyrrolo[2,1-f][1,2,4]triazin-5-yl]-2-fluorophenyl}-N'-[4-(morpholin-4-ylmethyl)-3-(trifluoromethyl)phenyl]urea

B. EVALUATION OF PHYSIOLOGICAL ACTIVITY

The in vitro effect of the compounds according to the invention can be demonstrated in the following assays:

Growth Factor Stimulated p-ERK Assay in HUVECs

Exponentially growing human endothelial HUVECs cells (human umbilical vein endothelial cells, cat#CC-2517, Cambrex, Walkersville, Md.) were seeded at twenty five thousand cells/well in 96 well plates in EBM-2 MV medium with growth factors (cat#CC-3202, Cambrex) and grown at 37° C. in 5% $CO_2$. Sixteen hours post-plating, the cells were changed to serum-free medium (RPMI 1640 containing 0.1% BSA (bovine serum albumin) and compounds were added at different concentrations for 2 hrs, after which the cells were stimulated for 10 min with 50 ng/ml of either VEGF (vascular endothelial growth factor, Protein Sciences, Meriden, Conn.) or bFGF (basic fibroblast growth factor cat#PHG0026, Biosource International, Camarillo, Calif.). The rest of the assay was performed per manufacturer indications for the ERK1/2 Bioplex assay (cat#171-304004, Bio-Rad, Hercules, Calif.). After removing culture medium by aspiration, the cells were quickly rinsed with 100 µl of cell wash buffer A to stop treatment reaction. Eighty microliters of cell lysis buffer were then immediately added to each well of the 96 well plate which was put on ice. Cells in each well were lysed by pipetting up and down 5 times with a multi-channel pipet. The plate was then agitated on a microtiter plate shaker at 300 rpm for 20 min at 4° C. Cellular debris were pelleted by centrifugation at 4500 g for 15 min at 4° C. and the supernatant was collected. Forty five microliters of supernatant was diluted with an equal volume of Bio-Plex phosphoprotein assay Buffer B, The coupled and color coated beads were added into a 96 well filter plate, and the prepared lysates were added. The beads and lysate mixture was incubated at room temperature for 15-18 hrs. The following day, the plate was vacuum-filtered and then washed 3×. Twenty-five microliters of detection antibody solution were added to each well and the plate was then incubated for 30 min at room temperature. The plate was then vacuum-filtered and washed as described previously. Fifty microliters of streptavidin-PE solution was added to each well, the plate was incubated for 10 min at room temperature and then was then vacuum-filtered and washed as described above. One hundred twenty-five microliters of resuspension buffer was added to each well and data were acquired on the Luminex 100 instrument (Bio-Rad). Compounds of examples 1, 8, 9, 12, 23, 27, 30, 32, 49, 59 and 70 demonstrate an inhibition greater than 50% @ 100 mM in the VEGF stimulated Phospho-ERK in HUVEC assay. Compounds of examples 11, 22, 24, 26, 29, 37, 39, 41, 47, 66, 75, 85, 93, 99, 100, 131, 143, 146 and 168 demonstrate an inhibition greater than 50% @ 1 µM but less than 50% @ 100 nM in the VEGF stimulated Phospho-ERK in HUVEC assay. Compounds of examples 14, 18, 62, 96, 98, 104 and 140 demonstrate an inhibition greater than 50% @ 10 µM but less than 50% @ 100 nM and 1 µM in the VEGF stimulated Phospho-ERK in HUVEC assay.

BRDU Growth Factor Stimulated Proliferation of HUVEC

Exponentially growing human umbilical vein endothelial cells (HUVEC; Cat #CC-2519A, Cambrex, Walkersville, Md.) were seeded at two thousand cells/well into Collagen IV-coated 96 well plates (Cat #35-4429, Becton Dickinson, Bedford, Mass.) in assay media containing RPMI-1640 (Cat #11875-093, Gibco, Carlsbad, Calif.), 0.5% charcoal-stripped serum (Cat #SH30068.03, HyClone, Logan, Utah), and 1% N-2 supplement (Cat #17502-048, Gibco, Carlsbad, Calif.). Fours hours after incubating the plates at 37° C. in 5% $CO_2$, the cells were treated with different concentrations of compound (diluted in assay media with a final DMSO concentration=0.1%) and then were immediately stimulated with 80 ng/ml of vascular endothelial growth factor (VEGF, Cat #100-20, PeproTech, Rocky Hill, N.J.) or 1.5 ng/ml of basic fibroblast growth factor (bFGF, Cat #100-18B, PeproTech, Rocky Hill, N.J.). Treated cells were incubated for 3 days at 37° C. in 5% $CO_2$. DNA synthesis was measured via the incorporation of bromodeoxyuridine (BrdU) into newly synthesized DNA using the Amersham Cell Proliferation BioTrack ELISA system (Cat #RPN250, Amersham, Piscataway, N.J.). Diluted BrdU solution (20 µl of stock BrdU diluted 1:20 fold into assay media) was added to each well and incubation proceeded for 6 hours at 37° C. in 5% $CO_2$. The media was removed and the cells were fixed according to the specifications of the Amersham assay kit for 30 minutes at room temperature. After removing the fixative, blocking buffer (supplied by Amersham kit; 200 µl/well) was added and the plates were stored at 4° C. overnight. The blocking buffer was aspirated and peroxidase-labeled anti-BrdU antibody (supplied by Amersham kit; 100 µl/well) was added and incubated for 3 hours at room temperature. The plates were washed three times with wash buffer (supplied by Amersham kit; 300 µl/well/wash). Immediately following the washes, 100 µl of the TMB-substrate was dispensed into each well and the plates were further incubated for 30 minutes at room temperature. The reaction was terminated by the addition of 25 µl of 1M $H_2SO_4$. Plates were read immediately at 450 nm using a SpectraMAX 250 spectrophotometer plate reader (Molecular Devices, Sunnyvale, Calif.). The software utilized was SoftMAX pro v.2.4.1.

Compounds of examples 70, 101, 218 and 226 demonstrate an $IC_{50}$ of less than 10 nM in the VEGFR stimulated HUVEC proliferation assay. Compounds of examples 103, 151, 155, 157, 159, 162, 223, 233, 234, 239 and 243 demonstrate an $IC_{50}$ greater than 10 nM but less than 100 nM in the VEGFR stimulated HUVEC proliferation assay. Compounds of examples 30, 99, 102, 152, 240 and 247 demonstrate an $IC_{50}$ greater than 100 nM but less than 500 nM in the VEGFR stimulated HUVEC proliferation assay. Compounds of examples 100 and 163 demonstrate an $IC_{50}$ greater than 500 nM but less than 2 µM in the VEGFR stimulated HUVEC proliferation assay.

Compounds of examples 70, 99, 101, 103, 151 and 223 demonstrate an $IC_{50}$ of less than 100 nM in the FGFR stimulated HUVEC proliferation assay. Compounds of examples 30, 102, 152, 155, 157, 159, 162, 218, 226, 233, 234, 239, 243 and 247 demonstrate an $IC_{50}$ greater than 100 nM but less than 500 nM in the FGFR stimulated HUVEC proliferation assay. Compound of example 240 demonstrates an $IC_{50}$ greater than 500 nM but less than 1 µm in the FGFR stimulated HUVEC proliferation assay.

Tumor Cell Proliferation

Human tumor cells (e.g., HCT116 or MDA-MB-231 cells), are seeded in a Costar 96-well plate at $3.0 \times 10^3$ cells/well and grown in 150 µl of RPMI complete media (Invitrogen Corporation, Grand Island, N.Y.) containing 10% fetal bovine serum (Hyclone, Logan, Utah) at 37° C. for 16 h in an incubator with 5% $CO_2$. To each well, 50 µl of additional growth media containing 40 µM to 18 nM concentrations of compound with 0.4% DMSO is added. Cells are grown for another 72 h at 37° C. with 5% $CO_2$. 20 µl of Alamar Blue (Trek Diagnostic Systems, Inc., Cleveland, Ohio) reagent is added to each well and incubated for 3 h at 37° C. Plates are read in a SpectraMax Gemini (Molecular Devices, CA) with 544 nm excitation and 590 nm emission wavelength. $IC_{50}$ values are determined by linear regression analysis of log drug concentration versus percent inhibition.

Compounds of examples 25, 70, 93, 155, 235 and 237 demonstrate an $IC_{50}$ of less than 500 nM in the HCT116 proliferation assay. Compounds of examples 59, 69, 71, 76, 156, 159, 161, 162, 223, 239, 241, 256 and 257 demonstrate an $IC_{50}$ greater than 500 nM but less than 1.5 µM in the HCT116 proliferation assay. Compounds of examples 30, 73, 74, 82, 99, 100, 102, 149, 157, 163, 217, 225, 226, 232, 233, 234, 240, 242, 243, 247, 248, 254 and 255 demonstrate an $IC_{50}$ greater than 1.5 µM but less than 5 µM in the HCT116 proliferation assay. Compounds of examples 84, 94, 103, 153 and 218 demonstrate an $IC_{50}$ greater than 5 µM but less than 10 µM in the HCT116 proliferation assay.

Compounds of examples 25, 70, 71, 155 and 156 demonstrate an $IC_{50}$ of less than 500 nM in the MDA-MB-231 proliferation assay. Compounds of examples 59, 82, 93, 99, 149, 159, 217, 223, 235, 239, 248, 251, 255, 256 and 257 demonstrate an $IC_{50}$ greater than 500 nM but less than 1.5 µM in the MDA-MB-231 proliferation assay. Compounds of examples 69, 73, 74, 76, 94, 100, 157, 161, 162, 163, 225, 226, 232, 233, 234, 237, 240, 241, 242, 243, 247 and 254 demonstrate an $IC_{50}$ greater than 1.5 µM but less than 5 µM in the MDA-MB-231 proliferation assay. Compounds of examples 102, 103, 153 and 218 demonstrate an $IC_{50}$ greater than 5 µM but less than 10 µM in the MDA-MB-231 proliferation assay.

p-Histone3

Compounds were assayed for the inhibition of histone 3 phosphorylation in colon carcinoma (HCT116). Briefly, 20,000 cells/well were seeded in a 96-well black-walled, poly-d-lysine plates in RPMI+10% FBS and incubated at 37° C. in 5% $CO_2$ overnight. The following day, the cells were treated with compounds for 24 hours at 37° C. Following compound treatment; plates were centrifuged at 1000 rpm for 2 minutes and washed twice with 100 µl of cold sterile TBS. Cells were then fixed with cold 3.7% formaldehyde in TBS (4° C. for 1 hour) and then permeabolized with 0.1% Triton-X-100 in TBS (room temperature for 30 minutes). Plates were then washed with of 0.25% BSA-TBS and blocked with BSA solution for 1 hour at room temperature while shaking. The supernatant was removed and replaced with diluted primary antibody (anti-phospho-histone 3, serine 10, Cell Signaling) at 1:250 in 0.25% BSA-TBS and incubated overnight at 4° C. The plates were washed and treated with diluted secondary antibody (anti-rabbit Eu-labeled) at 1:10000 in 0.25% BSA-TBS (room temperature for 1 hour). The antibody solution was removed from each well and washed eight times. The wash buffer was replaced with 50 µl pre-warmed enhancement solution and mixed on the orbital shaker for 10 minutes. Fluorescence was detected with a Victor V Fluorescence Detector. The data are expressed as percent inhibition: % inhibition=100−((Signal with inhibitor-background)/(Signal without inhibitor-background))×100. Compounds of examples 88, 92, 139, 164, 165, 171, 176 and 177 demonstrate an $IC_{50}$ of less than 500 nM in the p-histone3 assay. Compounds of examples 7, 13, 59, 167 and 204 demonstrate an $IC_{50}$ greater than 500 nM but less than 1 µM in the p-histone3 assay.

The in vivo effect of the compounds according to the invention can be demonstrated in tumor xenograft experiments, such as described in Wilhelm, S. et al. *Cancer Res.* 2004, 64, 7099-09.

C. OPERATIVE EXAMPLES RELATING TO PHARMACEUTICAL COMPOSITIONS

The compounds according to the invention can be converted into pharmaceutical preparations as follows:

Tablet:

Composition:

100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Suspension for Oral Administration:

Composition:

1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation:

The Rhodigel is suspended in ethanol and the active component is added to the suspension. The water is added with stirring. Stirring is continued for about 6 h until the swelling of the Rhodigel is complete.

Solution for Intravenous Administration 1:

Composition: 100-200 mg of the compound of Example 1, 15 g polyethylenglykol 400 and 250 g water optionally with up to 15% Cremophor EL, and optionally up to 15% ethyl alcohol, and optionally up to 2 equivalents of a pharmaceutically suitable acid such as citric acid or hydrochloric acid.

Preparation:

The compound of Example 1 and the polyethylenglykol 400 are dissolved in the water with stirring. The solution is sterile filtered (pore size 0.22 µm) and filled into heat sterilized infusion bottles under aseptical conditions. The infusion bottles are being sealed with rubber seals.

Solution for Intravenous Administration 2:

Composition: 100-200 mg of the compound of Example 1, saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid.

Preparation:

The compound of Example 1 is dissolved in the saline solution with stirring. Optionally Cremophor EL, ethyl alcohol or acid are added. The solution is sterile filtered (pore size 0.22 µm) and filled into heat sterilized infusion bottles under aseptical conditions. The infusion bottles are being sealed with rubber seals.

It should be apparent to one of ordinary skill in the art that changes and modifications can be made to this invention without departing from the spirit or scope of the invention as it is set forth herein.

The invention claimed is:

1. A compound of formula (I)

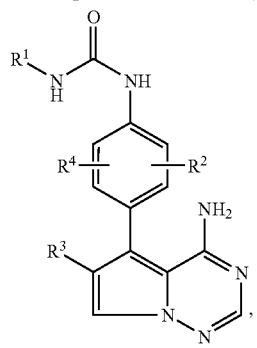

(I)

wherein $R^1$ is selected from the group consisting of unsubstituted aryl, substituted or unsubstituted benzyl, and unsubstituted heteroaryl, wherein benzyl can be substituted with 0, 1, 2 or 3 groups selected from halogen, $(C_1-C_3)$alkyl, and $(C_1-C_3)$alkoxy;

$R^2$ is selected from the group consisting of hydrogen, halogen, $(C_1-C_4)$alkyl and $(C_1-C_4)$alkoxy;

$R^3$ is selected from the group consisting of carboxyl, formyl, $(C_1-C_6)$alkylcarbonyl optionally substituted with 0, 1, 2, or 3 groups selected from fluorine, chlorine, hydroxy, $(C_1-C_6)$alkoxy, and heterocycle, $(C_3-C_6)$cycloalkylcarbonyl, $(C_1-C_6)$alkoxycarbonyl optionally substituted with 0, 1, 2, or 3 groups selected from amino, and $(C_1-C_6)$alkoxycarbonyl, aminocarbonyl, $(C_1-C_6)$alkylaminocarbonyl, wherein $(C_1-C_6)$alkylaminocarbonyl can optionally be substituted with 0, 1, 2 or 3 substituents independently selected from the group consisting of $(C_3-C_6)$cycloalkyl, halogen, amino, $(C_1-C_6)$alkylamino, hydroxy, $(C_1-C_6)$alkoxy, $(C_1-C_6)$alkoxycarbonyl, $(C_1-C_6)$alkylthio, $(C_1-C_6)$alkoxycarbonylamino, and methylsulfonyl, and wherein $(C_1-C_6)$alkylaminocarbonyl can optionally be substituted with or 0 or 1 heterocyclyl, wherein heterocyclyl can optionally be substituted with 0 or 1 $(C_1-C_6)$alkyl, and wherein $(C_1-C_6)$alkylaminocarbonyl can optionally be substituted with 0 or 1 phenyl, wherein phenyl can optionally be substituted with 0 or 1 halogen, $(C_1-C_6)$alkyl, or $(C_1-C_6)$alkoxy, heterocyclylcarbonyl optionally substituted with 0 or 1 amino, $(C_1-C_6)$alkylamino, cycloalkyl, or $(C_1-C_6)$alkyl, wherein $(C_1-C_6)$alkyl can optionally be substituted with 0 or 1 amino or $(C_1-C_6)$alkylamino, $(C_1-C_6)$alkyl optionally substituted with 0, 1, 2 or 3 substituents independently selected from the group consisting of a) hydroxyl, b) amino, c) $(C_1-C_6)$alkylamino, wherein $(C_1-C_6)$alkylamino can be substituted with 0, 1, 2, 3 or 4 substituents independently selected from the group consisting of halogen, amino, alkylamino, methoxy, methylthio, and methylsulfonyl, d) arylamino, wherein arylamino can be substituted with 0, 1 or 2 substituents independently selected from the group consisting of $(C_1-C_6)$alkyl, $(C_1-C_6)$alkoxy, and trifluoromethyl, e) heterocyclyl, wherein heterocyclyl can be substituted with 0, 1 or 2 $(C_1-C_6)$alkyl, wherein $(C_1-C_6)$alkyl can be substituted with 0, 1 or 2 hydroxy, methoxy or pyridyl, f) imidazolyl, g) pyridylamino, h) $(C_1-C_3)$alkoxy optionally substituted by fluoro, difluoro, trifluoro, or by heterocycle, wherein heterocycle can optionally be substituted by 0 or 1 $(C_1-C_6)$alkyl, i) $(C_1-C_3)$alkoxy$(C_2-C_3)$alkoxy, and j) $(C_1-C_6)$alkoxycarbonyl, k) $(C_3-C_6)$cycloalkyl, l) cyano, $(C_1-C_6)$alkoxy optionally substituted with 1, 2 or 3 substituents independently selected from the group consisting of amino, $(C_1-C_6)$alkylamino, and heterocyclyl, wherein heterocyclyl can be substituted with 0, 1, 2 or 3 $(C_1-C_6)$alkyl, ($C_3$-$C_6$)cycloalkylaminocarbonyl optionally substituted with ($C_1$-$C_3$)alkyl,
cyano,
heteroaryl, wherein heteroaryl can be substituted with 0, 1, 2, or 3 groups independently selected from the group consisting of
a) ($C_1$-$C_6$)alkyl, wherein ($C_1$-$C_6$)alkyl can be substituted with 0, 1, 2, or 3 halogen, 0 or 1 heterocyclyl, 0 or 1 alkylamino, or 0 or 1 hydroxy or methoxy,
b) halogen,
c) amino,
d) alkylamino,
e) ($C_1$-$C_6$)alkoxycarbonyl, and
f) ($C_3$-$C_6$)cycloalkyl,
heteroarylcarbonyl, which can be substituted with 0, 1, 2, or 3 groups independently selected from the group consisting of ($C_1$-$C_6$)alkyl, ($C_3$-$C_6$)cycloalkyl and halogen,
heterocyclyl, wherein heterocyclyl can be substituted with 0, 1, 2, or 3 groups independently selected from the group consisting of ($C_1$-$C_6$)alkyl and ($C_1$-$C_6$)alkoxycarbonyl; and
$R^4$ is selected from the group consisting of hydrogen, ($C_1$-$C_6$)alkyl, ($C_1$-$C_6$)alkoxy and halogen;
or a pharmaceutically acceptable salt thereof.

2. The compound of claim 1, wherein
$R^1$ is selected from the group consisting of unsubstituted phenyl and unsubstituted monocyclic heteroaryl having 5 or 6 ring atoms;
$R^2$ is selected from the group consisting of hydrogen, halogen, ($C_1$-$C_4$)alkyl and ($C_1$-$C_4$)alkoxy;
$R^3$ is selected from the group consisting of
carboxyl,
formyl,
($C_1$-$C_6$)alkylcarbonyl optionally substituted with 0, 1, 2, or 3 groups selected from fluorine, chlorine, hydroxy, ($C_1$-$C_6$)alkoxy, and monocyclic heterocycle having 5 or 6 ring atoms,
($C_3$-$C_6$)cycloalkylcarbonyl,
($C_1$-$C_6$)alkoxycarbonyl optionally substituted with 0, 1, 2, or 3 groups selected from amino, and ($C_1$-$C_6$)alkoxycarbonyl,
aminocarbonyl,
($C_1$-$C_6$)alkylaminocarbonyl, wherein ($C_1$-$C_6$)alkylaminocarbonyl can optionally be substituted with 0, 1, 2 or 3 substituents independently selected from the group consisting of ($C_3$-$C_6$)cycloalkyl, halogen, amino, ($C_1$-$C_6$)alkylamino, hydroxy, ($C_1$-$C_6$)alkoxy, ($C_1$-$C_6$)alkoxycarbonyl, ($C_1$-$C_6$)alkylthio, ($C_1$-$C_6$)alkoxycarbonylamino, and methylsulfonyl, and wherein ($C_1$-$C_6$)alkylaminocarbonyl can optionally be substituted with 0 or 1 hydroxyl or 0 or 1 monocyclic heterocyclyl having 5 or 6 ring atoms, wherein heterocyclyl can optionally be substituted with 0 or 1 ($C_1$-$C_6$)alkyl, and wherein ($C_1$-$C_6$)alkylaminocarbonyl can optionally be substituted with 0 or 1 phenyl, wherein phenyl can optionally be substituted with 0 or 1 halogen or ($C_1$-$C_6$)alkyl,
monocyclic heterocyclylcarbonyl having 5 or 6 ring atoms, optionally substituted with 0 or 1 amino, ($C_1$-$C_6$)alkylamino, ($C_3$-$C_6$)cycloalkyl, or ($C_1$-$C_6$)alkyl, wherein ($C_1$-$C_6$)alkyl can optionally be substituted with 0 or 1 amino or ($C_1$-$C_6$)alkylamino,
($C_1$-$C_6$)alkyl optionally substituted with 0, 1, 2 or 3 substituents independently selected from the group consisting of
a) hydroxyl,
b) amino,
c) ($C_1$-$C_6$)alkylamino, wherein ($C_1$-$C_6$)alkylamino can be substituted with 0, 1, 2, 3 or 4 substituents independently selected from the group consisting of halogen, amino, alkylamino, methoxy, methylthio, and methylsulfonyl,
e) monocyclic heterocyclyl having 5 or 6 ring atoms, wherein heterocyclyl can be substituted with 0, 1 or 2 ($C_1$-$C_6$)alkyl, wherein ($C_1$-$C_6$)alkyl can be substituted with 0, 1 or 2 hydroxy, methoxy or pyridyl,
f) imidazolyl,
h) ($C_1$-$C_3$)alkoxy optionally substituted by fluoro up to the perfluoro level, or by monocyclic heterocycle having 5 or 6 ring atoms, wherein heterocycle can optionally be substituted by 0 or 1 ($C_1$-$C_6$)alkyl,
i) ($C_1$-$C_3$)alkoxy($C_2$-$C_3$)alkoxy, and
j) ($C_1$-$C_6$)alkoxycarbonyl,
k) ($C_3$-$C_6$)cycloalkyl,
l) cyano,
($C_3$-$C_6$)cycloalkylaminocarbonyl optionally substituted with ($C_1$-$C_3$)alkyl,
cyano,
heteroaryl, wherein heteroaryl can be substituted with 0, 1, 2, or 3 groups independently selected from the group consisting of
a) ($C_1$-$C_6$)alkyl, wherein ($C_1$-$C_6$)alkyl can be substituted with 0, 1, 2, or 3 halogen, 0 or 1 monocyclic heterocyclyl having 5 or 6 ring atoms, 0 or 1 alkylamino, or 0 or 1 hydroxy or methoxy,
b) halogen,
e) ($C_1$-$C_6$)alkoxycarbonyl, and
f) ($C_3$-$C_6$)cycloalkyl,
monocyclic heteroarylcarbonyl having 5 or 6 ring atoms,
monocyclic heterocyclyl having 5 or 6 ring atoms, wherein heterocyclyl can be substituted with 0, 1, 2, or 3 groups independently selected from the group consisting of ($C_1$-$C_6$)alkyl and ($C_1$-$C_6$)alkoxycarbonyl; and
$R^4$ is selected from the group consisting of hydrogen and halogen;
or a pharmaceutically acceptable salt thereof.

3. The compound of claim 1, wherein
$R^1$ is selected from the group consisting of unsubstituted phenyl, unsubstituted pyrazolyl, unsubstituted oxazolyl, unsubstituted isoxazolyl, unsubstituted thiazolyl, unsubstituted pyridinyl, and unsubstituted pyrimidinyl;
$R^2$ is selected from the group consisting of hydrogen, fluoro and chloro;
$R^3$ is selected from the group consisting of
($C_1$-$C_6$)alkylcarbonyl optionally substituted with 0, 1, 2, or 3 groups selected from fluorine, chlorine, hydroxy, ($C_1$-$C_6$)alkoxy, piperazinyl, morpholinyl, pyrrolidinyl, and piperidinyl,
cyclopropylcarbonyl,
aminocarbonyl,
($C_1$-$C_6$)alkylaminocarbonyl, wherein ($C_1$-$C_6$)alkylaminocarbonyl can optionally be substituted with 0, 1, 2 or 3 substituents independently selected from the group consisting of ($C_3$-$C_6$)cycloalkyl, halogen, amino, ($C_1$-$C_6$)alkylamino, hydroxy, ($C_1$-$C_6$)alkoxy, ($C_1$-$C_6$)alkoxycarbonyl, ($C_1$-$C_6$)alkylthio, ($C_1$-$C_6$)alkoxycarbonylamino, and methylsulfonyl, and wherein ($C_1$-$C_6$)alkylaminocarbonyl can optionally be substituted with 0 or 1 hydroxyl, piperazinyl, morpholinyl, pyrrolidinyl or piperidinyl, wherein piperazinyl, morpholinyl, pyrrolidinyl or piperidinyl can optionally be substituted with 0 or 1 ($C_1$-$C_6$)alkyl, and wherein ($C_1$-$C_6$)alkylaminocarbonyl can optionally be substituted with 0 or 1 phenyl, wherein phenyl can optionally be substituted with 0 or 1 halogen or ($C_1$-$C_6$)alkyl, heterocyclylcarbonyl selected from piperazinylcarbonyl, morpholinylcarbonyl, pyrrolidinylcarbonyl or piperidinylcarbonyl, optionally substituted with 0 or 1 amino, ($C_1$-$C_6$)alkylamino, ($C_3$-$C_6$)cycloalkyl, or ($C_1$-$C_6$)alkyl, wherein ($C_1$-$C_6$)alkyl can optionally be substituted with 0 or 1 amino or ($C_1$-$C_6$)alkylamino, ($C_1$-$C_6$)alkyl optionally substituted with 0, 1, 2 or 3 substituents independently selected from the group consisting of a) hydroxyl,
c) ($C_1$-$C_6$)alkylamino, wherein ($C_1$-$C_6$)alkylamino can be substituted with 0, 1, 2, 3 or 4 substituents independently selected from the group consisting of halogen, alkylamino, and methoxy,
e) piperazinyl, morpholinyl, pyrrolidinyl or piperidinyl, wherein piperazinyl, morpholinyl, pyrrolidinyl or piperidinyl can be substituted with 0, 1 or 2 ($C_1$-$C_6$)alkyl, wherein ($C_1$-$C_6$)alkyl can be substituted with 0, 1 or 2 hydroxy or methoxy,
f) imidazolyl,
h) ($C_1$-$C_3$)alkoxy optionally substituted by fluoro up to the perfluoro level, or by monocyclic heterocycle having 5 or 6 ring atoms, wherein heterocycle can optionally be substituted by 0 or 1 ($C_1$-$C_6$)alkyl,
i) ($C_1$-$C_3$)alkoxy($C_2$-$C_3$)alkoxy, and
j) ($C_1$-$C_6$)alkoxycarbonyl,
k) ($C_3$-$C_6$)cycloalkyl,
l) cyano,
($C_3$-$C_6$)cycloalkylaminocarbonyl optionally substituted with ($C_1$-$C_3$)alkyl,
cyano,
pyrazolyl, oxazolyl, isoxazolyl, thiazolyl, isothiazolyl, pyridinyl, imidazolyl or pyrimidinyl, wherein pyrazolyl, oxazolyl, isoxazolyl, thiazolyl, isothiazolyl, pyridinyl, imidazolyl or pyrimidinyl can be substituted with 0, 1, 2, or 3 groups independently selected from the group consisting of
a) ($C_1$-$C_6$)alkyl, wherein ($C_1$-$C_6$)alkyl can be substituted with 0, 1, 2, or 3 halogen, 0 or 1 alkylamino, or 0 or 1 methoxy,
b) halogen, and
f) ($C_3$-$C_6$)cycloalkyl,
pyrazolylcarbonyl, oxazolylcarbonyl, isoxazolylcarbonyl, thiazolylcarbonyl, pyridinylcarbonyl or pyrimidinylcarbonyl; and $R^4$ is selected from the group consisting of hydrogen and fluoro;

or a pharmaceutically acceptable salt thereof.

4. A process for preparing a compound of claim 1, wherein a compound of formula (II)

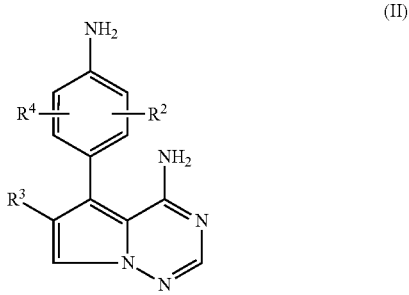

(II)

wherein $R^2$, $R^3$ and $R^4$ have the meaning indicated in claim 1, is reacted with an isocyanate compound of formula (III)

$R^1$—NCO (III)

or with an carbamate of formula (VI)

$R^1$—NH—C(O)—OPh (VI), wherein $R^1$ has the meaning indicated in claim 1; or a compound of formula (IV)

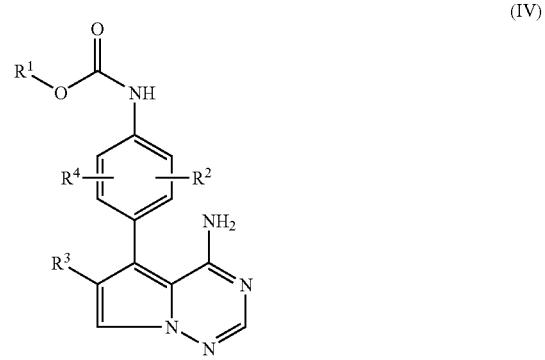

(IV)

wherein $R^1$, $R^2$, $R^3$ and $R^4$ have the meaning indicated in claim 1, is reacted with an amine of formula (V)

$R^1$—NH$_2$ (V), wherein $R^1$ has the meaning indicated in claim 1.

5. A pharmaceutical composition comprising a compound of claim 1 in combination with at least one pharmaceutically acceptable, pharmaceutically safe carrier or excipient.

6. A method of treating breast or colon cancer in a mammal, comprising administering to a mammal in need thereof a therapeutically effective amount of a compound of formula (I) according to claim 1.

7. The method of claim 6, wherein said therapeutically effective amount of a compound of formula (I) exhibits an effect on angiogenesis.

8. The compound of claim 1, wherein
$R^1$ is benzyl wherein benzyl is substituted with 1 halogen substituent.

* * * * *